US012599655B2

(12) United States Patent
Massari et al.

(10) Patent No.: US 12,599,655 B2
(45) Date of Patent: Apr. 14, 2026

(54) *NEISSERIA GONORRHOEAE* VACCINE COMPOSITIONS AND METHODS OF SELECTING ANTIGENS

(71) Applicant: Trustees of Tufts College, Medford, MA (US)

(72) Inventors: Paola Massari, Cambridge, MA (US); Caroline Genco, Medford, MA (US)

(73) Assignee: Trustees of Tufts College

(*) Notice: Subject to any disclaimer, the term of this patent is extended or adjusted under 35 U.S.C. 154(b) by 690 days.

(21) Appl. No.: 17/631,694

(22) PCT Filed: Jul. 30, 2020

(86) PCT No.: PCT/US2020/044187
    § 371 (c)(1),
    (2) Date: Jan. 31, 2022

(87) PCT Pub. No.: WO2021/022001
    PCT Pub. Date: Feb. 4, 2021

(65) Prior Publication Data
    US 2022/0280630 A1     Sep. 8, 2022

Related U.S. Application Data

(60) Provisional application No. 62/881,627, filed on Aug. 1, 2019.

(51) Int. Cl.
    *A61K 39/095*     (2006.01)
    *A61K 39/00*      (2006.01)
    (Continued)

(52) U.S. Cl.
    CPC ............ *A61K 39/095* (2013.01); *C12Q 1/689* (2013.01); *G16B 30/10* (2019.02); *A61K 2039/575* (2013.01)

(58) Field of Classification Search
    CPC ......................... A61K 39/095; A61K 2039/575
    See application file for complete search history.

(56) References Cited

U.S. PATENT DOCUMENTS 7,576,176 B1     8/2009  Fraser et al.
9,636,393 B2 *   5/2017  Giuliani ................. A61P 31/12
                 (Continued)

OTHER PUBLICATIONS

Dhillon et al. "Meningococcal Quadrivalent Tetanus Toxoid Conjugate Vaccine (MenACWY-TT; Nimenrix®): A Review", Nov. 1, 2017, Drugs, vol. 77, pp. 1881-1896. (Year: 2017).*
(Continued)

*Primary Examiner* — Daniel E Kolker
*Assistant Examiner* — Amelia Nicole Dickens
(74) *Attorney, Agent, or Firm* — NIXON PEABODY LLP; David S. Resnick; Nicole D. Kling

(57) ABSTRACT

Described herein are vaccine compositions and methods of selecting an antigen or fragment thereof for the preparation of a vaccine composition. The methods and vaccine compositions described herein are based, in part, on the discovery that certain polypeptides not previously identified or considered for potential use as antigens from pathogenic microorganisms (e.g., *N. gonorrhoeae*) can provoke an immune response in a subject. The methods of identifying and selecting the antigens described herein rely, in part, on approaches that identify polypeptides (e.g., hypothetical proteins) predicted to be immunogenic.

13 Claims, 17 Drawing Sheets

Specification includes a Sequence Listing.

(51) Int. Cl.
   *C12Q 1/689*       (2018.01)
   *G16B 30/10*      (2019.01)

(56)         References Cited

U.S. PATENT DOCUMENTS

| | | | |
|---|---|---|---|
| 2002/0187160 A1* | 12/2002 | Stein | A61K 39/39 424/191.1 |
| 2005/0260581 A1* | 11/2005 | Fontana | A61P 31/12 435/6.15 |
| 2008/0118535 A1 | 5/2008 | Yang et al. | |
| 2009/0298099 A1 | 12/2009 | Fontana et al. | |
| 2014/0017268 A1 | 1/2014 | Gebhart et al. | |
| 2015/0290311 A1 | 10/2015 | Aagaard et al. | |
| 2016/0067326 A1 | 3/2016 | Arico et al. | |
| 2018/0196047 A1 | 7/2018 | Alderete | |

OTHER PUBLICATIONS

Kasper et al. "Bactericidal Antibody in Genital Infection Due to Neisseria gonorrhoeae", Feb. 1977, The Journal of Infectious Diseases, vol. 135, No. 2, p. 243-251 (Year: 1977).*
Liu et al. "Experimental vaccine induces Th1-driven immune responses and resistance to Neisseria gonorrhoeae infection in a murine model", Nov. 2017, Mucosal Immunology, vol. 10, Issue 6, p. 1594-1608. (Year: 2017).*
Nudel et al. "Transcriptome Analysis of Neisseria gonorrhoeae during Natural Infection Reveals Differential Expression of Antibiotic Resistance Determinants between Men and Women" mSphere 3:e00312-18 (2018).
Almonacid-Medoza et al. "Structure of the recombinant Neisseria gonorrhoeae adhesin complex protein (rNg-ACP) and generation of murine antibodies with bactericidal activity against gonococci." Msphere 3.5: 10-1128 (2018).
Cole et al. "Opacity proteins increase Neisseria gonorrhoeae fitness in the female genital tract due to a factor under ovarian control." Infection and Immunity 78.4: 1629-1641 (2010).
Feinen et al. "Critical role of Th17 responses in a murine model of Neisseria gonorrhoeae genital infection." Mucosal Immunology 3.3: 312-321 (2010).
Feinen et al. "Contrasting roles of IL-22 and IL-17 in murine genital tract infection by Neisseria gonorrhoeae." Frontiers in Immunology 3: 11 (2012).
Gulati et al. "Properdin is critical for antibody-dependent bactericidal activity against Neisseria gonorrhoeae that recruit C4b-binding protein." The Journal of Immunology 188.7: 3416-3425 (2012).
Humbert et al. "Immunization with recombinant truncated Neisseria meningitidis-Macrophage Infectivity Potentiator (rT-Nm-MIP) protein induces murine antibodies that are cross-reactive and bactericidal for Neisseria gonorrhoeae." Vaccine 36.27: 3926-3936 (2018).

Islam et al. "Specific binding to differentially expressed human carcinoembryonic antigen-related cell adhesion molecules determines the outcome of Neisseria gonorrhoeae infections along the female reproductive tract." Infection and Immunity 86.8: 10-1128 (2018).
Jerse. "Experimental gonococcal genital tract infection and opacity protein expression in estradiol-treated mice." Infection and immunity 67.11: 5699-5708 (1999).
Jerse et al. "A gonococcal efflux pump system enhances bacterial survival in a female mouse model of genital tract infection." Infection and immunity 71.10: 5576-5582 (2003).
Jerse et al. "Vaccine research for gonococcal infections: where are we?." Sexually transmitted infections 89. Suppl 4: iv63-iv68 (2013).
Jerse et al. "Vaccines against gonorrhea: current status and future challenges." Vaccine 32.14: 1579-1587 (2014).
Li et al. "Neisseria gonorrhoeae NspA induces specific bactericidal and opsonic antibodies in mice." Clinical and Vaccine Immunology 18.11: 1817-1822 (2011).
Liu et al. "New concepts in immunity to Neisseria gonorrhoeae: innate responses and suppression of adaptive immunity favor the pathogen, not the host." Frontiers in microbiology 2: 52 (2011).
Liu et al. "Enhancement of adaptive immunity to Neisseria gonorrhoeae by local intravaginal administration of microencapsulated interleukin 12." The Journal of infectious diseases 208.11: 1821-1829 (2013).
Plante et al. "Intranasal Immunization with Gonococcal Outer Membrane Preparations Reduces the Duration of Vaginal Colonization of Mice by Neissevia gonorrhoeae." The Journal of infectious diseases 182.3: 848-855 (2000).
Rice et al. "Neisseria gonorrhoeae: drug resistance, mouse models, and vaccine development." Annual review of microbiology 71.1: 665-686 (2017).
Sarantis et al. "Defining the roles of human carcinoembryonic antigen-related cellular adhesion molecules during neutrophil responses to Neisseria gonorrhoeae." Infection and immunity 80.1: 345-358 (2012).
Semchenko et al. "MetQ of Neisseria gonorrhoeae is a surface-expressed antigen that elicits bactericidal and functional blocking antibodies." Infection and immunity 85.2: 10-1128 (2017).
Song et al. "Local and humoral immune responses against primary and repeat Neisseria gonorrhoeae genital tract infections of 17β-estradiol-treated mice." Vaccine 26.45: 5741-5751 (2008).
Wang et al. "Gonococcal MtrE and its surface-expressed Loop 2 are immunogenic and elicit bactericidal antibodies." Journal of Infection 77.3: 191-204 (2018).
Zhu et al. "Vaccines for gonorrhea: can we rise to the challenge?." Frontiers in microbiology 2: 124 (2011).
Zhang et al. "Comparison of PLA microparticles and alum as adjuvants for H5N1 influenza split vaccine: adjuvanticity evaluation and preliminary action mode analysis." Pharmaceutical research 31.4 (2014).

* cited by examiner

RNA-seq

*N. gonorrhoeae* global gene expression

2116 | 2151

\*Hypothetical protein genes shared predicted antigens mRNA expression < 50 RPKM

655 | 678

186 / 284

163

112 predicted localization

460 / 394 mRNA expression > 50 RPKM

69

43 non-cytosolic cytosolic

| | mRNA expression in vivo | | antigen | localization | | | | Size | annotation/homology | | Gene genome |
|---|---|---|---|---|---|---|---|---|---|---|---|
| | RPKM | | VaxiJen score | PSORTb PredictProtein Gneg-mPLoc | TMHMM | Phobius | SignalP* LipoP** | kDa | PubMed, BLASTp, PubMLST | | |
| NG00416 | 198 | 127 | 0.5 | periplasmic | 0 | non-cytosolic | *19-20: AFA-DR | 10.8 | hypothetical | NEIS0782 NMB0844 | v |
| NG00690 | 142 | 157 | 0.7 | outer membrane/periplasmic | 1 | TM: 5-27 non-cytosolic | **16-17: LGC-CA (+2=A) | 12.1 | hypothetical | NEIS1164 NMB1047 | v |
| NG00948 | 125 | 105 | 0.43 | outer membrane/periplasmic | 0 | non-cytosolic | ***16-17: LAA-CS (+2=S) | 44.8 | lipoprotein, NlpB/DapX/BamC | NEIS0906 NMB0928 | v |
| NG01043 | 1748 | 519 | 0.82 | outer membrane/periplasmic | 0 | non-cytosolic | | 10.2 | hypothetical | NEIS2446 NMB1468 | v |
| NG01215 | 180 | 292 | 0.67 | periplasmic | 0 | non-cytosolic | *19-20: VSA-AG | 16.1 | hypothetical, PduA/c | NEIS1474 NMB1557 | v |
| NG01701 | 127 | 121 | 0.41 | periplasmic | 0 | non-cytosolic | *24-25: ARA-HG | 14.4 | hypothetical, TAT Cys_rich four helix bundle protein | NEIS2720 | v |

FIG. 9

SEQUENCE LISTING

<160> NUMBER OF SEQ ID NOS: 74

<210> SEQ ID NO 1
<211> LENGTH: 88
<212> TYPE: PRT
<213> ORGANISM: Neisseria gonorrhoeae

<400> SEQUENCE: 1

```
Met Asn Gln Ala Val Ala Gln Phe Ala Pro Leu Val Leu Ile Met Val
1               5                   10                  15

Val Phe Tyr Phe Leu Ile Met Arg Pro Gln Gln Lys Lys Phe Lys Ala
            20                  25                  30

His Gln Ala Met Leu Ala Ala Leu Lys Ala Gly Asp Lys Val Val Leu
        35                  40                  45

Ala Ala Gly Phe Lys Gly Lys Val Thr Arg Val Gly Glu Gln Phe Phe
    50                  55                  60
```

-continued

Thr Val Asp Ile Gly Gln Gly Thr Lys Ile Glu Val Glu Val Glu Arg
65                  70                  75                  80

Asn Ala Ile Ala Ala Lys Val Asp
                85

<210> SEQ ID NO 2
<211> LENGTH: 169
<212> TYPE: PRT
<213> ORGANISM: Neisseria gonorrhoeae

<400> SEQUENCE: 2

Met Thr Met Ile Leu Ser Ile Leu Ser Leu Phe Phe Ile Ile Arg Leu
1               5                   10                  15

Leu Phe Leu Ala Val Ser Ile Lys His Glu Lys Ala Leu Ile Ala Lys
                20                  25                  30

Gly Ala Lys Gln Tyr Gly Lys Thr Asn Ser Thr Val Leu Ala Ala Val
            35                  40                  45

His Thr Leu Tyr Tyr Leu Ala Cys Phe Val Trp Val Trp Leu Ser Asp
        50                  55                  60

Thr Ala Phe Asn Gly Ile Ser Leu Ile Gly Thr Leu Thr Val Met Ala
65                  70                  75                  80

Ser Phe Val Ile Leu Ser Leu Ile Ile Lys Gln Leu Gly Glu Ile Trp
                85                  90                  95

Thr Val Lys Ile Tyr Ile Leu Pro Asn His Gln Ile Asn Arg Ser Trp
                100                 105                 110

Leu Phe Lys Thr Phe Arg His Pro Asn Tyr Phe Leu Asn Ile Ile Pro
            115                 120                 125

Glu Leu Ile Gly Ile Ala Leu Leu Cys Gln Ala Trp Tyr Val Leu Leu
    130                 135                 140

Ile Gly Leu Pro Ile Tyr Leu Leu Val Leu Phe Lys Arg Ile Arg Gln
145                 150                 155                 160

Glu Glu Gln Ala Met Ala Thr Leu Phe
            165

<210> SEQ ID NO 3
<211> LENGTH: 95
<212> TYPE: PRT
<213> ORGANISM: Neisseria gonorrhoeae

<400> SEQUENCE: 3

Met Asn Lys Glu Ile Val Gly Ile Phe Phe Ile Pro Met Gly Ile Ile
1               5                   10                  15

Ser Met Cys Met Ala Ala Leu Trp Gln Met Tyr Val Met Met Thr Glu
                20                  25                  30

Thr Tyr Thr Leu Asn Arg Phe Lys Asp Lys Glu Leu Val Trp Arg Val
            35                  40                  45

Ala Leu Leu Phe Ile Ser Phe Ser Leu Ala Val Tyr Leu Leu Cys Pro
    50                  55                  60

Asn Ser Arg Lys Lys Gly Ile Val Phe Phe Ile Leu Gly Gly Gly Gly
65                  70                  75                  80

Ala Val Met Tyr Leu Leu Ala Arg Met Trp Leu Pro Phe Ser Lys
                85                  90                  95

<210> SEQ ID NO 4
<211> LENGTH: 141
<212> TYPE: PRT
<213> ORGANISM: Neisseria gonorrhoeae

<400> SEQUENCE: 4

```
Met Thr Gln Glu Thr Ala Leu Gly Ala Ala Leu Lys Ser Ala Val Gln
1               5                   10                  15

Thr Met Ser Lys Lys Lys Gln Thr Glu Met Ile Ala Asp His Ile Tyr
                20                  25                  30

Gly Lys Tyr Asp Val Phe Lys Arg Phe Lys Pro Leu Ala Leu Gly Ile
            35                  40                  45

Asp Gln Asp Leu Ile Ala Ala Leu Pro Gln Tyr Asp Ser Ala Leu Ile
        50                  55                  60

Ala Arg Val Leu Ala Asn His Cys Arg Arg Pro Arg Tyr Leu Lys Ala
65                  70                  75                  80

Leu Ala Arg Gly Gly Lys Arg Phe Asp Leu Asn Asn Arg Phe Lys Gly
                85                  90                  95

Glu Val Thr Pro Glu Glu Gln Ala Ile Ala Gln Asn His Pro Phe Val
                100                 105                 110

Gln Gln Ala Leu Gln Gln Gln Ser Ala Gln Ala Ala Ala Glu Thr Pro
            115                 120                 125

Ser Val Glu Ala Glu Ala Ala Glu Ser Ser Ala Ala Glu
    130                 135                 140
```

<210> SEQ ID NO 5
<211> LENGTH: 144
<212> TYPE: PRT
<213> ORGANISM: Neisseria gonorrhoeae

<400> SEQUENCE: 5

```
Met Ala Phe Gly Ser Met Asn Ser Ser Asp Asp Ser Pro Met Ser Asp
1               5                   10                  15

Ile Asn Val Thr Pro Leu Val Asp Val Met Leu Val Leu Leu Ile Val
                20                  25                  30

Phe Met Ile Thr Met Pro Val Leu Thr His Ser Ile Pro Leu Glu Leu
            35                  40                  45

Pro Thr Ala Ser Glu Gln Ala Asn Lys Gln Asp Lys Gln Pro Lys Asp
        50                  55                  60

Pro Leu Arg Leu Thr Ile Asp Ala Asn Gly Gly Tyr Tyr Val Gly Gly
65                  70                  75                  80

Asp Ser Ala Ser Lys Val Glu Ile Gly Glu Val Glu Ser Arg Leu Lys
                85                  90                  95

Ala Ala Lys Glu Gln Asn Glu Asn Val Ile Val Ala Ile Ala Ala Asp
                100                 105                 110

Lys Ala Val Glu Tyr Asp Tyr Val Asn Lys Ala Leu Glu Ala Ala Arg
            115                 120                 125

Gln Ala Gly Ile Thr Lys Ile Gly Phe Val Thr Glu Thr Lys Ala Gln
    130                 135                 140
```

<210> SEQ ID NO 6
<211> LENGTH: 87
<212> TYPE: PRT
<213> ORGANISM: Neisseria gonorrhoeae

<400> SEQUENCE: 6

```
Met Asn Lys Ser Asn Phe Phe Leu Leu Leu Ala Val Cys Val Ser Ala
1               5                   10                  15

Phe Ser Val Val Met Gln Gln Asn Gln Tyr Arg Leu Asn Phe Thr Ala
                20                  25                  30
```

-continued

```
Leu Asp Lys Ala Lys Lys Gln Glu Ile Ala Leu Glu Gln Asp Tyr Ala
        35              40              45

Gln Met Arg Leu Gln Gln Ala Arg Leu Ala Asn His Glu Ala Ile Arg
    50              55              60

Ala Ala Ala Glu Lys Gln Asn Leu His Pro Pro Val Ser Gly Asn Thr
65              70              75              80

Phe Met Val Glu His Gln Arg
                85
```

```
<210> SEQ ID NO 7
<211> LENGTH: 289
<212> TYPE: PRT
<213> ORGANISM: Neisseria gonorrhoeae

<400> SEQUENCE: 7

Met Phe Met Asn Lys Phe Ser Gln Ser Gly Lys Gly Leu Ser Gly Phe
1               5               10              15

Phe Phe Gly Leu Ile Leu Ala Thr Val Ile Ile Ala Gly Ile Leu Leu
                20              25              30

Tyr Leu Asn Gln Gly Gly Gln Asn Ala Phe Lys Ile Pro Ala Pro Ser
        35              40              45

Lys Gln Pro Ala Glu Thr Glu Ile Leu Lys Leu Lys Asn Gln Pro Lys
    50              55              60

Glu Asp Ile Gln Pro Glu Pro Ala Asp Gln Asn Ala Leu Ser Glu Pro
65              70              75              80

Asp Val Ala Lys Glu Ala Glu Gln Ser Asp Ala Glu Lys Ala Ala Asp
                85              90              95

Lys Gln Pro Val Ala Asp Lys Ala Asp Glu Val Glu Glu Lys Ala Gly
            100             105             110

Glu Pro Glu Arg Glu Glu Pro Asp Gly Gln Ala Val Arg Lys Lys Ala
            115             120             125

Leu Thr Glu Glu Arg Glu Gln Thr Val Arg Glu Lys Ala Gln Lys Lys
        130             135             140

Asp Ala Glu Thr Val Lys Lys Gln Ala Val Lys Pro Ser Lys Glu Thr
145             150             155             160

Glu Lys Lys Ala Ser Lys Glu Glu Lys Lys Ala Ala Lys Glu Lys Val
            165             170             175

Ala Pro Lys Pro Thr Pro Glu Gln Ile Leu Asn Ser Gly Ser Ile Glu
            180             185             190

Lys Ala Arg Ser Ala Ala Ala Lys Glu Val Gln Lys Met Lys Thr Phe
            195             200             205

Gly Lys Ala Glu Ala Thr His Tyr Leu Gln Met Gly Ala Tyr Ala Asp
        210             215             220

Arg Arg Ser Ala Glu Gly Gln Arg Ala Lys Leu Ala Ile Leu Gly Ile
225             230             235             240

Ser Ser Glu Val Val Gly Tyr Gln Ala Gly His Lys Thr Leu Tyr Arg
            245             250             255

Val Gln Ser Gly Asn Met Ser Ala Asp Ala Val Lys Lys Met Gln Asp
            260             265             270

Glu Leu Lys Lys His Gly Val Ala Ser Leu Ile Arg Ala Ile Glu Gly
        275             280             285

Lys
```

```
<210> SEQ ID NO 8
<211> LENGTH: 193
```

<212> TYPE: PRT
<213> ORGANISM: Neisseria gonorrhoeae

<400> SEQUENCE: 8

Met Lys Val Arg Trp Arg Tyr Gly Ile Ala Phe Pro Leu Ile Leu Ala
1               5                   10                  15

Val Ala Leu Gly Ser Leu Ser Ala Trp Leu Gly Arg Ile Ser Glu Val
            20                  25                  30

Glu Ile Glu Glu Val Arg Leu Asn Pro Asp Glu Pro Gln Tyr Thr Met
        35                  40                  45

Asp Gly Leu Asp Gly Arg Arg Phe Asp Glu Gln Gly Tyr Leu Lys Glu
        50                  55                  60

His Leu Ser Ala Lys Gly Ala Lys Gln Phe Pro Glu Asn Ser Asp Ile
65                  70                  75                  80

His Phe Asp Ser Pro His Leu Val Phe Phe Gln Glu Gly Arg Leu Leu
                85                  90                  95

Tyr Glu Val Gly Ser Asp Glu Ala Val Tyr His Thr Glu Asn Lys Gln
            100                 105                 110

Val Leu Phe Lys Asn Asn Val Val Leu Thr Lys Thr Ala Asp Gly Arg
            115                 120                 125

Arg Gln Ala Gly Lys Val Glu Thr Glu Lys Leu His Val Asp Thr Glu
        130                 135                 140

Ser Gln Tyr Ala Gln Thr Asp Thr Pro Val Ser Phe Gln Tyr Gly Ala
145                 150                 155                 160

Ser His Gly Gln Ala Gly Gly Met Thr Tyr Asn His Lys Thr Gly Met
                165                 170                 175

Leu Asn Phe Ser Ser Lys Val Lys Ala Ala Ile Tyr Asp Thr Lys Asp
                180                 185                 190

Met

<210> SEQ ID NO 9
<211> LENGTH: 183
<212> TYPE: PRT
<213> ORGANISM: Neisseria gonorrhoeae

<400> SEQUENCE: 9

Met Lys Val Leu Asn Gly Trp Ser Asp Arg Lys Met Trp Arg Val Leu
1               5                   10                  15

Ser Ala Leu Pro Ile Gly Val Val Phe Phe Asp Leu Ile Tyr Gly Phe
            20                  25                  30

Val Leu Asn Val Leu Gln Gly Leu Asp Leu Gln Arg Ala Val Pro Asp
        35                  40                  45

Ser Glu Gly Val Leu Ala Val Thr Pro Asp Ile Ala Phe Asn Ser Leu
        50                  55                  60

Gln Ile Val Ala Asn Gly Gly Met Ala Ala Val Val Cys Phe Gly Leu
65                  70                  75                  80

Ala Val Val Phe Leu Leu Asn Arg Ser Val Arg Arg Arg Gln Val Leu
                85                  90                  95

Glu Ile Gly Val Phe Arg Met Leu Gly Leu Val Ala Val Leu Ala Phe
            100                 105                 110

Ser Ala Pro Ser Leu Trp Glu Trp Ala Asn Ala Leu Pro Leu Leu Leu
            115                 120                 125

Lys Gly Ala Asp Val Val Asn Thr Gly Asn Ala Arg Tyr Val Leu Thr
        130                 135                 140

Ala Leu Cys Met Pro Phe Pro Ala Val Ser Cys Ile Ile Gly Leu Val

-continued

```
145              150              155              160

Gly Arg Phe Arg Leu Gln Thr Ala Ser Gly Arg Val Ala Lys Ala Gly
                165              170              175

Gly Ala Val Lys Ala Gly Gly
        180

<210> SEQ ID NO 10
<211> LENGTH: 149
<212> TYPE: PRT
<213> ORGANISM: Neisseria gonorrhoeae

<400> SEQUENCE: 10

Met Lys Ile Gly Thr Thr Trp Gln Thr Ala Ser Ala Met Leu Val Leu
1               5               10              15

Arg Leu Phe Ala Ala Tyr Glu Phe Leu Glu Ser Gly Leu Gln Lys Trp
            20              25              30

Asn Gly Glu Asn Trp Phe Ser Glu Ile Asn Asp Gln Phe Pro Phe Pro
        35              40              45

Phe Asn Leu Leu Pro Asp Ala Leu Asn Trp Asn Leu Ala Met Tyr Ala
    50              55              60

Glu Leu Leu Leu Pro Val Leu Leu Leu Leu Gly Leu Ala Thr Arg Leu
65              70              75              80

Ser Ala Leu Gly Leu Met Val Val Thr Ala Val Ala Trp Ala Ala Val
            85              90              95

His Ala Gly Ser Gly Tyr Asn Val Cys Asp Asn Gly Tyr Lys Met Ala
            100             105             110

Leu Ile Tyr Ile Val Val Leu Ile Pro Leu Leu Phe Gln Gly Ala Gly
            115             120             125

Gly Trp Ser Leu Asp Thr Leu Leu Lys Lys Leu Phe Cys Pro Lys Cys
        130             135             140

Arg Leu Lys Gln Asp
145

<210> SEQ ID NO 11
<211> LENGTH: 282
<212> TYPE: PRT
<213> ORGANISM: Neisseria gonorrhoeae

<400> SEQUENCE: 11

Met Asp Phe Lys Gln Phe Asp Phe Leu His Leu Ile Ser Val Ser Gly
1               5               10              15

Trp Gly His Leu Ala Glu Lys Ala Trp Ala Phe Gly Leu Asn Leu Ala
            20              25              30

Ala Ala Leu Leu Ile Phe Leu Val Gly Lys Trp Ala Ala Lys Arg Ile
        35              40              45

Val Ala Val Met Arg Ala Ala Met Thr Arg Ala Gln Val Asp Ala Thr
    50              55              60

Leu Ile Ser Phe Leu Cys Asn Val Ala Asn Ile Gly Leu Leu Ile Leu
65              70              75              80

Val Ile Ile Ala Ala Leu Gly Arg Leu Gly Val Ser Thr Thr Ser Val
            85              90              95

Thr Ala Leu Ile Gly Gly Ala Gly Leu Ala Val Ala Leu Ser Leu Lys
            100             105             110

Asp Gln Leu Ser Asn Phe Ala Ala Gly Ala Leu Ile Ile Leu Phe Arg
            115             120             125

Pro Phe Lys Val Gly Asp Phe Ile Arg Val Gly Gly Phe Glu Gly Tyr
```

-continued

```
         130               135               140
Val Arg Glu Ile Lys Met Val Gln Thr Ser Leu Arg Thr Thr Asp Asn
145                 150               155               160

Glu Glu Val Val Leu Pro Asn Ser Val Val Met Gly Asn Ser Ile Val
                165               170               175

Asn Arg Ser Ser Leu Pro Leu Cys Arg Ala Gln Val Ile Val Gly Val
                180               185               190

Asp Tyr Asn Cys Asp Leu Lys Val Ala Lys Glu Ala Val Leu Lys Ala
            195               200               205

Ala Ala Glu His Pro Leu Ser Val Gln Asn Glu Glu Arg Gln Pro Ala
    210               215               220

Ala Tyr Ile Thr Ala Leu Gly Asp Asn Ala Ile Glu Ile Thr Leu Trp
225               230               235               240

Ala Trp Ala Asn Glu Ala Asp Arg Trp Thr Leu Gln Cys Asp Leu Asn
                245               250               255

Glu Gln Val Val Glu Asn Leu Arg Lys Val Asn Ile Asn Ile Pro Phe
                260               265               270

Pro Gln Arg Asp Ile His Ile Ile Asn Ser
            275               280
```

<210> SEQ ID NO 12
<211> LENGTH: 107
<212> TYPE: PRT
<213> ORGANISM: Neisseria gonorrhoeae

<400> SEQUENCE: 12

```
Met Lys Lys Cys Ile Leu Gly Ile Leu Thr Ala Cys Ala Ala Met Pro
1                   5                  10                  15

Ala Phe Ala Asp Arg Ile Ser Asp Leu Glu Ala Arg Leu Ala Gln Leu
                20                  25                  30

Glu His Arg Val Ala Val Leu Glu Ser Gly Gly Asn Thr Val Lys Ile
            35                  40                  45

Asp Leu Phe Gly Ser Asn Ser Thr Met Tyr Val Cys Ser Val Thr Pro
    50                  55                  60

Phe Gln Lys Thr Phe Glu Ala Ser Asp Arg Asn Glu Gly Val Ala Arg
65                  70                  75                  80

Gln Lys Val Arg Gln Ala Cys Asn Arg Glu Thr Ser Ala Met Phe Cys
                85                  90                  95

Gly Asp Glu Ala Ile Arg Cys Arg Lys Phe Asp
            100                 105
```

<210> SEQ ID NO 13
<211> LENGTH: 598
<212> TYPE: PRT
<213> ORGANISM: Neisseria gonorrhoeae

<400> SEQUENCE: 13

```
Met Arg Tyr Lys Pro Leu Leu Leu Ala Leu Met Leu Val Phe Ser Thr
1                   5                  10                  15

Pro Ala Val Ala Ala His Asp Ala Ala His Asn Arg Ser Ala Glu Val
                20                  25                  30

Lys Lys Gln Ala Lys Asn Lys Lys Glu Gln Pro Glu Ala Ala Glu Gly
            35                  40                  45

Lys Lys Glu Lys Gly Lys Asn Ala Ala Val Lys Asp Lys Lys Thr Gly
    50                  55                  60

Gly Lys Glu Ala Ala Lys Glu Phe Lys Lys Thr Ala Lys Asn Arg Lys
```

```
65              70              75              80

Glu Ala Glu Lys Glu Ala Thr Ser Arg Gln Ser Ala Arg Lys Gly Arg
            85              90              95

Glu Gly Asp Lys Glu Ser Lys Ala Glu His Lys Lys Ala His Gly Lys
            100             105             110

Pro Val Ser Gly Ser Lys Glu Lys Asn Ala Lys Thr Gln Pro Glu Asn
            115             120             125

Lys Gln Gly Lys Lys Gly Ala Lys Gly Gln Gly Asn Pro Arg Lys Gly
    130             135             140

Gly Lys Ala Glu Lys Asp Thr Val Ser Ala Asn Lys Lys Ala Arg Ser
145             150             155             160

Asp Lys Asn Gly Lys Ala Val Lys Gln Asp Lys Lys His Thr Glu Glu
            165             170             175

Lys Asn Ala Lys Thr Asp Ser Asp Glu Leu Lys Ala Ala Val Ala Ala
            180             185             190

Ala Thr Asn Asp Val Glu Asn Lys Lys Ala Leu Leu Lys Gln Ser Glu
            195             200             205

Gly Met Leu Leu His Val Ser Asn Ser Leu Lys Gln Leu Gln Glu Glu
    210             215             220

Arg Ile Arg Gln Glu Arg Ile Arg Gln Glu Arg Ile Arg Gln Ala Arg
225             230             235             240

Gly Asn Leu Ala Ser Val Asn Arg Lys Gln Arg Glu Ala Trp Asp Lys
            245             250             255

Phe Gln Lys Leu Asn Thr Glu Leu Asn Arg Leu Lys Thr Glu Val Ala
            260             265             270

Ala Thr Lys Ala Gln Ile Ser Arg Phe Val Ser Gly Asn Tyr Lys Asn
            275             280             285

Ser Arg Pro Asn Ala Val Ala Leu Phe Leu Lys Asn Ala Glu Pro Gly
    290             295             300

Gln Lys Asn Arg Phe Leu Arg Tyr Thr Arg Tyr Val Asn Ala Ser Asn
305             310             315             320

Arg Glu Val Val Lys Asp Leu Glu Lys Gln Gln Lys Ala Leu Ala Val
            325             330             335

Gln Glu Gln Lys Ile Asn Asn Glu Leu Ala Arg Leu Lys Lys Ile Gln
            340             345             350

Ala Asn Val Gln Ser Leu Leu Lys Lys Gln Gly Val Thr Asp Ala Ala
            355             360             365

Glu Gln Thr Glu Ser Arg Arg Gln Asn Ala Lys Ile Ser Lys Asp Ala
    370             375             380

Arg Lys Leu Leu Glu Gln Lys Gly Asn Glu Gln Gln Leu Asn Lys Leu
385             390             395             400

Leu Ser Asn Leu Glu Lys Lys Lys Ala Glu His Arg Ile Gln Asp Ala
            405             410             415

Glu Ala Lys Arg Lys Leu Ala Glu Ala Lys Leu Ala Ala Ala Glu Lys
            420             425             430

Ala Arg Lys Glu Ala Ala Gln Gln Lys Ala Glu Ala Arg Arg Ala Glu
            435             440             445

Met Ser Asn Leu Thr Ala Glu Asp Arg Asn Ile Gln Ala Pro Ser Val
    450             455             460

Met Gly Ile Gly Ser Ala Asp Gly Phe Ser Arg Met Gln Gly Arg Leu
465             470             475             480

Lys Lys Pro Val Asp Gly Val Pro Thr Gly Leu Phe Gly Gln Asn Arg
            485             490             495
```

-continued

```
Ser Gly Gly Asp Val Trp Lys Gly Val Phe Tyr Ser Thr Ala Pro Ala
        500                 505                 510

Thr Val Glu Ser Ile Ala Pro Gly Thr Val Ser Tyr Ala Asp Glu Leu
        515                 520                 525

Asp Gly Tyr Gly Lys Val Val Val Ile Asp His Gly Glu Asn Tyr Ile
        530                 535                 540

Ser Ile Tyr Ala Gly Leu Ser Glu Ile Ser Ala Gly Lys Gly Tyr Thr
545                 550                 555                 560

Val Ala Ala Gly Ser Lys Ile Gly Thr Ser Gly Ser Leu Pro Asp Gly
                565                 570                 575

Glu Glu Gly Leu Tyr Leu Gln Ile Arg Tyr Arg Gly Gln Val Leu Asn
                580                 585                 590

Pro Ser Gly Trp Ile Arg
        595
```

```
<210> SEQ ID NO 14
<211> LENGTH: 144
<212> TYPE: PRT
<213> ORGANISM: Neisseria gonorrhoeae

<400> SEQUENCE: 14
```

```
Met Pro Leu Pro Ala Pro Cys Arg Phe Ala Lys Pro Ala Ala Ser Phe
1               5                   10                  15

Leu Ser Met Ala Leu Leu Ser Cys Gln Leu Ser His Ala Ala Thr Ala
            20                  25                  30

Tyr Ile Pro Pro Asn Asp Phe Gln Pro Asn Cys Asp Ile Arg Arg Leu
            35                  40                  45

Gly Leu Thr Gln Gly Gln His Asn Glu Leu Arg Lys Ile Arg Ala Ala
        50                  55                  60

Phe Lys Met Ala Gly Asp Arg Ala Arg Leu Lys Val Met His Ser Glu
65                  70                  75                  80

His Ser Arg Arg Arg Ser Val Val Glu Ile Ile Ser Ser Asp Val Phe
                85                  90                  95

Asn Arg Asn Glu Ala Arg Asp Tyr Val Glu Ser Arg Tyr His Ser Ser
            100                 105                 110

Met Asp Phe Ala Val Asp Glu Leu Glu Ile Gln His Arg Phe Phe His
        115                 120                 125

Ile Leu Thr Pro Gln Gln Gln Gln Met Trp Leu Ser Ser Cys Leu Lys
        130                 135                 140
```

```
<210> SEQ ID NO 15
<211> LENGTH: 157
<212> TYPE: PRT
<213> ORGANISM: Neisseria gonorrhoeae

<400> SEQUENCE: 15
```

```
Met Lys Lys Leu Leu Ala Ala Val Met Met Ala Gly Leu Ala Gly Ala
1               5                   10                  15

Val Ser Ala Ala Gly Val His Val Glu Asp Gly Trp Ala Arg Thr Thr
            20                  25                  30

Val Glu Gly Met Lys Met Gly Gly Ala Phe Met Lys Ile Pro Asn Asp
        35                  40                  45

Glu Ala Lys Gln Asp Phe Leu Leu Val Gly Ser Ser Pro Val Ala Asp
        50                  55                  60

Arg Val Glu Val His Thr His Ile Asn Asp Asn Gly Val Met Arg Met
65                  70                  75                  80
```

-continued

```
Arg Glu Val Lys Gly Gly Val Pro Leu Glu Ala Lys Ser Val Thr Glu
                85                  90                  95

Leu Lys Pro Gly Ser Tyr His Val Met Phe Met Gly Leu Lys Lys Gln
            100                 105                 110

Leu Lys Glu Gly Asp Lys Ile Pro Val Thr Leu Lys Phe Lys Asn Ala
        115                 120                 125

Lys Ala Gln Thr Val Gln Leu Glu Val Lys Thr Ala Pro Met Ser Ala
    130                 135                 140

Met Asn His Gly His His His Gly Glu Ala His Gln His
145                 150                 155

<210> SEQ ID NO 16
<211> LENGTH: 192
<212> TYPE: PRT
<213> ORGANISM: Neisseria gonorrhoeae

<400> SEQUENCE: 16

Met Cys Phe Cys Leu Leu Leu Met Pro Lys Phe Tyr Phe Ser Cys Arg
1               5                   10                  15

Thr Ile Cys Phe Leu Lys Ala Asn Leu Ile Ile Met Ala Gly Met Lys
            20                  25                  30

Lys Tyr Leu Ile Pro Leu Ser Ile Ala Ala Val Leu Ser Gly Cys Gln
        35                  40                  45

Ser Ile Tyr Val Pro Thr Leu Thr Glu Ile Pro Val Asn Pro Ile Asn
    50                  55                  60

Thr Val Lys Thr Glu Ala Pro Ala Lys Gly Phe Arg Leu Ala Pro Ser
65                  70                  75                  80

His Trp Ala Asp Val Ala Lys Ile Ser Asp Glu Ala Thr Arg Leu Gly
                85                  90                  95

Tyr Gln Val Gly Ile Gly Lys Met Thr Lys Val Gln Ala Ala Gln Tyr
            100                 105                 110

Leu Asn Asn Phe Arg Lys Arg Leu Val Gly Arg Asn Ala Val Asp Asp
        115                 120                 125

Ser Met Tyr Glu Ile Tyr Leu Arg Ser Ala Val Asp Ser Gln Arg Gly
    130                 135                 140

Glu Ile Asn Thr Glu Gln Ser Lys Leu Tyr Ile Glu Asn Ala Leu Arg
145                 150                 155                 160

Gly Trp Gln Gln Arg Trp Lys Asn Met Asp Ala Lys Pro Asp Asn Pro
                165                 170                 175

Ala Phe Thr Asn Phe Leu Met Glu Val Met Lys Met Gln Pro Leu Lys
            180                 185                 190

<210> SEQ ID NO 17
<211> LENGTH: 261
<212> TYPE: PRT
<213> ORGANISM: Neisseria gonorrhoeae

<400> SEQUENCE: 17

Met Lys Thr Lys Leu Ile Lys Ile Leu Thr Pro Phe Thr Val Leu Pro
1               5                   10                  15

Leu Leu Ala Cys Gly Gln Thr Pro Val Ser Asn Ala Asn Ala Glu Ser
            20                  25                  30

Ala Val Lys Ala Glu Ser Ala Gly Lys Ser Val Ala Ala Ser Leu Lys
        35                  40                  45

Ala Arg Leu Glu Lys Thr Tyr Ser Ala Gln Asp Leu Lys Val Leu Ser
    50                  55                  60
```

```
Val Ser Glu Thr Pro Val Lys Gly Ile Tyr Glu Val Val Ser Gly
65              70                  75                  80

Arg Gln Ile Ile Tyr Thr Asp Ala Glu Gly Gly Tyr Met Phe Val Gly
                85                  90                  95

Glu Leu Ile Asn Ile Asp Thr Arg Lys Asn Leu Thr Glu Glu Arg Ala
            100                 105                 110

Ala Asp Leu Asn Lys Ile Asp Phe Ala Ser Leu Pro Leu Asp Lys Ala
            115                 120                 125

Ile Lys Glu Val Arg Gly Asn Gly Lys Leu Lys Val Ala Val Phe Ser
        130                 135                 140

Asp Pro Asp Cys Pro Phe Cys Lys Arg Leu Glu His Glu Phe Glu Lys
145                 150                 155                 160

Met Thr Asp Val Thr Val Tyr Ser Phe Met Met Pro Ile Ala Gly Leu
                165                 170                 175

His Pro Asp Ala Ala Arg Lys Ala Gln Ile Leu Trp Cys Gln Pro Asp
            180                 185                 190

Arg Ala Lys Ala Trp Thr Asp Trp Met Arg Lys Gly Lys Phe Pro Val
            195                 200                 205

Gly Gly Ser Ile Cys Asp Asn Pro Val Ala Glu Thr Thr Ser Leu Gly
        210                 215                 220

Glu Gln Phe Gly Phe Asn Gly Thr Pro Thr Leu Val Phe Pro Asn Gly
225                 230                 235                 240

Arg Thr Gln Ser Gly Tyr Ser Pro Met Pro Gln Leu Glu Glu Ile Ile
                245                 250                 255

Arg Lys Asn Gln Gln
            260

<210> SEQ ID NO 18
<211> LENGTH: 151
<212> TYPE: PRT
<213> ORGANISM: Neisseria gonorrhoeae

<400> SEQUENCE: 18

Met Asn Arg Arg Gln Phe Leu Gly Ser Ala Ala Ala Val Ser Leu Ala
1               5                   10                  15

Ser Ala Ala Ser Phe Ala Arg Ala His Gly His Ala Asp Tyr His His
            20                  25                  30

His His Asp Met Gln Pro Ala Ala Ala Ser Ala Tyr Thr Ala Val Arg
        35                  40                  45

Gln Thr Ala Ala His Cys Leu Asp Ala Gly Gln Val Cys Leu Thr His
    50                  55                  60

Cys Leu Ser Leu Leu Thr Gln Gly Asp Thr Ser Met Ser Asp Cys Ala
65              70                  75                  80

Val Ala Val Arg Gln Met Leu Ala Leu Cys Gly Ala Val His Asp Leu
                85                  90                  95

Ala Ala Gln Asn Ser Pro Leu Thr Arg Asp Ala Ala Lys Val Cys Leu
            100                 105                 110

Glu Ala Cys Lys Gln Cys Ala Lys Ala Cys Lys Glu His Ser Ala His
            115                 120                 125

His Ala Glu Cys Lys Ala Cys Tyr Glu Ser Cys Leu Asp Cys Ile Lys
        130                 135                 140

Glu Cys Glu Lys Leu Ala Ala
145                 150
```

```
<210> SEQ ID NO 19
<211> LENGTH: 199
<212> TYPE: PRT
<213> ORGANISM: Neisseria gonorrhoeae

<400> SEQUENCE: 19

Met Ala Phe Ile Thr Arg Leu Phe Lys Ser Ile Lys Gln Trp Leu Val
1               5                   10                  15

Leu Leu Pro Ile Leu Ser Val Leu Pro Asp Ala Ala Ala Glu Gly Ile
            20                  25                  30

Ala Ala Thr Arg Ala Glu Ala Arg Ile Thr Asp Gly Gly Arg Leu Ser
            35                  40                  45

Ile Ser Ser Arg Phe Gln Thr Glu Leu Pro Asp Gln Leu Gln Gln Ala
        50                  55                  60

Leu Arg Arg Gly Val Pro Leu Asn Phe Thr Leu Ser Trp Gln Leu Ser
65                  70                  75                  80

Ala Pro Thr Ile Ala Ser Tyr Arg Phe Lys Leu Gly Gln Leu Ile Gly
                85                  90                  95

Asp Asp Asp Asn Ile Asp Tyr Lys Leu Ser Phe His Pro Leu Thr Asn
            100                 105                 110

Arg Tyr Arg Val Thr Val Gly Ala Phe Ser Thr Asp Tyr Asp Thr Leu
            115                 120                 125

Asp Ala Ala Leu Arg Ala Thr Gly Ala Val Ala Asn Trp Lys Val Leu
            130                 135                 140

Asn Lys Gly Ala Leu Ser Gly Ala Glu Ala Gly Glu Thr Lys Ala Glu
145                 150                 155                 160

Ile Arg Leu Thr Leu Ser Thr Ser Lys Leu Pro Lys Pro Phe Gln Ile
                165                 170                 175

Asn Ala Leu Thr Ser Gln Asn Trp His Leu Asp Ser Gly Trp Lys Pro
            180                 185                 190

Leu Asn Ile Ile Gly Asn Lys
        195

<210> SEQ ID NO 20
<211> LENGTH: 196
<212> TYPE: PRT
<213> ORGANISM: Neisseria gonorrhoeae

<400> SEQUENCE: 20

Met Lys Lys Ser Ser Phe Ile Ser Ala Leu Gly Ile Gly Ile Leu Ser
1               5                   10                  15

Ile Gly Met Ala Phe Ala Ser Pro Ala Asp Ala Val Gly Gln Ile Arg
            20                  25                  30

Gln Asn Ala Thr Gln Val Leu Thr Ile Leu Lys Ser Gly Asp Ala Ala
            35                  40                  45

Ser Ala Arg Pro Lys Ala Glu Ala Tyr Ala Val Pro Tyr Phe Asp Phe
        50                  55                  60

Gln Arg Met Thr Ala Leu Ala Val Gly Asn Pro Trp Arg Thr Ala Ser
65                  70                  75                  80

Asp Ala Gln Lys Gln Ala Leu Ala Lys Glu Phe Gln Thr Leu Leu Ile
                85                  90                  95

Arg Thr Tyr Ser Gly Thr Met Leu Lys Phe Lys Asn Ala Thr Val Asn
            100                 105                 110

Val Lys Asp Asn Pro Ile Val Asn Lys Gly Gly Lys Glu Ile Val Val
            115                 120                 125

Arg Ala Glu Val Gly Ile Pro Gly Gln Lys Pro Val Asn Met Asp Phe
```

-continued

```
            130             135                 140

Thr Thr Tyr Gln Ser Gly Gly Lys Tyr Arg Thr Tyr Asn Val Ala Ile
145                 150                 155                 160

Glu Gly Thr Ser Leu Val Thr Val Tyr Arg Asn Gln Phe Gly Glu Ile
                    165                 170                 175

Ile Lys Ala Lys Gly Ile Asp Gly Leu Ile Ala Glu Leu Lys Ala Lys
                180                 185                 190

Asn Gly Gly Lys
        195

<210> SEQ ID NO 21
<211> LENGTH: 81
<212> TYPE: PRT
<213> ORGANISM: Neisseria gonorrhoeae

<400> SEQUENCE: 21

Met Lys Asp Ser Thr Gly Gln Met Arg Leu Ala Thr Lys Asp Leu Ala
1               5                   10                  15

Glu Ala Ile Lys Arg Gly Glu Val Arg Ser Ser Ala Phe Thr Thr Lys
                20                  25                  30

Gln Leu Lys Ala Ile Glu Lys Gly Lys Asp Lys Ile Pro Ser Tyr Thr
            35                  40                  45

Trp His His His Gln Asp Thr Gly Arg Met Gln Leu Val Pro Glu Trp
            50                  55                  60

Glu His Ser Lys Thr Gly His Ile Gly Gly Thr Ala Met Gly Lys Gly
65                  70                  75                  80

Lys

<210> SEQ ID NO 22
<211> LENGTH: 106
<212> TYPE: PRT
<213> ORGANISM: Neisseria gonorrhoeae

<400> SEQUENCE: 22

Met Asn Phe Gln Asp Tyr Leu Ala Thr Phe Pro Ser Ile Asp His Leu
1               5                   10                  15

Gly Gly Leu Asp Val Gln Asp Ala Glu Gly Lys Thr Val His His Ile
                20                  25                  30

Pro Ala Val Gln Gly Lys Leu Gly Ser Leu Lys Leu Tyr Asn Ala Leu
            35                  40                  45

Ala Glu Arg Phe Asp Gly Lys Leu Gly Lys Glu Ala Ala Glu Gln Gly
            50                  55                  60

Leu Ile Trp Phe Ala Glu His Val Ala Asp Ala Arg Ala His Pro Gly
65                  70                  75                  80

Lys His Pro Asn Ile Asp Leu Leu Glu Asn Val Val Gln Ser Gly Glu
                85                  90                  95

Thr Leu Leu Leu Lys Pro Leu Ala Ala Gln
            100                 105

<210> SEQ ID NO 23
<211> LENGTH: 160
<212> TYPE: PRT
<213> ORGANISM: Neisseria gonorrhoeae

<400> SEQUENCE: 23

Met Met Lys Lys Ile Leu Ala Val Ser Ala Leu Cys Leu Met Thr Ala
1               5                   10                  15
```

-continued

```
Ala Ala Gln Ala Ala Asp Thr Tyr Gly Tyr Leu Ala Val Trp Gln Asn
            20                  25                  30

Pro Gln Asp Ala Asn Asp Val Leu Gln Val Lys Thr Thr Lys Glu Asp
            35                  40                  45

Ser Ala Lys Ser Glu Ala Phe Ala Glu Leu Glu Ala Phe Cys Lys Gly
            50                  55                  60

Gln Asp Thr Leu Ala Gly Ile Ala Glu Asp Glu Pro Thr Gly Cys Arg
65                  70                  75                  80

Ser Val Val Ser Leu Asn Asn Thr Cys Val Ser Leu Ala Tyr Pro Lys
                    85                  90                  95

Ala Leu Gly Ala Met Arg Val Glu Asn Ala Val Val Ile Thr Ser Pro
                100                 105                 110

Arg Phe Thr Ser Val His Gln Val Ala Leu Asn Gln Cys Ile Lys Lys
                115                 120                 125

Tyr Gly Ala Gln Gly Gln Cys Gly Leu Glu Thr Val Tyr Cys Thr Ser
            130                 135                 140

Ser Ser Tyr Tyr Gly Gly Ala Val Arg Ser Leu Ile Gln His Leu Lys
145                 150                 155                 160

<210> SEQ ID NO 24
<211> LENGTH: 184
<212> TYPE: PRT
<213> ORGANISM: Neisseria gonorrhoeae

<400> SEQUENCE: 24

Met Lys Lys Ile Ile Ala Ser Ala Leu Ile Ala Thr Phe Ala Leu Thr
1                   5                   10                  15

Ala Cys Gln Asp Asp Thr Gln Ala Arg Leu Glu Arg Gln Gln Lys Gln
            20                  25                  30

Ile Glu Ala Leu Gln Gln Gln Leu Ala Gln Gln Ala Asp Asp Thr Val
            35                  40                  45

Tyr Gln Leu Thr Pro Glu Ala Val Lys Asp Thr Ile Pro Ala Gln Ala
            50                  55                  60

Gln Ala Asn Gly Asn Asn Gly Gln Pro Val Thr Gly Lys Asp Gly Gln
65                  70                  75                  80

Gln Tyr Ile Tyr Asp Gln Ser Thr Gly Ser Trp Leu Leu Gln Ser Leu
                    85                  90                  95

Ile Gly Ala Ala Ala Gly Ala Phe Ile Gly Asn Ala Leu Ala Asn Lys
                100                 105                 110

Phe Thr Arg Ala Gly Asn Gln Asp Ser Pro Val Ala Arg Arg Ala Arg
                115                 120                 125

Ala Ala Tyr His Gln Ser Ala Arg Pro Asn Ala Arg Thr Ser Arg Asp
            130                 135                 140

Leu Asn Thr Arg Ser Leu Arg Ala Lys Gln Gln Ala Ala Gln Ala Gln
145                 150                 155                 160

Arg Tyr Arg Pro Thr Thr Arg Pro Pro Val Asn Tyr Arg Arg Pro Ala
                165                 170                 175

Met Arg Gly Phe Gly Arg Arg Arg
            180

<210> SEQ ID NO 25
<211> LENGTH: 84
<212> TYPE: PRT
<213> ORGANISM: Neisseria gonorrhoeae

<400> SEQUENCE: 25
```

```
Met Asn Lys Leu Phe Val Thr Ala Leu Ser Ala Leu Ala Leu Ser Ala
1                   5                   10                  15

Cys Ala Gly Thr Trp Gln Gly Ala Lys Gln Asp Thr Ala Arg Asn Leu
                20                  25                  30

Asp Lys Thr Gln Ala Ala Ala Glu Arg Ala Ala Glu Gln Thr Gly Asn
            35                  40                  45

Ala Val Glu Lys Gly Trp Asp Lys Thr Lys Glu Ala Val Lys Lys Gly
        50                  55                  60

Gly Asn Ala Val Gly Arg Gly Ile Ser His Leu Gly Lys Lys Ile Glu
65                  70                  75                  80

Asn Ala Thr Glu

<210> SEQ ID NO 26
<211> LENGTH: 122
<212> TYPE: PRT
<213> ORGANISM: Neisseria gonorrhoeae

<400> SEQUENCE: 26

Met Asn Lys Thr Leu Ser Ile Leu Pro Ala Ala Ile Leu Leu Gly Gly
1                   5                   10                  15

Cys Ala Ala Gly Gly Asn Thr Phe Gly Ser Leu Asp Gly Gly Thr Gly
                20                  25                  30

Met Gly Gly Ser Ile Val Lys Met Thr Val Glu Ser Gln Cys Arg Ala
            35                  40                  45

Glu Leu Asp Arg Arg Ser Glu Trp Arg Leu Thr Ala Leu Ala Met Ser
        50                  55                  60

Ala Glu Lys Gln Ala Glu Trp Glu Asn Lys Ile Cys Gly Cys Ala Thr
65                  70                  75                  80

Glu Glu Ala Pro Asn Gln Leu Thr Gly Asn Asp Val Met Gln Met Leu
                85                  90                  95

Asn Gln Ser Thr Arg Asn Gln Ala Leu Ala Ala Leu Thr Val Lys Thr
                100                 105                 110

Val Ser Ala Cys Phe Lys Arg Leu Tyr Arg
                115                 120

<210> SEQ ID NO 27
<211> LENGTH: 872
<212> TYPE: PRT
<213> ORGANISM: Neisseria gonorrhoeae

<400> SEQUENCE: 27

Met Asn Gln Glu Gly Ile Thr Ala His Gly Asn Ala Thr Ile Thr Leu
1                   5                   10                  15

Lys Ala Lys Glu Asn Asn Lys Ile Thr Val Glu Asn Ala Ala Tyr Ser
                20                  25                  30

Ser Asp Gly Ile Ser Thr Leu Ile Asn Arg Thr Gly Ala Arg Pro Gly
            35                  40                  45

Thr Arg Asp Asp Gly Asn Lys Ile Ile Leu Glu Ala Gly Gly Asp Asn
        50                  55                  60

Ile Val Thr Met Lys Ser Gly Asp Ala Asp Ala Asp Tyr Val Asn Asn
65                  70                  75                  80

Ser Lys Val Leu Thr Glu Thr Pro Tyr Tyr Lys Ser Lys Arg Gly Ser
                85                  90                  95

Asn Gly Ile Phe Ala Tyr Gly Asp Lys Ser Leu Val Lys Leu Ile Gly
                100                 105                 110

Glu Asn Asn Ile Val Lys Ser Glu Ile Ser Glu Lys Ser Lys Ala Leu
```

-continued

```
          115                 120                 125

Asn Gly Gly Phe Arg His Ile Gly Ile Tyr Ser Trp Gln Asn Ala Lys
    130                 135                 140

Val Glu Leu Ser Ala Lys Ser Asp Asn Ile Val Gln Gly Gly Ile Trp
145                 150                 155                 160

Gly Leu Tyr Ser Asn Asn Ser Ser Ile Ser Leu Lys Gly Lys Asn Asn
                165                 170                 175

Val Ile Ser Asn Pro Lys Tyr Asn Val Phe Ala Tyr Lys Lys Ala Lys
                180                 185                 190

Val Asp Leu Thr Val Glu Asn Lys Asn Thr Leu Ser Asp Ala Glu Phe
                195                 200                 205

Gly Val Tyr Ala Leu Asn Thr Ser Met Val Asn Leu Ser Ser Lys Asp
                210                 215                 220

Asn Asn Glu Val Lys Ser Thr Gln Val Gly Leu Tyr Ser Gln Asp Gly
225                 230                 235                 240

Gly Ser Ile Asn Val Asp Arg Lys Asp Asn Ile Ile Glu Gly Asp Ala
                245                 250                 255

Val Ala Leu Val Gly Lys Gly Gly Ser Gln Asn Ile Arg Ala Ser Arg
                260                 265                 270

Thr Asn Leu Ile Ser Ser Lys Ser Leu Gly Ile His Ala Glu Gln Ala
                275                 280                 285

Ala Lys Ile Ala Ile Thr Gly Ala Ser Asn Thr Ile His Ala Ser Asn
                290                 295                 300

Ala Ala Ile Arg Ser Leu Asp Lys Ser Glu Val Lys Ile Asp Gly Gln
305                 310                 315                 320

Ile Thr Ile Asp Ser Asn Val Ala Asn Leu Ala Arg Gln Asp Gly Ser
                325                 330                 335

Ile His Leu Asn Tyr Lys Asp Asp Thr Arg Ile Thr Gly Ala Thr Val
                340                 345                 350

Ser Asp Lys Gly Leu Val Ala Ile Lys Pro Leu Asn Asn Thr Asn Ile
                355                 360                 365

Val Ala Asp Thr Ile His Tyr Lys Gly Asp Val Leu Ala Val Asn Lys
                370                 375                 380

Gly Lys Val Glu Leu Asp Phe Thr Pro Asn Ile Leu Leu Ala Gly Arg
385                 390                 395                 400

Leu Asp Asn Phe Ser Gly Leu Thr Asp Ser Lys His Lys Asn Leu Phe
                405                 410                 415

Glu Asn Tyr Val Ala Asn Leu Asp Ser Lys Ser Ala Gly Glu Ile Asn
                420                 425                 430

Phe Asn Leu Ala Lys Asp Ala Leu Trp Thr Met Thr Gly Gln Ser Trp
                435                 440                 445

Leu Asp Lys Leu Glu Gly Gln Gly Thr Ile Asp Phe Asn Asn Asp Ala
                450                 455                 460

Lys Thr Ser Gly Arg Ala Leu His Ile Gly Glu Leu Ala Gly Ala Asn
465                 470                 475                 480

Lys Phe Leu Met His Leu Asn Lys Asp Gly Ile His Ser Asp Met Leu
                485                 490                 495

Tyr Val Lys Lys Gly Thr Ser Thr Pro Gln Glu Val Val Lys Asn
                500                 505                 510

Leu Ser Glu Val Leu Asp Ser Met Asn Tyr Gly Glu Arg Leu Arg Phe
                515                 520                 525

Ala Thr Val Thr Asn Ser Lys Asn Glu Phe Val Asn Gly Lys Lys Tyr
                530                 535                 540
```

```
Ile Asp Asp Thr His Leu Met Glu Asp Ala Leu Thr Val Glu Tyr Ser
545                 550                 555                 560

Ala His Asn Gly Asp Lys Asn Asn Lys Asp Asp Tyr Asn Lys Ser Phe
                565                 570                 575

Asn Gly Ser Glu Met Thr Ala Glu Lys Ala Gly Asp Asp Tyr Val Asn
            580                 585                 590

Lys Thr Tyr Thr Asp Asn Arg Gln Asn Val Tyr Leu Val Lys Gln Ala
        595                 600                 605

Thr Gly Asn Pro Ser Arg Asn Val Lys Asn Ile Asn Asp Met Phe Asp
    610                 615                 620

Ser Thr Ala His Tyr Ala Phe Thr Leu Asp Thr Tyr Ala Lys Arg Glu
625                 630                 635                 640

Gly Glu Arg Ala Phe Ser Thr Leu Asp Lys Lys Glu Gly Asp Trp Ile
                645                 650                 655

Arg Leu Thr His Thr Arg Val Ile Gln Ser Asn Ala Phe Arg Phe His
                660                 665                 670

Asn Asn Asp Phe Glu Ile Gly Tyr Asp Arg Phe Ser Leu Asn Glu Gln
            675                 680                 685

Glu Lys Lys Arg Lys Trp Gly Ile Ser Leu Asp Tyr Gly His Gly Arg
        690                 695                 700

Thr Ser Leu Trp Asn Thr Phe Gly Lys Asp Lys Ile Arg Lys Tyr Glu
705                 710                 715                 720

Leu Ala Leu Tyr Asn Thr Thr Gln Tyr Ile Asp Lys Glu Gly Asp Glu
                725                 730                 735

Thr Gly Tyr Ile Asp Asn Val Leu Lys Ile Gly Lys Leu Arg Asn Arg
            740                 745                 750

Val Ile Ala Arg Asn His Met Gly Gln Leu Trp Gly Lys Gly Lys Tyr
        755                 760                 765

Ser Asn Thr Leu Phe Ser Ile Ser Thr Glu Tyr Gly Arg Arg Lys Phe
    770                 775                 780

Leu Asp Asp Asp Lys Leu Trp Arg Ile Thr Pro Gln Val Gln Leu Gln
785                 790                 795                 800

Tyr Ser Tyr Leu Arg Gly Thr Gly Tyr Arg Ile Asp Asn Gly Ile Asn
                805                 810                 815

Val Asn Leu Ser His Ala Asn Ser Leu Ile Gly Arg Leu Gly Leu Asp
            820                 825                 830

Val Val Arg Lys Phe Asp Gly Gly Lys Lys Leu Phe Tyr Ile Lys Gly
        835                 840                 845

Asn Ile Phe His Glu Phe Leu Gly Ser Arg Ser Phe Lys Ala Phe Glu
    850                 855                 860

Gly Lys Ser His Tyr Ala Gln Lys
865                 870
```

<210> SEQ ID NO 28
<211> LENGTH: 83
<212> TYPE: PRT
<213> ORGANISM: Neisseria gonorrhoeae

<400> SEQUENCE: 28

```
Met Trp Gln Ile Arg Lys Asn Arg Thr Glu Asn Leu His Asn Ala Pro
1               5                   10                  15

Asn Tyr Pro Ile Leu Leu Leu Lys Gln Asn Leu Phe Phe Lys Glu Asn
                20                  25                  30

Asn Glu Tyr Gln Glu Asn Leu Arg Phe Val Cys Cys Cys Arg Phe Tyr
```

-continued

```
             35                  40                  45

Cys Phe Asp Ser Leu Cys Gln Arg Asn Gln Asn Arg Cys Gln Gln His
    50                  55                  60

Ala Leu Phe Arg Ser Arg Arg Ala Lys Ala Gly Gly Asn Gly Ser Arg
65                  70                  75                  80

Tyr Gly Arg

<210> SEQ ID NO 29
<211> LENGTH: 82
<212> TYPE: PRT
<213> ORGANISM: Neisseria gonorrhoeae

<400> SEQUENCE: 29

Met Lys Met Lys Lys Leu Ile Leu Leu Ser Val Ala Ala Met Leu Val
1               5                   10                  15

Thr Ala Cys Thr Tyr Ala Asp Arg Arg Phe Val Thr Gln Glu Ser Ala
                20                  25                  30

Ala Glu Ile Gln Ala Lys Ser Arg Ala Ile Gln Ile Ser Glu Arg Ala
        35                  40                  45

Glu Arg Ala Glu Tyr Arg Lys Glu Arg Arg Glu Glu Met Met Asp Ala
    50                  55                  60

Ala Arg Ala Ile Lys Lys Ala Asn Glu Asn Ser Pro Asn Ile Tyr Phe
65                  70                  75                  80

Ile Arg

<210> SEQ ID NO 30
<211> LENGTH: 139
<212> TYPE: PRT
<213> ORGANISM: Neisseria gonorrhoeae

<400> SEQUENCE: 30

Met Lys Lys Leu Leu Met Ile Thr Leu Thr Gly Met Leu Ala Ala Cys
1               5                   10                  15

Ser Thr Gly Val Asn Val Gly Arg Leu Met Val Glu Met Pro Gln Gly
                20                  25                  30

Glu Arg Pro Val Val Val Gln Val Pro Ala Thr Asn Asn Pro Leu Ser
        35                  40                  45

Asp Ala Val Ala Val Gly Met Ile Lys Thr Ser Gly Ser Pro Ser Ala
    50                  55                  60

Ser Asn Met Ile Glu Met Leu Gly Ala Asp Asn Ile Asn Val Gly Val
65                  70                  75                  80

Ala Gly Gly Ser Gln Met Phe Asn Lys Ala Thr Ala Leu Tyr Ser Leu
                85                  90                  95

Asn His Ala Lys Lys Val Gly Asn Asn Val Ser Val Tyr Met Thr Gly
                100                 105                 110

Asp Ser Glu Ser Asp Lys Ala Asp Leu Glu Asn Ala Ala Asn Ala Lys
        115                 120                 125

Asn Ile Lys Leu His Tyr Phe Phe Asn Gln Lys
        130                 135

<210> SEQ ID NO 31
<211> LENGTH: 398
<212> TYPE: PRT
<213> ORGANISM: Neisseria gonorrhoeae

<400> SEQUENCE: 31

Met Pro Ser Glu Pro Phe Gly Arg His Asn Met Thr Asn Thr Leu Ile
```

-continued

```
1                    5                         10                        15
Ser Ile Thr Gln Asp Asp Thr Met Thr His Ile Lys Pro Val Ile Ala
                20                        25                        30

Ala Leu Ala Leu Ile Gly Leu Ala Ala Cys Ser Gly Ser Lys Thr Glu
                35                        40                        45

Gln Pro Lys Leu Asp Tyr Gln Ser Arg Ser His Arg Leu Ile Lys Leu
        50                        55                        60

Glu Val Pro Pro Asp Leu Asn Asn Pro Asp Gln Gly Asn Leu Tyr Arg
65                        70                        75                        80

Leu Pro Ala Gly Ser Gly Ala Val Arg Ala Ser Asp Leu Glu Lys Arg
                85                        90                        95

Arg Thr Pro Ala Val Gln Gln Pro Ala Asp Ala Glu Val Leu Lys Ser
                100                       105                       110

Val Lys Gly Val Arg Leu Glu Arg Asp Gly Ser Gln Arg Trp Leu Val
                115                       120                       125

Val Asp Gly Lys Ser Pro Ala Glu Ile Trp Pro Leu Leu Lys Ala Phe
        130                       135                       140

Trp Gln Glu Asn Gly Phe Asp Ile Glu Ser Glu Pro Ala Ile Gly
145                       150                       155                       160

Gln Met Glu Thr Glu Trp Ala Glu Asn Arg Ala Lys Ile Pro Gln Asp
                165                       170                       175

Ser Leu Arg Arg Leu Phe Asp Thr Val Gly Leu Gly Gly Ile Tyr Ser
                180                       185                       190

Thr Gly Glu Arg Asp Lys Phe Ile Val Arg Ile Glu Gln Gly Lys Asn
                195                       200                       205

Gly Val Ser Asp Ile Phe Phe Ala His Lys Ala Met Lys Glu Val Tyr
        210                       215                       220

Gly Asp Lys Asn Lys Asp Thr Thr Met Trp Gln Pro Ser Ala Ser Asp
225                       230                       235                       240

Pro Asn Leu Glu Ala Ala Phe Leu Thr Arg Phe Met Gln Tyr Leu Gly
                245                       250                       255

Val Asp Gly Arg Gln Ala Glu Asn Ala Leu Ala Lys Lys Pro Thr Leu
                260                       265                       270

Pro Ala Ala Asn Glu Met Ala Arg Ile Glu Gly Lys Ser Leu Ile Val
                275                       280                       285

Phe Gly Asp Tyr Gly Arg Asn Trp Arg Arg Thr Gly Leu Ala Leu Asp
        290                       295                       300

Arg Ile Gly Leu Thr Val Val Gly Gln Asn Thr Glu Arg His Ala Phe
305                       310                       315                       320

Leu Val Gln Lys Ala Pro Asn Glu Ser Asn Ala Val Thr Glu Gln Lys
                325                       330                       335

Pro Gly Leu Phe Lys Arg Leu Leu Gly Lys Gly Lys Ala Glu Lys Pro
                340                       345                       350

Ala Glu Gln Pro Glu Leu Ile Val Tyr Ala Glu Pro Val Ala Asp Gly
                355                       360                       365

Ser Arg Ile Val Leu Leu Asn Lys Asp Gly Ser Ala Tyr Ala Gly Lys
        370                       375                       380

Asp Ala Ser Ala Leu Leu Gly Lys Leu His Ser Glu Leu Arg
385                       390                       395
```

<210> SEQ ID NO 32
<211> LENGTH: 114
<212> TYPE: PRT
<213> ORGANISM: Neisseria gonorrhoeae -continued

<400> SEQUENCE: 32

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Ala Gln Ala Val
            20                  25                  30

Glu Ser Asp Val Lys Asp Thr Ala Ala Ser Ala Ala Glu Ser Ala Ala
        35                  40                  45

Ser Ala Val Glu Glu Ala Lys Gly Gln Val Lys Asp Ala Ala Ala Asp
        50                  55                  60

Ala Lys Ala Ser Ala Glu Glu Ala Val Thr Glu Ala Lys Asp Ala Ala
65                  70                  75                  80

Ala Glu Thr Lys Glu Ala Val Ser Glu Ala Ala Lys Asp Thr Leu Asn
                85                  90                  95

Lys Ala Ala Asp Ala Ala Gln Glu Ala Ala Asp Lys Met Lys Asp Ala
                100                 105                 110

Ala Lys

<210> SEQ ID NO 33
<211> LENGTH: 90
<212> TYPE: PRT
<213> ORGANISM: Neisseria gonorrhoeae

<400> SEQUENCE: 33

Met Lys Lys Thr Ser Lys Tyr Leu Ile Tyr Thr Ala Ala Phe Thr Ser
1               5                   10                  15

Phe Cys Phe Ala Phe Gln Glu Asn Arg Ser Glu Ala Lys Gln Pro Asp
            20                  25                  30

Ile Thr Leu Ser Ala Ser Leu Cys Glu Gln Phe Asn Met Leu Asn Ala
        35                  40                  45

Lys Asp Met Asp Thr Glu Gln Val Ser Leu Ser Lys Glu Cys Asp Ile
        50                  55                  60

Ile Glu Ser Ser His Asp Trp Glu Lys Glu Tyr Gly Asn Leu Asn Glu
65                  70                  75                  80

Gln Glu Met Leu Ala Gly Val Val Tyr Glu
                85                  90

<210> SEQ ID NO 34
<211> LENGTH: 108
<212> TYPE: PRT
<213> ORGANISM: Neisseria gonorrhoeae

<400> SEQUENCE: 34

Met Asn Ile Lys His Leu Leu Leu Thr Ala Ala Ala Thr Ala Leu Leu
1               5                   10                  15

Gly Ile Ser Ala Pro Ala Leu Ala His His Asp Gly His Gly Asp Asp
            20                  25                  30

Asp His Gly His Ala Ala His Gln His Gly Lys Gln Asp Lys Ile Ile
        35                  40                  45

Ser Arg Ala Gln Ala Glu Lys Ala Ala Trp Ala Arg Val Gly Gly Lys
        50                  55                  60

Ile Thr Asp Ile Asp Leu Glu His Asp Asp Gly Arg Pro His Tyr Asp
65                  70                  75                  80

Val Glu Ile Val Lys Asn Gly Gln Glu Tyr Lys Val Val Val Asp Ala
                85                  90                  95

Arg Thr Gly Arg Val Ile Ser Ser Arg Arg Asp Asp

```
        100                 105

<210> SEQ ID NO 35
<211> LENGTH: 185
<212> TYPE: PRT
<213> ORGANISM: Neisseria gonorrhoeae

<400> SEQUENCE: 35

Met Pro Ser Glu Ala Leu Gln Thr Ala Phe Arg Gly Asn Ile Arg Arg
1               5                   10                  15

Ser Phe Thr Met Ile Arg Leu Thr Arg Ala Phe Ala Ala Leu Ile
            20                  25                  30

Gly Leu Cys Cys Thr Thr Gly Ala His Ala Asp Thr Phe Gln Lys Ile
        35                  40                  45

Gly Phe Ile Asn Thr Glu Arg Ile Tyr Leu Glu Ser Lys Gln Ala Arg
    50                  55                  60

Asn Ile Gln Lys Thr Leu Asp Gly Glu Phe Ser Ala Arg Gln Asp Glu
65                  70                  75                  80

Leu Gln Lys Leu Gln Arg Glu Gly Leu Asp Leu Glu Arg Gln Leu Ala
                85                  90                  95

Gly Gly Lys Leu Lys Asp Ala Lys Lys Ala Gln Ala Glu Glu Lys Trp
            100                 105                 110

Arg Gly Leu Val Glu Ala Phe Arg Lys Lys Gln Ala Gln Phe Glu Glu
            115                 120                 125

Asp Tyr Asn Leu Arg Arg Asn Glu Glu Phe Ala Ser Leu Gln Gln Asn
    130                 135                 140

Ala Asn Arg Val Ile Val Lys Ile Ala Lys Gln Glu Gly Tyr Asp Val
145                 150                 155                 160

Ile Leu Gln Asp Val Ile Tyr Val Asn Thr Gln Tyr Asp Val Thr Asp
                165                 170                 175

Ser Val Ile Lys Glu Met Asn Ala Arg
            180                 185

<210> SEQ ID NO 36
<211> LENGTH: 112
<212> TYPE: PRT
<213> ORGANISM: Neisseria gonorrhoeae

<400> SEQUENCE: 36

Met Asn Lys Asn Ile Ala Ala Ala Leu Ala Gly Ala Leu Ser Leu Ser
1               5                   10                  15

Leu Ala Ala Gly Ala Val Ala Ala His Lys Pro Ala Ser Asn Ala Thr
            20                  25                  30

Gly Val Gln Lys Ser Ala Gln Gly Ser Cys Gly Ala Ser Lys Ser Ala
        35                  40                  45

Glu Gly Ser Cys Gly Ala Ser Lys Ser Ala Glu Gly Ser Cys Gly Ala
    50                  55                  60

Ala Ala Ser Lys Ala Gly Glu Gly Lys Cys Gly Glu Gly Lys Cys Gly
65                  70                  75                  80

Ala Thr Val Lys Lys Ala His Lys His Thr Lys Ala Ser Lys Ala Lys
                85                  90                  95

Ala Lys Ser Ala Glu Gly Lys Cys Gly Glu Gly Lys Cys Gly Ser Lys
            100                 105                 110

<210> SEQ ID NO 37
<211> LENGTH: 267
<212> TYPE: DNA
```

-continued

<213> ORGANISM: Neisseria gonorrhoeae

<400> SEQUENCE: 37

```
atgaatcaag ctgttgcaca atttgctcct ttggtgttga ttatggtggt gttctacttc        60
ctgatcatgc gcccccaaca aaagaaattc aaagcgcatc aggcaatgct tgccgccttg       120
aaagccggcg acaaagtggt cttggcggca ggtttcaagg gtaaggtaac cagagtcggc       180
gaacagtttt ttaccgtgga tatcggacag ggtacaaaaa tcgaggtcga agtggaacgc       240
aatgcgattg ccgcaaaagt cgattga                                           267
```

<210> SEQ ID NO 38
<211> LENGTH: 510
<212> TYPE: DNA
<213> ORGANISM: Neisseria gonorrhoeae

<400> SEQUENCE: 38

```
atgacaatga tttttaagcat tttaagcctg ttttttatca ttagactgtt atttttagcc       60
gtctctatta aacatgaaaa agccttgatt gccaaagggg cgaaacaata cggaaaaacc       120
aattccacgg tgcttgcggc agttcatacg ctttattatt tggcgtgttt tgtttgggta       180
tggctttctg acactgcttt taatggcata tccttgattg gtacactgac ggtgatggct       240
tcatttgtga tattatcatt gattattaag cagttggggg agatttggac ggttaaaatc       300
tatattttgc caaatcatca aattaatcgt tcgtggttgt ttaaaacatt ccgccacccg       360 aattatttt taaacatcat acccgaactg attggcatcg ccttattatg tcaagcgtgg       420
tatgttttat tgattggcct gcccatttat ttgctggtct tatttaagcg tatccgacaa       480
gaagaacagg cgatggcaac actttttaa                                         510
```

<210> SEQ ID NO 39
<211> LENGTH: 288
<212> TYPE: DNA
<213> ORGANISM: Neisseria gonorrhoeae

<400> SEQUENCE: 39

```
atgaacaaag aaatagtcgg tattttcttt ataccgatgg gcatcatcag catgtgtatg        60
gccgcattgt ggcagatgta tgtgatgatg accgaaactt atacgctcaa ccgtttcaaa       120
gataaagaat tggtttggcg cgtggcattg ttgtttatca gtttcagcct tgccgtttat       180
ctgctctgtc cgaattcgcg taaaaaaggc atcgtctttt ttattctcgg gggaggcggt       240
gcagtcatgt atctgctggc gcggatgtgg ttgcccttca gtaaatag                    288
```

<210> SEQ ID NO 40
<211> LENGTH: 426
<212> TYPE: DNA
<213> ORGANISM: Neisseria gonorrhoeae

<400> SEQUENCE: 40

```
atgacacaag aaaccgcttt gggcgcggca ctgaaatccg ccgtccaaac tatgagcaaa        60
aagaaacaga ccgaaatgat cgccgaccac atctacggca aatacgatgt attcaaacgc       120
ttcaaaccgt tggcgctcgg catcgatcag gatttgattg ccgctttgcc gcaatacgat       180
tccgcactga ttgcacgcgt cctcgccaac cactgccgcc gtccgcgcta tctgaaagcc       240
ttggcgcgcg gcggcaaacg tttcgatttg aacaaccgtt tcaaaggcga agttaccccc       300
gaagaacagg cgattgcgca aaaccatcct ttcgtgcagc aggctttgca acagcagtcc       360
gcccaagctg ccgccgaaac gccgtctgtt gaagccgaag cagccgaatc ttccgcagca       420
```

-continued

```
gaataa                                                                 426

<210> SEQ ID NO 41
<211> LENGTH: 426
<212> TYPE: DNA
<213> ORGANISM: Neisseria gonorrhoeae

<400> SEQUENCE: 41
atgacacaag aaaccgcttt gggcgcggca ctgaaatccg ccgtccaaac tatgagcaaa     60
aagaaacaga ccgaaatgat cgccgaccac atctacggca aatacgatgt attcaaacgc    120
ttcaaaccgt tggcgctcgg catcgatcag gatttgattg ccgctttgcc gcaatacgat    180
tccgcactga ttgcacgcgt cctcgccaac cactgccgcc gtccgcgcta tctgaaagcc    240
ttggcgcgcg cggcaaacg tttcgatttg aacaaccgtt tcaaaggcga agttacccccc    300 gaagaacagg cgattgcgca aaaccatcct ttcgtgcagc aggctttgca acagcagtcc    360
gcccaagctg ccgccgaaac gccgtctgtt gaagccgaag cagccgaatc ttccgcagca    420
gaataa                                                                 426

<210> SEQ ID NO 42
<211> LENGTH: 264
<212> TYPE: DNA
<213> ORGANISM: Neisseria gonorrhoeae

<400> SEQUENCE: 42
atgaacaaat cgaatttctt tctgctgctt gcggtgtgcg tttccgcttt ttccgttgtg     60
atgcagcaaa accagtacag gctcaacttc acagctttgg acaaggcgaa aaaacaggaa    120
atcgccttgg agcaggatta tgcgcaaatg aggctgcaac aggcgcgttt ggcgaatcac    180
gaagcgatca gggcggcggc agaaaaacaa aacctccatc cgccggtttc gggcaatacc    240
tttatggtgg aacatcaaag atag                                             264

<210> SEQ ID NO 43
<211> LENGTH: 870
<212> TYPE: DNA
<213> ORGANISM: Neisseria gonorrhoeae

<400> SEQUENCE: 43
atgtttatga acaaattttc ccaatccgga aaaggtctgt ccggtttctt cttcggtttg     60
atactggcaa cggtcattat tgccggtatt ttgctttatc tgaaccaggg cggtcaaaat    120
gcgttcaaaa tcccggctcc gtcgaagcag cctgcagaaa cggaaatcct gaaactgaaa    180
aaccagccta aggaagacat ccaacctgaa ccggccgatc aaaacgcctt gtccgaaccg    240
gatgttgcga agaggcaga gcagtcggat gcggaaaaag ctgccgacaa gcagcccgtt    300
gccgacaaag ccgacgaggt tgaagaaaag gcgggcgagc cggaacggga agagccggac    360
ggacaggcag tgcgcaagaa agcactgacg gaagagcgtg aacaaaccgt cagggaaaaa    420
gcgcagaaga aagatgccga aacggttaaa aaacaagcgg taaaaccgtc taaagaaaca    480
gagaaaaaag cttcaaaaga agagaaaaag gcggcgaagg aaaaagttgc acccaaaccg    540
accccggaac aaatcctcaa cagcggcagc atcgaaaaag cgcgcagtgc cgctgccaaa    600
gaagtgcaga aaatgaaaac gtttggcaag gcggaagcaa cgcattatct gcaaatgggc    660
gcgtatgccg accgccggag cgcggaaggg cagcgtgcca aactggcaat cttgggcata    720
tcttccgaag tggtcggcta tcaggcggga cataaaacgc tttaccgcgt gcaaagcggc    780
```

-continued

```
aatatgtctg ccgatgcggt gaaaaaaatg caggacgagt tgaaaaagca tggggttgcc      840
agcctgatcc gtgcgattga aggcaaataa                                        870

<210> SEQ ID NO 44
<211> LENGTH: 582
<212> TYPE: DNA
<213> ORGANISM: Neisseria gonorrhoeae

<400> SEQUENCE: 44
atgaaagtaa gatggcggta cggaattgcg ttcccattga tattggcggt tgccttgggc       60
agcctgtcgg catggttggg ccgtatcagc gaagtcgaaa tcgaggaagt caggctcaat      120
cccgacgaac ctcaatacac aatggacggc ttggacggaa ggcggtttga cgaacaggga      180
tacttgaaag aacatttgag cgcgaaaggt gcgaaacagt ttcccgaaaa cagcgacatc      240
cattttgatt cgccgcatct cgtgttcttc caagaaggca ggctgttgta cgaagtcggc      300
agcgatgaag ccgtttacca taccgaaaac aaacaggttc tttttaaaaa caacgttgtg      360
ctgaccaaaa ccgccgacgg caggcggcag gcgggtaaag tcgaaaccga aaaactgcac      420
gtcgataccg aatctcaata tgcccaaacc gatacgcctg tcagtttcca atatggcgcg      480
tcgcacggtc aggcgggcgg tatgacctac aaccacaaaa caggcatgtt gaacttctca      540
tctaaagtga aagccgcgat ttatgataca aaagatatgt aa                        582

<210> SEQ ID NO 45
<211> LENGTH: 552
<212> TYPE: DNA
<213> ORGANISM: Neisseria gonorrhoeae

<400> SEQUENCE: 45
atgaaggttt tgaacggttg gtcagatagg aagatgtggc gggtttttgag tgctttgccg       60 ataggcgtgg tgtttttttga tttgatctac ggttttgtgt tgaatgtgtt gcagggtttg     120
gatttgcagc gtgccgtgcc ggattcggaa ggcgtgttgg cggttacgcc cgatattgcg      180
ttcaacagtt tgcagattgt cgccaacggc ggtatggcgg cggtggtctg tttcgggttg      240
gcggttgtgt ttttgctcaa ccgttcggtg cggcggcggc aggtcttgga aatcggggtg      300
ttccggatgt tggggctggt ggcggtattg gcgttcagcg cgccttcgct gtgggagtgg      360
gcgaacgcgc tgccgctgct gctgaagggc gcggacgtgg tcaatacggg gaatgcgcgt      420
tatgtgctga cggctttgtg tatgccctttt ccggcggtgt cgtgcatcat cgggctggta      480
gggcggttca ggcttcagac ggcatcgggc agggtggcaa aggcaggggg tgcggtcaag      540
gcgggcggat ag                                                          552

<210> SEQ ID NO 46
<211> LENGTH: 450
<212> TYPE: DNA
<213> ORGANISM: Neisseria gonorrhoeae

<400> SEQUENCE: 46
atgaaaatcg aacaacttg gcagacggca tccgctatgc tggtttttgcg tctatttgcc       60 gcatatgaat ttttggaatc gggttttgcaa aaatggaacg gggagaattg gttttccgaa      120
atcaacgatc agtttccatt cccgttcaac ttgctgccgg acgcgttaaa ctggaatctc      180
gccatgtatg cggagctttt gctgcccgta ctgttgcttt tgggtttggc aacgcgcctg      240
tcggcattgg ggctgatggt cgttaccgcc gtcgcttggg ctgcggttca cgccggttcg      300
ggttacaatg tctgcgacaa cggttataaa atggctttaa tttatatcgt ggtattaatc      360
```

```
ccgctgcttt tccagggtgc gggcggatgg tcgctggata cgctgctgaa aaaactgttt     420
tgccccaaat gccgtctgaa acaagattga                                      450
```

<210> SEQ ID NO 47
<211> LENGTH: 849
<212> TYPE: DNA
<213> ORGANISM: Neisseria gonorrhoeae

<400> SEQUENCE: 47

```
atggacttca aacaatttga tttttttacac ctgatcagtg tttccggttg ggggcatctg      60
gctgaaaagg cgtgggcgtt cgggctgaac cttgccgccg cgctgcttat tttcttggtc     120
gggaaatggg cggcgaaacg cattgtcgcc gtaatgaggg cggcgatgac gcgcgcgcag     180
gtcgatgcca cgctgattag tttttttgtgt aatgttgcca atatcggctt attgattttg     240
gtgattattg ccgcattggg acggttgggc gtttccacaa catccgtaac cgccttaatc     300
ggcggcgcgg gtttggcggt ggcgttgtcc ttaaaagacc agctgtccaa ttttgccgcc     360
ggcgcgctga ttatcctgtt ccgcccgttc aaagtcggcg actttatccg tgtcggcggt     420
tttgaaggat atgtccggga aatcaaaatg gtgcagactt ctttgcggac gaccgacaac     480
gaagaagtcg tgctgcccaa cagcgtggtg atgggcaaca gcatcgtcaa ccgttccagc     540
ctgccgcttt gccgcgccca agtgatagtc ggcgtcgatt acaactgcga tttgaaagtg     600
gcgaaagagg cggtgttgaa agccgccgcc gaacacccct tgagcgttca aaacgaagag     660
cggcagcccg ccgcctacat caccgccttg ggcgacaatg ccatcgaaat cacattatgg     720
gcttgggcaa acgaagcaga ccgctggacg ctgcaatgcg acttgaacga caagtggtc     780 gaaaacctcc gcaaagtcaa tatcaacatc ccgttcccgc aacgcgacat acacatcatc     840
aattcttaa                                                            849
```

<210> SEQ ID NO 48
<211> LENGTH: 324
<212> TYPE: DNA
<213> ORGANISM: Neisseria gonorrhoeae

<400> SEQUENCE: 48

```
atgaaaaaat gtattttggg cattttgacc gcgtgtgccg ccatgcctgc atttgccgac      60
agaatcagcg atttggaagc acgtctggcg cagttggaac accgtgtcgc cgtattggaa     120
agcggcggca ataccgtcaa aatcgacctt ttcggttcaa attccaccat gtatgtatgc     180
agcgttacgc cttttcagaa gacgtttgag gcaagcgatc ggaatgaagg cgtggcgcgg     240
cagaaagtgc gtcaggcgtg caaccgcgaa acttcggcaa tgttttgcgg agatgaggca     300
atccgatgca gaaaattcga ttga                                            324
```

<210> SEQ ID NO 49
<211> LENGTH: 1797
<212> TYPE: DNA
<213> ORGANISM: Neisseria gonorrhoeae

<400> SEQUENCE: 49

```
atgcgctaca aaccccttct gcttgccctg atgctcgttt tttccacgcc cgccgttgcc      60
gcccacgacg cggcacacaa ccgttccgcc gaagtgaaaa acaggcgaa gaacaaaaaa     120 gaacagcccg aagcggcgga aggcaaaaaa gaaaaaggca aaaatgccgc agtgaaagat     180
aaaaaaacag gcggcaaaga ggcggcaaaa gagttcaaaa aaaccgccaa aaaccgcaaa     240
```

```
gaagcagaga aggaggcgac atccaggcag tctgcgcgca aaggacgcga aggggataag      300
gaatcgaagg cggaacacaa aaaggcacat ggcaagcccg tgtccggatc caaagaaaaa      360
aacgcaaaaa cacagcctga aaacaaacaa ggcaaaaaag gggcaaaagg acagggcaat      420
ccgcgcaagg gcggcaaggc ggaaaaagac actgtttctg caaataaaaa agcccgttcc      480
gacaagaacg gcaaagcagt gaaacaggac aaaaaacaca cggaagagaa aaatgccaaa      540
accgattccg acgaattgaa agccgccgtt gccgctgcca ccaatgatgt cgaaaacaaa      600
aaagccctgc tcaaacaaag cgaaggaatg ctgcttcatg tcagcaattc cctcaaacag      660
cttcaggaag agcgtatccg ccaagaacgt atccgccaag agcgtatccg tcaggcgcgc      720
ggcaaccttg cttccgtcaa ccgcaaacag cgcgaggctt gggacaaatt ccaaaaactc      780
aataccgagc tgaaccgttt gaaaacggaa gtcgccgcta cgaaagcgca gatttcccgt      840
ttcgtatcgg ggaactataa aaacagccgg ccgaatgcgg ttgccctgtt cctgaaaaac      900
gccgaaccgg gtcagaaaaa ccgctttttg cgttatacgc gttatgtaaa cgcctccaat      960
cgggaagttg tcaaggattt ggaaaaacag cagaaggctt tggcggtaca agagcagaaa     1020
atcaacaatg agcttgcccg tttgaagaaa attcaggcaa acgtgcaatc cctgctgaaa     1080
aaacagggtg taaccgatgc ggcggaacag acggaaagcc gcagacagaa tgccaaaatc     1140
tccaaagatg cccgaaaact gctggaacag aaagggaacg agcagcagct gaacaagctc     1200
ttgagcaatt tggagaaaaa aaaagccgaa caccgcattc aggatgcgga agcaaaaaga     1260
aaattggctg aagccaaact ggcggcagcc gaaaaagcca gaaaagaagc ggcgcagcag     1320
aaggctgaag cgcgacgtgc ggaaatgtcc aacctgaccg ccgaagacag gaacatccaa     1380
gcgccttcgg ttatgggtat cggcagtgcc gacggtttca gccgcatgca gggacgtttg     1440
aaaaaaccgg ttgacggtgt gccgaccggg ctttttcgggc agaaccggag cggcggcgat     1500
gtttggaaag gcgtgttcta ttccactgcg cctgcaacgg ttgaaagcat tgcgccggga     1560
acggtaagct atgcggacga gttggacggc tacggcaaag tggtcgtgat cgatcacggc     1620
gagaactaca tcagcatcta tgccggtttg agcgaaattt ccgccggcaa gggttatacg     1680
gtcgcggcag gaagcaaaat cggcacgagc gggtcgctgc cggacgggga agaggggctt     1740
tacctgcaaa tacgttatcg aggtcaggtg ttgaaccctt cgggctggat acgttga       1797
```

```
<210> SEQ ID NO 50
<211> LENGTH: 435
<212> TYPE: DNA
<213> ORGANISM: Neisseria gonorrhoeae

<400> SEQUENCE: 50
gtgccgctgc ctgctccctg ccgtttttgcc aaacctgccg cctcttttttt aagtatggct       60 ttgctttcct gccagctttc ccacgccgcc acggcttata tccccccgaa cgattttcaa      120
ccgaactgcg acatacgccg gctcgggctg acacagggtc agcacaatga gctgcgtaaa      180
atccgcgccg ccttcaaaat ggcggcgac agggcgcgtt tgaaggttat gcattccgaa      240
cacagccgcc gccgctctgt cgtcgaaatc atttcttcgg atgtttttaa tcggaacgag      300
gcgcgcgatt atgtcgaaag ccgctaccac tccagcatgg attttgcggt ggacgaattg      360
gaaatccaac accgcttctt ccatattctc acaccgcaac agcagcaaat gtggctttct      420
tcctgcctca aataa                                                       435
```

```
<210> SEQ ID NO 51
<211> LENGTH: 474
```

```
<212> TYPE: DNA
<213> ORGANISM: Neisseria gonorrhoeae

<400> SEQUENCE: 51
atgaaaaaat tattggcagc cgtgatgatg gcaggtttgg caggcgcggt ttccgccgcc        60
ggagtccatg tcgaggacgg ctgggcgcgc accactgtcg aaggtatgaa aatgggcggc       120
gcgttcatga aaatccccaa cgacgaagcc aaacaagact ttttgctcgt cggaagcagc       180
cccgttgccg accgcgtcga agtgcatacc cacatcaacg acaacggcgt gatgcgtatg       240
cgcgaagtca aaggcggcgt gcctttggag gcgaaatccg ttaccgaact caaacccggc       300
agctatcacg tgatgtttat gggtttgaaa aaacaactga agagggcga caagattccc        360 gttaccctga aatttaaaaa cgccaaagcg caaaccgtcc aactggaagt caaaaccgcg       420
ccgatgtcgg caatgaacca cggtcatcac cacggcgaag cgcatcagca ctaa             474

<210> SEQ ID NO 52
<211> LENGTH: 579
<212> TYPE: DNA
<213> ORGANISM: Neisseria gonorrhoeae

<400> SEQUENCE: 52 atgtgtttt gcctgcttct gatgccgaaa ttttatttt cttgccgaac aatttgtttt         60
ctcaaggcaa acttgattat aatggcgggt atgaaaaaat accttatccc tctttccatt       120
gcggcagtcc tttccgggtg ccagtctatt tatgtgccca cattgacgga aatccccgtg       180
aatcccatca ataccgtcaa aacggaagca cctgcaaaag gttttcgcct cgcccccttcg      240 cattgggcgg atgttgccaa aatcagcgat gaagcgacgc gcttgggcta tcaggtgggt      300
atcggtaaaa tgaccaaggt tcaggcggcg caatatctga caacttcag aaaacgcctg        360 gtcggacgca atgccgtcga tgacagtatg tatgaaatct acctgcgttc ggcggtagac      420
agccagcgcg gcgaaatcaa tacggaacag tccaagctgt atatcgagaa tgccttgcgc      480
ggctggcagc agcgttggaa aaatatggat gccaaacccg ataatcccgc atttaccaac       540
tttttgatgg aagtgatgaa gatgcagccc ttgaaatga                            579

<210> SEQ ID NO 53
<211> LENGTH: 786
<212> TYPE: DNA
<213> ORGANISM: Neisseria gonorrhoeae

<400> SEQUENCE: 53
atgaaaacca agttaatcaa aatcttgacc cccttaccg tcctgccgct gctggcttgc         60
gggcaaacgc ccgtttccaa tgccaacgcc gaatccgccg tcaaagccga tccgccggc        120 aaatccgttg ccgcttcttt gaaagcgcgt ttggaaaaaa cctattccgc ccaagatttg       180
aaagtgttga gcgtcagcga aacaccggtc aaaggcattt acgaagtcgt cgtcagcggc       240
aggcagatta tctacaccga tgccgaaggc ggctatatgt tcgtcggcga actcatcaac       300
atcgacacgc gcaaaaacct gaccgaagaa cgcgccgccg atttgaacaa aatcgacttc       360
gcctccctgc ctttggacaa agccatcaaa gaagtacgcg gcaacggcaa gctgaaagtc       420
gccgtcttct ccgaccccga ttgtccgttc tgcaaacgct tggaacatga gtttgaaaaa       480
atgaccgacg tgacggttta cagctttatg atgcccattg ccggcctgca cccagatgcc       540
gcgcgcaagg cgcaaatctt atggtgtcag cccgaccgtg ccaaagcgtg gacggattgg       600
atgcgtaaag gcaaattccc ggtcggcggc agcatctgcg acaatcccgt cgcggaaacc       660
```

```
acttccttgg gcgaacagtt cggcttcaac ggcacgccga ccctcgtctt ccccaacggg        720
cgcacccaaa gcggttacag cccgatgccc caactggagg aaatcatccg caaaaaccag        780
cagtaa                                                                   786

<210> SEQ ID NO 54
<211> LENGTH: 456
<212> TYPE: DNA
<213> ORGANISM: Neisseria gonorrhoeae

<400> SEQUENCE: 54
atgaaccgtc gtcaattttt gggcagcgcc gctgccgtct ctttggcttc cgccgcctct         60
ttcgcgcgtg cgcacggaca cgccgactac caccatcatc acgatatgca gcctgccgcc        120
gcatccgcct acaccgccgt ccgccaaact gccgcacact gtctggatgc cggacaggtt        180
tgcctgaccc actgcctgtc cctgctcact cagggcgaca cgtctatgtc cgactgtgcg        240
gttgccgtgc gccagatgct tgccttatgc ggcgcggtgc acgaccttgc cgcacaaaat        300
tcccctctga cacgcgacgc ggcaaaagtg tgcctcgaag cgtgcaaaca gtgtgccaaa        360
gcctgtaaag aacactccgc ccaccatgcg gaatgcaaag cctgttacga gtcctgcctc        420
gactgtatca aagaatgcga aaaactcgcc gcctga                                  456

<210> SEQ ID NO 55
<211> LENGTH: 600
<212> TYPE: DNA
<213> ORGANISM: Neisseria gonorrhoeae

<400> SEQUENCE: 55
atggctttta ttacgcgctt attcaaaagc attaaacaat ggcttgtgct gttgccgata         60
ctctccgttt tgccggacgc ggcggcggag ggcattgccg cgacccgcgc cgaagcgagg        120
ataaccgacg gcgggcggct ttccatcagc agccgcttcc aaaccgagct gcccgaccag        180
ctccaacagg cgttgcgccg gggcgtaccg ctcaacttta ccttaagctg gcagctttcc        240
gccccgacaa tcgcttctta tcggtttaaa ttggggcaac tgattggcga tgacgacaat        300
attgactaca aactaagttt ccatccgctg accaaccgct accgcgttac cgtcggcgca        360
ttttccaccg attacgacac tttggatgcg gcattgcgcg cgaccggcgc ggttgccaac        420
tggaaagtcc tgaacaaagg cgcgttgtcc ggtgcggaag caggggaaac caaggcggaa        480
atccgcctga cgctgtccac ttcaaaactg cccaagcctt tccaaatcaa cgcattgact        540
tctcaaaact ggcatttgga ttcgggttgg aaacctctaa acatcatcgg gaacaaataa        600

<210> SEQ ID NO 56
<211> LENGTH: 591
<212> TYPE: DNA
<213> ORGANISM: Neisseria gonorrhoeae

<400> SEQUENCE: 56
atgaaaaaat cctccttcat cagcgcattg ggcatcggta tttttgagcat cggcatggca         60 tttgcctccc cggccgacgc agtgggacaa atccgccaaa cgccacaca ggttttgacc        120 atcctcaaaa gcggcgacgc ggcttctgca cgcccaaaag ccgaagccta tgcggttccc        180
tatttcgatt ccaacgtat gaccgcattg gcggtcggca acccttggcg taccgcgtcc        240
gacgcgcaaa acaagcgtt ggccaaagaa tttcaaaccc tgctgatccg cacctattcc        300
ggcacgatgc tgaaattcaa aaacgcgacc gtcaacgtca agacaatcc catcgtcaat        360 aagggcggca aggaaatcgt cgtccgtgcc gaagtcggca tccccggtca gaagcccgtc        420
```

```
aatatggact ttaccaccta ccaaagcggc ggcaaatacc gtacctacaa cgtcgccatc        480
gaaggcacga gcctggttac cgtgtaccgc aaccaattcg gcgaaatcat caaagccaaa        540
ggcatcgacg ggctgattgc cgagttgaaa gccaaaaacg gcggcaaata a                 591
```

<210> SEQ ID NO 57
<211> LENGTH: 246
<212> TYPE: DNA
<213> ORGANISM: Neisseria gonorrhoeae

<400> SEQUENCE: 57

```
ttgaaggatt ctacagggca aatgaggctg gcaaccaagg atttggcgga agccattaaa         60
cgaggagaag tacgtagttc tgcttttaca acaaagcaac taaaggcaat cgaaaaaggc        120
aaagacaaaa tccctagcta cacttggcat catcatcaag atacagggag aatgcagctt        180
gtgcctgaat gggaacattc taaaaccggt cacataggag ggacggcaat ggggaagggt        240
aaataa                                                                     246
```

<210> SEQ ID NO 58
<211> LENGTH: 321
<212> TYPE: DNA
<213> ORGANISM: Neisseria gonorrhoeae

<400> SEQUENCE: 58

```
atgaatttcc aagactatct cgccacattt ccttcaatcg accatctggg cggtttggat         60
gttcaggatg ccgaaggcaa aacggttcac cacattcccg ccgttcaggg caagctcggt        120
tcgctcaagc tgtacaatgc cttggcggaa cgttttgatg gaaaattggg taaagaagcg        180
gcagaacagg gtttgatatg gtttgccgaa catgttgccg acgcgcgcgc ccatccgggg        240
aagcatccga acatcgattt gctggaaaat gtcgtgcaaa gcggcgaaac cctcctgctc        300
aaaccgcttg ccgcgcaata a                                                   321
```

<210> SEQ ID NO 59
<211> LENGTH: 483
<212> TYPE: DNA
<213> ORGANISM: Neisseria gonorrhoeae

<400> SEQUENCE: 59

```
atgatgaaaa agatactggc agtatcggca ctatgcctga tgactgcggc ggcacaggct         60
gccgatactt acggctatct cgccgtttgg cagaatccgc aggatgcaaa cgatgttttg        120
caggttaaaa ccacaaaaga agattcggcg aaaagcgaag cgtttgccga gttggaagcc        180
ttttgcaaag gtcaggacac gcttgcgggc attgccgaag acgagccgac cggatgccgg        240
tcggtcgtgt cgctgaacaa tacctgtgtc tcgctggcat acccgaaagc cttgggcgcg        300
atgcgcgttg aaaacgccgt cgtgattact tctccgcgtt ttacgagcgt tcatcaggtc        360
gcactcaacc agtgcataaa aaaatacggc gcacagggac aatgcggctt ggaaacagtg        420
tattgcacgt catcttctta ttacggcggg gctgttcgct ccttaatcca acacctgaaa        480
taa                                                                        483
```

<210> SEQ ID NO 60
<211> LENGTH: 555
<212> TYPE: DNA
<213> ORGANISM: Neisseria gonorrhoeae

<400> SEQUENCE: 60

-continued

```
atgaaaaaaa tcatcgcctc cgcgcttatc gcaacattcg cactcaccgc ctgccaagac      60
gacacgcagg cgcggctcga acggcagcag aaacagattg aagccctgca acagcagctc     120
gcacagcagg cagacgatac ggtttaccaa ctgactcccg aagcagtcaa agacaccatt     180
cctgcccagg cgcaggcaaa cggcaacaac ggtcagcccg ttaccggcaa agacgggcag     240
cagtatattt acgaccaatc gacaggaagc tggctgctgc aaagcctgat tggcgcggcg     300
gcaggcgcgt ttatcggcaa cgcgctggca aacaaattca cacgggcggg caaccaagac     360
agccccgtcg cccgtcgcgc gcgtgctgcc taccatcagt ccgcacgccc caatgcgcgc     420
accagcaggg atttgaacac gcgcagcctc cgtgcaaaac aacaggcggc gcaggcgcag     480
cgttaccgcc cgacaacgcg cccgcccgtc aattaccgcc gtcccgctat gcgcggtttc     540
ggcagaaggc ggtaa                                                       555
```

```
<210> SEQ ID NO 61
<211> LENGTH: 255
<212> TYPE: DNA
<213> ORGANISM: Neisseria gonorrhoeae

<400> SEQUENCE: 61
atgaacaaac ttttcgttac cgccctgtcc gccctcgcct tgtccgcctg cgccggcact      60
tggcagggcg cgaaacaaga caccgcccgc aaccttgaca aaacacaggc cgccgccgaa     120
cgcgccgccg aacaaacagg caacgccgtc gaaaaaggtt gggacaaaac caaagaagcc     180
gtcaaaaaag cgggcaatgc cgtcggacgc ggcatttccc atctcggcaa aaaaatcgaa     240
aacgccaccg aataa                                                       255
```

```
<210> SEQ ID NO 62
<211> LENGTH: 369
<212> TYPE: DNA
<213> ORGANISM: Neisseria gonorrhoeae

<400> SEQUENCE: 62
atgaataaaa ccttgtctat tttgccggcg gcaatcttac tcggcgggtg cgccgccggc      60
ggcaacacat tcggcagctt agacggcggc acgggtatgg gtggcagcat cgtcaaaatg     120
acggtagaaa gccaatgccg tgcggaattg gacaggcgca gcgaatggcg tttgaccgcg     180
ctggcgatga gtgccgaaaa acaggcggaa tgggaaaaca agatttgcgg ctgcgctacc     240
gaagaagcac ctaaccagct gaccggcaac gatgtgatgc agatgctgaa ccagtccacg     300
cgcaatcagg cacttgccgc cctgaccgtc aaaacggttt ccgcctgctt caaacgcctg     360
taccgctaa                                                              369
```

```
<210> SEQ ID NO 63
<211> LENGTH: 2619
<212> TYPE: DNA
<213> ORGANISM: Neisseria gonorrhoeae

<400> SEQUENCE: 63
atgaaccaag aagggattac cgctcacgga atgccacga ttaccctcaa ggcgaaagaa       60
aacaataaaa ttaccgtgga aaacgccgca tacagcagcg acggcatttc gactctgatt     120
aacagaacgg gggcaagacc cggaacaagg gatgatggaa ataaaatcat actggaagcc     180
ggcggcgata atattgttac catgaaatcc ggcgatgcgg atgcggatta tgtaaacaat     240
tccaaagtat taacggagac accatattat aaaagcaaac gaggttccaa cggcatttt      300 gcctatggcg acaaatcgct ggtcaaactg attggcgaga ataatatcgt taagagtgaa     360
```

-continued

```
atcagtgaaa aatctaaggc attaaatggg ggatttcgcc atatcggcat ttattcatgg      420
caaaacgcga aagtcgaatt gtctgcgaag agcgacaata tcgtacaagg cggaatttgg      480
ggcttatact ccaacaactc ctcaatttcc ctcaaggggga aaaataatgt gatttcaaac      540
ccgaaatata atgttttcgc ctacaaaaag gcaaaggtgg atttgactgt cgaaaataaa      600
aacacattat ctgatgcgga atttggcgta tatgccttaa acacaagtat ggttaatttg      660
tcttcaaaag ataataacga ggtaaaaagc acccaagtgg gtctgtattc gcaagacggc      720
ggttcaatca atgtagatag gaaggataat attattgaag gcgacgcggt tgccttggtg      780
ggaaaaggtg gaagtcaaaa cattcgggca agccgtacaa acctgattag ttcaaaaagc      840
ttaggaattc atgctgaaca agctgcaaaa atagccataa ccggcgcaag caatacaatt      900
catgcaagca atgccgctat tcgttcatta gacaaaagcg aagttaagat tgacggtcaa      960
attaccattg actccaacgt tgccaatctt gcaaggcaag atggttcaat tcatttgaat     1020
tataaagacg atacccgtat cacaggggca accgtatctg ataagggttt ggtagccatc     1080
aaacctttga ataacacgaa tattgttgcc gacactattc actataaagg cgatgtcttg     1140
gcggtaaata agggtaaagt ggaattagat ttcacgccga acatcctttt agcgggacgt     1200
ttggataatt ttagcggctt aaccgattcc aaacataaaa atttattcga aaactatgtt     1260
gcaaatttag acagcaaaag tgcgggcgaa attaactttta atttagccaa agacgcatta     1320
tggacgatga caggtcaaag ctggctggat aaattggaag gacaaggcac tatcgatttt     1380
aataatgatg ctaaaacaag tggacgcgcc ttacatatcg gcgaattggc gggtgccaat     1440
aaattcttga tgcatctgaa taaagacggc attcacagcg atatgctcta tgtgaaaaaa     1500
ggcacttcga caccgcaaga agtcgtcgtc aaaaatctgt ccgaagtgct cgacagtatg     1560
aattacggcg aacgtttgcg tttcgctaca gtaacaaact caaaaaatga atttgtgaac     1620
ggtaaaaaat atattgacga tacgcacctt atggaggatg ccctgactgt cgaatactcc     1680
gcacataacg gcgataaaaa caacaaggat gactataata aatcctttaa cggctctgaa     1740
atgacggcgg aaaaagctgg agacgattat gtcaataaaa cctataccga caacaggcaa     1800
aatgtctatt tggtcaaaca ggctaccggc aatccgagcc gaaatgtcaa aaatatcaat     1860
gatatgttcg attcaaccgc acattatgcg ttcactttgg atacttatgc caaacgcgaa     1920
ggggagcggg cttttttcaac gttggataaa aaagaaggcg attggataag gctgacgcat     1980
acccgtgtga ttcaatccaa tgcgtttagg tttcataaca acgattttga aatcggatat     2040
gaccgattca gcctcaacga gcaggagaaa aaacgcaaat ggggcataag tctcgactac     2100
ggccacggca ggacatcatt atggaatacg tttggcaagg acaaaatcag gaaatatgaa     2160
ttggctctgt acaatactac ccaatacata gataaagaag gagacgaaac agggtatatc     2220
gacaatgtat taaaaatagg aaaactgcgt aaccgtgtga ttgcacgaaa tcatatgggg     2280
caattatggg gcaagggaaa atatagcaac accctattct ctatcagcac cgaatacggc     2340
cgccgtaaat ttttggatga cgataaattg tggcggatta caccgcaagt acagttgcaa     2400
tattcctatt tgagaggtac cggctatcgg atcgataacg gcataaacgt caatttaagc     2460
cacgcaaaca gcctgatagg ccgcttgggt ttggatgtcg tgagaaaatt tgacggaggc     2520
aaaaaacttt tctatatcaa aggcaatatc tttcatgaat ttttgggcag tcgttccttt     2580
aaggcatttg agggcaaaag tcattatgct caaaaatga                             2619
```

<210> SEQ ID NO 64

-continued

```
<211> LENGTH: 252
<212> TYPE: DNA
<213> ORGANISM: Neisseria gonorrhoeae

<400> SEQUENCE: 64
atgtggcaaa ttcggaaaaa caggacggaa aacttgcaca acgcgccgaa ctaccctatc        60
cttctcttga aacaaaacct tttctttaag gaaaacaatg aatatcagga aaatctccgc       120
tttgtgtgct gttgccgttt ttactgtttc gacagcctat gccaaagaaa tcaaaatcga       180
tgccaacaac acgccttatt ccgaagccga cgcgcaaaag ctggcggcaa cggcagtcgg       240
tatgggcgtt aa                                                          252

<210> SEQ ID NO 65
<211> LENGTH: 249
<212> TYPE: DNA
<213> ORGANISM: Neisseria gonorrhoeae

<400> SEQUENCE: 65
atgaaaatga agaaactgat tttgttgtcg gtggctgcga tgttggtgac ggcatgtact        60
tacgcagacc gccgttttgt aactcaagaa tctgcagcgg aaatacaggc gaaaagtcgt       120
gccattcaga taagcgagcg tgccgagcgt gccgaatacc gtaaagaacg ccgggaagaa       180
atgatggatg cggcacgcgc catcaaaaag gcaaacgaaa attcacccaa tatttatttt       240
atccgataa                                                             249

<210> SEQ ID NO 66
<211> LENGTH: 420
<212> TYPE: DNA
<213> ORGANISM: Neisseria gonorrhoeae

<400> SEQUENCE: 66
atgaaaaaac ttctaatgat aaccctcacc ggtatgcttg cagcttgttc aacaggtgtc        60
aatgtcggcc ggttgatggt tgaaatgccg caggagaaac gccctgttgt cgtgcaggtt       120
cccgcgacga ataacccgct ttccgatgcg gtggctgtcg gaatgattaa aacatccgga       180
tcgccttcgg catcaaatat gattgaaatg ctcggcgcgg acaatatcaa cgtcggcgtg       240
gcgggaggca gccaaatgtt taataaggcg accgcacttt attccttaaa ccatgcaaag       300
aaagtcggaa ataatgtcag tgtctatatg acgggcgata gcgaaagcga caaggccgat       360
ttggaaaacg cggcaaatgc caaaaatatt aaattacatt atttctttaa ccaaaaataa       420

<210> SEQ ID NO 67
<211> LENGTH: 1197
<212> TYPE: DNA
<213> ORGANISM: Neisseria gonorrhoeae

<400> SEQUENCE: 67
atgccgtctg aaccgttcgg acggcataac atgacaaaca ctttaatatc catcacacag        60
gatgacacga tgacccatat caaacccgtc attgccgcgc tcgcactcat cgggcttgcc       120
gcctgctccg gcagcaaaac cgaacagccc aagctcgact accaaagccg gtcgcaccgc       180
ctgatcaaac tcgaagtccc gcctgatttg aacaaccccg accaaggcaa cctctaccgc       240
ctgcctgccg gttcgggagc cgtccgcgcc agcgatttgg aaaaacgccg cacacccgcc       300
gtccaacagc cagccgatgc cgaagtattg aaaagcgtca aggcgtccg cctcgagcgc       360 gacggcagcc aacgctggct tgtcgttgac ggcaaatccc ccgccgaaat ctggccgctt       420
ctgaaagcct tttggcagga aaacggcttc gacatcgaat ccgaagaacc cgccatcgga       480
```

```
caaatggaaa ccgagtgggc ggaaaaccgt gccaaaatcc cccaagacag cttgcgccgc       540
ctattcgaca cagtcggttt gggcggcatc tactccaccg gcgagcgcga caaattcatc       600
gtccgtatcg aacagggcaa aaacggcgtt tccgacatct tcttcgccca caaagcgatg       660
aaagaagtgt atggcgacaa aaacaaagac acgaccatgt ggcagccttc cgcttccgac       720
cccaaccttg aggccgcttt cctgacgcgc tttatgcaat atttgggcgt tgacggacgg       780
caggcggaaa acgcattggc aaaaaaaccg acccttcccg ccgccaacga aatggcgcgt       840
atcgaaggca aaagcctgat tgtctttggc gactacggca gaaactggcg gcgcaccggc       900
cttgccctcg accgcatcgg actgaccgtc gtcggtcaaa acaccgaacg ccacgccttc       960
ctggttcaaa aagccccgaa cgaaagcaat gcagttaccg aacaaaaacc ggggctgttc      1020
aaacgcctac tgggcaaagg caaagcggag aaacctgccg aacagccgga actgattgtc      1080
tatgccgagc ctgtcgccga cggttcgcgc atcgtcctgc tcaacaaaga cggcagcgca      1140
tatgccggca aagacgcatc cgcactgtta ggcaaactcc attccgaact gcgttaa       1197

<210> SEQ ID NO 68
<211> LENGTH: 345
<212> TYPE: DNA
<213> ORGANISM: Neisseria gonorrhoeae

<400> SEQUENCE: 68
atgaaaaaat tattgattgc cgcaatgatg gcggctgcct tggcagcttg ttcgcaagaa        60
gccaaacagg aggttaaaga agcggcccaa gccgttgagt ccgatgttaa agacactgcg       120
gcttctgccg ccgagtctgc cgcttctgcc gtcgaagaag cgaaaggcca agtcaaagat       180
gctgcggctg atgcaaaggc aagtgccgag gaagctgtaa ctgaagccaa agacgcggca       240
gccgaaacca agaagcggt aagcgaagcg gctaaagaca ctttgaacaa agctgccgac       300
gcggctcagg aagcggcaga caaaatgaaa gacgccgcca aataa                        345

<210> SEQ ID NO 69
<211> LENGTH: 273
<212> TYPE: DNA
<213> ORGANISM: Neisseria gonorrhoeae

<400> SEQUENCE: 69
atgaagaaaa ccagcaaata tcttatctat actgcggcat ttacctcatt ctgctttgcc        60
ttccaagaaa accgttctga agccaaacag cccgacatca ctttatccgc atccctgtgc       120
gaacaattca acatgctgaa cgccaaagat atggatacaa aacaagtctc cctttccaaa       180
gaatgcgaca tcatcgagtc ttcacacgac tgggaaaaag agtacggcaa cttgaacgaa       240
caggaaatgc tcgccggcgt cgtctatgaa taa                                     273

<210> SEQ ID NO 70
<211> LENGTH: 327
<212> TYPE: DNA
<213> ORGANISM: Neisseria gonorrhoeae

<400> SEQUENCE: 70
atgaacatca aacaccttct cttgaccgcc gccgcaaccg cactgttggg catttccgcc        60
cccgcactcg cccaccacga cggacacggc gatgacgacc acggacacgc cgcacaccaa       120
cacggcaaac aagacaaaat catcagccgc gcccaagcca aaaaagcggc ttgggcgcgt       180
gtcggcggca aaatcaccga catcgatctc gaacacgacg acggccgtcc gcactatgat       240
```

-continued

```
gtcgaaatcg tcaaaaacgg acaggaatac aaagtcgttg tcgatgcccg taccggccgc      300
gtgatttcct cccgccgcga cgactga                                         327

<210> SEQ ID NO 71
<211> LENGTH: 558
<212> TYPE: DNA
<213> ORGANISM: Neisseria gonorrhoeae

<400> SEQUENCE: 71
atgccgtctg aagcccttca gacggcattt cgcggcaaca tccgaaggag ttttaccatg       60
atccgtttga cccgcgcgtt tgccgccgcc ctgatcggtt tatgctgcac cacaggcgcg      120
cacgccgaca ccttccaaaa aatcggcttt atcaacaccg agcgcatcta cctcgaatcc      180
aagcaggcgc gcaacatcca aaaaacgctg gacggcgaat tttccgcccg tcaggacgaa      240
ttgcaaaaac tgcaacgcga aggcttggat ttggaaaggc agctcgccgg cggcaaactt      300
aaggacgcaa aaaaggcgca agccgaagaa aaatggcgcg ggctggtcga agcgttccgc      360
aaaaaacagg cgcagtttga agaagactac aacctccgcc gcaacgaaga gtttgcctcc      420
ctccagcaaa acgccaaccg cgtcatcgtc aaaatcgcca acaggaagg ttacgatgtc       480 attttgcagg acgtgattta cgtcaacacc caatacgacg ttaccgacag cgtcattaaa      540
gaaatgaacg cccgctga                                                   558

<210> SEQ ID NO 72
<211> LENGTH: 339
<212> TYPE: DNA
<213> ORGANISM: Neisseria gonorrhoeae

<400> SEQUENCE: 72
atgaacaaaa atattgctgc cgcactcgcc ggtgctttat ccctgtctct ggccgccggc       60
gccgttgccg cccacaaacc ggcaagcaac gcaacaggcg ttcaaaaatc cgcccaaggc      120
tcttgcggcg catccaaatc tgccgaaggt tcgtgcggcg catccaaatc tgccgaaggt      180
tcgtgcggcg cggctgcttc taaagcaggc gaaggcaaat gcggcgaggg caaatgcggt      240
gcaactgtaa aaaaagccca caaacacacc aaagcatcta aagccaaagc caaatctgcc      300
gaaggcaaat gcggcgaagg caaatgcggt tctaaataa                            339

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 73

His His His His His His
1               5

<210> SEQ ID NO 74
<211> LENGTH: 21
<212> TYPE: DNA
<213> ORGANISM: Neisseria gonorrhoeae

<400> SEQUENCE: 74
gccgccgagt ctgcggcttc t                                               21
```

NEISSERIA GONORRHOEAE VACCINE COMPOSITIONS AND METHODS OF SELECTING ANTIGENS

CROSS-REFERENCE TO RELATED APPLICATIONS

This application is a 35 U.S.C. § 371 National Phase Entry Application of International Application No. PCT/US2020/044187, filed Jul. 30, 2020, which designates the U.S. and which claims benefit under 35 U.S.C. § 119(e) of U.S. Provisional Application No. 62/881,627, filed Aug. 1, 2019, the contents of each of which are incorporated herein by reference in their entireties.

GOVERNMENT SUPPORT

This invention was made with Government support under Grant Nos. AI107821, AI116969, and AI131004 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 29, 2020, is named 700355-095660WOPT_SL.txt and is 91,331 bytes in size.

TECHNICAL FIELD

The technology described herein relates to vaccine compositions, methods of selecting an antigen or fragment thereof for the preparation of a vaccine composition, and uses thereof.

BACKGROUND

Vaccines are used to stimulate the immune system to generate an effective response to a pathogenic infection. Existing vaccines, however, do not always provide protection from mucosal infections by microorganisms. In particular, there is a lack of vaccines to prevent sexually transmitted infections (STIs) such as gonorrhea, chlamydia, or syphilis, that are major public health concerns worldwide. The discovery of new antigens for vaccine compositions would provide more effective prevention and treatment of pathogenic infections and would greatly reduce the spread of diseases associated with pathogenic microorganisms.

SUMMARY

The methods and vaccine compositions described herein are based, in part, on the discovery that certain polypeptides not previously identified or considered for potential use as antigens from pathogenic microorganisms (e.g., *N. gonorrhoeae*) can provoke an immune response in a subject. The methods of identifying and selecting the antigens described herein rely, in part, on approaches that identify polypeptides (e.g., hypothetical proteins) predicted to be immunogenic.

In one aspect, described herein is a vaccine composition comprising at least one antigen or fragment thereof, or a nucleic acid encoding such antigen or fragment thereof, derived from a pathogenic bacterium wherein the antigen or fragment thereof is expressed by a bacteria during an infection of a host at a level that is increased compared with a reference level.

In another aspect, described herein is a vaccine composition comprising at least one antigen or fragment thereof, or a nucleic acid encoding such antigen or fragment thereof, derived from a pathogenic bacterium wherein the antigen or fragment thereof is expressed by a bacteria during an infection of a host at a level that is decreased compared with a reference level.

In another aspect, described herein is a vaccine composition comprising at least one antigen or fragment thereof, or a nucleic acid encoding such antigen or fragment thereof, derived from a pathogenic bacterium wherein the antigen or fragment thereof has a Reads per Kilobase of transcript per Million (RPKM) level greater than 25.

In one embodiment, the RPKM level is from a host subject identified with the pathogen.

In another aspect, described herein is a vaccine composition comprising at least one antigen or fragment thereof, or a nucleic acid encoding such antigen or fragment thereof, derived from a pathogenic bacterium wherein the antigen or fragment thereof has a Reads per Kilobase of transcript per Million (RPKM) level greater than 50.

In one embodiment of either of these aspects, the RPKM level is from a host subject identified with the pathogen.

In another embodiment, the pathogenic bacterium is a mucosal bacterium.

In another embodiment, the pathogenic bacterium is *Neisseria gonorrhoeae*.

In another embodiment, the antigen is selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947.

In another embodiment, the vaccine composition comprises two or more antigens or nucleic acids encoding such antigens are selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947.

In another embodiment, the vaccine composition comprises at least one antigen or nucleic acids encoding such antigens are selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947, and at least one further antigen, or a nucleic acid encoding at least one further antigen.

In another embodiment, the at least one further antigen is selected from the group consisting of: porin, pilin, TbpA, TbpB, LOS, MetQ, SliC, MtrE, BamA, ACP.

In another embodiment, the antigen is expressed by multiple strains of *Neisseria gonorrhoeae*.

In another embodiment, the bacterium infects a mucous membrane in the host subject.

In another embodiment, the host subject is a mammal.

In another embodiment, the host subject is a human.

In another embodiment, the bacterium infects the host subject's genitals, mouth, eyelids, nose, skin, and/or rectum.

In another embodiment, the vaccine composition further comprises an adjuvant. In another embodiment, the vaccine composition further comprises outer membrane vesicles. In another embodiment, at least a portion of the one or more antigens or fragment thereof or nucleic acid encoding an antigen or fragment thereof is present in or on the outer membrane vesicles. In another embodiment, the adjuvant is alum.

In another embodiment, at least one antigen or fragment thereof is a hypothetical protein.

In another embodiment, at least one antigen or fragment thereof is a lipoprotein.

In another aspect, described herein is a vaccine composition comprising a NGO0416 polypeptide or a fragment thereof or a nucleic acid encoding such antigen or fragment thereof, and an antigen selected from the group consisting of NGO0188, NGO0449, NGO0914, NGO1332, NGO1377, NGO1543, NGO1549, NGO1607, NGO1880, NGO1948, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947 polypeptide or a fragment thereof or a nucleic acid encoding such antigen or fragment thereof.

In another aspect, described herein is a vaccine composition comprising a NGO0690 polypeptide or a fragment thereof or a nucleic acid encoding such antigen or fragment thereof, and an antigen selected from the group consisting of NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0694, NGO0768, NGO0861, NGO0891, NGO0948, NGO1043, NGO1428, NGO1729, NGO1802, and NGO1947 polypeptide or a fragment thereof or a nucleic acid encoding such antigen or fragment thereof.

In another aspect, described herein is a vaccine composition comprising a NGO0948 polypeptide or a fragment thereof or a nucleic acid encoding such antigen or fragment thereof, and an antigen selected from the group consisting of NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO1043, NGO1428, NGO1729, NGO1802, and NGO1947 polypeptide or a fragment thereof or a nucleic acid encoding such antigen or fragment thereof.

In another aspect, described herein is a vaccine composition comprising a NGO1043 polypeptide or a fragment thereof or a nucleic acid encoding such antigen or fragment thereof, and an antigen selected from the group consisting of NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO1428, NGO1729, NGO1802, and NGO1947 polypeptide or a fragment thereof or a nucleic acid encoding such antigen or fragment thereof.

In another aspect, described herein is a vaccine composition comprising NGO1215 polypeptide or a fragment thereof or a nucleic acid encoding such antigen or fragment thereof, and an antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO1043, NGO1428, NGO1729, NGO1802, and NGO1947 polypeptide or a fragment thereof or a nucleic acid encoding such antigen or fragment thereof.

In another aspect, described herein is a vaccine composition comprising a NGO1701 polypeptide or a fragment thereof or a nucleic acid encoding such antigen or fragment thereof, and an antigen selected from the group consisting of NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1868, NGO2119-NGO0227, NGO0354, NGO0588, NGO0648, NGO0678, NGO0690, NGO0694, NGO0768, NGO0861, NGO0891, NGO1043, NGO1428, NGO1729, NGO1802, and NGO1947 polypeptide or a fragment thereof or a nucleic acid encoding such antigen or fragment thereof.

In another aspect, described herein is a vaccine composition, comprising the following antigen polypeptides or a nucleic acids encoding such antigen polypeptides: NGO0416; NGO0690; NGO0948; NGO1043; NGO1215; and NGO1701 or a fragment thereof.

In another aspect, described herein is a vaccine composition comprising a NGO0690 polypeptide or a fragment thereof or a nucleic acid encoding such antigen or fragment thereof, and a NGO1701 polypeptide or a fragment thereof or a nucleic acid encoding such antigen or fragment thereof.

In another aspect, described herein is a vaccine composition comprising a NGO690 polypeptide or a fragment thereof or a nucleic acid encoding such antigen or fragment thereof, a NGO0948 polypeptide or a fragment thereof, and a NGO1701 polypeptide or a fragment thereof or a nucleic acid encoding such antigen or fragment thereof.

In another aspect, described herein is a method of provoking an immune response to a pathogenic bacterium in a subject, the method comprising: administering to a subject a vaccine composition as described herein.

In one embodiment, the subject is a mammal.

In another embodiment, the subject is a human.

In another embodiment, the administering is by injection, oral, or intranasal administration.

In another embodiment, the bacterium is *Neisseria gonorrhoeae*.

In another embodiment, the vaccine composition provokes an immune response that is protective against a plurality of strains of the bacteria.

In another embodiment, the vaccine composition provokes an immune response that is protective against multiple strains of *Neisseria gonorrhoeae*.

In another aspect, described herein is a method of selecting an antigen for the preparation of a vaccine composition, the method comprising:

(a) sequencing RNA from a sample from a subject infected with a bacterium, wherein the sample comprises RNA expressed by the bacterium;

(b) comparing the RNA sequence information obtained in step (a) to RNA sequence information obtained from the bacteria grown in culture, and identifying a candidate set of transcripts with a modulation in the level of expression during an infection when compared with a reference level;

(c) detecting, for an open reading frame of the set of candidate transcripts identified in step (b), one or more of the following properties:

i. a level of Reads per Kilobase of transcript per Million (RPKM) greater than 25;

ii. an immunogenic probability score of at least 0.4;

iii. the cellular localization of an encoded polypeptide is within the cell membrane, periplasm or outer cell membrane;

iv. the encoded polypeptide does not have an amino acid sequence that is conserved between human and other bacterial species;

v. the encoded polypeptide has an amino acid sequence that is conserved across multiple strains of the bacteria; and vi. the encoded polypeptide is a hypothetical protein wherein an encoded polypeptide comprising one or more of the properties is selected as a candidate antigen for a vaccine composition.

In one embodiment, the encoded polypeptide comprises two or more of the properties in step c. is selected as a candidate antigen for a vaccine composition.

In another embodiment, the encoded polypeptide comprises three or more of the properties in step c. is selected as a candidate antigen for a vaccine composition.

In another embodiment, the encoded polypeptide comprises four or more of the properties in step c. is selected as a candidate antigen for a vaccine composition.

In another embodiment, the encoded polypeptide comprising five or more of the properties in step c. is selected as a candidate antigen for a vaccine composition.

In another embodiment, the encoded polypeptide comprises each of the properties in step c. is selected as a candidate antigen for a vaccine composition.

In another embodiment, the method further comprises isolating a biological sample from a subject.

In another embodiment, the biological sample is epidermal tissue, mucosal tissue, mucus, bodily fluid, blood, buffy coat, saliva, or lower genital tract fluid.

In another embodiment, the subject is a mammal.

In another embodiment, the subject is a human.

In another embodiment, the method further comprises synthesizing or transcribing a nucleic acid encoding the candidate antigen.

In another embodiment, the method further comprises cloning the antigen or a fragment thereof into an expression vector.

In another embodiment, the method further comprises expressing and isolating the candidate antigen or fragment thereof.

In another embodiment, the method further comprises formulating the antigen or fragment thereof with a pharmaceutically acceptable carrier, and optionally an adjuvant. In one embodiment, the adjuvant comprises outermembrane vesicles.

In another aspect, described herein is a vaccine composition comprising an antigen or fragment thereof identified or produced by any one of the methods described herein.

In another aspect, described herein is a method of immunizing a subject, the method comprises administering a vaccine composition comprising an antigen or antigen fragment thereof identified or produced by a method described herein.

In another aspect, described herein is a polypeptide comprising an amino acid sequence of an antigen or antigen fragment thereof selected by any one of the methods described herein.

In one embodiment, the amino acid sequence is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, and SEQ ID NO: 36.

In another aspect, described herein is a vector comprising a nucleic acid encoding an antigen or antigen fragment thereof selected by any one of the methods described herein.

In one embodiment, the nucleic acid sequence is selected from the group consisting of: SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and SEQ ID NO: 72.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of immunization and immune response. A subject can be male or female.

A subject can be one who has been previously diagnosed with or identified as suffering from or having a condition (e.g., has been diagnosed with an infection) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition (e.g., an infection).

As used herein, a "host subject" is a subject that has been infected with a pathogen, microorganism, or bacteria. The host subject can be symptomatic or asymptomatic. The host subject can also be a carrier for the microorganism. In some embodiments of any of the aspects, the host subject is a mammal. In some embodiments of any of the aspects, the host subject is a human.

As used herein, an "immune response" refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus (e.g., to a vaccine composition, antigen or fragment thereof). In some embodiments of the aspects described herein, the response is specific for at least one particular antigen (e.g., an antigen of *Neisseria gonorrhoeae*), and refers to a response by a CD4 T cell, CD8 T cell, or B cell via their antigen-specific receptor. Such responses by these cells can include, for example, cytotoxicity, proliferation, antibody, cytokine, or chemokine production, trafficking, or phagocytosis, and can be dependent on the nature of the immune cell undergoing the response.

As used herein, the term "provoking an immune response" refers to stimulation of an immune response, an induction, or increase in the immune response to a pathogenic microorganism. The term "provoking an immune response" as used herein can mean any one or more of the following: (i) the prevention of infection or re-infection, as in a traditional vaccine, (ii) the reduction in the severity of, or, in the elimination of symptoms, and (iii) the substantial or complete elimination of the pathogenic microorganism or disorder in question. Hence, provoking an immune response may be effected prophylactically (prior to infection) or therapeutically (following infection). In the present methods described herein, prophylactic treatment is the preferred mode. According to a particular embodiment, the vaccine compositions and methods described herein treat, including prophylactically and/or therapeutically immunize, a host animal against a microbial infection (e.g., a bacterium). The methods of the present technology are useful for conferring prophylactic and/or therapeutic immunity to a subject. The methods described herein can also be practiced on subjects for biomedical research applications.

As used herein, the terms "infection" or "infection of a host" or "infectious disease" or "microbial infection" refers to the growth, proliferation, spread, and/or presence of a microorganism in a subject. In some cases, the infection can elicit an immune response by the host that leads to symptoms associated with a disease. The infection can be transmitted from one subject to another by contact, contact with aerosolized liquid droplets (coughing, sneezing, etc.), contaminated needles, contaminated bodily fluids, or via sexual transmission. The infection can be characterized by at least one symptom of a disease, such as pain, increased mucosal secretions, bleeding, coughing, headaches, abnormalities of the skin, fever, sore throat, swollen lymph nodes, hair loss, muscle aches, sores, or any other symptom associated with an infection. Exemplary infections or infectious diseases include but are not limited to gonorrhea, syphilis, chlamydia, acquired immune deficiency syndrome (AIDS), hepatitis, candidiasis, human papillomavirus (HPV) infection, trichomoniasis, herpes, tuberculosis, streptococcal infections (e.g., strep throat), *E. coli* infection, influenza, pneumonia, ear infections, the common cold, chicken pox, cat scratch disease, rabies, adenovirus, bronchiolitis, croup, encephalitis, fifth disease, hand foot and mouth disease, impetigo, botulism, *listeria* infection, MRSA infection, measles, meningitis, mumps, polio, pinkeye, Rocky Mountain Spotted Fever, *Salmonella* infections, *Shingella* infections, shingles, sinusitis, staph infections, tetanus, tonsillitis, toxic shock syndrome, urinary tract infections, warts, whooping cough, Zika virus infections, or any other infection caused by a microorganism known in the art.

The term "vaccine composition" used herein is defined as a composition used to provoke or stimulate an immune response against an antigen or fragment thereof within the composition in order to protect or treat an organism against disease. In some embodiments of any of the aspects, the vaccine composition is a suspension of attenuated or killed microorganisms (e.g., bacteria, viruses, or fungi) or of antigenic proteins or nucleic acids derived from them, administered for prevention, amelioration, or treatment of infectious diseases. The terms "vaccine composition" and "vaccine" are used interchangeably.

As used herein, a "pathogenic bacteria" or "pathogenic bacterium" is a bacterial microorganism that causes an infectious disease or an infection. Exemplary bacteria include but are not limited to *Neisseria gonorrhoeae, Neisseria meningitides, Treponema pallidum, Ureaplasma urealyticum, Trichomona vaginalis, Bartonella henselae, Escherichia coli, Pseudomonas aeruginosa, Helicobacter pyloris, Borelia burgdorferi, Legionella pneumophilia, Mycobacteria* sps (such as. *M, genitalium, M. hominis, M tuberculosis, M. avium, M intracellulare, M. kansaii, M. gordonae), Staphylococcus aureus, Neisseria meningitidis, Listeria monocytogenes, Streptococcus pyogenes* (Group A *Streptococcus), Streptococcus agalactiae* (Group B *Streptococcus), Streptococcus (viridans* group), *Streptococcus faecalis, Streptococcus epidermidis, Streptococcus (anaerobic* sps.), *Streptococcus pneumoniae,* pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Brucella abortus, Pasteurella multocida, Bacteroides* sp., *Fusobacterium nucleatum, Streptobacillus moniliformis, Treponema pertenue, Leptospira, Nocadia brasiliensis, Borrelia hermsii, Borrelia burgdorferi,* and *Actinomyces israelli.*

As used herein, the term "antigen" refers to a molecule that is derived from a pathogenic microorganism (e.g., a bacterium, virus, or parasite). Typically, antigens are bound by the host subject's antibody ligands and are capable of raising or causing an antibody immune response in vivo by the host subject. An antigen can be a polypeptide, protein, nucleic acid or other molecule. The term "antigenic determinant" refers to an epitope on the antigen recognized by an antigen-binding molecule (e.g., an antibody, antibody reagent, or a polypeptide fragment thereof), and more particularly, by the antigen-binding site of said molecule.

As used herein, the term "antigen fragment" refers to one or more portions of an antigen that retain the ability to provoke an immune response. The fragment can be a nucleic acid encoding a portion of the antigen or a polypeptide.

As used herein, the terms "protein" and "polypeptide" and "encoded polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, a polypeptide or nucleic acid as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are also typically still referred to as "engineered" even though the actual manipulation was performed on a prior entity.

As used herein, the term "derived from" refers to the aspect of a molecule, substance. polypeptide, nucleic acid, sugar, lipid, etc. as being from a parent substance (e.g., a cell or membrane) or organism (e.g., a microorganism). In the context of antigens and fragments thereof, the term "derived from" encompasses an antigen or fragment thereof that is expressed by, purified, or isolated from a microorganism as described herein. By way of example only, the antigen, NGO1701 is derived from *Neisseria gonorrhoeae*.

As used herein, the term "pharmaceutical composition" refers to the antigen or fragment thereof as described herein in combination with a pharmaceutically acceptable carrier e.g. a carrier commonly used in the pharmaceutical industry. The phrase "pharmaceutically acceptable" is employed herein to refer to those antigens, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a vaccine composition, antigen, or antigen fragment thereof as described herein into a subject by a method or route which results in at least partial delivery of the vaccine composition at a desired site. Pharmaceutical and vaccine compositions comprising the antigens or fragments of antigens described herein can be administered by any appropriate route which results in an effective treatment in the subject.

As used herein, the term "multiple" refers to a number of at least two, more than two, or greater than two. In the context of strains of bacteria, multiple refers to two or more strains known in the art for that given bacteria.

The terms "decreased", "reduced", "reduction", or "inhibit" are all used herein to mean a decrease by a statistically significant amount. In some embodiments of any of the aspects, "reduce," "reduction" or "decreased" or "inhibit" typically means a decrease by at least 10% as compared to a reference level (e.g. the absence of a given treatment or vaccine composition) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statistically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a "reference" level. In the context of a marker or symptom, a "increase" is a statistically significant increase in such level.

As used herein, the term "modulates" or "modulation" refers to an effect including increasing or decreasing a given parameter as those terms are defined herein.

As used herein a "reference level" refers to a level of a given parameter measured or detected in a normal, otherwise unaffected, or untreated population of microorganisms (e.g., bacteria cultured in vitro, bacteria from a healthy subject, or bacteria obtained from a subject at a prior time point) or in a subject (e.g., a subject that does not have an infection). One of skill in the art would be able to choose the appropriate reference level for the desired experiment or test. For example, the microorganisms (e.g., bacteria) cultured in vitro can be cultured in chemically defined medium with or without iron supplementation.

Generally, a reference level refers to the level of an antigen or fragment thereof, or a nucleic acid encoding an antigen or fragment thereof expressed by a microorganism (e.g., bacteria) which is not present in a subject (i.e., a microorganism which is not in vivo), not genetically modified, and is grown in culture in vitro. For example, the microorganism (e.g., bacteria) can be commercially available bacteria or bacteria that were not cultured directly from a host subject or a strain originally obtained from a host subject but which is cultured in vitro at the time the reference level was determined The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempl gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), *The Encyclopedia of Molecular Cell Biology and Molecular Medicine*, published by Blackwell Science Ltd., 1999-2012 (ISBN 9783527600908); and Robert A. Meyers (ed.), *Molecular Biology and Biotechnology: a Comprehensive Desk Reference*, published by VCH Publishers, Inc., 1995 (ISBN 1-56081-569-8); *Immunology* by Werner Luttmann, published by Elsevier, 2006; *Janeway's Immunobiology*, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, *Molecular Cloning: A Laboratory Manual*, 4th ed., Cold Spring Harbor Laboratory Press, Cold Spring Harbor, N.Y., USA (2012) (ISBN 1936113414); Davis et al., *Basic Methods in Molecular Biology*, Elsevier Science Publishing, Inc., New York, USA (2012) (ISBN 044460149X); *Laboratory Methods in Enzymology: DNA*, Jon Lorsch (ed.) Elsevier, 2013 (ISBN 0124199542); *Current Protocols in Molecular Biology* (*CPMB*), Frederick M. Ausubel (ed.), John Wiley and Sons, 2014 (ISBN 047150338X, 9780471503385), *Current Protocols in Protein Science* (*CPPS*), John E. Coligan (ed.), John Wiley and Sons, Inc., 2005; and *Current Protocols in Immunology* (*CPI*) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the vaccine compositions and methods described herein.

BRIEF DESCRIPTION OF THE DRAWINGS

FIG. 3A demonstrate hypothetical protein position in the gonococcal gene expression network. FIG. 3B demonstrate the degree (y-axis) and betweenness (x-axis) values of gonococcal genes in the network. The position of NGO0690 and NGO0948 are indicated.

FIG. 4B) NGO0690; FIG. 4C) NGO0948; FIG. 4D) NGO1043; FIG. 4E) NGO1215 and FIG. 4F) NGO1701 with alum as adjuvant. Preimmune (Pr) and immune sera (wk2, wk4 and wk6) are shown. * p significant (0.001-0.05) by one-way ANOVA with Tukey's multiple comparisons test.

FIG. 5A shows the immunoblot of FF *N. gonorrhoeae* strains F62, FA1090, U08401 and U08402 (2-4×108 total organisms/slot) incubated with pooled mouse immune sera (wk6) to each of 6 hypothetical proteins (1:200 dilution). FIG. 5B shows an SDS-PAGE gel and Coomassie staining of bacteria as in FIG. 5A.

FIG. 6B) NGO0690; FIG. 6C) NGO0948; FIG. 6D) NGO1043; FIG. 6E) NGO1215 and FIG. 6F) NGO1701 tested against FF *N. gonorrhoeae* strains F62 (black bars), FA1090 (gray bars), U08401 (striped bars) and U08402 (dotted bars). Preimmune sera (white bars) and pooled immune sera (wk6) (1:100). *,**** p significant by one-way ANOVA with Tukey's multiple comparisons test.

FIG. 7A shows an immunoblot of OMPs from *N. gonorrhoeae* F62 and FA1090 strains (5 µg of total protein content) were spotted on nitrocellulose and incubated with pooled mouse immune sera (wk6) to each of 6 hypothetical proteins and to porin as a control (1:200 dilution). FIG. 7B shows formalin fixed (FF) *N. gonorrhoeae* strains F62, FA1090, U08401 and U08402 incubated with immune mouse sera to NGO0690, to NGO0948 and to NGO1701 and pre-immune sera (1:200). Antibody surface binding was detected by flow cytometry with a FITC-labeled secondary anti-mouse IgG antibody. Unstained bacteria controls (dark gray histograms); FITC-labeled anti-mouse secondary antibody controls (light gray histograms). Fluorescence peak shift to the right indicates antibody binding. Histograms are representative of triplicate experiments.

FIG. 8C) incubation with anti-NGO0690+anti-NGO1701 sera. 10% NHS control: gray bars. Adjuvant control sera: white bars. Immune sera: black bars. *, , *, **** p significant by one-way ANOVA with uncorrected Fisher's LSD test.

FIG. 9 shows Table 2: CASS summary of the 6 gonococcal hypothetical protein candidates.

FIG. 12A: anti-NGO0690/NGO1701 mouse sera (checkered bars); FIG. 12B: anti-NGO0948 (gray bars) and FIG. 12C: anti-NGO0690/NGO1701/NGO0948 (thick striped bars) at the indicated dilutions. *,  ** p significant by one-way ANOVA with Dunnett's multiple comparison test vs adjuvant control.

DETAILED DESCRIPTION

Figure 1:
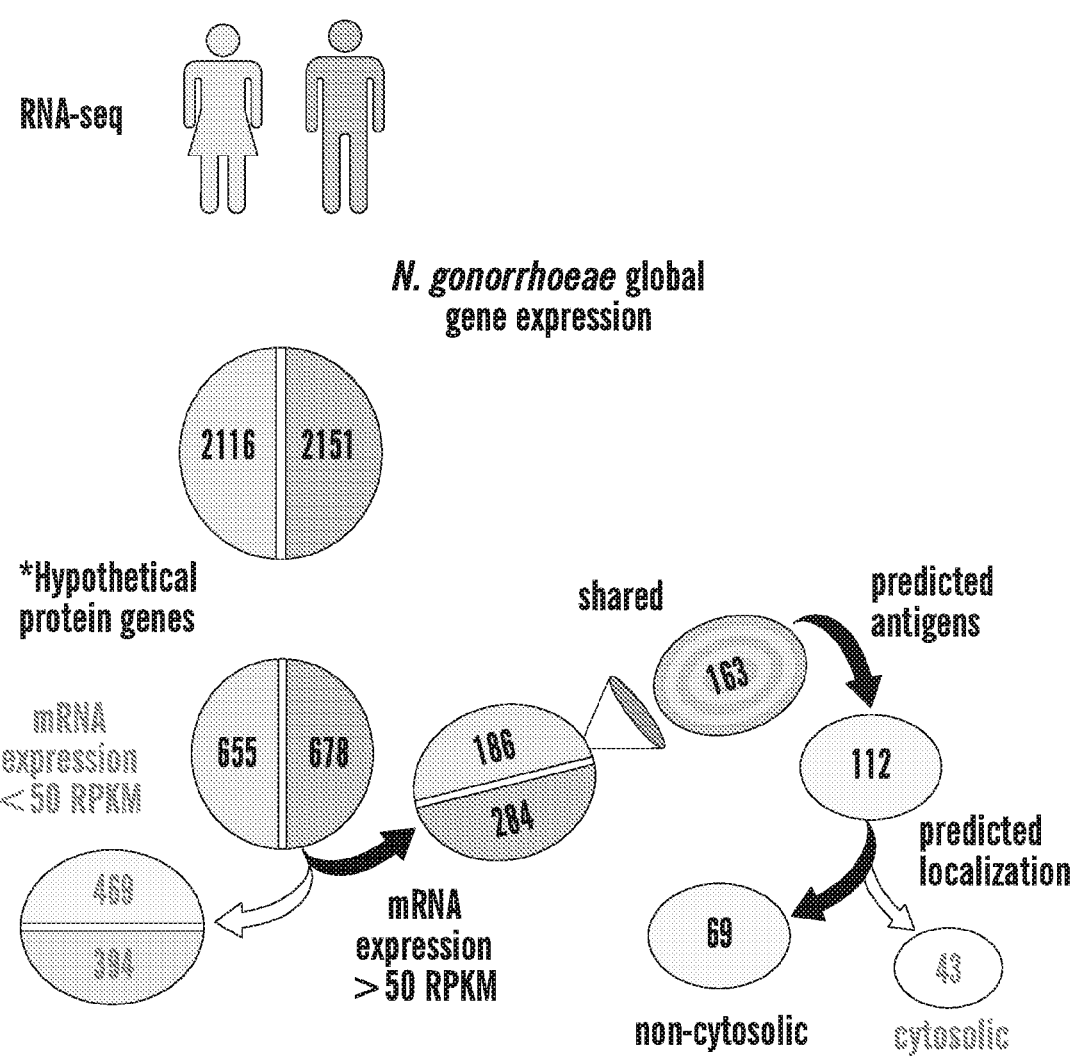
FIG. 1 shows candidate antigen selection strategy (CASS): Discovery Phase 1 (DP-1). Gonococcal genes expressed during natural mucosal infection in female and male subjects encode for 163 hypothetical proteins* with mRNA expression above 50 RPKM (Reads per Kilobase of transcript per Million mapped reads) in both datasets. In silico analysis of the 163 candidates with VaxiJen predicted 112 proteins to be antigenic; cell localization analysis with Psort, Protein Predict, Gneg-mPLoc predicted 43 proteins to be cytosolic and 69 to be non-cytosolic. * Rockhopper analysis

Infectious microorganisms are one of the world's leading causes of mortality and vaccines have emerged as promising biomedical interventions to reduce this burden. Vaccines also prevent the exacerbation of the spread of infections from one host to another. However, vaccines developed using traditional antigen selection principles has largely failed for certain microorganisms, e.g., *Neisseria gonorrhoeae*. Attempts to use antigens that traditional vaccine development would suggest, such as capsular polysaccharide antigens or other surface proteins have not yielded effective vaccines. As described herein, this appears to be due in part to the fact that the mechanisms of protective immunity in these infections is not completely understood and the available models do not accurately reproduce the interplay of microorganism and host immune system. Described herein is the selection of antigens that are actually immune protective, by identifying proteins whose expression is differentially regulated during the relevant host infection or which are highly expressed (e.g., during the relevant host infection). In particular, proteins currently classed as hypothetical have proved to be an excellent source of immune protective antigens.

It is demonstrated herein that these novel antigens from pathogenic microorganisms (e.g., *N. gonorrhoeae*) can provoke an immune response in a subject. The methods of identifying and selecting the antigens described herein rely, in part approaches that identify polypeptides (e.g., hypothetical proteins) predicted to be immunogenic and membrane-associated, conserved across multiple strains of the microorganism.

*Neisseria gonorrhoeae* is the causative agent of the sexually transmitted infection (STI) gonorrhea, a disease with high morbidity worldwide with an estimated 87 million cases annually *N. gonorrhoeae* infection in women can lead to reproductive tract complications (pelvic inflammatory disease (PID)), ectopic pregnancy, infertility, and disseminated gonococcal infections (DGI)). Current therapeutic and pharmacologic approaches against gonorrhea have been compromised by a worldwide increased in antibiotic resistance, including to the last FDA-approved antibiotic, cefixime. Drug-resistant *N. gonorrhoeae* is now listed by the Center for Disease Control (CDC) in the urgent threat category. There is a pressing need for an effective vaccine against *N. gonorrhoeae*. Development of such vaccines has been delayed primarily by a scarcity of successful antigens, inadequate animal models to mimic *N. gonorrhoeae* infection and a lack of correlates of immunity.

Infections by a microorganism as described herein have been found to have environmentally-dictated gene expression in the host subject. Accordingly, the methods and vaccine compositions described herein relate, in part, to the discovery of new antigens expressed by *Neisseria gonorrhoeae*.

In one aspect of any of the embodiments, described herein is a method of selecting an antigen based on in vivo gene expression or mRNA transcript expression greater than 25 Reads per Kilobase of transcript per Million.

In one aspect, described herein is a vaccine composition comprising at least one antigen or fragment thereof, or a nucleic acid encoding such antigen or fragment thereof, derived from, expressed by, or encoded by a microorganism (e.g., a pathogenic bacterium) wherein the antigen or fragment thereof is expressed by a microorganism (e.g. a bacterium) during an infection of a host at a level that is increased compared with a reference level.

In another aspect, described herein is a vaccine composition comprising at least one antigen or fragment thereof, or a nucleic acid encoding such antigen or fragment thereof, derived from, expressed by, or encoded by a microorganism (e.g., a pathogenic bacterium) wherein the antigen or fragment thereof is expressed by a microorganism (e.g., a bacterium) during an infection of a host at a level that is decreased compared with a reference level.

In another aspect, described herein is a vaccine composition comprising at least one antigen or fragment thereof, or a nucleic acid encoding such antigen or fragment thereof, derived from, expressed by, or encoded by a microorganism (e.g., a pathogenic bacterium) wherein the antigen or fragment thereof has a Reads per Kilobase of transcript per Million (RPKM) of 25 or greater. In some embodiments of any of the aspects, the RPKM is 25 or greater, 30 or greater, 35 or greater, 40 or greater, 45 or greater, or 50 or greater. In some embodiments of any of the aspects, the RPKM is 50 or greater. In some embodiments of any of the aspects, the RPKM is the RPKM during infection of a host.

In some embodiments of any of the aspects, the at least one antigen or fragment thereof, or a nucleic acid encoding such antigen or fragment thereof, derived from, expressed by, or encoded by a microorganism (e.g., a pathogenic bacterium) wherein the antigen or fragment thereof has a Reads per Kilobase of transcript per Million (RPKM) of 25 or greater and the antigen or fragment thereof is expressed by a microorganism (e.g. a bacterium) during an infection of a host at a level that is modulated compared with a reference level.

The pathogenic microorganism that expresses an antigen during an infection of a host, can be collected by isolating or removing a biological sample from a host. Preferable the biological sample is removed from the site of infection. The biological sample can be taken from any area on the host (e.g., genitals, throat, or any other mucosal area). By way of example only, a swab of the affected area can be collected.

Following collection of the biological sample, the expression level of the antigens can be measured and compared with a reference level. Any method for measuring expression of a nucleic acid or polypeptide known in the art can be used. Non-limiting examples of assays that can be used to measure nucleic acid or polypeptide expression include DNA and RNA sequencing, next-generation sequencing, RT-PCR, microarrays, proteomics, fluorescent assays, transcriptomics, gene chip assays, whole-genome sequencing, methylation specific oligonucleotide arrays, and microfluidic assays.

The level of nucleic acid or polypeptide expression by a microorganism isolated from an infected host subject can exhibit an increase in the expression level of the nucleic acid or polypeptide by at least 10% or more, e.g. by 10% or more, 50% or more, 100% or more, 200% or more, 500% or more, or 1000% or more when compared with a reference level.

Similarly, the level of nucleic acid or polypeptide expression by a microorganism isolated from an infected host subject can exhibit a decrease in the expression level and/or activity of the nucleic acid or polypeptide by at least 10% or more, e.g. by 10% or more, 50% or more, 100% or more, 200% or more, 500% or more, or 1000% or more when compared with a reference level.

In the context of RNA sequencing, the level of Reads per Kilobase of transcript per Million (RPKM) can be used to determine the expression level of a nucleic acid from a microorganism isolated during the infection of a host.

It is known in the art that the level of iron in the host microenvironment may be depleted and alter the expression level of various antigens when the microorganism is infecting a host subject. It is contemplated herein that other changes in the host microenvironment can modulate gene expression of the microorganism during an infection (e.g., pH, immune cell secretions, osmolality, temperature, oxygen availability, anaerobic condition, the presence of other microorganisms, etc.).

The reference level described herein can be from a microorganism that is cultured in vitro. The culture conditions for a microorganism in vitro can be culture conditions that permit proliferation and/or growth of that microorganism known in the art.

For example, the microorganism cultured in vitro can be cultured in nutrient broth including but not limited to gonococcal (GC) broth, or cultured in chemically defined media (CDM). The microorganism cultured in vitro can further be cultured with iron supplementation to the media. The culture medium can be supplemented with any molecule, agent, or compound known in the art that permits proliferation and/or growth of the microorganism in vitro. Microorganisms can also be cultured with cells from a mammalian subject. For example, the microorganism can be cultured with blood cells, immune cells (e.g., polymorphonuclear neutrophils), or epithelial cells from a human subject.

Preferably, the microorganism cultured in vitro is substantially the same microorganism that expresses an antigen during an infection of a host as described herein for the comparison of the in vitro and in vivo environments that affect the expression of a given antigen.

Pathogenic microorganisms can express a number of antigens, including but not limited to antigens that relate to their ability to infect a host subject and proliferate. The antigens described herein can be used, for example, to detect the organism's presence in a host subject, produce antibodies to the antigens, or to generate new therapeutics for infection.

In some embodiments of any of the aspects, the antigen or fragment thereof is derived from a pathogenic bacterium. In some embodiments of any of the aspects, the antigen or fragment thereof is derived from a bacterium that infects a mucous membrane in the host subject. In some embodiments of any of the aspects, the antigen or fragment thereof is derived from *Neisseria gonorrhoeae*.

In some embodiments of any of the aspects, the antigen or fragment thereof is a polypeptide expressed by a pathogenic bacterium. In some embodiments of any of the aspects, the antigen or fragment thereof is a polypeptide expressed by a bacterium that infects a mucous membrane in the host subject. In some embodiments of any of the aspects, the antigen or fragment thereof is a polypeptide expressed by *Neisseria gonorrhoeae*. In some embodiments of any of the aspects, the antigen is a polypeptide expressed by multiple strains of *Neisseria gonorrhoeae*.

In some embodiments of any of the aspects, the antigen or fragment thereof is encoded by a nucleic acid in the genome of a pathogenic bacterium. In some embodiments of any of the aspects, the antigen or fragment thereof is encoded by a nucleic acid in the genome of a bacterium that infects a mucous membrane in the host subject. In some embodiments of any of the aspects, the antigen or fragment thereof is encoded by a nucleic acid in the genome of *Neisseria gonorrhoeae*.

The antigens (or fragments thereof, or nucleic acids encoding the foregoing) can be antigens expressed by or encoded by multiple strains of a bacteria, e.g, *N. gonorrhoeae*. In some embodiments of any of the aspects, the antigens (or fragments thereof, or nucleic acids encoding the foregoing) can be antigens expressed by or encoded by at least 10%, at least 20%, at least 30%, at least 40%, at least 50%, at least 60%, at least 70%, at least 80%, at least 90%, at least 95%, or a greater percentage of all known strains of a bacteria, e.g, *N. gonorrhoeae*. In some embodiments of any of the aspects, the antigens (or fragments thereof, or nucleic acids encoding the foregoing) can be antigens expressed by or encoded by at least 10%, at least 20%, at least 30%, at least 40%, at least 50%, at least 60%, at least 70%, at least 80%, at least 90%, at least 95%, or a greater percentage of all known pathogenic strains of a bacteria, e.g, *N. gonorrhoeae*.

In some embodiments of any of the aspects, the antigens (or fragments thereof, or nucleic acids encoding the foregoing) can be antigens expressed by or encoded by at least 10%, at least 20%, at least 30%, at least 40%, at least 50%, at least 60%, at least 70%, at least 80%, at least 90%, at least 95%, or a greater percentage of all strains of a bacteria which are known to have been present in cases of the disease in the last year. In some embodiments of any of the aspects, the antigens (or fragments thereof, or nucleic acids encoding the foregoing) can be antigens expressed by or encoded by at least 10%, at least 20%, at least 30%, at least 40%, at least 50%, at least 60%, at least 70%, at least 80%, at least 90%, at least 95%, or a greater percentage of all strains of a bacteria which are known to have been present in cases of the disease in the last decade. In some embodiments of any of the aspects, the antigens (or fragments thereof, or nucleic acids encoding the foregoing) can be antigens expressed by or encoded by at least 10%, at least 20%, at least 30%, at least 40%, at least 50%, at least 60%, at least 70%, at least 80%, at least 90%, at least 95%, or a greater percentage of all strains of a bacteria which are known to have been present in cases of the disease in 2018. In some embodiments of any of the aspects, the antigens (or fragments thereof, or nucleic acids encoding the foregoing) can be antigens expressed by or encoded by at least 10%, at least 20%, at least 30%, at least 40%, at least 50%, at least 60%, at least 70%, at least 80%, at least 90%, at least 95%, or a greater percentage of all strains of a bacteria which are known to have been present in cases of the disease from 2009-2018.

In some embodiments of any of the aspects, the antigens (or fragments thereof, or nucleic acids encoding the foregoing) can be antigens expressed by or encoded by at least 10%, at least 20%, at least 30%, at least 40%, at least 50%, at least 60%, at least 70%, at least 80%, at least 90%, at least 95%, or a greater percentage of the 4198 gonococcal gnomes available in the PubMLST database as of April 2019. In some embodiments of any of the aspects, the antigens (or fragments thereof, or nucleic acids encoding the foregoing) can be antigens expressed by or encoded by at least 10%, at least 20%, at least 30%, at least 40%, at least 50%, at least 60%, at least 70%, at least 80%, at least 90%, at least 95%, or a greater percentage of the 4198 gonococcal gnomes available in the PubMLST database as of April 2019 and absent from the 288 *N. lactamica* genomes available in the PubMSLT database as of April 2019.

In some embodiments of any of the aspects, the antigens (or fragments thereof, or nucleic acids encoding the foregoing) can be antigens expressed by or encoded in a global manner. As used herein, "global manner" means that the antigen is expressed or encoded in at least one clinical isolate from each of Africa, Europe, Asia, South America, and North America. In some embodiments of any of the aspects, the antigens (or fragments thereof, or nucleic acids encoding the foregoing) can be antigens expressed by or encoded in a global manner within the last year. In some embodiments of any of the aspects, the antigens (or fragments thereof, or nucleic acids encoding the foregoing) can be antigens expressed by or encoded in a global manner within the last decade. In some embodiments of any of the aspects, the antigens (or fragments thereof, or nucleic acids encoding the foregoing) can be antigens expressed by or encoded in a global manner during 2018. In some embodiments of any of the aspects, the antigens (or fragments thereof, or nucleic acids encoding the foregoing) can be antigens expressed by or encoded in a global manner from 2009-2018.

In some embodiments of any of the aspects, the antigens (or fragments thereof, or nucleic acids encoding the foregoing) can be antigens expressed by or encoded in a multi-hemispherical manner. As used herein, "multi-hemispherical manner" means that the antigen is expressed or encoded in at least one clinical isolate from at least two hemispheres. In some embodiments of any of the aspects, the antigens (or fragments thereof, or nucleic acids encoding the foregoing) can be antigens expressed by or encoded in a multi-hemispherical manner within the last year. In some embodiments of any of the aspects, the antigens (or fragments thereof, or nucleic acids encoding the foregoing) can be antigens expressed by or encoded in a multi-hemispherical manner within the last decade. In some embodiments of any of the aspects, the antigens (or fragments thereof, or nucleic acids encoding the foregoing) can be antigens expressed by or encoded in a multi-hemispheric manner during 2018. In some embodiments of any of the aspects, the antigens (or fragments thereof, or nucleic acids encoding the foregoing) can be antigens expressed by or encoded in a multi-hemispherical manner from 2009-2018.

Where an antigen is said to be expressed by or encoded in a genome, naturally-occurring alleles are encompassed. Naturally-occurring alleles can be alleles with at least 60%, at least 65%, at least 70%, at least 75%, at least 80%, at least 90%, at least 95%, or greater sequence similarity or identity over the entire length of the antigen sequence. Sequences with less than 60% sequence similar or identity are not considered to be alleles represented in the naturally occurring *N. gonorrhoeae* strains, and would not be basis for a determination that an antigen is expressed by or encoded in a given genome.

The antigens and fragments thereof can provoke an immune response in a subject. The antigen or fragment thereof described herein comprises an epitope that is recognized by the immune system. The term "epitope" is a region or portion of an antigen that is bound by a binding protein, and includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope can be determined by obtaining an X-ray crystal structure of an antibody: antigen complex and determining which residues on the antigen are within a specified distance of residues on the antibody of interest, wherein the specified distance is, 5 Å or less, e.g., 5 Å, 4 Å, 3 Å, 2 Å, 1A or any distance in between. In some embodiments, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

In some embodiments of any of the aspects, at least one antigen or fragment thereof is a lipoprotein. As used herein, a "lipoprotein" refers to any group of soluble proteins that combine with and/or transport lipids. In the context of bacterial lipoproteins, the lipoprotein can be a component of the bacterial cell wall or a surface antigen.

In some embodiments of any of the aspects, the at least one antigen or fragment thereof is a hypothetical protein. As used herein, the term "hypothetical protein" refers to a protein or polypeptide that has been predicted to be encoded by a nucleic acid as determined by nucleic acid sequencing and bioinformatics analysis but for which there is a lack experimental evidence of its translation or functional activity. With regard to *Neisseria gonorrhoeae*, mRNA transcription for numerous gonococcal hypothetical proteins with variable levels have been predicted. A full list of *Neisseria gonorrhoeae* sequences can be found, for example, on the world wide web at pubmlst.org/*neisseria*. In some embodiments of any of the aspects, a hypothetical protein is a protein for which there is no experimental evidence of the translation or function of the predicted polypeptide as of the filing date of this application. In some embodiments of any of the aspects, a hypothetical protein is a *N. gonorrhoeae* protein for which there is no experimental evidence of the translation or function of the predicted polypeptide as of the filing date of this application. In some embodiments of any of the aspects, a hypothetical protein is a *N. gonorrhoeae* protein for which there is no experimental evidence of the translation or function of the predicted polypeptide as of Apr. 1, 2019.

The hypothetical proteins described herein, can exhibit any one or more of the following properties: (i) a level of Reads per Kilobase of transcript per Million (RPKM) greater than 25; (ii) an immunogenic probability of at least 0.4; (iii) the cellular localization of the encoded polypeptide is within the cell membrane, periplasm or outer cell membrane; (iv) the encoded polypeptide does not have an amino acid sequence that is conserved between human and bacterial amino acid sequences of other species of bacteria; and (v) the encoded polypeptide has an amino acid sequence that is conserved across multiple strains of the bacteria; and (vi) the hypothetical protein has less than 4 transmembrane domains.

Examples of such *N. gonorrhoeae* hypothetical proteins are provided herein below and at PubMLST available on the world wide web at <pubMLST.org/*Neisseria*> and the Gene Expression Omnibus available on the world wide web at <ncbi.nlm.nih.gov/geo>.

Exemplary hypothetical proteins and antigens for *Neisseria gonorrhoeae* and corresponding amino acid and nucleotide sequence identification numbers (SEQ ID NOs) are shown in the table below.

TABLE 1: *Neisseria gonorrhoeae* antigens

TABLE 1

| *Neisseria gonorrhoeae* antigens | | |
| --- | --- | --- |
| Hypothetical protein name | Amino Acid Sequence (SEQ ID NO:) | Nucleic Acid Sequence (SEQ ID NO:) |
| NGO0188 | SEQ ID NO: 1 | SEQ ID NO: 37 |
| NGO0449 | SEQ ID NO: 2 | SEQ ID NO: 38 |
| NGO0914 | SEQ ID NO: 3 | SEQ ID NO: 39 |
| NGO1332 | SEQ ID NO: 4 | SEQ ID NO: 40 |
| NGO1377 | SEQ ID NO: 5 | SEQ ID NO: 41 |
| NGO1543 | SEQ ID NO: 6 | SEQ ID NO: 42 |
| NGO1549 | SEQ ID NO: 7 | SEQ ID NO: 43 |

TABLE 1-continued

| Neisseria gonorrhoeae antigens | | |
| --- | --- | --- |
| Hypothetical protein name | Amino Acid Sequence (SEQ ID NO:) | Nucleic Acid Sequence (SEQ ID NO:) |
| NGO1607 | SEQ ID NO: 8 | SEQ ID NO: 44 |
| NGO1880 | SEQ ID NO: 9 | SEQ ID NO: 45 |
| NGO1948 | SEQ ID NO: 10 | SEQ ID NO: 46 |
| NGO2057 | SEQ ID NO: 11 | SEQ ID NO: 47 |
| NGO0416 | SEQ ID NO: 12 | SEQ ID NO: 48 |
| NGO0571 | SEQ ID NO: 13 | SEQ ID NO: 49 |
| NGO0757 | SEQ ID NO: 14 | SEQ ID NO: 50 |
| NGO1215 | SEQ ID NO: 15 | SEQ ID NO: 51 |
| NGO1251 | SEQ ID NO: 16 | SEQ ID NO: 52 |
| NGO1438 | SEQ ID NO: 17 | SEQ ID NO: 53 |
| NGO1701 | SEQ ID NO: 18 | SEQ ID NO: 54 |
| NGO1868 | SEQ ID NO: 19 | SEQ ID NO: 55 |
| NGO2119 | SEQ ID NO: 20 | SEQ ID NO: 56 |
| NGO0227 | SEQ ID NO: 21 | SEQ ID NO: 57 |
| NGO0354 | SEQ ID NO: 22 | SEQ ID NO: 58 |
| NGO0588 | SEQ ID NO: 23 | SEQ ID NO: 59 |
| NGO0648 | SEQ ID NO: 24 | SEQ ID NO: 60 |
| NGO0678 | SEQ ID NO: 25 | SEQ ID NO: 61 |
| NGO0690 | SEQ ID NO: 26 | SEQ ID NO: 62 |
| NGO0694 | SEQ ID NO: 27 | SEQ ID NO: 63 |
| NGO0768 | SEQ ID NO: 28 | SEQ ID NO: 64 |
| NGO0861 | SEQ ID NO: 29 | SEQ ID NO: 65 |
| NGO0891 | SEQ ID NO: 30 | SEQ ID NO: 66 |
| NGO0948 | SEQ ID NO: 31 | SEQ ID NO: 67 |
| NGO1043 | SEQ ID NO: 32 | SEQ ID NO: 68 |
| NGO1428 | SEQ ID NO: 33 | SEQ ID NO: 69 |
| NGO1729 | SEQ ID NO: 34 | SEQ ID NO: 70 |
| NGO1802 | SEQ ID NO: 35 | SEQ ID NO: 71 |

TABLE 1-continued

| Neisseria gonorrhoeae antigens | | |
| --- | --- | --- |
| Hypothetical protein name | Amino Acid Sequence (SEQ ID NO:) | Nucleic Acid Sequence (SEQ ID NO:) |
| NGO1947 | SEQ ID NO: 36 | SEQ ID NO: 72 |

Without imitations, the vaccine compositions described herein can comprise any one of the polypeptide antigens or fragments thereof from Table 1 above (SEQ ID NOs: 1-36). Accordingly, the vaccine compositions described herein can be made by synthesizing or translating any of the antigens or a fragment thereof from Table 1 above (SEQ ID NOs: 37-72) using any method known in the art. Alternatively or additionally, the vaccine compositions described herein can comprise a nucleic acid encoding one of the polypeptide antigens or fragments thereof from Table 1 above (e.g., a nucleic acid of any of SEQ ID NOs: 37-72). Accordingly, the vaccine compositions described herein can be made by synthesizing or transcribing a nucleic acid encoding any of the antigens or a fragment thereof from Table 1 above (SEQ ID NOs: 37-72) using any method known in the art. The vaccine compositions can comprise any combination of the antigens or fragments thereof or nucleic acids encoding the antigens or fragments thereof as described herein.

The table below provides all of the possible combinations of antigens that can be used. Contemplated exemplary combinations of antigens are indicated by "X."

First table (columns NGO0188 through NGO1701):

| | NGO0188 | NGO0449 | NGO0914 | NGO1332 | NGO1377 | NGO1543 | NGO1549 | NGO1607 | NGO1880 | NGO1948 | NGO2057 | NGO0416 | NGO0571 | NGO0757 | NGO1215 | NGO1251 | NGO1438 | NGO1701 |
|---|---|---|---|---|---|---|---|---|---|---|---|---|---|---|---|---|---|---|
| NGO0188 | | | | | | | | | | | | | | | | X | X | X |
| NGO0449 | X | | | | | | | | | | | | | | | X | X | X |
| NGO0914 | X | X | | | | | | | | | | | | | | X | X | X |
| NGO1377 | X | X | X | X | | | | | | | | | | | | X | X | X |
| NGO1543 | X | X | X | X | X | | | | | | | | | | | X | X | X |
| NGO1549 | X | X | X | X | X | X | | | | | | | | | | X | X | X |
| NGO1607 | X | X | X | X | X | X | X | | | | | | | | | X | X | X |
| NGO1880 | X | X | X | X | X | X | X | X | | | | | | | | X | X | X |
| NGO1948 | X | X | X | X | X | X | X | X | X | | | | | | | X | X | X |
| NGO2057 | X | X | X | X | X | X | X | X | X | X | | | | | | X | X | X |
| NGO0416 | X | X | X | X | X | X | X | X | X | X | X | | | | | X | X | X |
| NGO0571 | X | X | X | X | X | X | X | X | X | X | X | X | | | | X | X | X |
| NGO0757 | X | X | X | X | X | X | X | X | X | X | X | X | X | | | X | X | X |
| NGO1215 | X | X | X | X | X | X | X | X | X | X | X | X | X | X | | X | X | X |
| NGO1251 | X | X | X | X | X | X | X | X | X | X | X | X | X | X | X | | X | X |
| NGO1438 | X | X | X | X | X | X | X | X | X | X | X | X | X | X | X | X | | X |
| NGO1701 | X | X | X | X | X | X | X | X | X | X | X | X | X | X | X | X | X | |
| NGO1868 | X | X | X | X | X | X | X | X | X | X | X | X | X | X | X | X | X | X |
| NGO2119 | X | X | X | X | X | X | X | X | X | X | X | X | X | X | X | X | X | X |
| NGO0227 | X | X | X | X | X | X | X | X | X | X | X | X | X | X | X | X | X | X |
| NGO0354 | X | X | X | X | X | X | X | X | X | X | X | X | X | X | X | X | X | X |
| NGO0588 | X | X | X | X | X | X | X | X | X | X | X | X | X | X | X | X | X | X |
| NGO0648 | X | X | X | X | X | X | X | X | X | X | X | X | X | X | X | X | X | X |
| NGO0678 | X | X | X | X | X | X | X | X | X | X | X | X | X | X | X | X | X | X |
| NGO0690 | X | X | X | X | X | X | X | X | X | X | X | X | X | X | X | X | X | X |
| NGO0694 | X | X | X | X | X | X | X | X | X | X | X | X | X | X | X | X | X | X |
| NGO0768 | X | X | X | X | X | X | X | X | X | X | X | X | X | X | X | X | X | X |
| NGO0861 | X | X | X | X | X | X | X | X | X | X | X | X | X | X | X | X | X | X |
| NGO0891 | X | X | X | X | X | X | X | X | X | X | X | X | X | X | X | X | X | X |
| NGO0948 | X | X | X | X | X | X | X | X | X | X | X | X | X | X | X | X | X | X |
| NGO1043 | X | X | X | X | X | X | X | X | X | X | X | X | X | X | X | X | X | X |
| NGO1428 | X | X | X | X | X | X | X | X | X | X | X | X | X | X | X | X | X | X |
| NGO1729 | X | X | X | X | X | X | X | X | X | X | X | X | X | X | X | X | X | X |
| NGO1802 | X | X | X | X | X | X | X | X | X | X | X | X | X | X | X | X | X | X |
| NGO1947 | X | X | X | X | X | X | X | X | X | X | X | X | X | X | X | X | X | X |

Second table (columns NGO1868 through NGO1947):

| | NGO1868 | NGO2119 | NGO0227 | NGO0354 | NGO0588 | NGO0648 | NGO0678 | NGO0690 | NGO0694 | NGO0768 | NGO0861 | NGO0891 | NGO0948 | NGO1043 | NGO1428 | NGO1729 | NGO1802 | NGO1947 |
|---|---|---|---|---|---|---|---|---|---|---|---|---|---|---|---|---|---|---|
| NGO0188 | X | X | X | X | X | X | X | X | X | X | X | X | X | X | X | X | X | X |
| NGO0449 | X | X | X | X | X | X | X | X | X | X | X | X | X | X | X | X | X | X |
| NGO0914 | X | X | X | X | X | X | X | X | X | X | X | X | X | X | X | X | X | X |
| NGO1332 | X | X | X | X | X | X | X | X | X | X | X | X | X | X | X | X | X | X |
| NGO1377 | X | X | X | X | X | X | X | X | X | X | X | X | X | X | X | X | X | X |
| NGO1543 | X | X | X | X | X | X | X | X | X | X | X | X | X | X | X | X | X | X |
| NGO1549 | X | X | X | X | X | X | X | X | X | X | X | X | X | X | X | X | X | X |
| NGO1607 | X | X | X | X | X | X | X | X | X | X | X | X | X | X | X | X | X | X |
| NGO1880 | X | X | X | X | X | X | X | X | X | X | X | X | X | X | X | X | X | X |

-continued

| | | | | | | | | | | | | | | | | |
|---|---|---|---|---|---|---|---|---|---|---|---|---|---|---|---|---|
| NGO1948 | | | | | | | | | | | | | | | | |
| NGO2057 | | | | | | | | | | | | | | | | |
| NGO0416 | | | | | | | | | | | | | | | | |
| NGO0571 | | | | | | | | | | | | | | | | |
| NGO0757 | | | | | | | | | | | | | | | | |
| NGO1215 | | | | | | | | | | | | | | | | |
| NGO1251 | | | | | | | | | | | | | | | | |
| NGO1438 | | | | | | | | | | | | | | | | |
| NGO1701 | | | | | | | | | | | | | | | | |
| NGO1868 | | | | | | | | | | | | | | | | |
| NGO2119 | | | | | | | | | | | | | | | | |
| NGO0227 | | | | | | | | | | | | | | | | |
| NGO0354 | | | | | | | | | | | | | | | | |
| NGO0588 | | | | | | | | | | | | | | | | |
| NGO0648 | | | | | | | | | | | | | | | | |
| NGO0678 | | | | | | | | | | | | | | | | |
| NGO0690 | | | | | | | | | | | | | | | | |
| NGO0694 | | | | | | | | | | | | | | | | |
| NGO0768 | | | | | | | | | | | | | | | | |
| NGO0861 | | | | | | | | | | | | | | | | |
| NGO0891 | | | | | | | | | | | | | | | | |
| NGO0948 | | | | | | | | | | | | | | | | |
| NGO1043 | | | | | | | | | | | | | | | | |
| NGO1428 | | | | | | | | | | | | | | | | |
| NGO1729 | | | | | | | | | | | | | | | | |
| NGO1802 | | | | | | | | | | | | | | | | |
| NGO1947 | | | | | | | | | | | | | | | | |

27
28

In one embodiment of any of the aspects, the vaccine composition described herein comprises at least one antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, NGO1947, and fragments thereof. In one embodiment of any of the aspects, the vaccine composition described herein comprises at least one antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947.

In another embodiment of any of the aspects, the vaccine composition described herein comprises two or more antigens selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, NGO1947, and fragments thereof. In another embodiment of any of the aspects, the vaccine composition described herein comprises two or more antigens selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947.

In another embodiment of any of the aspects, the vaccine composition described herein comprises at least one antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, NGO1947, and fragments thereof; and at least one further antigen.

In another embodiment of any of the aspects, the vaccine composition described herein comprises at least one antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947; and at least one further antigen.

A further antigen referred to herein with respect to the vaccine compositions can be antigens already known in the art. In some embodiments of any of the aspects, the at least one further antigen is selected from the group consisting of porin, pilin, TbpA, TbpB, LOS, MetQ, SliC, MtrE, BamA, ACP, and nucleic acids encoding any of the foregoing antigens. Non-limiting examples of antigens known in the art can be found in Edwards et al. *Curr Opin Infect Dis.* (2018); Baarda et al. *Front Immunol.* (2018); and Vincent et al. *Vaccine.* (2018), which are incorporated herein by reference in their entireties.

In another aspect, described herein is a vaccine composition comprising i) a NGO0416 polypeptide or a fragment thereof, or a nucleic acid encoding such antigen or fragment thereof and ii) at least one antigen selected from the group consisting of: NGO0188, NGO0449, NGO0914, NGO1332, NGO1377, NGO1543, NGO1549, NGO1607, NGO1880, NGO1948, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947 polypeptide or a fragment thereof or a nucleic acid encoding such antigen or fragment thereof.

In another aspect, described herein is a vaccine composition comprising i) a NGO0690 polypeptide or a fragment thereof or a nucleic acid encoding such antigen or fragment thereof, and ii) at least one antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0694, NGO0768, NGO0861, NGO0891, NGO0948, NGO1043, NGO1428, NGO1729, NGO1802, and NGO1947 polypeptide or a fragment thereof or a nucleic acid encoding such antigen or fragment thereof.

In another aspect, described herein is a vaccine composition comprising i) a NGO0948 polypeptide or a fragment thereof or a nucleic acid encoding such antigen or fragment thereof, and ii) at least one antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO1043, NGO1428, NGO1729, NGO1802, and NGO1947 polypeptide or a fragment thereof or a nucleic acid encoding such antigen or fragment thereof.

In another aspect, described herein is a vaccine composition comprising i) a NGO1043 polypeptide or a fragment thereof or a nucleic acid encoding such antigen or fragment thereof, and ii) at least one antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO1428, NGO1729, NGO1802, and NGO1947 polypeptide or a fragment thereof or a nucleic acid encoding such antigen or fragment thereof.

In another aspect, described herein is a vaccine composition comprising i) a NGO1215 polypeptide or a fragment thereof or a nucleic acid encoding such antigen or fragment thereof, and ii) at least one antigen selected from the group consisting of NGO0188, NGO0449, NGO0914, NGO1332, NGO1377, NGO1543, NGO1549, NGO1607, NGO1880, NGO1948, NGO2057-NGO0416, NGO0571, NGO0757, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO1043, NGO1428, NGO1729, NGO1802, and NGO1947 polypeptide or a fragment thereof or a nucleic acid encoding such antigen or fragment thereof.

In another aspect, described herein is a vaccine composition comprising i) a NGO1701 polypeptide or a fragment thereof or a nucleic acid encoding such antigen or fragment thereof, and ii) at least one antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1868, NGO2119-NGO0227, NGO0354, NGO0588, NGO0648, NGO0678, NGO0690, NGO0694, NGO0768, NGO0861, NGO0891, NGO1043, NGO1428, NGO1729, NGO1802, and NGO1947 polypeptide or a fragment thereof or a nucleic acid encoding such antigen or fragment thereof.

In another aspect, described herein is a vaccine composition comprising the polypeptides NGO0416; NGO0690; NGO0948; NGO1043; NGO1215; andNGO1701. In another aspect, described herein is a vaccine composition comprising the polypeptides, fragments thereof, or nucleic acids encoding each of NGO0416; NGO0690; NGO0948; NGO1043; NGO1215; and NGO1701.

In another aspect, described herein is a vaccine composition comprising a NGO0690 polypeptide or a fragment thereof or a nucleic acid encoding such antigen or fragment thereof, and a NGO1701 polypeptide or a fragment thereof or a nucleic acid encoding such antigen or fragment thereof.

In another aspect, described herein is a vaccine composition comprising a NGO0690 polypeptide or a fragment thereof or a nucleic acid encoding such antigen or fragment thereof, a NGO0948 polypeptide or a fragment thereof, and a NGO1701 polypeptide or a fragment thereof or a nucleic acid encoding such antigen or fragment thereof.

In another aspect, described herein is a polypeptide comprising an amino acid sequence of an antigen or antigen fragment thereof selected by the methods described herein. In some embodiments of any of the aspects, the amino acid sequence of the antigen is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, and SEQ ID NO: 36.

In another aspect, described herein is a vector comprising a nucleic acid encoding an antigen or antigen fragment thereof selected by the methods described herein. In some embodiments of any of the aspects, the nucleic acid sequence is selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and SEQ ID NO: 72.

The antigens or fragments thereof described herein can be expressed in a vector (e.g., an expression vector). The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide (e.g., the antigens or fragments thereof as described herein) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

The antigens (or fragments thereof or nucleic acids encoding the foregoing) can be produced in a cell, a recombinant cell, or a cell-free system. Exemplary systems for vaccine component production include, e.g., The Xpress CF™ platform (Sutrovax; Foster City, CA).

As described herein, nucleic acids encoding antigen polypeptides can be used in vaccine compositions. The use of nucleic acid vaccines and production thereof is known in the art, and can include, e.g., liposomes, modified nucleosides and conjugation of targeting moieities. For further discussion, see e.g., Servick, Kelly (1 Feb. 2017). "This mysterious $2 billion biotech is revealing the secrets behind its new drugs and vaccines" *Science*; which is incorporated by reference herein in its entirety.

Described herein is a comprehensive, high-throughput in silico screening approach (candidate antigen selection strategy or CASS) to identify vaccine targets based on predicted immunogenicity, membrane association/surface exposure, conservation and with structure features favorable for future scale up and manufacturing.

In one aspect, described herein are vaccine compositions comprising an antigen or fragment thereof produced by the methods described herein.

In another aspect, described herein is a method of selecting an antigen for the preparation of a vaccine composition, wherein the method comprises:

a. sequencing or detecting RNA from a sample from a subject infected with a bacterium, wherein the sample comprises RNA expressed by the bacterium;

b. comparing the RNA information obtained in step (a) to RNA sequence information obtained from the same species (or optionally, same strain) of bacterium grown in culture to establish a reference level, and identifying a candidate set of transcripts with a modulation in the level of expression during an infection as compared with the reference level;

c. detecting, measuring, or determining for, the set of candidate transcripts identified in step (b) (or for an open reading frame thereof), one or more of the following properties:

i. a level of Reads per Kilobase of transcript per Million (RPKM) greater than 25;

ii. an immunogenic probability score of at least 0.4;

iii. the cellular localization of the encoded polypeptide is within the cell membrane, periplasm or outer cell membrane;

iv. the encoded polypeptide does not have an amino acid sequence that is conserved between human and other bacterial species;

v. the encoded polypeptide has an amino acid sequence that is conserved across multiple strains of the bacteria; and vi. the encoded polypeptide is a hypothetical protein wherein an encoded polypeptide comprising one or more of the properties is selected as a candidate antigen for a vaccine composition.

In some embodiments of any of the aspects, the encoded polypeptide comprising two or more of the properties in step c. is selected as a candidate antigen for a vaccine composition. In some embodiments of any of the aspects, the encoded polypeptide comprising three or more of the properties in step c. is selected as a candidate antigen for a vaccine composition. In some embodiments of any of the aspects, the encoded polypeptide comprising four or more of the properties in step c. is selected as a candidate antigen for a vaccine composition. In some embodiments of any of the aspects, the encoded polypeptide comprising five or more of the properties in step c. is selected as a candidate antigen for a vaccine composition. In some embodiments of any of the aspects, the encoded polypeptide comprises each of the properties in step c. is selected as a candidate antigen for a vaccine composition.

Sequencing or detecting nucleic acids (e.g., RNA) from a sample from a subject infected with a microorganism (e.g., bacteria) can be accomplished by methods known in the art. See for example, McClure R et al. *PLoS ONE*. (2015); and U.S. Pat. Nos. 6,271,002 B1; 6,518,019 B2; 8,206,913 B1; 6,524,829 B1; and 2016/0122753 A1, which are incorporated herein by reference in their entireties.

Comparison of the nucleic acid (e.g., RNA) sequence information obtained in step (a) to sequence information obtained from the microorganism (e.g., bacteria grown in culture), and identifying a candidate set of transcripts with a modulation in the level of expression during an infection compared with a reference level can be performed by RNA sequencing or any method of detecting the level of expression of a nucleic acid or polypeptide known in the art (e.g., DNA and RNA sequencing, next-generation sequencing, RT-PCR, microarrays, proteomics, fluorescent assays, transcriptomics, gene chip assays, whole-genome sequencing, methylation specific oligonucleotide arrays, and microfluidic assays).

The Reads per Kilobase of transcript per Million (RPKM) is a unit of transcript expression. Raw read counts from sequencing assays alone can be affected by factors such as transcript length, total number of reads, and sequencing biases. The measure RPKM (reads per kilobase of exon model per million reads) is a within-sample normalization method that removes the feature-length and library-size effects. The RPKM is calculated by first determining the number of millions of total reads in a set of sequence data, dividing the read counts by the number of millions of total reads to yield reads per million, then dividing by the length of the gene in kb. This measure and its subsequent derivatives FPKM (fragments per kilobase of exon model per million mapped reads), a within-sample normalized transcript expression measure analogous to RPKs, and TPM (transcripts per million) are the most frequently reported RNA-seq gene expression values.

One method for identifying and selecting an antigen or fragment thereof as a candidate antigen for a vaccine composition, is by selecting transcripts with an RPKM level greater than 25, greater than 30, greater than 35, greater than 40, greater than 45, greater than 50.

The properties of step c, particularly elements ii. and iii., can either be predicted (e.g., on the basis of sequence information) or experimentally determined. Several bioinformatic analyses and prediction tools can be used to analyze and prioritize candidate antigens with the properties in step c. One of skill in the art would know which prediction tool to use based on which property was desired for a specific candidate antigen.

For example, VaxiJen can be used for prediction of antigenicity, immunogenic probability, and protective potential (cut-off of 0.4); PSORTb v3.0, PredictProtein and GnegmPLoc for protein subcellular localization (52-54); Vaxgen found on the world wide web at <www.violinet.org/vaxgen/index.php> and BLASTp (BLAST 2.2.26+) for protein sequence analyses. Amino acid sequence similarity with human/mouse/*E. coli* proteins, *N. gonorrhoeae* and *N. lactamica* proteins can also be assessed.

As used herein, the term "immunogenic probability" refers to a probability that a given antigen or fragment thereof has multiple epitopes (e.g., T cell and B cell epitopes) and/or can provoke an immune response. See for example, Jain R, et al., *J Theor Biol*. 2016; 410:36-43, which incorporated herein by reference in its entirety. In some embodiments of any of the aspects, the immunogenic probability is the immunogenic probability as calculated by VaxiJen. In some embodiments, the immunogenic probability is at least 0.4.

Protein structure features can be examined with HMTMM for prediction of presence and number of trans-membrane domains, with Phobius for prediction of topology, and with SignalP v5.0 and SecretomeP for prediction of presence/type of signal peptides, cleavage site and post-translational modifications. Protein functional analyses can be further evaluated with BLAST, UniProtKB, PFAM and by PubMed records.

Gene presence, alleles distribution and sequence conservation can be examined for pathogenic bacteria (e.g., *N. gonorrhoeae* (4198 strains) and *N. lactamica* (288 strains)) using PubMLST found on the world wide web at <pubMLST.org>. Protein sequence conservation can be deduced from from BLASTp in NCBI.

Generally, an amino acid or nucleic acid sequence is considered conserved when the sequence of the selected polypeptide or nucleic acid encoding the polypeptide (e.g., an antigen) has at least a 50% or greater, 60% or greater, 70% or greater, 80% or greater, 90% or greater, or 100% or greater homology to a sequence of another polypeptide or nucleic acid encoding a polypeptide.

In the various embodiments of any of the aspects, it is contemplated that variants (naturally occurring or otherwise), alleles, homologs, conservatively modified variants, and/or conservative substitution variants of any of the particular antigen polypeptides described are encompassed. As to amino acid sequences (e.g., SEQ ID NOs: 1-36), one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. ligand-mediated receptor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments of any of the aspects, an antigen polypeptide or fragment thereof as described herein can be a variant of a polypeptide or antigen as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 80%, at least 90%, at least 91%, at least 92%, at least 93%, at least 94%, at least 95%, at least 96%, at least 97%, at least 98%, at least 99%, identical to a native or reference sequence (e.g. SEQ ID NOs: 1-72). The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are incorporated herein by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

In some embodiments of any of the aspects, the method described herein further comprises isolating a biological sample from a subject. The biological sample can be obtained or isolated by methods known in the art such as a swab, blood draw, or surgical methods.

In some embodiments of any of the aspects, the biological sample is epidermal tissue, mucosal tissue, mucus, bodily fluid, blood, buffy coat, saliva, or lower genital tract fluid. The biological sample can be removed from any subject as described herein. In some embodiments of any of the aspects, the subject is a mammal. In some embodiments of any of the aspects, the subject is a human.

In some embodiments of any of the aspects, the method described herein further comprises cloning the antigen or a fragment thereof into an expression vector. Methods of cloning are well known in the art. By way of example only, the nucleic acid encoding the candidate antigen or fragment thereof described herein can be cloned into a plasmid (e.g., pET17b). The plasmid can have an antibiotic-resistance cassette (e.g., ampicillin or kanamycin) The plasmid is then transformed into a bacterium (e.g., E. coli BL21 (DE3)) for recombinant expression. Transformed bacterial cultures can then be inoculated in a medium with the appropriate antibiotics followed by induction (e.g., by isopropyl β-D-1-thiogalactopyranoside (IPTG)) to evaluate the antigen or antigen fragment expression.

Other methods of making, expressing, delivering, or preparing an antigen or fragment thereof can also be used. For example, mRNA vaccine compositions can be used. See U.S. Pat. Nos. 9,192,651 B2 and 10,022,435B2 which have been incorporated by reference herein in their entirety. See also, polypeptide-antigen conjugates in US 2018/0333484 Å1 and 2019/0192645 Å1, which have been incorporated by reference herein in their entirety.

In some embodiments of any of the aspects, the method further comprises expressing and isolating the candidate antigen or fragment thereof.

By way of example only, after induction, bacteria can be collected by centrifugation and proteins can then be purified by methods known in the art (e.g., column purification). Dot blots can be used to verify the antigen-positive fractions using an antibody and detection reagents. Protein concentration can then be quantified by methods known in the art.

The resulting antigens or fragments thereof can be tested and verified by immunizing an animal model or a subject with purified recombinant proteins and measuring an immune response to the antigen. Methods of measuring an immune response are known in the art. An immune response can be determined experimentally by evaluating the levels of immune molecules or cells in a biological sample from a subject exposed to the antigen or fragment thereof. Methods of detecting an immune response include but are not limited to antibody ELISA (e.g., IgG antibody), cytokine ELISA (e.g., measuring the presence of cytokines such as IL-4, IL-12, IL-6, IFN-γ, or TNF-α), flow cytometry, or a bactericidal assay (SBA).

The vaccine compositions and methods described herein provoke an immune response, e.g., an immune response which is protective against infections by one or more microorganisms.

The terms "microorganism" or "pathogenic microorganism" or "infectious microorganism" are used interchangeably herein to refer to any organism, particularly microscopic organisms, that can infect a subject and lead to an infectious disease or disorder. Examples of infectious organisms or pathogens include, but are not limited to, viruses, bacteria, protozoa, mycoplasma, and fungi. Infectious diseases can impact any bodily system, be acute (short-acting) or chronic/persistent (long-acting), occur with or without fever, strike any age group, and overlap with other infectious organisms.

As used herein, the term "pathogen" refers to an organism that causes a disease or disorder in a subject. For example, pathogens include but are not limited to viruses, fungi, bacteria, parasites and other infectious organisms or molecules therefrom, as well as taxonomically related macroscopic organisms within the categories algae, fungi, yeast, protozoa, or the like. In some embodiments, the pathogen is a human pathogen.

As used herein, a "bacterial infection" refers to any infection caused by a bacterium. A bacterial infection as described herein can be caused by any bacteria type currently known, or yet to be discovered that results in a pathogenic disease. Pathogenic bacteria and diseases are well known in the art.

Mammals are diagnosed as having an infection according to any standard method known in the art and described, for example, in U.S. Pat. Nos. 6,368,832, 6,579,854, and 6,808, 710 and U.S. Patent Application Publication Nos. 20040137577, 20030232323, 20030166531, 20030064380, 20030044768, 20030039653, 20020164600, 20020160000, 20020110836, 20020107363, and 20020106730, all of which are hereby incorporated by reference in their entireties.

In another aspect, described herein is a method of provoking an immune response to a microorganism (e.g., a pathogenic bacterium) in a subject, wherein the method comprises administering to a subject a vaccine composition as described herein. In some embodiments of any of the aspects, the vaccine composition provokes an immune response that is protective against a pathogenic bacterium. In some embodiments of any of the aspects, the vaccine composition provokes an immune response that is protective against a plurality of strains of the bacteria. In some embodiments of any of the aspects, the vaccine composition provokes an immune response that is protective against multiple strains of *Neisseria gonorrhoeae*. Exemplary strains of *Neisseria gonorrhoeae* include but are not limited to F62, FA1090, U08401, and U08402.

An immune response can be characterized as any stimulation of any immune cell, such as release of antibodies, cytokines, proliferation of an immune cell, phagocytosis, or any known function of an immune cell known in the art. Provoking an immune response as described herein can include the presence of an antibody or an increase in antibody production by B cells wherein the antibody can bind to an antigen expressing or an infecting pathogen following administration of the antigens, fragments thereof, or vaccine compositions described herein and thereby target the microorganism for killing or inactivation.

As known to those of skill in the art, the term "antibody" broadly refers to any immunoglobulin (Ig) molecule and immunologically active portions of immunoglobulin molecules (i.e., molecules that contain an antigen binding site that immunospecifically bind an antigen) comprised of four polypeptide chains, two heavy (H) chains and two light (L) chains, or any functional fragment, mutant, variant, or derivation thereof, which retains the essential epitope binding features of an Ig molecule. The antibody or immunoglobulin molecules can be of any type (e.g., IgG, IgE, IgM, IgD, IgA and IgY), class (e.g., IgG1, IgG2, IgG3, IgG4, IgAQ1 and IgA2) or subclass of immunoglobulin molecule, as is understood by one of skill in the art.

The presence or an increase in antibody production in a subject compared with a reference level can be measured by any method known in the art including enzyme-linked immunosorbent assay (ELISA). In addition, the presence or an increase in cytokine production by immune cells compared with a reference level can be measured by any method known in the art including an ELISPOT assay.

In some embodiments of any of the aspects, the vaccine compositions and methods described herein are for use against bacterial infections, i.e., when the antigen or fragment thereof comprises a molecule derived from bacteria.

Bacteria are unicellular organisms which multiply asexually by binary fission. They are classified and named based on their morphology, staining reactions, nutrition and metabolic requirements, antigenic structure, chemical composition, and genetic homology. Bacteria can be classified into three groups based on their morphological forms, spherical (coccus), straight-rod (bacillus) and curved or spiral rod (vibrio, campylobacter, spirillum, and spirochaete). Bacteria are also more commonly characterized based on their staining reactions into two classes of organisms, gram-positive and gram-negative. Gram refers to the method of staining which is commonly performed in microbiology labs. Gram-positive organisms retain the stain following the staining procedure and appear a deep violet color. Gram-negative organisms do not retain the stain but take up the counter-stain and thus appear pink.

Non-limiting examples of bacteria include: *Neisseria gonorrhoeae, Neisseria meningitides, Treponema pallidum, Ureaplasma urealyticum, Trichomona vaginalis, Bartonella henselae, Escherichia coli, Pseudomonas aeruginosa, Helicobacter pyloris, Borelia burgdorferi, Legionella pneumophilia, Mycobacteria* sps (such as. *M. genitalium, M. hominis, M. tuberculosis, M. avium, M. intracellulare, M. kansaii, M. gordonae*), *Staphylococcus aureus, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus epidermidis, Streptococcus* (*anaerobic* sps.), *Streptococcus pneumoniae,* pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Brucella abortus, Pasteurella multocida, Bacteroides* sp., *Fusobacterium nucleatum, Streptobacillus moniliformis, Treponema pertenue, Leptospira, Nocadia brasiliensis, Borrelia hermsii, Borrelia burgdorferi,* and *Actinomyces israelli.*

In some embodiments of any of the aspects, the bacteria can infect a mucous membrane in the host subject.

As used herein, a "mucosal bacteria" refers to any bacteria that can colonize or infect a mucous membrane of a host subject. The mucosal bacteria can be commensal bacteria (e.g., non-disease causing) or pathogenic bacteria (e.g., disease-causing). Exemplary mucosal bacteria include *Neisseria gonorrhoeae, Neisseria meningitides, Treponema pallidum, Ureaplasma urealyticum, Trichomona vaginalis, Bartonella henselae, Escherichia coli, Mycobacteria* sps (such as. *M. genitalium, M. hominis, M. tuberculosis*).

The methods and vaccine compositions described herein can be used for the prevention and treatment of a mucosal infection in a host subject. Mucosal infections caused by microorganisms (e.g., bacteria) can include sexually transmitted infections (STI) (e.g., gonorrhea). Exemplary STIs include chlamydia, gonorrhea, HIV infection, trichomoniasis, genital herpes, or syphilis. Left untreated, STIs can lead to an increased risk of giving or getting other infections (e.g., HIV), cause long-term pelvic and abdominal discomfort, or an inability to conceive a pregnancy or cause pregnancy complications.

Individuals diagnosed or at risk of having an STI may be symptomatic or asymptomatic. A subject is at risk for having an STI if they have been exposed to another individual with an STI. STIs can be transmitted from one individual to another in several ways, such as sexual transmission, contact with an infected individual, exposure to contaminated needles, exposure to contaminated biological fluids, etc. Symptoms associated with STIs (e.g., gonorrhea) include pain, pain when urinating, increased mucosal secretions, bleeding, headaches, abnormalities of the skin, fever, swollen lymph nodes, hair loss, muscle aches, sores, and the like. Diagnosis of an STI can be made by a physician or practitioner using a laboratory test such as a urine test or a swab of the affected area.

The affected area of the infection can be located within mucous membranes of the subject. As used herein, the term "mucous membrane" refers to a biological membrane layer that lines various cavities of the body and covers the surface of internal organs. The mucous membranes of organs can comprise one or more layers of epithelial cells that secrete mucus and an underlying lamina propria of loose connective tissue. Non-limiting examples of organs that have mucous membranes include the genitals, mouth, lips, ears, eyelids, nose, skin, bronchi, tongue, gastrointestinal tract, and/or rectum.

In addition to bacterial microorganisms, it is contemplated that the methods of selecting an antigen for making a vaccine composition described herein can be used to identify candidate antigens from other microorganisms such as parasites, viruses, or fungi.

Parasites are organisms which depend upon other organisms in order to survive and thus must enter, or infect, another organism to continue their life cycle. The infected organism, i.e., the host, provides both nutrition and habitat to the parasite. Although in its broadest sense the term parasite can include all infectious agents (i.e., bacteria, viruses, fungi, protozoa and helminths), generally speaking, the term is used to refer solely to protozoa, helminths, and ectoparasitic arthropods (e.g., ticks, mites, etc.). Protozoa are single-celled organisms which can replicate both intracellularly and extracellularly, particularly in the blood, intestinal tract or the extracellular matrix of tissues. Helminths are multicellular organisms which almost always are extracellular (an exception being *Trichinella* spp.). Helminths normally require exit from a primary host and transmission into a secondary host in order to replicate. In contrast to these aforementioned classes, ectoparasitic arthropods form a parasitic relationship with the external surface of the host body.

Parasites include intracellular parasites and obligate intracellular parasites. Examples of parasites include but are not limited to *Plasmodium falciparum, Plasmodium ovale, Plasmodium malariae, Plasmdodium vivax, Plasmodium knowlesi, Babesia microti, Babesia divergens, Trypanosoma cruzi, Toxoplasma gondii, Trichinella spiralis, Leishmania major, Leishmania donovani, Leishmania braziliensis, Leishmania tropica, Trypanosoma gambiense, Trypanosoma rhodesiense* and *Schistosoma mansoni.*

Viruses are small infectious agents which generally contain a nucleic acid core and a protein coat, but are not independently living organisms. Viruses can also take the form of infectious nucleic acids lacking a protein. A virus cannot replicate in the absence of a living host cell. Viruses enter specific living cells either by endocytosis or direct injection of DNA and multiply, causing disease. The multiplied virus can then be released and infect additional cells. Some viruses are DNA-containing viruses and others are RNA-containing viruses.

Specific examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Hepacivruses (hepatitis C viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxyiridae (variola viruses, vaccinia viruses, pox viruses); Iridoviridae (e.g., African swine fever virus); and unclassified viruses (e.g., the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted); Norwalk and related viruses, and astroviruses.

Fungi are eukaryotic organisms, only a relative few of which cause infection in vertebrate mammals. Because fungi are eukaryotic organisms, they differ significantly from prokaryotic bacteria in size, structural organization, life cycle and mechanism of multiplication. Fungi are classified generally based on morphological features, modes of reproduction and culture characteristics. Although fungi can cause different types of disease in subjects, such as respiratory infection or allergies following inhalation of fungal antigens, fungal intoxication due to ingestion of toxic substances, such as *Amanita phalloides* toxin and phallotoxin produced by poisonous mushrooms and aflatoxins, produced by *Aspergillus* species, not all fungi cause infectious disease.

Infectious fungi can cause systemic or superficial infections. Primary systemic infection can occur in normal healthy subjects, and opportunistic infections are most frequently found in immunocompromised subjects. The most common fungal agents causing primary systemic infection include *Blastomyces, Coccidioides*, and *Histoplasma*. Common fungi causing opportunistic infection in immunocompromised or immunosuppressed subjects include, but are not limited to, *Candida albicans, Cryptococcus neoformans*, and various *Aspergillus* species. Systemic fungal infections are invasive infections of the internal organs. The organism usually enters the body through the lungs, gastrointestinal tract, or intravenous catheters. These types of infections can be caused by primary pathogenic fungi or opportunistic fungi.

Superficial fungal infections involve growth of fungi on an external surface without invasion of internal tissues. Typical superficial fungal infections include cutaneous fungal infections involving skin, hair, or nails.

Diseases associated with fungal infection include aspergillosis, blastomycosis, candidiasis, chromoblastomycosis, coccidioidomycosis, cryptococcosis, fungal eye infections, fungal hair, nail, and skin infections, histoplasmosis, lobomycosis, mycetoma, otomycosis, paracoccidioidomycosis, disseminated *Penicillium marneffei*, phaeohyphomycosis, rhinosporidioisis, sporotrichosis, and zygomycosis.

Other medically relevant microorganisms have been described extensively in the literature, e.g., see C. G. A Thomas, Medical Microbiology, Bailliere Tindall, Great Britain 1983, the entire contents of which is hereby incorporated by reference. Each of the foregoing lists is illustrative and is not intended to be limiting.

Several medications for the treatment of an infection (e.g., a bacterial or viral infection) have been developed. Treatments for infections can include (1) vaccines comprising inactivated bacterial cells, (ii) a live attenuated vaccine containing genetically manipulated viruses, (iii) conjugates of pathogen lipopolysaccharides within a fusion protein or polypeptide, (iv) antibiotics and antiviral medications administered following infection.

In particular, treatments for STIs can be found in Workowski K A et al. Sexually transmitted diseases treatment guidelines, 2015. *MMWR Recomm Rep.* 2015; 64(RR-03): 1-137.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians' Desk Reference, and The Pharmacological Basis of Therapeutics, and they include, without limitation, medications; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject.

Exemplary therapeutic agents and vaccines for infections include but are not limited to penicillin, ceftriaxone, azithromycin, amoxicillin, doxycycline, cephalexin, ciprofloxacin, clindamycin, metronidazole, azithromycin, sulfamethoxazole, trimethoprim, meningococcal polysaccharide vaccine, tetanus toxoid, cholera vaccine, typhoid vaccine, pneumococcal 7-valent vaccine, pneumococcal 13-valent vaccine, pneumococcal 23-valent vaccine, haemophilus b conjugate, anthrax vaccine, acyclovir, adefovir, amantadine, cidofovir, combivir, dolutegravir, delavirdine, didanosine, emtricitabine, entecavir, famicolovir, fosamprenavir, imunovir, indinavir, inosine, lopinavir, lovaride, maravirox, nevirapine, nucleoside analogues, oseltamivir, penciclovir, rimantidine, pyrimidine, saquinavir, stavudine, tenofovir, trizivir, tromantadine, truvada, valaciclovir, ciramidine, zanamivir, zidovudine, MMR vaccine, DTaP vaccine, hepatitis vaccines, Hib vaccine, HPV vaccine, influenza vaccine, polio vaccine, rotavirus vaccine, shingles vaccine, Tdap vaccine, tetanus vaccine, fluconazole, ketoconazole, amphotericin B, and sulfadoxine/pyrimethamine.

In some embodiments of any of the aspects, the method further comprises formulating the antigen or fragment thereof with a pharmaceutically acceptable carrier, and optionally an adjuvant or outer membrane vesicles. In some embodiments of any of the aspects, a composition described herein comprises an antigen (or fragment thereof or nucleic acid encoding the antigen or fragment), at least one of a pharmaceutically acceptable carrier, an adjuvant, and outer membrane vesicles.

In some embodiments of any of the aspects, a composition described herein comprises an antigen (or fragment thereof or nucleic acid encoding the antigen or fragment) and does not comprise an adjuvant. In some embodiments of any of the aspects, a composition described herein comprises an antigen (or fragment thereof or nucleic acid encoding the antigen or fragment) and does not comprise alum.

In one aspect, described herein is a method of immunizing a subject, the method comprising administering a vaccine composition made by the methods described herein. In another aspect, described herein are vaccine compositions comprising any of the antigens or a fragments thereof as described herein, or a nucleic acid encoding such antigens or fragments thereof as described herein.

In some embodiments of any of the aspects, the vaccine or vaccine composition comprises at least one antigen. In some embodiments of any of the aspects, the vaccine or vaccine composition comprises multiple antigens. In some embodiments of any of the aspects, multiple antigens are administered. In some embodiments of any of the aspects, multiple vaccines or vaccine compositions are administered. The multiple vaccines or vaccine compositions can be, e.g., identical or different, e.g., two different vaccines comprising different antigens or antigen combinations, or two vaccine compositions comprising the same antigen or antigen combination (e.g, as in booster vaccines or repeated immunization protocols).

In some embodiments of any of the aspects, the vaccine is or can comprise an attenuated vaccine. Attenuated vaccines comprise weakened or compromised versions or variants of a microorganism. Attenuated vaccines can include mutated or engineered strains of a microorganism and/or strains which have been passaged in culture, thereby resulting in a loss of pathogenicity.

In some embodiments of any of the aspects, the vaccine composition can be or can comprise a subunit vaccine, including a recombinant subunit vaccine. A subunit vaccine does not comprise entire disease-causing microorganism, but only a subset of antigens obtained from or derived from the disease-causing microorganism. A subunit vaccine can comprise multiple different antigens. Subunit vaccines in which the antigens are produced via recombinant technologies are termed recombinant subunit vaccines.

In some embodiments of any of the aspects, at least one antigen is comprised by a conjugate vaccine. In conjugate vaccines, polysaccharides from a pathogenic microorganism (e.g., polysaccharides found on the surface of the microbe) are administered in combination with (e.g., conjugated to) an antigen which the subject's immune system already recognizes or which the subject's immune system will readily respond to. This increases the patient's response to the polysaccharides and the antigens and provides increased protection against live versions of the pathogenic microorganism. In some embodiments of any of the aspects, the vaccine composition described herein further comprises a polysaccharide.

A vaccine composition as described herein can be used, for example, to protect or treat a subject against disease. The terms "immunize" and "vaccinate" tend to be used interchangeably in the field. However, in reference to the administration of the vaccine compositions as described herein to provide protection against disease, e.g., infectious disease caused by a pathogen that expresses the antigen, it should be understood that the term "immunize" refers to the passive protection conferred by the administered vaccine composition.

For the clinical use of the methods described herein, administration of the antigen or antigen fragment thereof described herein can include formulation into pharmaceutical compositions or pharmaceutical formulations for parenteral administration, e.g., intravenous; mucosal, e.g., intranasal; ocular, or other mode of administration. In some embodiments, the antigen or antigen fragment described herein can be administered along with any pharmaceutically acceptable carrier compound, material, or composition which results in an effective treatment in the subject. Thus, a pharmaceutical formulation for use in the methods described herein can contain antigen or antigen fragment as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an antigen or fragment thereof. Each carrier must be "acceptable" in the sense of being compatible with the other ingredients of the formulation and not injurious to the patient. The terms "excipient", "carrier", "pharmaceutically acceptable carrier" or the like are used interchangeably herein.

The antigen or fragment thereof described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) transdermally; or (3) transmucosally. Additionally, an antigen or antigen fragment thereof can be implanted into a patient or injected using a drug delivery system. See, for example, Urquhart, et al., *Ann. Rev. Pharmacol. Toxicol.* 24: 199-236 (1984); Lewis, ed. "Controlled Release of Pesticides and Pharmaceuticals" (Plenum Press, New York, 1981); U.S. Pat. Nos. 3,773,919; and 35 3,270,960, which are incorporated herein by reference in their entireties.

Therapeutic formulations of the antigen or fragment thereof described herein can be prepared for storage by mixing the antigen or antigen fragments having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ PLURONICS™ or polyethylene glycol (PEG). Exemplary lyophilized antigen or antigen fragment formulations are described in WO 97/04801, expressly incorporated herein by reference.

Optionally, but preferably, the formulations comprising the vaccine compositions described herein contain a pharmaceutically acceptable salt, typically, e.g., sodium chloride, and preferably at about physiological concentrations. Optionally, the formulations of the vaccine compositions described herein can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the vaccine compositions described herein can include a pharmaceutically acceptable surfactant at a concentration of 0.005 to 0.02%.

The therapeutic formulations of the vaccine compositions comprising antigens or fragments thereof as described herein can also contain more than one active compound as necessary for the particular indication being treated, preferably those with complementary activities that do not adversely affect each other. Alternatively, the composition can comprise a cytotoxic agent, cytokine, or growth inhibitory agent, for example. Such molecules are suitably present in combination in amounts that are effective for the purpose intended.

The active ingredients of the vaccine compositions comprising an antigen or fragment thereof described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, sustained-release preparations can be used. Suitable examples of sustained-release preparations include semipermeable matrices of solid hydrophobic polymers containing an antigen or fragment thereof described herein in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated, the antigen or fragment thereof can remain in the body for a long time, denature, or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S-bond formation through thio-disulfide interchange, stabilization can be achieved by modifying sulfhydryl residues, lyophilizing from acidic solutions, controlling moisture content, using appropriate additives, and developing specific polymer matrix compositions.

The therapeutic formulations to be used for in vivo administration, such as parenteral administration, in the methods described herein can be sterile, which is readily accomplished by filtration through sterile filtration membranes, or other methods known to those of skill in the art.

An antigen or fragment thereof or vaccine composition, can be formulated, dosed, and administered in a fashion consistent with good medical practice. Factors for consideration in this context include the particular disorder being treated, the particular subject being treated, the clinical condition of the individual subject, the cause of the disorder, the site of delivery of the vaccine composition, the method of administration, the scheduling of administration, and other factors known to medical practitioners. The "therapeutically effective amount" of the antigen or fragment thereof or vaccine composition to be administered are governed by such considerations, and refers to the minimum amount necessary to ameliorate, treat, or stabilize an infection; to increase the time until progression (duration of progression free survival) or to treat or prevent the occurrence or recurrence of an infection or tumor. The antigen or fragment thereof or vaccine composition can be optionally formulated, in some embodiments, with one or more additional therapeutic agents currently used to prevent or treat the infection, for example. The effective amount of such other agents depends on the amount of antigen or antigen fragment present in the formulation, the type of disorder or treatment, and other factors discussed above. These are generally used in the same dosages and with administration routes as used herein before or about from 1 to 99% of the heretofore employed dosages.

The dosage ranges for the vaccine composition depend upon the potency, and encompass amounts large enough to produce the desired effect. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 100 mg/kg body weight. In some embodiments, the dose range is from 5 µg/kg body weight to 100 µg/kg body weight. Alternatively, the dose range can be titrated to maintain serum levels between 1 µg/mL and 1000 µg/mL For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 7.5 mg/kg, 10 mg/kg, 15 mg/kg, 20 mg/kg, 25 mg/kg, 30 mg/kg, 40 mg/kg, 50 mg/kg, or more. These doses can be administered by one or more separate administrations, or by continuous infusion. For repeated administrations over several days or longer, depending on the condition, the treatment is sustained until, for example, the infection is treated, as measured by the methods described above or known in the art. However, other dosage regimens can be useful.

The vaccine compositions described herein can be administered to a subject in need of vaccination, immunization, and/or stimulation of an immune response. In some embodiments of any of the aspects, the methods described herein comprise administering an effective amount of vaccine compositions described herein, e.g. to a subject in order to stimulate an immune response or provide protection against the relevant pathogen or microorganism (e.g., bacteria) the antigen was derived from. Providing protection against the relevant pathogen is stimulating the immune system such that later exposure to the antigen or fragment thereof (e.g., on or in a live pathogen) triggers a more effective immune response than if the subject was naïve to the antigen. Protection can include faster clearance of the pathogen, reduced severity and/or time of symptoms, and/or lack of development of disease or symptoms. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or topical, administration. Administration can be local or systemic. In some embodiments of any of the aspects, the administration can be intramuscular or subcutaneous. In some embodiments of any of the aspects, the administration can be by injection, oral administration, or intranasal administration.

The term "effective amount" as used herein refers to the amount of an antigen or fragment thereof or a vaccine composition needed to alleviate or prevent at least one or more symptom of an infection, disease or disorder, and relates to a sufficient amount of pharmacological composition to provide the desired effect, e.g., reduce the level of pathogenic microorganisms at a site of infection, reduce pathology, or any symptom associated with or caused by the pathogenic microorganism. The term "therapeutically effective amount" therefore refers to an amount of an antigen or fragment thereof or vaccine composition described herein using the methods as disclosed herein, that is sufficient to effect a particular effect when administered to a typical subject. An effective amount as used herein would also include an amount sufficient to delay the development of a symptom of the disease, alter the course of a symptom disease (for example, but not limited to, slow the progression of a symptom of the disease), or reverse a symptom of the disease. Thus, it is not possible to specify the exact "effective amount." However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the antigen or fragment thereof), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The antigen or fragment thereof or vaccine compositions as described herein can be administered to a subject in need thereof by any appropriate route which results in an effective treatment in the subject. As used herein, the terms "administering," and "introducing" are used interchangeably and refer to the placement of a vaccine composition, antigen or fragment thereof into a subject by a method or route which results in at least partial localization of such vaccine compositions at a desired site, such as a site of infection, such that a desired effect(s) is produced. An antigen or fragment thereof or vaccine composition can be administered to a subject by any mode of administration that delivers the vaccine composition systemically or to a desired surface or target, and can include, but is not limited to, injection, infusion, instillation, and inhalation administration. To the extent that antigen or fragment thereof or vaccine composition can be protected from inactivation in the gut, oral administration forms are also contemplated. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of a therapeutic agent other than directly into a target site, tissue, or organ, such as a tumor site, such that it enters the subject's circulatory system and, thus, is subject to metabolism and other like processes. In other embodiments, the antibody or antigen-binding fragment thereof is administered locally, e.g., by direct injections, when the disorder or location of the infection permits, and the injections can be repeated periodically.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with an infection. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation or at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

As used herein "preventing" or "prevention" refers to any methodology where the disease state does not occur due to the actions of the methodology (such as, for example, administration of an antigen or fragment thereof or vaccine composition as described herein). In one aspect, it is understood that prevention can also mean that the disease is not established to the extent that occurs in untreated controls. Accordingly, prevention of a disease encompasses a reduction in the likelihood that a subject can develop the disease, relative to an untreated subject (e.g. a subject who is not treated with the methods or compositions described herein).

The duration of a therapy using the methods described herein will continue for as long as medically indicated or until a desired therapeutic effect (e.g., those described herein) is achieved. In certain embodiments, the administration of the vaccine composition described herein is continued for 1 month, 2 months, 4 months, 6 months, 8 months, 10 months, 1 year, 2 years, 3 years, 4 years, 5 years, 10 years, 20 years, or for a period of years up to the lifetime of the subject.

As will be appreciated by one of skill in the art, appropriate dosing regimens for a given vaccine composition can comprise a single administration/immunization or multiple ones. Subsequent doses may be given repeatedly at time periods, for example, about two weeks or greater up through the entirety of a subject's life, e.g., to provide a sustained preventative effect. Subsequent doses can be spaced, for example, about two weeks, about three weeks, about four weeks, about one month, about two months, about three months, about four months, about five months, about six months, about seven months, about eight months, about nine months, about ten months, about eleven months, or about one year after a primary immunization.

The precise dose to be employed in the formulation will also depend on the route of administration and should be decided according to the judgment of the practitioner and each patient's circumstances. Ultimately, the practitioner or physician will decide the amount of antigen, antigen fragment, or vaccine composition to administer to particular subjects.

In some embodiments of these methods and all such methods described herein, the antigen or antigen fragment thereof is administered in an amount effective to provide short-term protection against an infection. In some embodiments, the infection is a bacterial infection. In some embodiments, the bacterial infection is caused by *Neisseria gonorrhoeae.*

As used herein, "short-term protection" refers to protection from an infection, such as a malarial infection, lasting at least about 2 weeks, at least about 1 month, at least about 6 weeks, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. Such protection can involve repeated dosing.

"Alleviating a symptom of a persistent infection" is ameliorating any condition or symptom associated with the persistent infection. Alternatively, alleviating a symptom of a persistent infection can involve reducing the infectious microbial (such as viral, bacterial, fungal or parasitic) load in the subject relative to such load in an untreated control. As compared with an equivalent untreated control, such reduction or degree of prevention is at least 5%, 10%, 20%, 40%, 50%, 60%, 80%, 90%, 95%, or 100% as measured by any standard technique. Desirably, the persistent infection is completely cleared as detected by any standard method known in the art, in which case the persistent infection is considered to have been treated. A patient who is being treated for a persistent infection is one who a medical practitioner has diagnosed as having such a condition. Diagnosis may be by any suitable means. Diagnosis and monitoring may involve, for example, detecting the level of microbial load in a biological sample (for example, a tissue biopsy, blood test, or urine test), detecting the level of a surrogate marker of the microbial infection in a biological sample, detecting symptoms associated with persistent infections, or detecting immune cells involved in the immune response typical of persistent infections (for example, detection of antigen specific T cells that are anergic and/or functionally impaired). A patient in whom the development of a persistent infection is being prevented may or may not have received such a diagnosis. One in the art will understand that these patients may have been subjected to the same standard tests as described above or may have been identified, without examination, as one at high risk due to the presence of one or more risk factors (such as family history or exposure to infectious agent).

For the treatment of diseases or infection, as described herein, the appropriate dosage of an antigen or fragment thereof will depend on the type of disease to be treated, as defined above, the severity and course of the disease, whether the antigen or fragment thereof is administered for preventive or therapeutic purposes, previous therapeutic indications, the subject's clinical history and response to the antigen or fragment thereof, and the discretion of the attending physician. The antigen or fragment thereof or a vaccine composition described herein is suitably administered to the subject at one time or over a series of treatments. In a combination therapy regimen, the antigen or fragment thereof and the one or more additional therapeutic agents described herein are administered in a therapeutically effective or synergistic amount. As used herein, a therapeutically effective amount is such that co-administration of an antigen or fragment thereof and one or more other therapeutic agents, or administration of a composition described herein, results in reduction or inhibition or prevention of a disease or disorder as described herein. A therapeutically synergistic amount is that amount of an antigen or fragment thereof and one or more other therapeutic agents necessary to synergistically or significantly reduce, prevent, or eliminate conditions or symptoms associated with a particular disease. In some cases, the antigen or fragment thereof can be co-administered with one or more additional therapeutically effective agents to give an additive effect resulting in a significantly reduction, prevention, or elimination of conditions or symptoms associated with a particular disease, but with a much reduced toxicity profile due to lower dosages of one or more of the additional therapeutically effective agents.

In one aspect, the vaccine composition described herein can further comprise an adjuvant or outer membrane vesicles.

As used herein in the context of immunization, immune response and vaccination, the term "adjuvant" refers to any substance than when used in combination with a specific antigen that produces a more robust immune response than the antigen alone. When incorporated into a vaccine formulation, an adjuvant acts generally to accelerate, prolong, or enhance the quality of specific immune responses to the vaccine antigen(s).

Adjuvants promote the accumulation and/or activation of accessory cells to enhance antigen-specific immune responses. Adjuvants are used to enhance the efficacy of vaccines, i.e., antigen-containing compositions used to induce protective immunity against the antigen.

Adjuvants, in general, include adjuvants that create a depot effect, immune-stimulating adjuvants, and adjuvants that create a depot effect and stimulate the immune system. An adjuvant that creates a depot effect as used herein is an adjuvant that causes the antigen to be slowly released in the body, thus prolonging the exposure of immune cells to the antigen. This class of adjuvants includes but is not limited to alum (e.g., aluminum hydroxide, aluminum phosphate); emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720; AirLiquide, Paris, France); MF-59 (a squalene-in-water emulsion stabilized with Span 85 and Tween 80; Chiron Corporation, Emeryville, Calif.); and PROVAX™ (an oil-in-water emulsion containing a stabilizing detergent and a micelle-forming agent; IDEC Pharmaceuticals Corporation, San Diego, Calif).

An immune-stimulating adjuvant is an adjuvant that causes activation of a cell of the immune system. It may, for instance, cause an immune cell to produce and secrete cytokines. This class of adjuvants includes but is not limited to saponins purified from the bark of the *Q. saponaria* tree, such as QS21 (a glycolipid that elutes in the 21st peak with HPLC fractionation; Aquila Biopharmaceuticals, Inc., Worcester, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). This class of adjuvants also includes CpG DNA.

Adjuvants that create a depot effect and stimulate the immune system are those compounds which have both of the above-identified functions. This class of adjuvants includes but is not limited to ISCOMS (immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

In some embodiments of any of the aspects, the adjuvant is alum.

In some embodiments of any of the aspects, the vaccine composition is formulated with outer membrane vesicles.

As used herein, "outer membrane vesicles" or "OMVs" refers to vesicles of lipids from the outer membrane of a microorganism (e.g., a bacterium). The OMVs are released by microorganisms to communicate with other microorganisms in their environment and with a host. The OMVs are involved in bacterial signaling and traffic bacterial biochemicals to target cells.

Outer membrane vesicles (OMV) that are both naturally released by bacteria or induced in OMV-based vaccines (e.g., meningococcal vaccine, BEXERO®). Outer membrane vesicles can be used to enhance the immune response to an infection. Thus, OMVs can be used in place of an adjuvant or in combination with another adjuvant.

In some embodiments of any of the aspects, at least a portion of the one or more antigens or fragments thereof or nucleic acid encoding an antigen or fragment thereof is present in or on the outer membrane vesicles. The antigen can be added to the OMV by a mixing process, or expressing the antigen in the cell or system which produces the OMV.

Some embodiments of the various aspects described herein can be described as in the following paragraphs:

1. A vaccine composition comprising at least one antigen or fragment thereof, or a nucleic acid encoding such antigen or fragment thereof, derived from a pathogenic bacterium wherein the antigen or fragment thereof is expressed by a bacteria during an infection of a host at a level that is increased compared with a reference level.

2. A vaccine composition comprising at least one antigen or fragment thereof, or a nucleic acid encoding such antigen or fragment thereof, derived from a pathogenic bacterium wherein the antigen or fragment thereof is expressed by a bacteria during an infection of a host at a level that is decreased compared with a reference level.

3. A vaccine composition comprising at least one antigen or fragment thereof, or a nucleic acid encoding such antigen or fragment thereof, derived from a pathogenic bacterium wherein the antigen or fragment thereof has a Reads per Kilobase of transcript per Million (RPKM) level greater than 50.

4. The vaccine composition of any one of paragraphs 1-3, wherein the pathogenic bacterium is a mucosal bacterium.

5. The vaccine composition of any one of paragraphs 1-4, wherein the pathogenic bacterium is *Neisseria gonorrhoeae*.

6. The vaccine composition of any one of paragraphs 1-5, wherein the antigen is selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947.

7. The vaccine composition of any one of paragraphs 1-5, comprising two or more antigens selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947.

8. The vaccine composition of any one of paragraphs 1-5, comprising at least one antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947, and at least one further antigen.

9. The vaccine composition of any one of paragraphs 1-8, wherein the at least one further antigen is selected from the group consisting of: porin, pilin, TbpA, TbpB, LOS, MetQ, SliC, MtrE, BamA, ACP, and nucleic acids encoding any of the foregoing antigens.

10. The vaccine composition of any one of paragraphs 1-9, wherein the antigen is expressed by multiple strains of *Neisseria gonorrhoeae*.

11. The vaccine composition of any one of paragraphs 1-10, wherein the bacterium infects a mucous membrane in the host subject.

12. The vaccine composition of any one of paragraphs 1-11, wherein the host subject is a mammal.

13. The vaccine composition of any one of paragraphs 1-12, wherein the host subject is a human.

14. The vaccine composition of any one of paragraphs 1-13, wherein the bacterium infects the host subject's genitals, mouth, eyelids, nose, skin, and/or rectum.

15. The vaccine composition any one of paragraphs 1-14, further comprising an adjuvant or outer membrane vesicles.

16. The vaccine composition any one of paragraphs 1-15, wherein at least a portion of the one or more antigens or fragment thereof or nucleic acid encoding an antigen or fragment thereof is present in or on the outer membrane vesicles.

17. The vaccine composition of paragraph 15, wherein the adjuvant is alum.

18. The vaccine composition of any one of paragraphs 1-17, wherein at least one antigen or fragment thereof is a hypothetical protein.

19. The vaccine composition of any one of paragraphs 1-18, wherein at least one antigen or fragment thereof is a lipoprotein.

20. A vaccine composition comprising a NGO0416 polypeptide or a fragment thereof or a nucleic acid encoding such antigen or fragment thereof, and an antigen selected from the group consisting of: NGO0188, NGO0449, NGO0914, NGO1332, NGO1377, NGO1543, NGO1549, NGO1607, NGO1880, NGO1948, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947 polypeptide or a fragment thereof or a nucleic acid encoding such antigen or fragment thereof.

21. A vaccine composition comprising a NGO0690 polypeptide or a fragment thereof or a nucleic acid encoding such antigen or fragment thereof, and an antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0694, NGO0768, NGO0861, NGO0891, NGO0948, NGO1043, NGO1428, NGO1729, NGO1802, and NGO1947 polypeptide or a fragment thereof or a nucleic acid encoding such antigen or fragment thereof.

22. A vaccine composition comprising a NGO0948 polypeptide or a fragment thereof or a nucleic acid encoding such antigen or fragment thereof, and an antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO1043, NGO1428, NGO1729, NGO1802, and NGO1947 polypeptide or a fragment thereof or a nucleic acid encoding such antigen or fragment thereof.

23. A vaccine composition comprising a NGO1043 polypeptide or a fragment thereof or a nucleic acid encoding such antigen or fragment thereof, and an antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO1428, NGO1729, NGO1802, and NGO1947 polypeptide or a fragment thereof or a nucleic acid encoding such antigen or fragment thereof.

24. A vaccine composition comprising NGO1215 polypeptide or a fragment thereof or a nucleic acid encoding such antigen or fragment thereof, and an antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1251, NGO1438, NGO1701, NGO1868, NGO2119-NGO0227, NGO0354, NGO0588, NGO0648, NGO0678, NGO0690, NGO0694, NGO0768, NGO0861, NGO0891, NGO1043, NGO1428, NGO1729, NGO1802, and NGO1947 polypeptide or a fragment thereof or a nucleic acid encoding such antigen or fragment thereof.

25. A vaccine composition comprising a NGO1701 polypeptide or a fragment thereof or a nucleic acid encoding such antigen or fragment thereof, and an antigen selected from the group consisting of: NGO0188, NGO0449, NGO0914, NGO1332, NGO1377, NGO1543, NGO1549, NGO1607, NGO1880, NGO1948, NGO2057-NGO0416, NGO0571, NGO0757, NGO1215, NGO1251, NGO1438, NGO1868, NGO2119-NGO0227, NGO0354, NGO0588, NGO0648, NGO0678, NGO0690, NGO0694, NGO0768, NGO0861, NGO0891, NGO1043, NGO1428, NGO1729, NGO1802, and NGO1947 polypeptide or a fragment thereof or a nucleic acid encoding such antigen or fragment thereof.

26. A vaccine composition, comprising the following antigen polypeptides or a nucleic acids encoding such antigen polypeptides: NGO0416; NGO0690; NGO0948; NGO1043; NGO1215; and NGO1701 or a fragment thereof.

27. A vaccine composition comprising a NGO0690 polypeptide or a fragment thereof or a nucleic acid encoding such antigen or fragment thereof, and aNGO1701 polypeptide or a fragment thereof or a nucleic acid encoding such antigen or fragment thereof.

28. A vaccine composition comprising a NGO690 polypeptide or a fragment thereof or a nucleic acid encoding such antigen or fragment thereof, a NGO0948 polypeptide or a fragment thereof, and a NGO1701 polypeptide or a fragment thereof or a nucleic acid encoding such antigen or fragment thereof.

29. A method of provoking an immune response to a pathogenic bacterium in a subject, the method comprising: administering to a subject a vaccine composition of any one of paragraphs 1-28.

30. The method of paragraph 29, wherein the subject is a mammal.

31. The method of any one of paragraphs 29-30, wherein the subject is a human.

32. The method of paragraph 29, wherein the administering is by injection, oral, or intranasal administration.

33. The method of paragraph 29, wherein the bacterium is *Neisseria gonorrhoeae.*

34. The method of any one of paragraphs 29-33, wherein the vaccine composition provokes an immune response that is protective against a plurality of strains of the bacteria.

35. The method of any one of paragraphs 29-34, wherein the vaccine composition provokes an immune response that is protective against multiple strains of *Neisseria gonorrhoeae.*

36. A method of selecting an antigen for the preparation of a vaccine composition, the method comprising:

a. sequencing RNA from a sample from a subject infected with a bacterium, wherein the sample comprises RNA expressed by the bacterium;

b. comparing the RNA sequence information obtained in step (a) to RNA sequence information obtained from the bacteria grown in culture, and identifying a candidate set of transcripts with a modulation in the level of expression during an infection when compared with a reference level;

c. detecting for, an open reading frame of the set of candidate transcripts identified in step (b), one or more of the following properties:

i. a level of Reads per Kilobase of transcript per Million (RPKM) greater than 25;

ii. an immunogenic probability score of at least 0.4;

iii. the cellular localization of an encoded polypeptide is within the cell membrane, periplasm or outer cell membrane;

iv. the encoded polypeptide does not have an amino acid sequence that is conserved between human and other bacterial species;

ii. the encoded polypeptide has an amino acid sequence that is conserved across multiple strains of the bacteria; and iii. the encoded polypeptide is a hypothetical protein wherein an encoded polypeptide comprising one or more of the properties is selected as a candidate antigen for a vaccine composition.

37. The method of paragraph 36, wherein the encoded polypeptide comprising two or more of the properties in step c. is selected as a candidate antigen for a vaccine composition.

38. The method of paragraph 36, wherein the encoded polypeptide comprising three or more of the properties in step c. is selected as a candidate antigen for a vaccine composition.

39. The method of paragraph 36, wherein the encoded polypeptide comprising four or more of the properties in step c. is selected as a candidate antigen for a vaccine composition.

40. The method of paragraph 36, wherein the encoded polypeptide comprising five or more of the properties in step c. is selected as a candidate antigen for a vaccine composition.

41. The method of paragraph 36, wherein the encoded polypeptide comprises each of the properties in step c. is selected as a candidate antigen for a vaccine composition.

42. The method of any one of paragraphs 36-41, further comprising isolating a biological sample from a subject.

43. The method of paragraph 42, wherein the biological sample is epidermal tissue, mucosal tissue, mucus, bodily fluid, blood, buffy coat, saliva, or lower genital tract fluid.

44. The method of any one of paragraphs 36-43, wherein the subject is a mammal.

45. The method of any one of paragraphs 36-44, wherein the subject is a human.

46. The method of any one of paragraphs 36-45, further comprising synthesizing or transcribing a nucleic acid encoding the candidate antigen.

47. The method of any one of paragraphs 36-46, further comprising cloning the antigen or a fragment thereof into an expression vector.

48. The method of any one of paragraphs 36-47, further comprising expressing and isolating the candidate antigen or fragment thereof.

49. The method of any one of paragraphs 36-48, further comprising formulating the antigen or fragment thereof with a pharmaceutically acceptable carrier, and optionally an adjuvant or outermembrane vesicles.

50. A vaccine composition comprising an antigen or fragment thereof produced by the method of any one of paragraphs 36-49.

51. A method of immunizing a subject, the method comprising administering a vaccine composition made by the method of any one of paragraphs 36-49.

52. A polypeptide comprising an amino acid sequence of an antigen or antigen fragment thereof selected by the method of any one of paragraphs 36-49.

53. The polypeptide of paragraph 52, wherein the amino acid sequence is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, and SEQ ID NO: 36.

54. A vector comprising a nucleic acid encoding an antigen or antigen fragment thereof selected by the method of any one of paragraphs 36-49.

55. The vector of paragraph 54, wherein the nucleic acid sequence is selected from the group consisting of: SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and SEQ ID NO: 72.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Example 1: Discovery of New *Neisseria Gonorrhoeae* Vaccine Antigens Expressed During Natural Mucosal Infection Using Integrated Bioinformatic Approaches In the last decade, an increasingly severe trend of antibiotic-resistant *Neisseria gonorrhoeae* strains has been reported worldwide, emphasizing the need for new therapeutic strategies to treat this sexually-transmitted infection. There is an urgent need to develop a vaccine to prevent gonococcal infections. Unfortunately, this has been delayed by the scarcity of suitable vaccine antigens, along with the elusiveness of the correlates of protective immunity in humans and insufficient animal models of gonococcal reproductive tract infection for testing protection. In the current study, hypothetical proteins expressed during natural human mucosal infection as compared to during in vitro growth were mined using a "reverse vaccinology"-like approach together with bioinformatic tools for the discovery of new candidate vaccine antigens. A Candidate Antigen Selection Strategy (CASS) was designed, divided into Discovery Phases DP-1 and DP-2. This strategy allowed for the identification of 36 gonococcal hypothetical proteins predicted to be immunogenic and membrane-associated, conserved in *N. gonorrhoeae* strains and with structural features suitable for recombinant expression and manufacturing. Six antigens were selected for immune characterization in mice, showing induction of cross-reactive immune responses across *N. gonorrhoeae* laboratory strains and clinically-relevant strains. Antisera to three hypothetical proteins exhibited bactericidal activity against all gonococcal strains tested, and one additional antiserum showed strain-dependent bacterial killing. These results support the CASS as a tool for discovery of new antigens among gonococcal hypothetical proteins expressed during human natural infection and their inclusion in the pool of vaccine candidates for an improved gonococcal vaccine.

Introduction

*Neisseria gonorrhoeae* is the causative agent of the sexually transmitted infection (STI) gonorrhea, a multi-faceted disease with high morbidity worldwide and an estimated 87 million cases annually (1). *N. gonorrhoeae* infections in men are mostly symptomatic (urethritis), while gonorrhea in women is often asymptomatic, leading to reproductive tract complications (pelvic inflammatory disease (PID), ectopic pregnancy and infertility), and disseminated gonococcal infections (DGI) (1). Once easily treated by a standard antibiotic course, the current therapeutic and pharmacologic approaches to treat *N. gonorrhoeae* infections are now complicated by the onset of fluoroquinolone resistance and rising levels of resistance to the last FDA-approved antibiotic, cefixime (2-7). Presently, the CDC recommends treatment with ceftriaxone and azithromycin, but resistance to cefixime and ceftriaxone has already developed outside the U.S. leading to the potential spread of untreatable gonorrhea. There is an urgent need to develop a vaccine to prevent gonococcal infections. Alternative options to failing antibiotic treatment include vaccination. Unfortunately, the elusiveness of the correlates of protective immunity in natural mucosal infections combined with insufficient animal models of gonococcal reproductive tract infection for testing protection, and importantly, the scarcity of suitable vaccine antigens has delayed vaccine development (8).

Major limitations of the existing mouse models of gonococcal female genital tract infection include requirement of hormone/antibiotics treatment, mouse strain specificity and genetic manipulation to ensure bacterial colonization and survival (9-12). A human volunteer male urethral infection model has been used to address the acute infection phase, however it is limited in that it does not replicate chronic female reproductive tract infections (13-16). Historical subunit antigens that have been tested in animal models and in the human male volunteer model have only shown limited protection (generally confined to homologous strains) defined by the production of antibodies with bactericidal activity (SBA). Correlates of protection and mechanisms of protective immunity in humans are unknown, and likely different from those in mice, impacting vaccine evaluation in vivo. Re-infection with both homologous and heterologous strains in humans suggests unsatisfactory memory responses. Furthermore, immune evasion or immune suppression mechanisms have also been shown, for example induction of low-titered non-protective or even blocking antibodies (i.e. anti-Rmp antibodies (17)).

*N. gonorrhoeae* does not possess the highly immune-protective capsular polysaccharide antigens (CPS) expressed by the closely related organism, *N. meningitidis* (18). To date, only two protein antigen vaccines have been tested in clinical trials and failed to show protection against heterologous infections (8). Other gonococcal surface proteins have been explored as antigens in a mouse model of infection, but the majority remain scarcely protective against heterologous strain infection. This is mostly due to high amino acid sequence and phase variability (i.e. pilin, porins, transferrin binding proteins TbpA and TbpB, efflux pump proteins (MtrC-MtrD-MtrE, FarA/B) (19-25)). More recent candidates include MetQ (26), MrsA/B (27), BamA (28) and ACP (29). The 2C7 LOS epitope-based vaccine has gained ground as a protective candidate (30-33), and interest in outer membrane vesicle vaccines has also been renewed, due to evidence of cross-reactive protection by the meningococcal OMV-based vaccine against *N. gonorrhoeae* (34-39).

Previous approaches based on reverse vaccinology (initially developed for the *N. meningitidis* serogroup B vaccine 4CMenB (40-42)), genomics- and proteomics-based strategies have investigated antigens previously undiscovered by conventional methods. (43-48). When lavage specimens from naturally infected human urethral and cervico-vaginal subjects are examined, it is revealed that 1) the gonococcus specifically responds to the male and female reproductive tract environments by expressing genes at different levels; and 2) gonococcus expresses and regulates gene expression differently in vitro. Genes detected as expressed at higher levels in vivo than in vitro are termed in vivo expressed factors (IVEFs). Additionally, about 30% of the gonococcal genes expressed during human infection encode for hypothetical proteins.

In the current study focusing on the gonococcal hypothetical proteins, a comprehensive, high-throughput in silico screening approach (candidate antigen selection strategy or CASS) was designed to identify new vaccine targets based on predicted immunogenicity, membrane association/surface exposure, conservation and with structure features favorable for future scale up and manufacturing. Two Discovery Phases (DP) were employed for identification of 36 hypothetical protein targets. Six of these 36 hypothetical proteins were expressed recombinantly and used to immunize mice. Immune characterization revealed induction of cross-reactive antibodies against *N. gonorrhoeae* laboratory and clinical strains, and strain-specific serum bactericidal activity. These studies supported discovery of new gonococcal antigen via the CASS approach and based on transcriptome analysis of gonococci during natural human mucosal infection.

Materials and Methods

Candidate antigen selection strategy (CASS) and computational tools. The following bioinformatic analyses and prediction tools were used to analyze and prioritize candidate antigens: VaxiJen for prediction of antigenicity and protective potential (cut-off of 0.4) (44, 51); PSORTb v3.0, PredictProtein and Gneg-mPLoc for protein subcellular localization (52-54); Vaxign found on the world wide web at <violinet.org/vaxgen/index.php> and BLASTp (BLAST 2.2.26+) (55, 56) for protein sequence analyses, amino acid sequence similarity with human/mouse/*E. coli* proteins, *N. gonorrhoeae* and *N. lactamica* proteins. Protein structure features were examined with HMTMM for prediction of presence and number of trans-membrane domains (57), with Phobius for prediction of topology (58), and with SignalP v5.0 and SecretomeP (59-61) for prediction of presence/type of signal peptides, cleavage site and post-translational modifications. Protein functional analyses were evaluated with BLAST, UniProtKB (62), PFAM (63) and by PubMed records. Gene presence, alleles distribution and sequence conservation were examined in *N. gonorrhoeae* (4198 strains) and *N. lactamica* (288 strains) using PubMLST available on the world wide web at <pubMLST.org/*Neisseria*> (64). Protein sequence conservation (deduced from from *N. gonorrhoeae* FA1090 (Gen Bank accession number AE004969)) was examined by BLASTp in NCBI.

Bacterial strains and growth conditions. *N. gonorrhoeae* strains F62 and FA1090 were used as laboratory reference strains. Two representative strains isolated from a Nanjing cohort strain selection were also used (49): *N. gonorrhoeae* strains U08401 and U08402, obtained from an infected male and his self-reporting monogamous female partner, respectively. Bacteria were grown overnight on GC agar plates supplemented with 1% IsoVitaleX at 37° C. with 5% $CO_2$ or in liquid culture in CDM for 1-3 h ($OD_{600}$ of $1=1-2\times10^9$ bacteria/ml) and resuspended at the desired concentration for each experiment. For formalin-fixing (FF), bacteria were incubated with 1% paraformaldehyde for 1 h at 4° C., washed and resuspended in PBS. *E. coli* strain BL21 was grown on LB agar plates at 37° C. with 5% $CO_2$ or in LB liquid cultures using kanamycin (50 μg/ml) or carbenicillin (100 μg/ml) as selection antibiotics.

Cloning and expression of recombinant gonococcal hypothetical proteins. NGO0416, NGO0690, NGO1043, NGO1215 and NGO1701 were cloned into a pET17b plasmid with an ampicillin-resistance cassette, and NGO0948 in a pET30a plasmid with kanamycin resistance (Genscript, Piscataway, NJ) and subsequently transformed into *E. coli* BL21 (DE3) for recombinant expression. Primers were codon-optimized based on the available protein sequences of *N. gonorrhoeae* FA1090. All constructs included a C-terminal 6x His-tag; NGO0948 was cloned as a full-length protein, and NGO0416, NGO0690, NGO1043, NGO1215 and NGO1701 were cloned as truncated proteins without the signal sequence. Transformed *E. coli* cultures inoculated in LB broth with the appropriate antibiotics were grown overnight at 22° C. in the presence of 1 mM IPTG for NGO0416 and NGO1043 expression, or overnight at 37° C. followed by IPTG induction the next day for 4 h at 37° C. for NGO0690, NGO0948, NGO1215 and NGO1701 expression.

Chromatography purification of recombinant hypothetical proteins. After induction, bacteria were collected by centrifugation at 5000 rpm for 15 min. at 4° C., resuspended in 3 ml of Buffer A (50 mM sodium phosphate, 300 mM NaCl, pH 7.8, 1× protease inhibitor cocktail (Sigma)) per gram of cells, and lysed with lysozyme and deoxycholate (0.1 mg/ml and 4 mg/gram of cell pellet) at room temperature until viscous. DNAse I (0.02 mg/gram of cell) was then added until the suspension returned non-viscous, followed by centrifugation (10,000×rpm for 20 min. at 4° C.) to separate the soluble protein fraction and the inclusion bodies. All proteins were purified on a $Ni^{++}$ fast-flow agarose (ThermoScientific) column using an AKTAprime plus chromatography system (GE). NGO1043, NGO1215 and NGO1701 resulted 50% or more soluble and were purified from the soluble fraction in Buffer A and a 10-300 mM imidazole gradient. The NGO0416, NGO0690 and NGO0948 inclusion bodies were solubilized in denaturing Buffer A (containing 10 mM imidazole and 6 M guanidine). Purification was carried out in denaturing Buffer B (50 mM sodium phosphate, 300 mM NaCl, pH 7.8, 1× protease inhibitor cocktail, 10 mM imidazole and 8 M urea) and a 10-300 mM imidazole gradient. The column flow-through, wash and elution fractions were examined by SDS-PAGE/Coomassie staining to assess protein purity. Dot blot was used to verify the positive fractions using a mouse anti-His tag HRP-conjugated antibody (Invitrogen) and 1-Step TNB detection (ThermoScientific). The pooled fractions were extensively dialyzed against PBS/0.02% $NaN_3$ and the protein concentration was measured by BCA assay (Pierce).

Immunization of mice. Female BALB/c mice (4 weeks old) (Jackson Labs) were housed and cared for according to National Institutes of Health (NIH) and Tufts University protocols. Groups of eight mice each were immunized subcutaneously (s.c.) three times at two-week intervals with purified recombinant proteins (10 μg/mouse/immunization)

formulated with alum (Imject) (ThermoScientific) at 1:1 v/v ratio in a total volume of 100 µl/immunization. A control group was immunized with PBS and alum as above (adjuvant control). Preimmune sera were collected prior to the first immunization and immune sera were collected two weeks after each immunization. Sera were stored at –80° C. until use.

Immunoblotting. Formalin-fixed (FF) bacteria ($2\text{-}4\times10^8$ CFU total) or outer membrane protein (OMPs) fractions isolated using Sarkosyl (26) (5 µg total) were spotted on a nitrocellulose filter using a slot-blot apparatus (Hoefer). The membranes were air-dried, blocked with 1% BSA in TBS/Tween 20 (TBS-T) and incubated with aliquots of pooled immune mouse sera (1:200 dilution) overnight at 4° C. An anti-mouse IgG secondary AP-conjugated antibody (Southern Biotech) was used to detect immunoreactive dots with NBT/BCIP chromogenic substrate (Biorad).

Antibody ELISA. For purified antigens, high binding ELISA plates were coated with 2 µg/well of each hypothetical protein in carbonate buffer pH 9.0, in PBS overnight at 4° C. Plates were washed, blocked with 1% BSA in PBS/0.05% Tween-20 for 2 h at room temperature and incubated overnight at 4° C. with serial dilutions of mouse pre-immune and immune sera. The next day, plates were washed, incubated with AP-conjugated secondary anti-mouse total IgG, IgG1 or IgG2a antibodies (Southern Biotech) followed by 1-step PNPP reagent (ThermoScientific) and spectrophotometric detection at $OD_{405}$. For whole bacteria, ELISA plates were coated with FF *N. gonorrhoeae* ($1\text{-}1.5\times107$ bacteria/well), incubated with sera at a 1:100 dilution and secondary antibody as above. Sera from individual mice were tested in duplicate wells, and pooled mouse sera aliquots were tested in quadruplicate wells. A reference standard curve was used to quantify the total IgG and the IgG subclasses in µg/ml with a linear regression function (65). The Th2/Th1 ratio was determined as IgG1/IgG2a.

Cytokine ELISA. IL-4 and IL-10 (Th2 cytokines), IL-12 and IFN-γ (Th1 cytokines), IL-6 and TNF-α (pro-inflammatory cytokines) were measured in mouse sera by ELISA using Opt-EIA kits (BD Biosciences) according to the manufacturer's specifications. Preimmune and immune sera from individual mice or pooled sera aliquots were tested as above. Cytokines were expressed in pg/ml and normalized to the pre-immune sera.

Flow cytometry. FF *N. gonorrhoeae* ($10^8$/ml) were incubated with pooled pre-immune and immune mouse sera (1:200) in 2% FBS/PBS for 30 minutes at 4° C., washed and stained with an anti-mouse IgG FITC-labeled secondary antibody (eBioscience) (1:1000) for 30 minutes at 4° C. Negative controls included bacteria alone and bacteria incubated only with FITC-labeled secondary antibody. The samples were examined with on a FACScan™ flow cytometer using CellQuest acquisition software (Becton Dickinson, Mountain View, CA) and analyzed with FlowJo software (Tufts University Flow Cytometry Core). Gating was used to exclude cellular debris. The histograms shown are representative of a minimum of two separate experiments.

Bactericidal assay (SBA). The SBA were carried out in 96-well U-bottom plates in a 75 µl total volume. Normal human serum depleted of IgG and IgM was used as a source of complement (Pel-Freez Biologicals). Briefly, *N. gonorrhoeae* liquid cultures at $OD_{600}$ of $0.2\text{=}2\text{-}4\times10^8$ CFU/ml were serially diluted to obtain $2\text{-}4\times10^4$ CFU/ml. For each experimental condition, 12.5 µl of bacteria were seeded per well in HBSS containing 0.15 mM $CaCl_2$) and 1 mM $MgCl_2$ (HBSS$^{++}$) and incubated for 20 min. at room temperature with serial dilutions of heat-inactivated (56° C. for 30 min.)

pooled mouse pre-immune and immune sera previously depleted of the IgM fraction. For FA1090, 20% NHS was added to each well, and for F62, U08401 and U08402, 10% NHS was used. 10 µl aliquots of bacterial suspension were immediately plated on IsoVitalex-GC agar plates (Time 0). The 96-well plates were incubated at 37° C. for 30 min. with gentle shaking, and aliquots were plated as above (Time 30). The next day, bacterial killing was evaluated by CFU counting; survival was expressed as percent of bacterial viability at T30/T0±SEM. The bactericidal titer was defined as the reciprocal of the lowest serum dilution with ≥50% killing after 30 minutes (32). Controls included bacteria alone, bacteria incubated with NHS alone (negative controls), and with sera from PBS/alum-immunized mice (adjuvant control).

Statistical analysis. Statistical significance was examined with unpaired t-test for comparisons of two samples/conditions, and with one-way analyses of variance (ANOVA) to determine significance between multiple groups with Tukey's multiple comparisons or uncorrected Fisher LSD tests. Differences were considered significant at a minimum p value of 0.05, as indicated in the text and in the description of the Figures.

Results

Gonococcal Candidate Antigen Selection Strategy (CASS).

RNA-seq analysis of urethral and cervico-vaginal lavage specimens from a cohort of naturally-infected subjects attending the National Center for STD Control (NCSTD) in Nanjing, China, was carried out in a previous study (49, 50). The gonococcal strains isolated from infected males and their female partners shared DNA sequence identity by whole DNA sequencing and high homology with *N. gonorrhoeae* FA1090, and had higher antibiotic resistance than strains isolated in the US (Gonococcal Isolate Surveillance Project (GISP) (6, 66, 67)). Analysis of the gonococcal transcriptome expressed during natural human mucosal infection revealed that approximately 30% of the total expressed genes encoded hypothetical proteins (49). These totaled 678 genes in the specimens from infected males and 655 genes in the female specimens (FIG. 1). These were mined with a multi-pronged candidate antigen selection strategy (CASS) designed to prioritize hypothetical proteins expressed in vivo during male and female infections, and potentially immunogenic, surface-exposed and not hypervariable, via the following two Discovery Phase (DP).

Discovery Phase (DP) 1: Hypothetical proteins were segregated into either low-expression or high-expression groups by applying a gene expression unit cut-off of 50 RPKM (RNA-seq gene expression=unit of transcript expression in RPKM or Reads per Kilobase of transcript per Million mapped reads). Proteins with RPMK<50 were excluded (469 in the female dataset and 394 in the male dataset) (FIG. 1), and those with RPKM>50 (186 in the female dataset and 284 in the male dataset) were matched to identify those present in both datasets, resulting in a pool of 163 shared hypothetical proteins (FIG. 1).

Moving towards a manageable number of candidates, the 163 hypothetical proteins were filtered using high throughput bioinformatic tools. First, the probability for these being immunogenic was examined with VaxiJen (51), which assigns an unbiased antigen probability score based on the amino acid sequence. Setting a cut-off threshold of 0.4 (44), this analysis predicted 112 hypothetical proteins to be putative antigens (FIG. 1). Next, analysis of protein cellular distribution with PSORTb v3.0, PredictProtein and GnegmPLoc (52-54) predicted 43 hypothetical proteins to be cytosolic; these were excluded. The remaining 69 hypothetical proteins predicted to be non-cytosolic were advanced to Discovery Phase 2 (DP-2) (FIG. 1).

Figure 2:
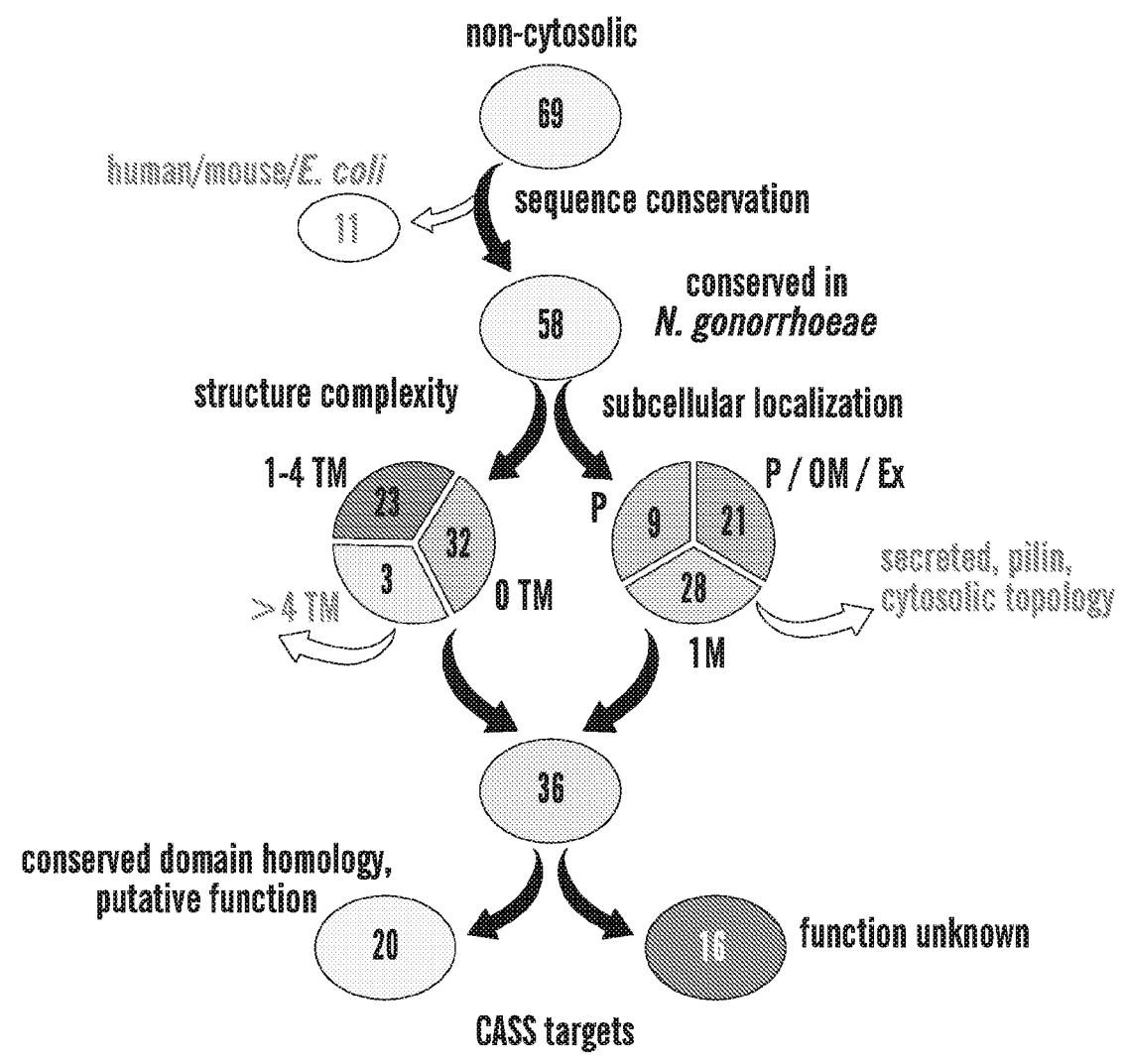
FIG. 2 shows CASS: Discovery Phase 2 (DP-2). In silico analyses of 69 non-cytosolic gonococcal hypothetical proteins from DP-1 with Vaxgen found on the world wide web at <violinet.org/vaxgen/index.php> and BLASTp (BLAST 2.2.26+) predicted 11 hypothetical proteins to share high amino acid sequence similarity to human, mouse and *E. coli* proteins. Amino acid sequence analyses of the remaining 58 hypothetical proteins by BLASTp predicted conservation in *N. gonorrhoeae*. Structure complexity analyses with HMTMM predicted 3 proteins to possess >4 trans-membrane domains (TM) and 55 with 0-4 TMs. Membrane localization analyses with Psort, Protein Predict and Gneg-mPLoc predicted 28 hypothetical proteins to be associated with the inner membrane (IM), 9 with the periplasm (P) and 21 with the outer membrane (OM) (facing the periplasm or the extracellular space (P/OM/Ex)). Topology and signal peptide analyses with Phobius, SecretomeP and SignalP 5.0 predicted 9 IM hypothetical proteins with cytosolic topology/function, 3 extracellular proteins and 7 putative pilin-associated proteins. The final CASS pool was composed of 36 hypothetical proteins: 20 had putative function or conserved domain similarity to other bacterial proteins in NCBI BLAST, UniProtKB, PFAM analyses, and 16 were fully hypothetical proteins with unknown function.

Discovery Phase (DP) 2: The amino acid sequence of the 69 hypothetical proteins was examined for conservation with human, mouse and *E. coli* proteins using Vaxign available on the world wide web at <violinet.org/vaxgen/index.php> and BLASTp (BLAST 2.2.26+) (55, 56) (FIG. 2). Hypothetical proteins with an E-value >1e-10 versus human/mouse genes were considered potential autoantigens and were excluded (3 proteins). Proteins with >40% sequence similarity >70% of the gene length in *E. coli*, considered widespread bacterial housekeeping genes, were also excluded (8 proteins). The remaining 58 hypothetical proteins were assessed for amino acid sequence conservation within the available *N. gonorrhoeae* genomes in NCBI by BLAST searches and all had >40% sequence similarity across >70% of the amino acid sequence in multiple *N. gonorrhea* strains (FIG. 2).

By analysis of presence and number of trans-membrane domain (TM) with TMHMM Server v.2.0 (57), 3 hypothetical proteins out of the 58 candidates were predicted to have >4 TMs and were considered proteins with a potentially high structure constraints; 23 candidates were predicted to have 1-4 TMs (considered low/moderate structure constraints) and 32 candidates did not possess TM domains (FIG. 2). Concurrently, the hypothetical proteins association with the bacterial membranes compartment was parsed in detail, also aided by topology and secretion predictions with Phobius, SignalP and SecretomeP (58-61): 28 hypothetical proteins were likely associated with the inner membrane (IM), 9 with the periplasm (P) and 21 with the outer membrane, either facing the periplasm or the extracellular space (P/OM/EX) (FIG. 2). The IM-predicted proteins were revised by PSI-Blast and manually curated to exclude those with likely involvement in cytosolic processes (9 proteins). Post-translational structure modifications such as presence and type of signal peptide (SP) indicated that 20 hypothetical proteins were not predicted to contain a SP; 16 hypothetical proteins contained a classical SP, and 11 had a SP typical of outer membrane-exposed lipoproteins (inner membrane lipoproteins have an aspartic acid (D) in position +2 after the cleavage site); 7 hypothetical proteins contained a TatP-predicted SP and 5 were non-classically exported membrane proteins (special folding requirements or part of large protein complexes) (not shown). Based on these results, 3 hypothetical proteins predicted to be extracellular were excluded, and 7 putative pilin-associated proteins (FIG. 2). Overall, completion of DP-2 led to a total of 36 hypothetical proteins, 16 of which were fully hypothetical and 20 had putative function or conserved domains similarity to other bacterial proteins in NCBI BLAST, UniProtKB, PFAM analyses (FIG. 2).

In this study, six initial hypothetical protein candidates were selected for immunologic characterization. Table 2 (FIG. 9) summarizes the CASS features for these candidates. NGO0416 is a predicted periplasmic protein with putative conserved domain (CD) similarity to the N-terminal domain of the LamB sugarporin (68); NGO0690 is a putative lipoprotein predicted to be associated with both the periplasm and the OM (P/OM); NGO0948 is also a P/OM putative lipoprotein, possibly a member of the NlpB/DapX family (COG3317) and has homology to BamC (a potential meningococcal vaccine antigen (69-71)); NGO1043 is a putative P/OM lipoprotein, possibly glycosylated, with homology to the meningococcal antigen Ag473 (42, 72);

NGO1215 is a predicted periplasmic protein with CD homology to a copper chaperone PCu(A)C superfamily (COG2847) (potential virulence factor) (73), and NGO1701 is a membrane protein predicted to be periplasmic with CD homology to a TAT_Cys_rich four helix bundle copper-binding protein of the DUF326 superfamily.

Sequence Analysis and Conservation of the Hypothetical Protein Candidates.

A detailed gene and protein sequence analysis of these candidates was carried out by assessing gene presence and sequence conservation in a total of 4198 gonococcal genomes available in the PubMLST database available on the world wide web at <pubmlst.org/*neisseria*/> (64) (accessed April 2019)). This was a globally representative collection of *N. gonorrhoeae* strains spanning 6 decades (1960-2018) and included strains from the Nanjing collection. The 6 hypothetical proteins were present in all gonococci examined and were part of the gonococcal core genome (Ng cgMLST v1.0). Corresponding NEIS nomenclature for these proteins is NEIS0782 (NGO0416), NEIS0906 (NGO0948), NEIS1164 (NGO0690) NEIS1474 (NGO1215), NEIS2446 (NGO1043) and NEIS2720 (NGO1701) (Table 3). Differing numbers of alleles were identified, indicating some sequence diversity. The most conserved protein was NGO0416, with only 6 alleles (p-distance=0.006) while the most diverse was NGO0948 (p-distance=0.005) with 55 alleles, although alleles could not be assigned for 8 strains, due to incomplete sequence data as genes were located at the end of contigs. This was also the case for NGO1215 in 2 isolates. A total of 27 strains also had incomplete NGO1043 genes, and a 21 bp repeat region at nt 127 (5'-GCCGCCGAGTCTGCGGCTTCT-3') was present 3 times in allele 138, twice in allele 137 and once in the remaining alleles except allele 141. Due to the large number of alleles for some genes, only those corresponding to the most represented are shown, specifically those with above 5% representation in the total strains (Table 3). For example, 3069 *N. gonorrhoeae* strains possessed NGO0416 allele 17, equivalent to 73% of the total 4198 isolates. The non-synonymous amino acid sequence mutations in the most represented alleles are also indicated in Table 3.

TABLE 3

Hypothetica protein alleles distribution in *N. gonorrhoeae* (4198 strains in PubMLST).

| Gene | Total alleles n. | [1]Allele/ isolates | [2]% of total isolates (4198) | p-distance | Non-synonymous mutations |
|---|---|---|---|---|---|
| ngo0416 | 6 | 17/3069 | 73 | 0.006 | — |
| (neis0782) | | 26/124 | 26.7 | | — |
| ngo0690 | 17 | 7/3332 | 79.3 | 0.01 | — |
| (neis1164) | | 32/815 | 19.4 | | 32.1/S38R |
| ngo0948 | 55 | 12/2354 | 57 | 0.005 | — |
| (neis0906) | | 28/363 | 8.6 | | 28.1/A319R |
| | | 32/324 | 7.7 | | 32.1/I18M-T19K |
| | | 214/248 | 5.9 | | 214.1/Q49R |
| ngo1043 | 27 | 57/2720 | 64.7 | 0.01 | — |
| (neis2446) | | 64/691 | 16.4 | | 64.1/V65A |
| | | 58/283 | 6.7 | | 58.1/V65A-A116T |
| | | 80/262 | 6.2 | | 80.1/V65A |

TABLE 3-continued

Hypothetica protein alleles distribution in *N. gonorrhoeae* (4198 strains in PubMLST).

| Gene | Total alleles | [1]Allele/ n. isolates | [2]% of total isolates (4198) | p-distance | Non-synonymous mutations |
|---|---|---|---|---|---|
| ngo1215 (neis1474) | 13 | 13/3817 16/273 | 91 7 | 0.012 | 13.1/x143P 16.1/x143S |
| ngo1701 (neis2720) | 11 | 1/3379 2/803 | 80.4 19.12 | 0.005 | — 2.1/E126A |

[1]Most frequent alleles in the highest number of strains.
[2]Percent of strains expressing a given allele within the total number of isolates examined. Data collected from the world wide web at <pubmlst.org/bigsdb?db = pubmlst_neisseria_isolates> accessed on April 2019.

The distribution of the 6 hypothetical proteins was also assessed in *N. lactamica* (a total of 288 genomes) in Pub-MLST. NGO0416 was absent in all *N. lactamica* genomes and no allelic overlap with gonococci was observed for the other 5 hypothetical protein genes. Comparison of the most prevalent alleles from each species for each locus revealed low conservation (Table 4). BLASTp analysis of the amino acid sequences of the 6 candidates with *N. lactamica* proteins available in NCBI revealed that only NGO1043 shared a maximum of 60% amino acid sequence identity over the entire protein length. Upon analysis of protein conservation of all the 36 gonococcal hypothetical proteins derived by CASS, only 4 additional proteins besides NGO1043 shared a maximum of 60% sequence similarity with *N. lactamica* proteins (not shown).

TABLE 4

PubMLST analysis of the 6 hypothetical protein candidate alleles in *N. lactamica*[1]

| Gene | Total alleles | [1]Allele/n. isolates | [2]% of total isolates (288) | p-distance | Alleles comparison to *N. gonorrhoeae* |
|---|---|---|---|---|---|
| ngo0416 (neis0782) | — | —/288 | 0 | 0 | 0 |
| ngo0690 (neis1164) | 13 | 3/229 5/23 | 79.5 7.9 | 0.054 | 3 vs 7 |
| ngo0948 (neis0906) | 17 | 3/225 70/21 | 78.1 7.2 | 0.062 | 3 vs 12 |
| ngo1043 (neis2446) | 8 | 28/242 77/21 | 84 7.3 | 0.032 | 28 vs 57 |
| ngo1215 (neis1474) | 10 | 34/214 7/23 | 74.3 7.9 | 0.034 | 34 vs 13 |
| ngo1701 (neis2720) | 10 | 20/225 24/823 | 78.1 7.9 | 0.024 | 20 vs 1 |

[1]Most frequent alleles in the highest number of strains.
[2] Percent of strains expressing a given allele within the total number of isolates examined. Data collected from the world wide web at <pubmlst.org/bigsdb?db=pubmlst_neisseria_isolates> accessed on April 2019.

Network—Centrality Analysis of Target Genes.

Figure 3A:
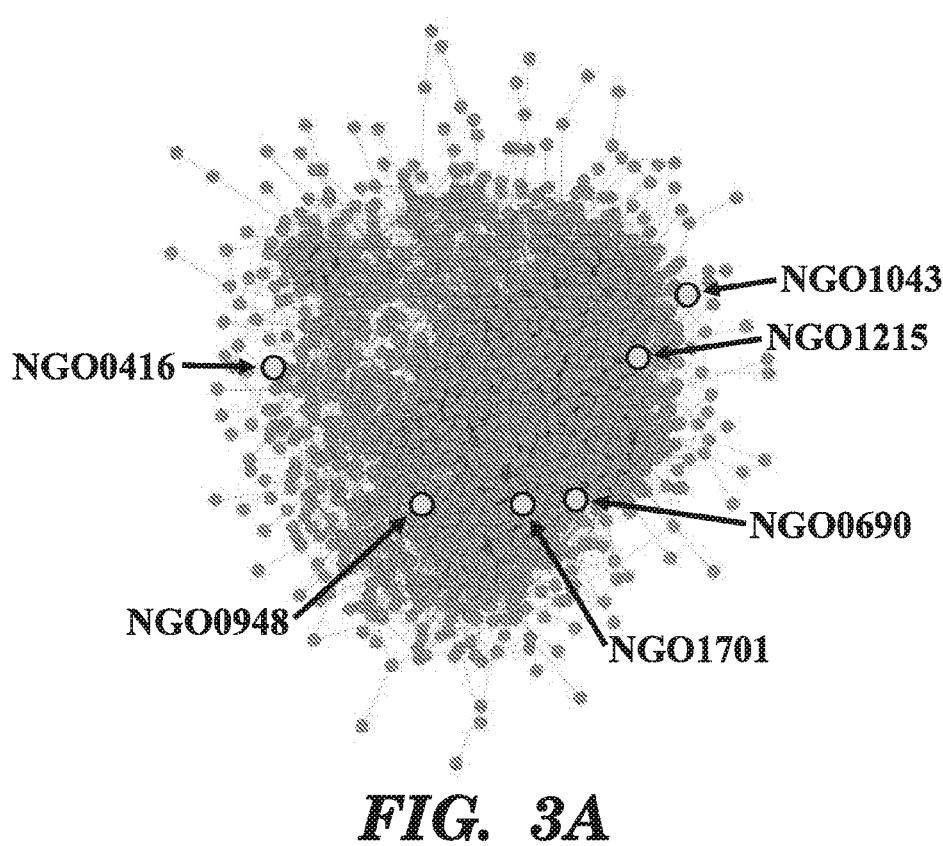
FIG. 3A-3B shows network analysis of the 6 hypothetical protein candidates.
Figure 3B:
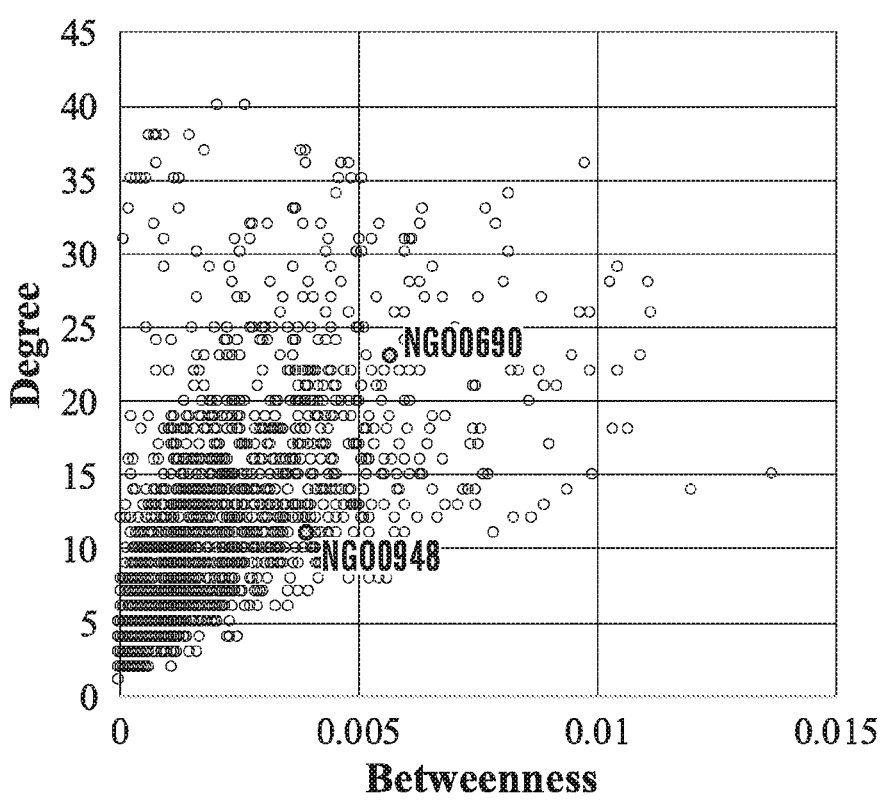

As a further analysis of gene expression in correlation with growth conditions and environment, a transcriptome data was merged with a collection of additional RNA-seq datasets derived from different and multiple *N. gonorrhoeae* experiments (74-77). A network linking genes by their co-expression was generated (McClure et al.), where each gene represents is represented by a node and each instance of high correlation among two nodes by an edge. Within these networks, the position of a gene in respect to the total genes reflects its centrality, measured in degrees and betweenness. The degree refers to the number of edges a node has with other nodes, and the betweenness is a measure of how much a single node connects two larger clusters of nodes. The network inferred for *N. gonorrhoeae* contained ~1000 genes (FIG. 3A). The centrality scores of the 6 hypothetical protein candidates within this network were examined and revealed that NGO0948 had both a high degree and a high betweenness value, NGO690 had a high betweenness value (FIG. 3B) and the remaining 4 genes had average centrality values for both measurements (not shown). Information on a gene's centrality adds to its potential as putative vaccine target, although lower or even lack of centrality are not exclusion criteria.

Cloning, Expression and Purification of the 6 Hypothetical Protein Candidates.

NGO0416, NGO0690, NGO0948, NGO1043, NGO1215, NGO1701 were cloned as truncated proteins without the SP, and NGO0948 was cloned as a full-length protein. NGO1043, NGO1215 and NGO1701 were 50% or more soluble and were purified by Ni[++] affinity chromatography in native condition; NGO0416, NGO00690 and NGO0948 were purified in denaturing conditions from inclusion bodies. The positive fractions were identified by dot-blot analysis with a mouse anti-His antibody, and the protein purity was examined by SDS-PAGE and Coomassie staining based on the predicted molecular weight of each protein (not shown).

Gonococcal Hypothetical Proteins are Immunogenic in Mice.

Figures 4A, 4B, 4C:
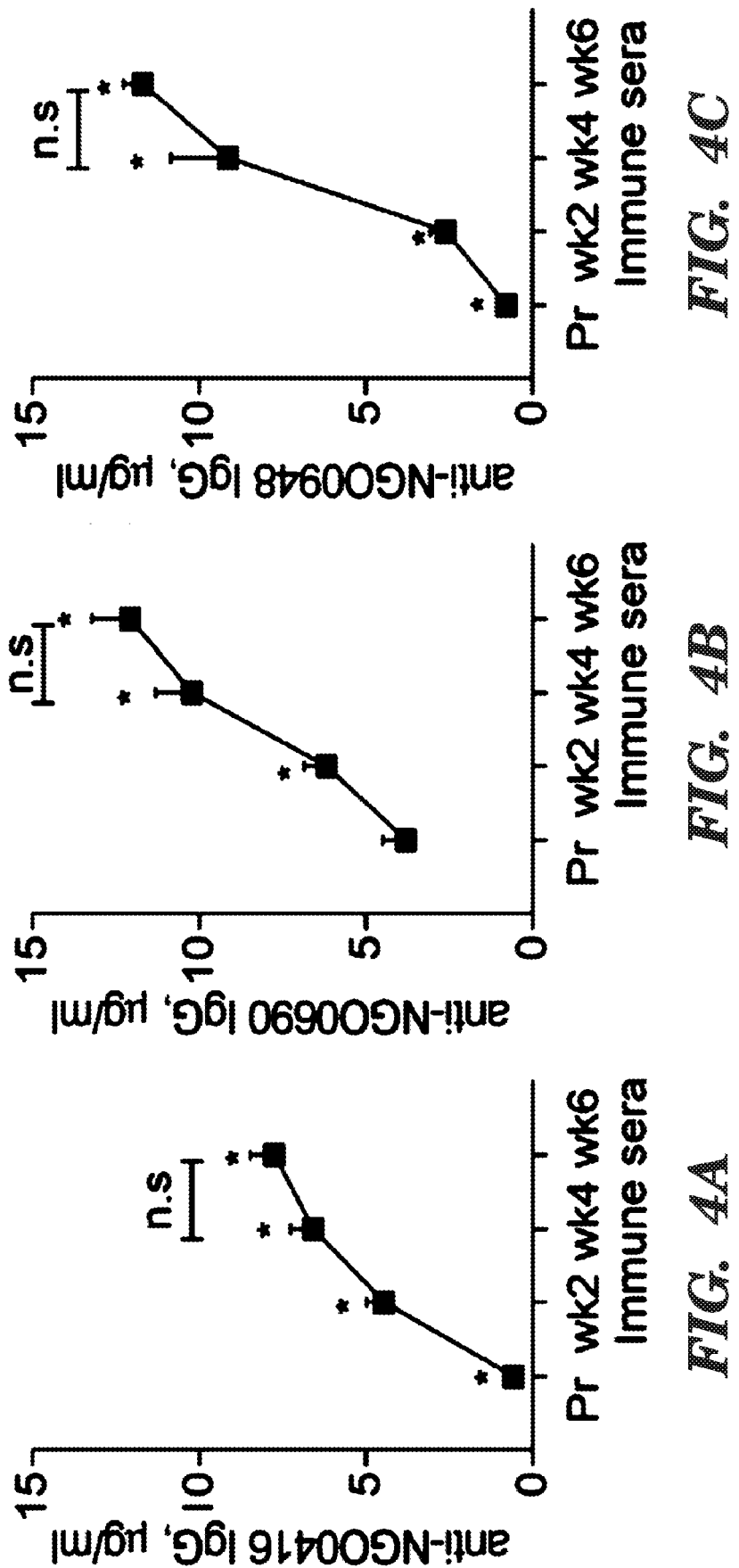
FIG. 4A-4F shows gonococcal hypothetical proteins are immunogenic. Total IgG (µg/ml±SEM) measured by ELISA in sera from mice immunized with FIG. 4A) NGO0416.
Figures 4D, 4E, 4F:
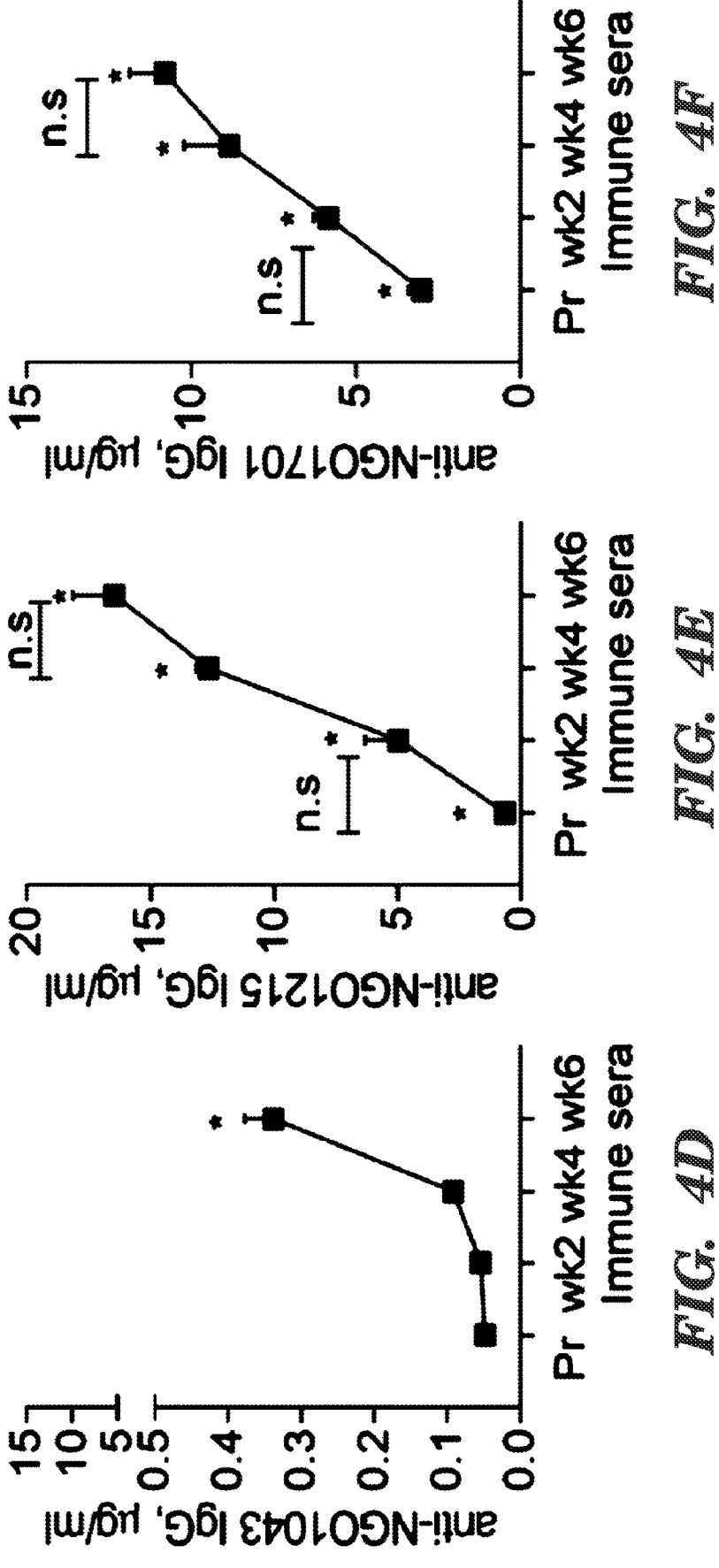

The purified proteins were used to immunize female BALB/c mice subcutaneously with alum as an adjuvant. Preimmune sera (Pr) and immune sera were tested for presence and amounts of antigen-specific antibodies by ELISA. A robust production of antigen-specific IgG was induced by immunization with NGO0416, NGO0690, NGO0948, NGO1215 and NGO1701 (FIGS. 4A-C and 3E-F), while NGO1043 induced substantially lower IgG amounts (FIG. 4D). Values were considered significantly different for p between 0.001 and 0.05 by one-way ANOVA with Tukey's multiple comparisons test, indicated by *. Analysis and quantification of the IgG subclasses revealed abundant levels of IgG1, typically observed in the Th2-type response elicited when using alum as adjuvant (Table 5). The IgG1/IgG2 ratio indicated a strong Th2 bias for NGO0690 and NGO1043 (ratio >10), and possibly a more balanced Th2/Th1 bias for NGO1701 (IgG1/IgG2a ratio close to 1).

TABLE 5

IgG subclasses. Serum IgG1 and IgG2a (µg/ml ± SEM) and IgG1/IgG2a ratio.

| Group | IgG1 | IgG2a | IgG1/IgG2a |
|---|---|---|---|
| NGO0416 | 16.6 ± 0.8 [a] | 2.86 ± 0.4 | >1 [b] |
| NGO0690 | 17 ± 0.3 [a] | 0.007 ± 0.002 | >>1 [a] |
| NGO0948 | 16 ± 2.4 [a] | 4.2 ± 0.6 | >1 [b] |
| NGO1043 | 0.42 ± 0.15 | $1.9 \cdot 10^{-5} \pm 6.4 \cdot 10^{-6}$ | >>1 [a] |
| NGO1215 | 8.3 ± 0.09 [a] | 0.89 ± 0.3 | >1 [b] |
| NGO1701 | 30.6 ± 0.8 | 35.3 ± 1.37 | ~1 [c] |

[a] strong Th2 bias
[b] Th2 bias
[c] balanced Th1/Th2

Gonococcal Hypothetical Proteins Induce Serum Cytokines Production in Mice.

Serum cytokines were measured by ELISA and expressed in pg/ml normalized to the pre-immune sera. Immunization with NGO0416 and NGO0690 induced the highest levels of IL-4, while NGO1043 induced low IL-4 and IL-10 levels (Table 6). All the antigens induced comparable IL-12p70 levels, while NGO0416 and NGO1701 induced higher IFN-γ than the other antigens. Immunization with NGO0690 and NGO1701 induced high IL-6 levels, and TNF-α was elevated in response to NGO0416, NGO0948 and NGO1701 (Table 6). Overall, the variability in serum cytokine levels induced by each antigen, despite being used with the same adjuvant, suggested a potential antigen-specific contribution to the inflammatory profile elicited by immunization.

TABLE 6

Serum cytokines. IL-4, IL-10, IL-12p70, IFN-γ, IL-6 and TNF-α (pg/ml, ratio to pre-immune sera ± SEM)

| Gene | IL-4 | IL-10 | IL-12p70 | IFN-γ | IL-6 | TNF-α |
|------|------|-------|----------|-------|------|-------|
| NGO0416 | 14.6 ± 1.6 [a] | 8.7 ± 2.5 [b] | 2.2 ± 0.6 [d] | 5.6 ± 0.5 [a] | 1.8 ± 0.6 | 4 ± 0.7 |
| NGO0690 | 9.5 ± 0.4 [a] | 4.4 ± 0.6 | 1.2 ± 0.1 | 1.8 ± 0.2 | 6.4 ± 2 | 0.8 ± 0.2 [c] |
| NGO0948 | 2.2 ± 0.7 | 3.6 ± 0.7 | 0.8 ± 0.1 | 0.9 ± 0.4 | 1.4 ± 0.3 [c] | 3.4 ± 0.5 |
| NGO1043 | 0.5 ± 0.1 | 1.7 ± 0.2 [c] | 1.4 ± 0.1 | 1.2 ± 0.1 [c] | 1 ± 0.1 [c] | 1.1 ± 0.2 [c] |
| NGO1215 | 1.7 ± 0.2 | 2.1 ± 0.2 | 1.3 ± 0.08 | 1 ± 0.2 [c] | 1.2 ± 0.1 [c] | 1 ± 0.2 [c] |
| NGO1701 | 2.8 ± 0.3 | 5.6 ± 0.7 | 1.6 ± 0.3 | 3.2 ± 1 | 11 ± 7.2 | 5.5 ± 2.9 |

[a] significant by one-way ANOVA with Tukey's multiple comparison test vs all groups;
[b] vs NG01215;
[c] vs NG01701;
[d] vs NG00948

Gonococcal Hypothetical Proteins are Expressed in Diverse N. gonorrhoeae Strains and Elicit Cross-Reactive Antibodies.

Figures 5A, 5B:
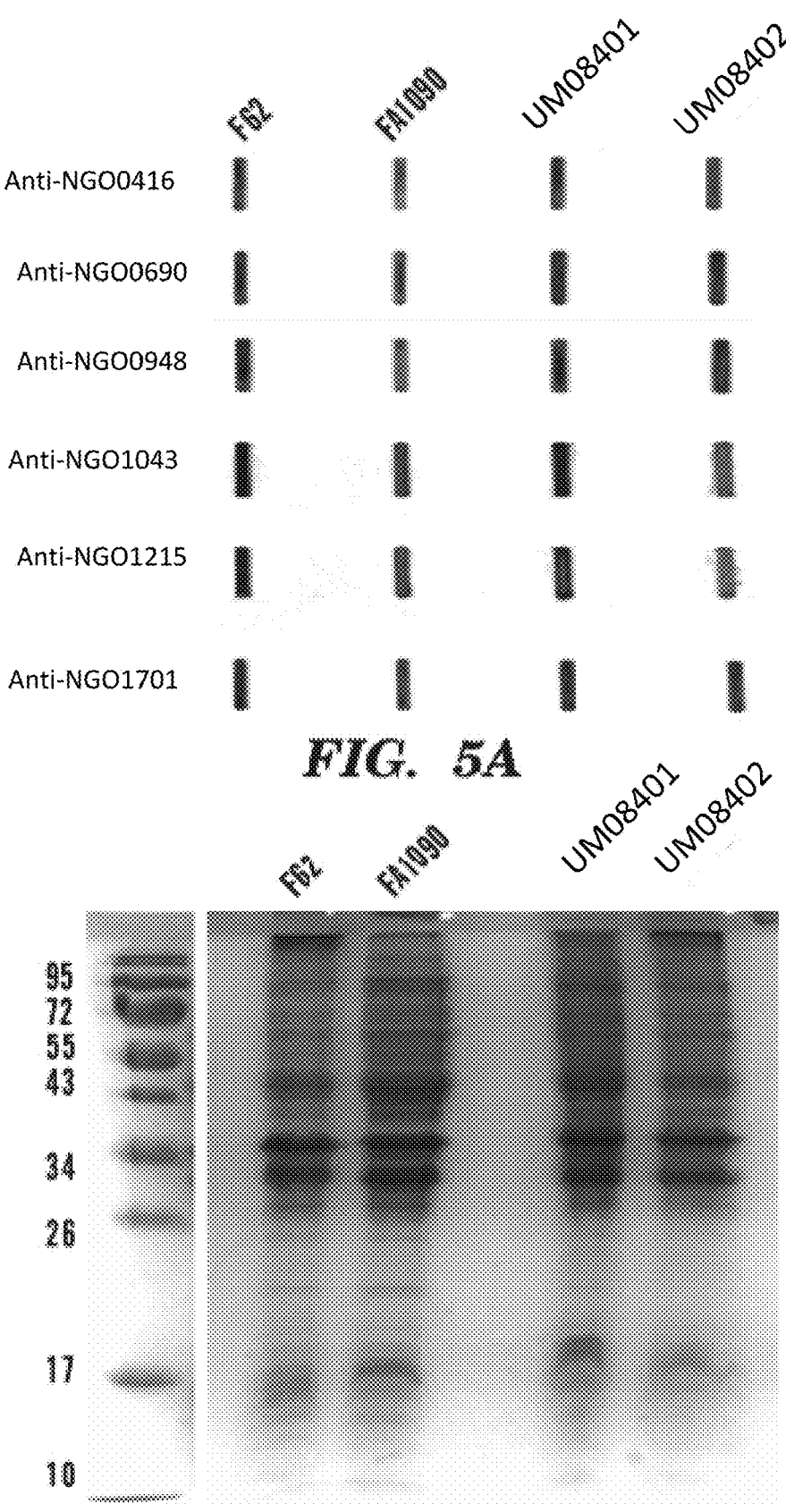
FIG. 5A-5B shows sera cross-reactivity with whole *N. gonorrhoeae* organisms.

To confirm immune recognition of the 6 hypothetical proteins in whole bacteria, the antisera were tested by slot blot against formalin fixed (FF)N. gonorrhoeae strains F62 and FA1090 and two strains from a Nanjing cohort collection, U08401 and U08402 (49, 50). Pooled mouse immune mouse sera to each of the hypothetical proteins recognized these four strains, indicating presence and immune reactivity of each of the six candidates in whole bacteria (FIG. 5A). Equal total protein content in the spotted bacteria aliquots was verified by SDS-PAGE and Coomassie staining of an equivalent bacterial volume, showing consistent bands distribution and intensity in all the samples (FIG. 5B).

Figures 6A, 6B, 6C:
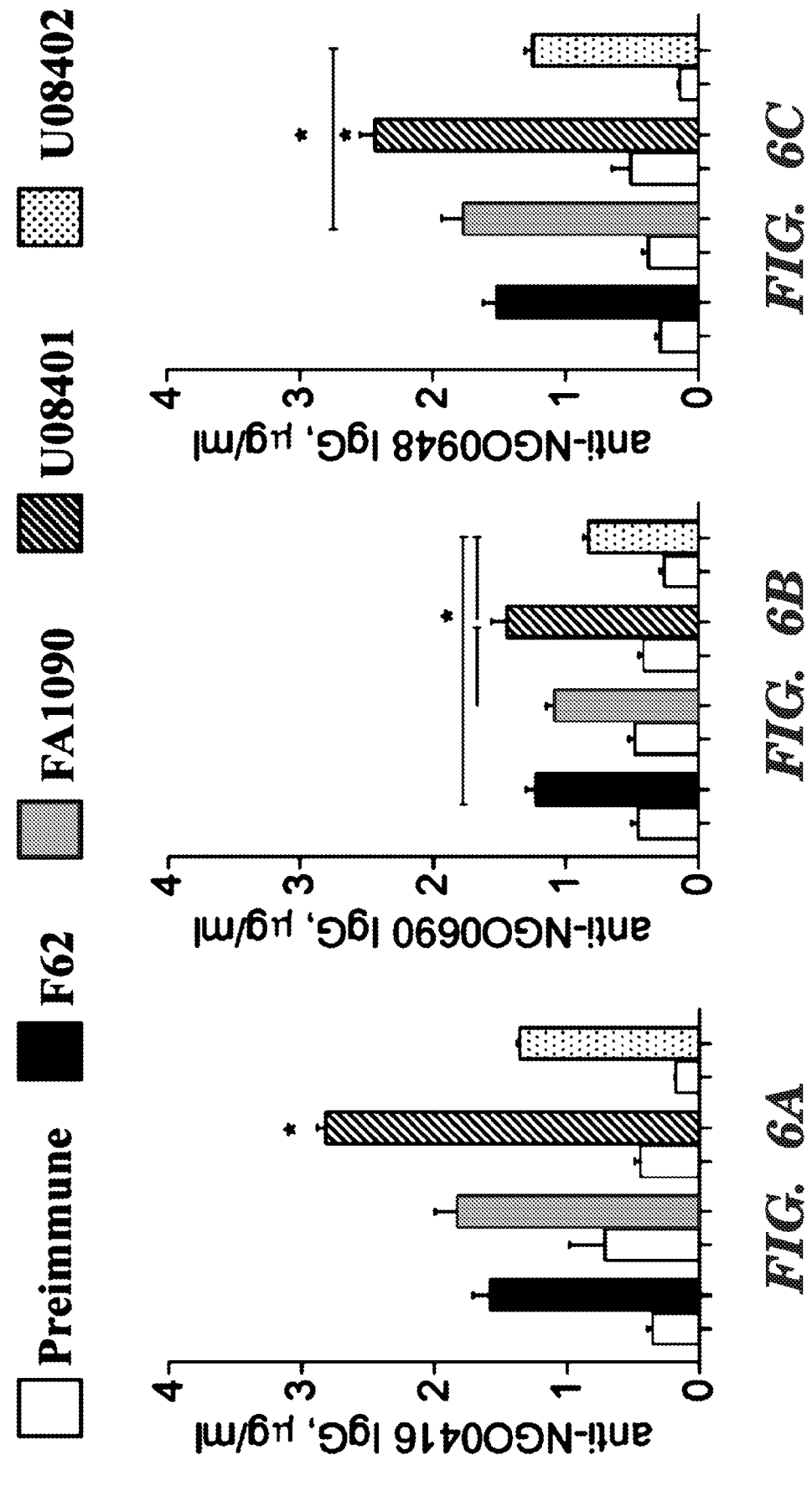
FIG. 6A-6F show sera cross-reactivity with whole *N. gonorrhoeae* organisms by ELISA. Total IgG (µg/ml±SEM) measured by ELISA in sera from mice immunized with FIG. 6A) NGO0416.
Figures 6D, 6E, 6F:
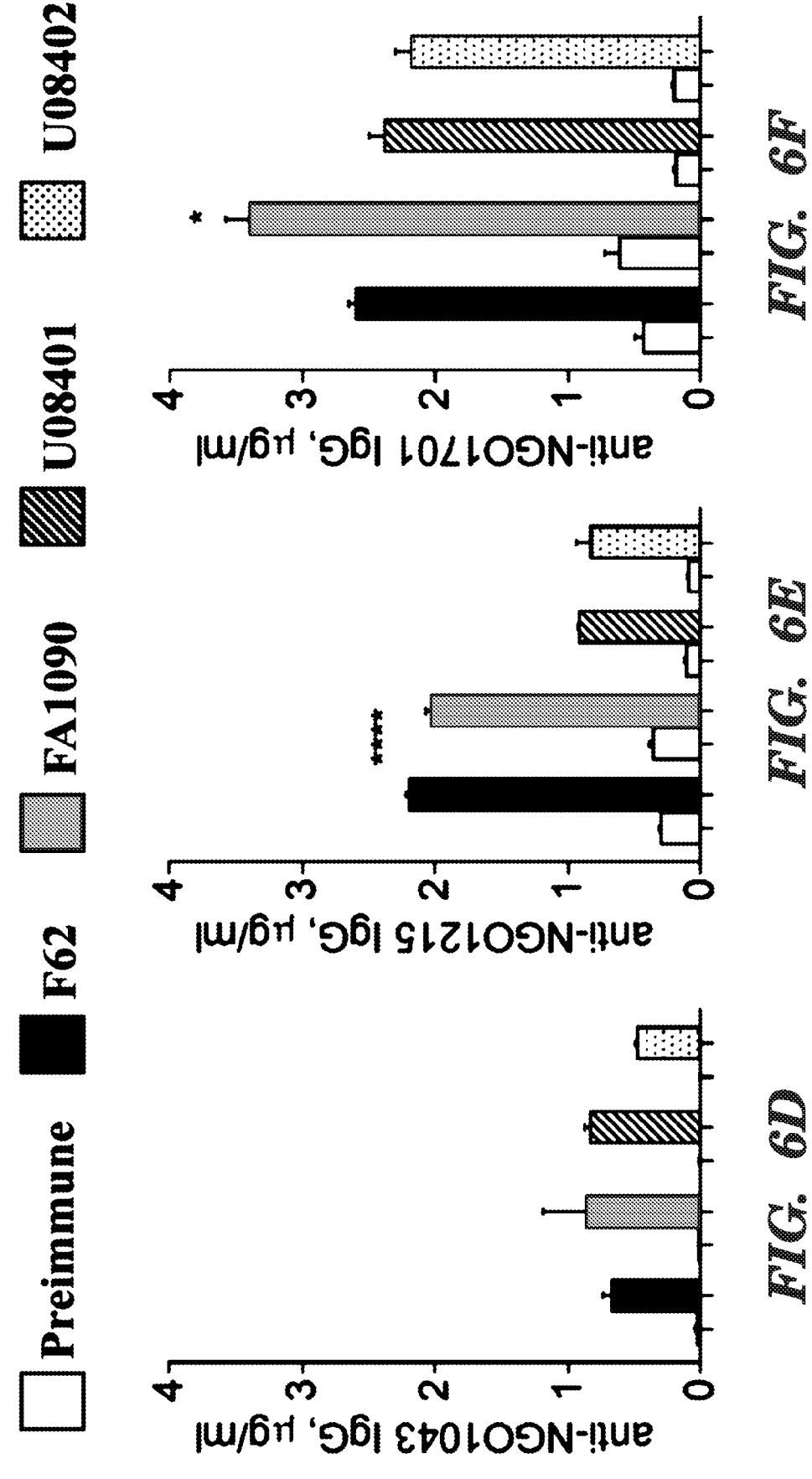

Sera cross-reactivity was then quantified by whole-cell ELISA of FF bacteria and IgGs were expressed as μg/ml±SEM. A significantly higher anti-NGO0416 and anti-NGO0948 IgG amount was detected against N. gonorrhoeae strain U08401 compared to the other three strains tested, and a similar trend was also observed for anti-NGO0690 (FIG. 6A-C, striped bars). IgG levels to NGO1043 were low but consistent among the four strains (FIG. 6D) and lastly, a trend of higher IgG amounts to NGO1215 and NGO1701 against N. gonorrhoeae F62 and FA1090 strains than to the clinical isolate strains was observed (FIG. 6E-F, black and gray bars) particularly for anti-NGO1215 sera. Overall, the slot blot analysis and the ELISA results indicated that the 6 hypothetical proteins were expressed and recognized by the corresponding mouse antisera in diverse whole N. gonorrhoeae strains with an apparent strain-specificity. This may be due to variable expression of these specific proteins in vitro among the four N. gonorrhoeae strains.

Gonococcal Hypothetical Proteins Localization in the Bacterial Membrane.

Figure 7A:
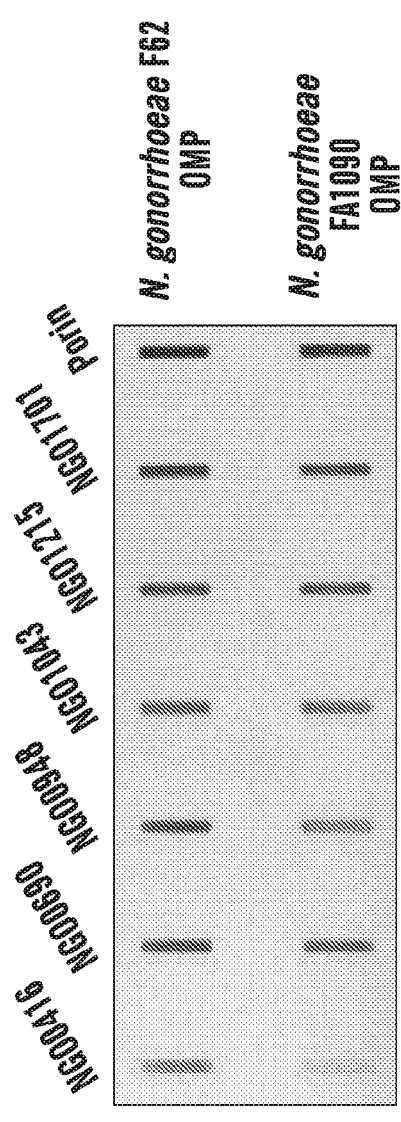
FIG. 7A-7B shows membrane localization and surface expression of gonococcal hypothetical proteins in whole *N. gonorrhoeae* organisms.

To verify the protein localization predictions, outer membrane protein (OMP) fractions from N. gonorrhoeae F62 and FA1090 were examined by immunoblot blot analysis with the mouse immune sera to each of the hypothetical protein. FIG. 7A shows a representative immunoblot of OMPs (5 μg total protein content); the hypothetical proteins were recognized in OMPs from both N. gonorrhoeae strains with variable intensity. NGO0416 was the least immunoreactive in both strains, possibly due to only partial presence/exposure in the OMP fractions and/or to low expression levels particularly in N. gonorrhoeae FA1090. Similarly, NGO0948 also showed an apparent lower immunoreactivity in OMPs from N. gonorrhoeae FA1090, while NGO0690, NGO1043, NGO1215 and NGO1701 were consistent in both strains (FIG. 7A). An anti-porin mouse antibody was used as a control for the OMP content and showed high immunoreactivity in both OMP fractions (porins represent >60% of the neisserial OMPs).

Figure 7B:
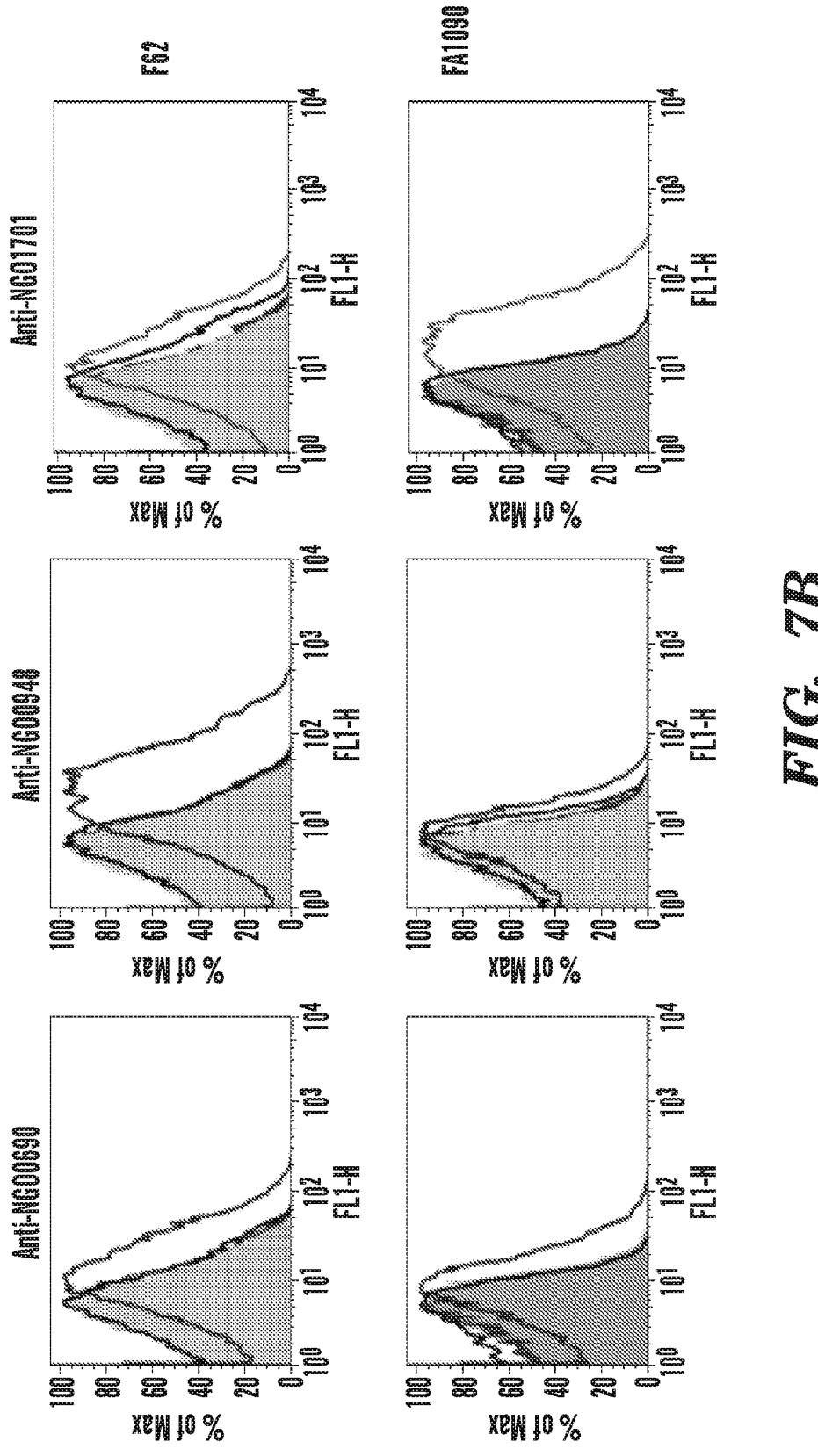
Figure 7B:
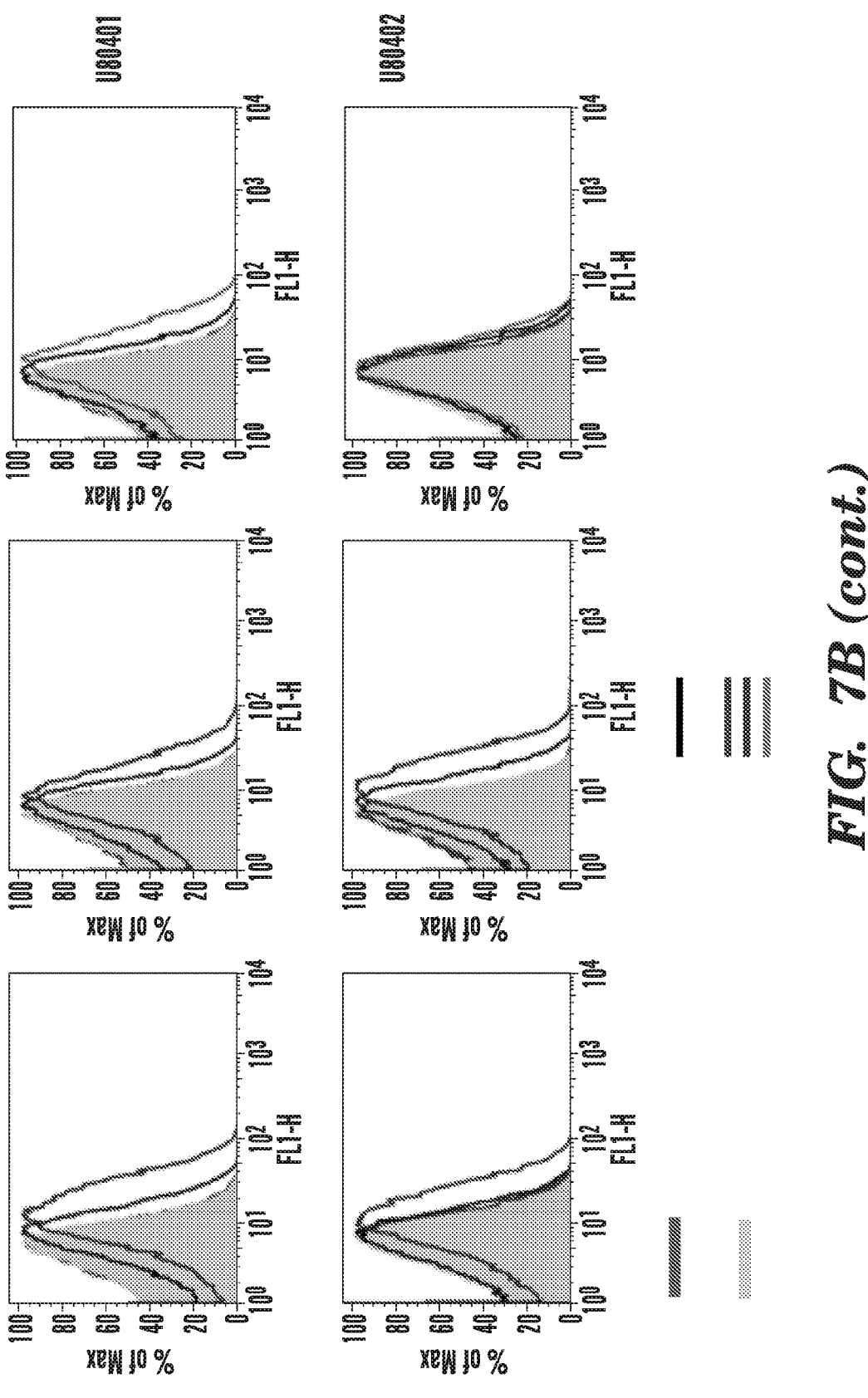

To examine immune recognition of the hypothetical proteins on the surface of whole intact bacteria, FF N. gonorrhoeae F62, FA1090, U08401 and U08402 strains were examined by flow cytometry with mouse antisera to each of the hypothetical proteins. Preimmune sera were used as a negative control (FIG. 7B, thin line histograms) and additional controls included bacteria only incubated with the FITC-conjugated anti-mouse secondary antibody (FIG. 7B, gray histograms) and without any antibody (FIG. 7B, dark gray histograms). No fluorescence shift indicative of antibody binding to the bacterial surface was detected with anti-NGO0416 sera, anti-NGO1043 and anti-NGO1215 sera in any of the four N. gonorrhoeae strains examined (not shown). In contrast, antibody binding to the bacterial surface was detected with anti-NGO0690 sera (FIG. 7B), anti-NGO00948 sera (FIG. 7B) and anti-NGO1701 sera (FIG. 7B) in all the four strains. Consistent with the immunoblot results in FIG. 7A, a greater antibody binding to NGO0948 was detected in N. gonorrhoeae F62 than in FA1090, as well as in strains U08401 and U08402 (FIG. 7B). However, surface recognition of NGO1701 appeared quite higher in N. gonorrhoeae FA1090 than in F62 and the clinical strains (FIG. 7B) although this difference was not detected by immunoblot. These results confirmed antibody cross-reactivity to different N. gonorrhea strains and supported recognition of NGO0690, NGO0948 and NGO1710 on the bacterial surface.

Antibodies to the Gonococcal Hypothetical Proteins are bactericidaL

The antibodies ability to kill N. gonorrhoeae was investigated by serum bactericidal assay (SBA). For all strains, no killing was detected by NHS alone (not shown) (reported as % bacterial survival at T30/T0). Sera from mice immunized with PBS/alum (adjuvant control) induced 0-15% killing at a 1/10 dilution, which was considered negligible (Table 7). No significant bacterial killing activity was detected with anti-NGO0416 sera with any of the N. gonorrhoeae strains tested (Table 7). A pronounced strain-dependent killing activity was detected for anti-NGO1215 sera, which only killed *N. gonorrhea* strain U08401 with a titer of 1/10 (the killing titer represents the reciprocal of the sera dilution that killed 50% or more bacteria). Anti-NGO1043 sera also had a killing titer of 1/10 against strains F62, U08401 and U08402, but also failed to kill *N. gonorrhea* strain FA1090 (Table 7). Anti-NGO0948 sera showed a consistent 1/10 killing titer against *N. gonorrhea* F62, U80401 and U08402 strains, and a 1/5 titer against FA1090. Similar results were shown for anti-NGO0690 and anti-NGO1701 sera, with titers reaching 1/40 against *N. gonorrhoeae* F62 (Table 7). These two antisera were further investigated to determine whether bacterial killing was enhanced by sera combination. As shown in FIG. 8C, combination of anti-NGO0690 and anti-NGO1701 sera both at 1/40 dilution increased killing of *N. gonorrhoeae* strain F62 to a 1/80 titer, suggesting an additive effect.

TABLE 7

Serum bactericidal titers. Percent of bacterial killing (CFUs at T30/T0) and sera dilutions (in parentheses)

| Group | *N. gonorrhoeae* strains | | | |
| | FA1090 | F62 | U08401 | U08402 |
| --- | --- | --- | --- | --- |
| Adjuvant control | 0-15% (1/10) | | | |
| NGO0416 | 30% (1/5) | 5% (1/10) | 30% (1/10) | 10% (1/10) |
| NGO0690 | 50% (1/5) | 50% (1/40) | 50% (1/10) | 60% (1/20) |
| NGO0948 | 50% (1/5) | 55% (1/10) | 45% (1/20) | 50% (1/20) |
| NGO1043 | 15% (1/5) | 45% (1/10) | 56% (1/10) | 50% (1/10) |
| NGO1215 | 0% (1/5) | 20% (1/10) | 60% (1/10) | 25% (1/10) |
| NGO1701 | 50% (1/5) | 50% (1/40) | 56% (1/10) | 50% (1/20) |

Summary of Experimental Results

Using a customized high-throughput in silico pipeline designed for antigen discovery, termed candidate antigen selection strategy (CASS), over 600 gonococcal hypothetical proteins were mined and expressed during natural human mucosal *N. gonorrhoeae* infections to identify new vaccine targets. The CASS was built on a reverse vaccinology approach integrated with bioinformatics and divided into 2 Discovery Phases (DP), which ultimately led to a pool of 36 hypothetical protein candidates. One of the primary attributes of these candidates was stable and sustained expression during natural infection in men and women, along with traditional attributes such as immunogenicity and membrane surface exposure.

Based on results from gonococcal transcriptome studies, the hypothetical proteins that were expressed below a cut-off level of 50 RPKM in both the male and female specimens were excluded because their potentially scarce expression may not only influence antibody recognition in vivo but could also be insufficient when testing immune responses in in vitro-based platforms. However, it was not excluded that when immune responses are forced by vaccination, proteins in this group would still act as immune antigens. In addition, the group of genes expressed at RPKM<50 encompassed hypothetical proteins that were regulated in a different manner during natural mucosal infection in male and female subjects; for example, those expressed with RPKM<50 in the male dataset and >50 in the female dataset, and vice versa. It has been previously reported that there is gender-related variability in antimicrobial resistance gene expression during natural human infections (49, 50).

Focusing the CASS on discovery of universal vaccine candidates, the starting point was from the 169 hypothetical proteins expressed with RPKM>50 in both male and female datasets and narrowed down the candidates to 36 hypothetical proteins, a manageable number of antigens for in vitro and in vivo testing. The CASS in silico analyses converged on crucial requirements of vaccine candidates, such as predictions of immunogenicity and bacterial cell localization. Once non-immunogenic and cytosolic proteins were eliminated, the amino acid sequence conservation of the remaining candidates was examined and aimed at excluding proteins that were conserved in humans and mouse to avoid self-reactive antigens. These pose an obvious problem in humans, but autoreactivity in mice is also adverse for pre-clinical vaccine studies. In addition, proteins with high degree of conservation with *E. coli* were also excluded to avoid immunity to widespread housekeeping factors. In *Neisseria*, antigenic conservation is a double-edged sword: both proteins that are very conserved and highly variable have failed as vaccine candidates because they either do not induce robust adaptive and protective immune responses, or do not protect against heterologous strain infections. Analysis of amino acid sequence conservation by BLASTp against the available *N. gonorrhoeae* protein sequences in NCBI revealed that the CASS candidates were present in the gonococcal strain database and shared variable degrees of conservation.

The next major CASS attribute that was considered was antigen structure complexity, based on the assumption that structure constrains that limit recombinant protein expression and purification would not be desirable for future manufacturability, and the candidates would be limited to pre-clinical analyses. An example is the *Chlamydia* outer membrane protein MOMP, one of the best protective antigens in *Chlamydia* experimental models of infection, but unsuitable for recombinant production due to refolding issues (78). Proteins with high structure hierarchy and number of trans-membrane domains were excluded, thereby enriching the CASS list with candidates with low to moderate structure constrains. The pool was further consolidated by excluding proteins predicted to be localized at the inner membrane/cytosolic interface and secreted proteins via prediction of cellular localization, topology and secretion pathways. Optimal vaccine candidates should be surface expressed for easy access to neutralizing antibodies. However, those predicted to be periplasmic were also included for two reasons: 1) predictions are not 100% accurate, and 2) periplasmic proteins are included in outer membrane vesicles (OMV) that are both naturally released by bacteria or induced in OMV-based vaccines, such as the meningococcal vaccine BEXERO®. This is very relevant, due to the recent observation that BEXERO® induces a partial cross-reactive immunity to *N. gonorrhoeae* in vaccinated subjects and in animal models, likely attributable to conserved and cross-reactive antigens (34-39). For the same reason, prediction of protein association with the inner membrane but facing the periplasm could be considered. The final CASS pool consisted of 36 hypothetical proteins, 16 of which were fully hypothetical and 20 with some conserved domain and motif homology with other bacterial proteins.

Six hypothetical proteins were selected from the CASS pool for immunological characterization. The six genes were assigned to the *N. gonorrhoeae* core genome defined within a wide global population of *N. gonorrhoeae* strains in the PubMLST database available on the world wide web at <pubmlst.org/*neisseria*/> (64)), which includes laboratory-adapted strains and clinical strains. Analysis of allelic distribution showed that NGO0948 and NGO1043 were the most variable candidates, and NGO0416 was the most conserved within the entire *N. gonorrhoeae* population (over 4000 strains), with no non-synonymous mutations within the total of 6 alleles carrying this gene. The amino acid sequences of these 6 candidates also showed conservation within the *N. gonorrhoeae* strains available in the NCBI database, suggesting potential for recognition and cross-reactivity in a broad range of gonococcal strains. While cross-reactivity may be desirable for "universal" immunity to pathogenic *Neisseria*, it may be less desirable against commensal *Neisseria*. For example, *N. lactamica* colonization of the nasopharynx at early age is thought to contribute to induction of natural immunity to *N. meningitidis* and influence meningococcal carriage (79). In case of interference by anti-gonococcal immunity, these natural immune responses may be attenuated. By examining the reservoir of hypothetical protein genes in *N. lactamica* present in the PubMLST database, there was no allelic overlap between the candidates, and that the ngo0416 gene was absent in *N. lactamica*. Furthermore, the amino acid sequences of the six candidates in *N. lactamica* revealed limited sequence identity with the corresponding *N. gonorrhoeae* proteins, suggesting unlikely robust responses to commensal organisms.

It was contemplated that the first gene co-expression network of *N. gonorrhoeae* utilizing several gonococcal transcriptomic datasets obtained from experimental studies examining the gonococcus grown under a variety of conditions including during mucosal infection. In such networks, transcripts or proteins are defined as nodes, and these are connected by co-abundance or co-expression levels, indicated as edges. Interrogation of the gonococcal gene expression network indicated that NGO0690 and NGO0948 had high centrality scores. Centrality has been used as a metric to rank gene importance in a biological system, including human pathogens or cancer (80-83). Studies suggest that genes more central in a network are more important for bacterial growth, metabolism and infection, providing additional rationale for the choice of NGO00690 and NGO0948 as potential candidates. Analysis of the centrality and the edges can also infer placement of a given gene into a defined genes module based on function enrichment. Thus, interrogation of networks can assist in function assignment of hypothetical proteins with a process termed Guilt-by-Association (GBA), an approach that has been used with other bacterial species to predict functions of unknown genes based on the edges they have with well-characterized genes in the network (84). This sophisticated process can provide context for characterizing the function of the 36 hypothetical proteins, short of generating deletion mutants in future studies.

Despite the challenges associated with recombinant expression and correct folding of proteins with limited or no structure information, the purified gonococcal antigens were able to elicit robust IgG responses in mice; the candidate that was the least immunogenic was NGO1043. Immunizations were carried out using alum as an adjuvant and, accordingly, a Th2-skewed immune response was observed with high IgG1, low IgG2a and IgG1/IgG2a ratio >1 except for NGO1701 (IgG1/IgG2a ratio of 0.86). This was also mirrored by the serum cytokine levels in response to NGO1701 and NGO0416 with higher IFN-γ, IL-6 and TNF-α, and to NGO0690 (higher IL-6). These results suggested that different antigens had an intrinsically different effect on inflammatory responses in mice despite all being used with the same adjuvant. Th1-type immune responses, important for promoting cell-mediated immunity and antibody class switching to IgG2a (important for complement binding and bacterial killing (85)) (86, 87), contribute specifically to clearance of infection in a gonococcal mouse infection model and lead to protective memory response (88, 89). It is possible that enhancing Th1-type responses to NGO0690 and NGO1701 by using different adjuvants (possibly mucosal) would be beneficial for a tailored and robust anti-gonococcal response.

Mouse antisera to each of the six hypothetical proteins were cross-reactive with different gonococcal strains and suggested presence of potentially heterologous cross-reactive epitopes. When targeting an extracellular pathogen such as *N. gonorrhoeae*, antigen recognition in the context of whole bacteria is a critical step for protective immunity against infection/colonization. However, using substrate-bound bacteria in immunoblot and ELISA analyses could not verify whether the candidates were surface-exposed; it is possible that they were indiscriminately accessible to antibody recognition in immobilized whole bacteria. Extraction of outer membrane proteins with Sarkosyl, known to preferentially solubilize inner-membrane proteins (90), was used to prove the localization of the six hypothetical proteins; those predicted to be periplasmic but associated with the inner membrane side within the periplasmic space may be solubilized with the proteins from this compartment during the OMP preparation. The hypothetical proteins were detected with variable intensity in the *N. gonorrhoeae* OMPs; the least immunoreactive was NGO1043, suggesting either a limited OM exposure, or low antibody specificity (this protein was also the least immunoreactive by ELISA). Both these possibilities could also explain lack of recognition of NGO1043 by flow cytometry. Interestingly, NGO00416 and NGO1215 were recognized in the OMP fraction by immunoblot blot but failed to show surface recognition in whole bacteria by FACS. NGO0690, NGO0948 and NGO1701 were detected by immunoblot blot of the OMPs and by flow cytometry of whole bacteria, indicating display of antibody-accessible epitopes on the bacterial membrane.

Antibodies that bind to the bacteria may neutralize them via complement-mediated bactericidal killing, opsonophagocytic killing or by inhibiting host cell adhesion/invasion at the colonization site. Such antibodies would be considered protective. The current best available in vitro surrogate of protection for gonorrhea is the serum bactericidal assay (SBA), since other correlates of immune protection are currently unknown. Not surprisingly, antibodies to NGO0416 had negligible bactericidal activity. Sera raised to NGO1215 killed only *N. gonorrhoeae* strain U08401, proving an unsatisfactory candidate; interestingly, despite NGO1043 was not recognized on the bacterial surface by flow cytometry, the anti-NGO1043 mouse sera had a low-titered bactericidal activity against three diverse *N. gonorrhoeae* strains, supporting the possibility that antibodies raised to this antigen were directed to limited epitopes on the bacterial surface. In contrast, sera raised to NGO0690, NGO0948 and NGO1701 had bactericidal activity against all the strains tested with titers up to 1/40. Furthermore, combination of NGO0690 and NGO1701 antisera doubled the killing titers, in support of the use of multiple antigens to induce a more potent protective immune response.

Targeting multiple microbial processes simultaneously, i.e. colonization and invasion, immune evasion and nutrient acquisition would provide a wider net protective strategy. Not much is known about the function of NGO0690, a fully hypothetical protein; NGO1701 has conserved domain homology with a Tat_Cys_rich four-helix bundle copper-binding protein and NGO0948 with BamC, a periplasmic protein part of the BamABCDE (BAM) complex for β-barrel proteins folding and insertion into the OM (91). In *N.*

*meningitidis*, a BamC homolog elicited antibodies with bactericidal activity (69, 71) and other components of the Bam complex are being explored as vaccine targets for *N. gonorrhoeae* (28, 92). Construction of mutants lacking expression of these proteins will clarify their role in the metabolism and pathogenesis of *N. gonorrhoeae*.

In conclusion, stable and sustained antigen expression during natural infection must be added to the requirements for successful vaccine that elicits neutralizing antibodies against colonization and infection formulated with adjuvants that provide appropriate T cell help for a long-lasting immune response. It is demonstrated herein that new antigens gonococcal antigens can be identified within hypothetical proteins expressed during gonococcal natural infection in humans by applying in silico tools and predictions leading to a pool of potential candidates that warrants further analysis in a mouse model of gonococcal infection in vivo.

REFERENCES

1. Rice P A, Shafer W M, Ram S, Jerse A E. *Neisseria gonorrhoeae*: Drug Resistance, Mouse Models, and Vaccine Development. *Annu Rev Microbiol.* 2017; 71:665-86. Epub 2017/09/10. doi: 10.1146/annurev-micro-090816-093530. PubMed PMID: 28886683.
2. CDC. 2016 Sexually Transmitted Diseases Surveillance. 2018.
3. CDC Grand Rounds: the growing threat of multidrug-resistant gonorrhea. *MMWR Morb Mortal Wkly Rep.* 2013; 62(6):103-6.
4. Workowski K A, Bolan G A. Sexually transmitted diseases treatment guidelines, 2015. *MMWR Recomm Rep.* 2015; 64(RR-03):1-137.
5. Thakur S D, Araya P, Borthagaray G, Galarza P, Hernandez A L, Payares D, Sanabria Cruz O M, Carvallo M E, Corredor A H, Dillon J R. Resistance to Ceftriaxone and Azithromycin in *Neisseria gonorrhoeae* Isolates From 7 Countries of South America and the Caribbean: 2010-2011. *Sex Transm Dis.* 2017; 44(3):157-60.
6. Li S, Su X H, Le W J, Jiang F X, Wang B X, Rice P A. Antimicrobial susceptibility of *Neisseria gonorrhoeae* isolates from symptomatic men attending the Nanjing sexually transmitted diseases clinic (2011-2012): genetic characteristics of isolates with reduced sensitivity to ceftriaxone. *BMC Infect Dis.* 2014; 14:622.
7. George C R R, Enriquez R P, Gatus B J, Whiley D M, Lo Y R, Ishikawa N, Wi T, Lahra M M. Systematic review and survey of *Neisseria gonorrhoeae* ceftriaxone and azithromycin susceptibility data in the Asia Pacific, 2011 to 2016. *PLoS One.* 2019; 14(4): e0213312. Epub 2019/04/04. doi: 10.1371/journal.pone.0213312.
8. Gottlieb S L, Johnston C. Future prospects for new vaccines against sexually transmitted infections. *Curr Opin Infect Dis.* 2017; 30(1):77-86.
9. Jerse A E, Wu H, Packiam M, Vonck R A, Begum A A, Garvin L E. Estradiol-Treated Female Mice as Surrogate Hosts for *Neisseria gonorrhoeae* Genital Tract Infections. *Front Microbiol.* 2011; 2:107. Epub 2011/07/13. doi: 10.3389/fmicb.2011.00107. PubMed PMID: 21747807; PMCID: PMC3129519.
10. Plante M, Jerse A, Hamel J, Couture F, Rioux C R, Brodeur B R, Martin D. Intranasal Immunization with Gonococcal Outer Membrane Preparations Reduces the Duration of Vaginal Colonization of Mice by *Neisseria gonorrhoeae*. *J Infect Dis.* 2000; 182(3):848-55.
11. Islam E A, Shaik-Dasthagirisaheb Y, Kaushic C, Wetzler L M, Gray-Owen S D. The reproductive cycle is a pathogenic determinant during gonococcal pelvic inflammatory disease in mice. *Mucosal Immunol.* 2015.
12. Francis I P, Islam E A, Gower A C, Shaik-Dasthagirisaheb Y B, Gray-Owen S D, Wetzler L M. Murine host response to *Neisseria gonorrhoeae* upper genital tract infection reveals a common transcriptional signature, plus distinct inflammatory responses that vary between reproductive cycle phases. *BMC Genomics.* 2018; 19(1):627. Epub 2018/08/24. doi: 10.1186/s12864-018-5000-7. PubMed PMID: 30134832; PMCID: PMC6106831.
13. Hobbs M M, Sparling P F, Cohen M S, Shafer W M, Deal C D, Jerse A E. Experimental Gonococcal Infection in Male Volunteers: Cumulative Experience with *Neisseria gonorrhoeae* Strains FA1090 and MS11mkC. *Front Microbiol.* 2011; 2:123. Epub 2011/07/08. doi: 10.3389/fmicb.2011.00123. PubMed PMID: 21734909; PMCID: PMC3119411.
14. Jerse A E, Cohen M S, Drown P M, Whicker L G, Isbey S F, Seifert H S, Cannon J G. Multiple gonococcal opacity proteins are expressed during experimental urethral infection in the male. *J Exp Med.* 1994; 179: 911-20.
15. Seifert H S, Wright C J, Jerse A E, Cohen M S, Cannon J G. Multiple gonococcal pilin antigenic variants are produced during experimental human infections. *J Clin Invest.* 1994; 93:2744-9.
16. Lenz J D, Dillard J P. Pathogenesis of *Neisseria gonorrhoeae* and the Host Defense in Ascending Infections of Human Fallopian Tube. *Front Immunol.* 2018; 9:2710. Epub 2018/12/14. doi: 10.3389/fimmu.2018.02710. PubMed PMID: 30524442; PMCID: PMC6258741.
17. Rosenqvist E, Musacchio A, Aase A, Hoiby E A, Namork E, Kolberg J, Wedege E, Delvig A, Dalseg R, Michaelsen T E, Tommassen J. Functional activities and epitope specificity of human and murine antibodies against the class 4 outer membrane protein (Rmp) of *Neisseria meningitidis*. *Infect Immun.* 1999; 67(3): 1267-76.
18. Tan L K, Carlone G M, Borrow R. Advances in the development of vaccines against *Neisseria meningitidis*. *N Engl J Med.* 2010; 362(16):1511-20. Epub 2010/04/23. doi: 10.1056/NEJMra0906357. PubMed PMID: 20410516.
19. Siegel M, Olsen D, Critchlow C, Buchanan T M. Gonococcal pili: safety and immunogenicity in humans and antibody function in vitro. *J Infect Dis.* 1982; 145(3):300-10.
20. Zhu W, Thomas C E, Chen C J, Van Dam C N, Johnston R E, Davis N L, Sparling P F. Comparison of immune responses to gonococcal PorB delivered as outer membrane vesicles, recombinant protein, or Venezuelan equine encephalitis virus replicon particles. *Infect Immun.* 2005; 73(11):7558-68.
21. Wetzler L M, Blake M S, Gotschlich E C. Protein I (Por) of *Neisseria gonorrhoeae* as an immunogen: liposomes, proteosomes and the lack of blocking antibodies. Transactions of the American Association of Physicians. 102 ed. Baltimore, M D: Waverly Press; 1989. p. 78-90.
22. Fegan J E, Calmettes C, Islam E A, Ahn S K, Chaudhuri S, Yu R H, Gray-Owen S D, Moraes T F, Schryvers A B. Utility of Hybrid Transferrin Binding Protein Antigens for Protection Against Pathogenic *Neisseria* Species. *Front Immunol.* 2019; 10:247. Epub 2019/03/07. doi: 10.3389/fimmu.2019.00247. PubMed PMID: 30837995; PMCID: PMC6389628.

23. Price G A, Masri H P, Hollander A M, Russell M W, Cornelissen C N. Gonococcal transferrin binding protein chimeras induce bactericidal and growth inhibitory antibodies in mice. *Vaccine.* 2007; 25(41):7247-60.

24. Wang S, Xue J, Lu P, Ni C, Cheng H, Han R, van der Veen S. Gonococcal MtrE and its surface-expressed Loop 2 are immunogenic and elicit bactericidal antibodies. *J Infect.* 2018; 77(3):191-204. Epub 2018/06/15. doi: 10.1016/j.jinf2018.06.001. PubMed PMID: 29902495.

25. Lee E H, Shafer W M. The farAB-encoded efflux pump mediates resistance of gonococci to long-chained antibacterial fatty acids. *Mol Microbiol.* 1999; 33(4):839-45. Epub 1999/08/14. PubMed PMID: 10447892.

26. Semchenko E A, Day C J, Seib K L. MetQ of *Neisseria gonorrhoeae* Is a Surface-Expressed Antigen That Elicits Bactericidal and Functional Blocking Antibodies. *Infect Immun.* 2017; 85(2).

27. Jen F E, Semchenko E A, Day C J, Seib K L, Jennings M P. The *Neisseria gonorrhoeae* Methionine Sulfoxide Reductase (MsrA/B) Is a Surface Exposed, Immunogenic, Vaccine Candidate. *Front Immunol.* 2019; 10:137. Epub 2019/02/23. doi: 10.3389/fimmu.2019.00137. PubMed PMID: 30787927; PMCID: PMC6372556.

28. Zielke R A, Wierzbicki I H, Baarda B I, Gafken P R, Soge 00, Holmes K K, Jerse A E, Unemo M, Sikora A E. Proteomics-driven Antigen Discovery for Development of Vaccines Against Gonorrhea. *Mol Cell Proteomics.* 2016; 15(7):2338-55. Epub 2016/05/04. doi: 10.1074/mcp.M116.058800. PubMed PMID: 27141096; PMCID: PMC4937508.

29. Almonacid-Mendoza H L, Humbert M V, Dijokaite A, Cleary D W, Soo Y, Hung M C, Orr C M, Machelett M M, Tews I, Christodoulides M. Structure of the Recombinant *Neisseria gonorrhoeae* Adhesin Complex Protein (rNg-ACP) and Generation of Murine Antibodies with Bactericidal Activity against Gonococci. *mSphere.* 2018; 3(5). Epub 2018/10/12. doi: 10.1128/mSphere.00331-18. PubMed PMID: 30305317; PMCID: PMC6180225.

30. Ngampasutadol J, Rice P A, Walsh M T, Gulati S. Characterization of a peptide vaccine candidate mimicking an oligosaccharide epitope of *Neisseria gonorrhoeae* and resultant immune responses and function. *Vaccine.* 2006; 24(2):157-70.

31. Gulati S, Zheng B, Reed G W, Su X, Cox A D, St M F, Stupak J, Lewis L A, Ram S, Rice P A. Immunization against a saccharide epitope accelerates clearance of experimental gonococcal infection. *PLoS Pathog.* 2013; 9(8):e1003559.

32. Ram S, Ngampasutadol J, Cox A D, Blom A M, Lewis L A, St Michael F, Stupak J, Gulati S, Rice P A. Heptose I glycan substitutions on *Neisseria gonorrhoeae* lipooligosaccharide influence C4b-binding protein binding and serum resistance. *Infect Immun.* 2007; 75(8):4071-81. Epub 2007/05/29. doi: 10.1128/IAIL01109-06. PubMed PMID: 17526744; PMCID: PMC1952009.

33. Gulati S, Shaughnessy J, Ram S, Rice P A. Targeting Lipooligosaccharide (LOS) for a Gonococcal Vaccine. *Front Immunol.* 2019; 10:321. Epub 2019/03/16. doi: 10.3389/fimmu.2019.00321. PubMed PMID: 30873172; PMCID: PMC6400993.

34. Gorringe A R, Pajon R. Bexsero: a multicomponent vaccine for prevention of meningococcal disease. *Hum Vaccin Immunother.* 2012; 8(2):174-83. Epub 2012/03/20. doi: 10.4161/hv.18500. PubMed PMID: 22426368.

35. Paynter J, Goodyear-Smith F, Morgan J, Saxton P, Black S, Petousis-Harris H. Effectiveness of a Group B Outer Membrane Vesicle Meningococcal Vaccine in Preventing Hospitalization from Gonorrhea in New Zealand: A Retrospective Cohort Study. Vaccines (Basel). 2019; 7(1). Epub 2019/01/10. doi: 10.3390/vaccines7010005. PubMed PMID: 30621260.

36. Semchenko E A, Tan A, Borrow R, Seib K L. The serogroup B meningococcal vaccine Bexsero elicits antibodies to *Neisseria gonorrhoeae. Clin Infect Dis.* 2018. Epub 2018/12/15. doi: 10.1093/cid/ciy1061. PubMed PMID: 30551148.

37. Petousis-Harris H, Paynter J, Morgan J, Saxton P, McArdle B, Goodyear-Smith F, Black S. Effectiveness of a group B outer membrane vesicle meningococcal vaccine against gonorrhoea in New Zealand: a retrospective case-control study. *Lancet.* 2017; 390(10102):1603-10. Epub 2017/07/15. doi: 10.1016/S0140-6736(17)31449-6. PubMed PMID: 28705462.

38. Ochoa-Azze R F. Cross-protection induced by VA-MENGOC-BC(R) vaccine. Hum *Vaccin Immunother.* 2018; 14(5):1064-8. Epub 2018/02/09. doi: 10.1080/21645515.2018.1438028. PubMed PMID: 29420119.

39. Beernink P T, Ispasanie E, Lewis L A, Ram S, Moe G R, Granoff D M. A Meningococcal Native Outer Membrane Vesicle Vaccine With Attenuated Endotoxin and Overexpressed Factor H Binding Protein Elicits Gonococcal Bactericidal Antibodies. *J Infect Dis.* 2019; 219(7):1130-7. Epub 2018/10/23. doi: 10.1093/infdis/jiy609. PubMed PMID: 30346576; PMCID: PMC6420169.

40. Pizza M, Scarlato V, Masignani V, Giuliani M M, Arico B, Comanducci M, Jennings G T, Baldi L, Bartolini E, Capecchi B, Galeotti C L, Luzzi E, Manetti R, Marchetti E, Mora M, Nuti S, *Ratti* G, Santini L, Savino S, Scarselli M, Stori E, Zuo P, Broeker M, Hundt E, Knapp B, Blair E, Mason T, Tettelin H, Hood D W, Jeffries A C, Saunders N J, Granoff D M, Venter J C, Moxon E R, Grandi G, Rappuoli R. Identification of vaccine candidates against serogroup B meningococcus by whole-genome sequencing [see comments]. *Science.* 2000; 287(5459):1816-20.

41. Serruto D, Bottomley M J, Ram S, Giuliani M M, Rappuoli R. The new multicomponent vaccine against meningococcal serogroup B, 4CMenB: immunological, functional and structural characterization of the antigens. Vaccine. 2012; 30 Suppl 2:B87-B97.

42. Hsu C A, Lin W R, Li J C, Liu Y L, Tseng Y T, Chang C M, Lee Y S, Yang C Y. Immunoproteomic identification of the hypothetical protein NMB1468 as a novel lipoprotein ubiquitous in *Neisseria meningitidis* with vaccine potential. Proteomics. 2008; 8(10):2115-25.

43. Williams J N, Weynants V, Poolman J T, Heckels J E, Christodoulides M. Immuno-proteomic analysis of human immune responses to experimental *Neisseria meningitidis* outer membrane vesicle vaccines identifies potential cross-reactive antigens. *Vaccine.* 2014; 32(11):1280-6.

44. Jain R, Sonkar S C, Chaudhry U, Bala M, Saluja D. In-silico Hierarchical Approach for the Identification of Potential Universal Vaccine Candidates (PUVCs) from *Neisseria gonorrhoeae. J Theor Biol.* 2016; 410:36-43.

45. Connor D O, Zantow J, Hust M, Bier F F, von Nickisch-Rosenegk M. Identification of Novel Immunogenic Proteins of *Neisseria gonorrhoeae* by Phage Display. *PLoS ONE.* 2016; 11(2):e0148986.

46. Baarda B I, Martinez F G, Sikora A E. Proteomics, Bioinformatics and Structure-Function Antigen Mining For Gonorrhea Vaccines. *Front Immunol.* 2018; 9:2793. Epub 2018/12/20. doi: 10.3389/fimmu.2018.02793. PubMed PMID: 30564232; PMCID: PMC6288298.

47. El-Rami F E, Zielke R A, Wi T, Sikora A E, Unemo M. Quantitative Proteomics of the 2016 WHO *Neisseria gonorrhoeae* Reference Strains Surveys Vaccine Candidates and Antimicrobial Resistance Determinants. *Mol Cell Proteomics.* 2019; 18(1):127-50. Epub 2018/10/26. doi: 10.1074/mcp.RA118.001125. PubMed PMID: 30352803; PMCID: PMC6317477.

48. Altindis E, Cozzi R, Di P B, Necchi F, Mishra R P, Fontana M R, Soriani M, Bagnoli F, Maione D, Grandi G, Liberatori S. Protectome analysis: a new selective bioinformatics tool for bacterial vaccine candidate discovery. *Mol Cell Proteomics.* 2015; 14(2):418-29.

49. McClure R, Nudel K, Massari P, Tjaden B, Su X, Rice P A, Genco C A. The Gonococcal Transcriptome during Infection of the Lower Genital Tract in Women. *PLoS ONE.* 2015; 10(8):e0133982.

50. Nudel K, McClure R, Moreau M, Briars E, Abrams A J, Tjaden B, Su X H, Trees D, Rice P A, Massari P, Genco C A. Transcriptome Analysis of *Neisseria gonorrhoeae* during Natural Infection Reveals Differential Expression of Antibiotic Resistance Determinants between Men and Women. *mSphere.* 2018; 3(3). Epub 2018/06/29. doi: 10.1128/mSphereDirect.00312-18. PubMed PMID: 29950382; PMCID: PMC6021601.

51. Doytchinova I A, Flower D R. VaxiJen: a server for prediction of protective antigens, tumour antigens and subunit vaccines. *BMC Bioinformatics.* 2007; 8:4.

52. Yu N Y, Wagner J R, Laird M R, Melli G, Rey S, Lo R, Dao P, Sahinalp S C, Ester M, Foster L J, Brinkman F S. PSORTb 3.0: improved protein subcellular localization prediction with refined localization subcategories and predictive capabilities for all prokaryotes. *Bioinformatics.* 2010; 26(13):1608-15. Epub 2010/05/18. doi: 10.1093/bioinformatics/btq249. PubMed PMID: 20472543; PMCID: PMC2887053.

53. Yachdav G, Kloppmann E, Kajan L, Hecht M, Goldberg T, Hamp T, Honigschmid P, Schafferhans A, Roos M, Bemhofer M, Richter L, Ashkenazy H, Punta M, Schlessinger A, Bromberg Y, Schneider R, Vriend G, Sander C, Ben-Tal N, Rost B. PredictProtein—an open resource for online prediction of protein structural and functional features. *Nucleic Acids Res.* 2014; 42(Web Server issue):W337-43. Epub 2014/05/07. doi: 10.1093/nar/gku366. PubMed PMID: 24799431; PMCID: PMC4086098.

54. Shen H B, Chou K C. Gneg-mPLoc: a top-down strategy to enhance the quality of predicting subcellular localization of Gram-negative bacterial proteins. *J Theor Biol.* 2010; 264(2):326-33. Epub 2010/01/23. doi: 10.1016/j.jtbi.2010.01.018. PubMed PMID: 20093124.

55. He Y, Racz R, Sayers S, Lin Y, Todd T, Hur J, Li X, Patel M, Zhao B, Chung M, Ostrow J, Sylora A, Dungarani P, Ulysse G, Kochhar K, Vidri B, Strait K, Jourdian G W, Xiang Z. Updates on the web-based VIOLIN vaccine database and analysis system. Nucleic Acids Res. 2014; 42(Database issue):D1124-32. Epub 2013/11/22. doi: 10.1093/nar/gkt1133. PubMed PMID: 24259431; PMCID: PMC3964998.

56. Altschul S F, Gish W, Miller W, Myers E W, Lipman D J. Basic local alignment search tool. *J Mol Biol.* 1990; 215(3):403-10.

57. Krogh A, Larsson B, von H G, Sonnhammer E L. Predicting transmembrane protein topology with a hidden Markov model: application to complete genomes. *J Mol Biol.* 2001; 305(3):567-80.

58. Kall L, Krogh A, Sonnhammer E L. Advantages of combined transmembrane topology and signal peptide prediction—the Phobius web server. *Nucleic Acids Res.* 2007; 35(Web Server issue):W429-32. Epub 2007/05/08. doi: 10.1093/nar/gkm256. PubMed PMID: 17483518; PMCID: PMC1933244.

59. Almagro Armenteros J J, Tsirigos K D, Sonderby C K, Petersen T N, Winther O, Brunak S, von Heijne G, Nielsen H. SignalP 5.0 improves signal peptide predictions using deep neural networks. *Nat Biotechnol.* 2019; 37(4):420-3. Epub 2019/02/20. doi: 10.1038/s41587-019-0036-z. PubMed PMID: 30778233.

60. Bendtsen J D, Jensen L J, Blom N, Von Heijne G, Brunak S. Feature-based prediction of non-classical and leaderless protein secretion. *Protein Eng Des Sel.* 2004; 17(4):3-[9-56. Epub 2004/04/30. doi: 10.1093/protein/gzh037. PubMed PMID: 15115854.

61. Juncker A S, Willenbrock H, Von Heijne G, Brunak S, Nielsen H, Krogh A. Prediction of lipoprotein signal peptides in Gram-negative bacteria. *Protein Sci.* 2003; 12(8):1652-62. Epub 2003/07/24. doi: 10.1110/ps.0303703. PubMed PMID: 12876315; PMCID: PMC2323952.

62. UniProt C. UniProt: a worldwide hub of protein knowledge. *Nucleic Acids Res.* 2019; 47(D1):D506-D15. Epub 2018/11/06. doi: 10.1093/nar/gky1049. PubMed PMID: 30395287; PMCID: PMC6323992.

63. El-Gebali S, Mistry J, Bateman A, Eddy S R, Luciani A, Potter S C, Qureshi M, Richardson L J, Salazar G A, Smart A, Sonnhammer ELL, Hirsh L, Paladin L, Piovesan D, Tosatto SCE, Finn R D. The Pfam protein families database in 2019. *Nucleic Acids Res.* 2019; 47(D1):D427-D32. Epub 2018/10/26. doi: 10.1093/nar/gky995. PubMed PMID: 30357350; PMCID: PMC6324024.

64. Jolley K A, Maiden M C. BIGSdb: Scalable analysis of bacterial genome variation at the population level. *BMC Bioinformatics.* 2010; 11:595. Epub 2010/12/15. doi: 10.1186/1471-2105-11-595. PubMed PMID: 21143983; PMCID: PMC3004885.

65. Liu X, Wetzler L M, Massari P. The PorB porin from commensal *Neisseria* lactamica induces Th1 and Th2 immune responses to ovalbumin in mice and is a potential immune adjuvant. Vaccine. 2008; 26(6):786-96.

66. Chen S C, Yin Y P, Dai X Q, Unemo M, Chen X S. First nationwide study regarding ceftriaxone resistance and molecular epidemiology of *Neisseria gonorrhoeae* in China. *J Antimicrob Chemother.* 2016; 71(1):92-9.

67. Kirkcaldy R D, Kidd S, Weinstock H S, Papp J R, Bolan G A. Trends in antimicrobial resistance in *Neisseria gonorrhoeae* in the USA: the Gonococcal Isolate Surveillance Project (GISP), January 2006-June 2012. *Sex Transm Infect.* 2013; 89 Suppl 4:iv5-10.

68. Andersen C, Rak B, Benz R. The gene bglH present in the bgl operon of *Escherichia coli*, responsible for uptake and fermentation of beta-glucosides encodes for a carbohydrate-specific outer membrane porin. *Mol Microbiol.* 1999; 31(2):499-510. Epub 1999/02/23. PubMed PMID: 10027967.

69. Delgado M, Yero D, Niebla O, Gonzalez S, Climent Y, Perez Y, Cobas K, Caballero E, Garcia D, Pajon R. Lipoprotein NMB0928 from *Neisseria meningitidis* serogroup B as a novel vaccine candidate. *Vaccine.* 2007; 25(50):8420-31. Epub 2007/11/13. doi: 10.1016/j.vaccine.2007.09.053. PubMed PMID: 17996338.

70. Pajon R, Yero D, Niebla O, Climent Y, Sardinas G, Garcia D, Perera Y, Llanes A, Delgado M, Cobas K, Caballero E, Taylor S, Brookes C, Gorringe A. Identification of new meningococcal serogroup B surface antigens through a systematic analysis of neisserial genomes. *Vaccine.* 2009; 28(2):532-41.

71. Awanye A M, Chang C M, Wheeler J X, Chan H, Marsay L, Dold C, Rollier C S, Bird L E, Nettleship J E, Owens R J, Pollard A J, Derrick J P. Immunogenicity profiling of protein antigens from capsular group B *Neisseria meningitidis. Sci Rep.* 2019; 9(1):6843. Epub 2019/05/03. doi: 10.1038/s41598-019-43139-0. PubMed PMID: 31048732.

72. Chu C L, Yu Y L, Kung Y C, Liao P Y, Liu K J, Tseng Y T, Lin Y C, Hsieh S S, Chong P C, Yang C Y. The immunomodulatory activity of meningococcal lipoprotein Ag473 depends on the conformation made up of the lipid and protein moieties. *PLoS One.* 2012; 7(7): e40873. Epub 2012/07/31. doi: 10.1371/journal.pone.0040873. PubMed PMID: 22844415; PMCID: PMC3402496.

73. Ladomersky E, Petris M J. Copper tolerance and virulence in bacteria. Metallomics. 2015; 7(6):957-64. Epub 2015/02/06. doi: 10.1039/c4mt00327f. PubMed PMID: 25652326; PMCID: PMC4464932.

74. Gangaiah D, Raterman E L, Wu H, Fortney K R, Gao H, Liu Y, Jerse A E, Spinola S M. Both MisR (CpxR) and MisS (CpxA) Are Required for *Neisseria gonorrhoeae* Infection in a Murine Model of Lower Genital Tract Infection. *Infect Immun.* 2017; 85(9). Epub 2017/06/28. doi: 10.1128/IAI.00307-17. PubMed PMID: 28652307; PMCID: PMC5563589.

75. Yu C, Genco C A. Fur-mediated global regulatory circuits in pathogenic *Neisseria* species. *J Bacteriol.* 2012; 194(23):6372-81.

76. Quillin S J, Hockenberry A J, Jewett M C, Seifert H S. *Neisseria gonorrhoeae* Exposed to Sublethal Levels of Hydrogen Peroxide Mounts a Complex Transcriptional Response. *mSystems.* 2018; 3(5). Epub 2018/10/16. doi: 10.1128/mSystems.00156-18. PubMed PMID: 30320218; PMCID: PMC6172773.

77. Velez Acevedo R N, Ronpirin C, Kandler J L, Shafer W M, Cornelissen C N. Identification of regulatory elements that control expression of the tbpBA operon in *Neisseria gonorrhoeae. J Bacteriol.* 2014; 196(15): 2762-74. Epub 2014/05/20. doi: 10.1128/JB.01693-14. PubMed PMID: 24837286; PMCID: PMC4135677.

78. Madico G, Gursky O, Fairman J, Massari P. Structural and Immunological Characterization of Novel Recombinant MOMP-Based Chlamydial Antigens. *Vaccines* (Basel). 2017; 6(1).

79. Deasy A M, Guccione E, Dale A P, Andrews N, Evans C M, Bennett J S, Bratcher H B, Maiden M C, Gorringe A R, Read R C. Nasal Inoculation of the Commensal *Neisseria lactamica* Inhibits Carriage of *Neisseria meningitidis* by Young Adults: A Controlled Human Infection Study. *Clin Infect Dis.* 2015; 60(10):1512-20.

80. McDermott J E, Taylor R C, Yoon H, Heffron F. Bottlenecks and hubs in inferred networks are important for virulence in *Salmonella typhimurium. J Comput Biol.* 2009; 16(2):169-80. Epub 2009/01/31. doi: 10.1089/cmb.2008.04TT. PubMed PMID: 19178137.

81. McDermott J E, Diamond D L, Corley C, Rasmussen A L, Katze M G, Waters K M. Topological analysis of protein co-abundance networks identifies novel host targets important for HCV infection and pathogenesis. *BMC Syst Biol.* 2012; 6:28. Epub 2012/05/02. doi: 10.1186/1752-0509-6-28. PubMed PMID: 22546282; PMCID: PMC3383540.

82. Song H S, McClure R S, Bernstein H C, Overall C C, Hill E A, Beliaev A S. Integrated in silico Analyses of Regulatory and Metabolic Networks of Synechococcus sp. PCC 7002 Reveal Relationships between Gene Centrality and Essentiality. Life (Basel). 2015; 5(2): 1127-40. Epub 2015/04/01. doi: 10.3390/life5021127. PubMed PMID: 25826650; PMCID: PMC4500133.

83. Chou W C, Cheng A L, Brotto M, Chuang C Y. Visual gene-network analysis reveals the cancer gene co-expression in human endometrial cancer. *BMC Genomics.* 2014; 15:300. Epub 2014/04/25. doi: 10.1186/1471-2164-15-300. PubMed PMID: 24758163; PMCID: PMC4234489.

84. Wolfe C J, Kohane I S, Butte A J. Systematic survey reveals general applicability of "guilt-by-association" within gene coexpression networks. *BMC Bioinformatics.* 2005; 6:227. Epub 2005/09/16. doi: 10.1186/1471-2105-6-227. PubMed PMID: 16162296; PMCID: PMC1239911.

85. Bungener L, Geeraedts F, Ter Veer W, Medema J, Wilschut J, Huckriede A. Alum boosts TH2-type antibody responses to whole-inactivated virus influenza vaccine in mice but does not confer superior protection. *Vaccine.* 2008; 26(19):2350-9. Epub 2008/04/11. doi: 10.1016/j.vaccine.2008.02.063. PubMed PMID: 18400340.

86. Finkelman F D, Holmes J, Katona I M, Urban J, J. F., Beckmann M P, Park L S, Schooley K A, Coffman R L, Mosmann T R, Paul W E. Lymphokine control of in vivo immunoglobulin isotype selection. *Ann Rev Immunol.* 1990; 8:303-33.

87. Mosmann T R, Cherwinski H M, Bond M W, Giedlin M A, Coffman R L. Two types of murine helper T cell clones:1. definition according to the profiles of lymphokine activity and secreted proteins. *J Immunol.* 1986; 136:2348-57.

88. Liu Y, Feinen B, Russell M W. New concepts in immunity to *Neisseria gonorrhoeae*: innate responses and suppression of adaptive immunity favor the pathogen, not the host. *Front Microbiol.* 2011; 2:52. Epub 2011/08/13. doi: 10.3389/fmicb.2011.00052. PubMed PMID: 21833308; PMCID: PMC3153028.

89. Liu Y, Perez J, Hammer L A, Gallagher H C, De Jesus M, Egilmez N K, Russell M W. Intravaginal Administration of Interleukin 12 during Genital Gonococcal Infection in Mice Induces Immunity to Heterologous Strains of *Neisseria gonorrhoeae. mSphere.* 2018; 3(1). Epub 2018/02/07. doi: 10.1128/mSphere.00421-17. PubMed PMID: 29404418; PMCID: PMC5793040.

90. Filip C, Fletcher G, Wulff J L, Earhart C F. Solubilization of the cytoplasmic membrane of *Escherichia coli* by the ionic detergent sodium-lauryl sarcosinate. *J Bacteriol.* 1973; 115(3):717-22. Epub 1973/09/01. PubMed PMID: 4580564; PMCID: PMC246312.

91. Plummer A M, Fleming K G. From Chaperones to the Membrane with a BAM!*Trends Biochem Sci.* 2016; 41(10):872-82. Epub 2016/07/28. doi: 10.1016/j.tibs.2016.06.005. PubMed PMID: 27450425; PMCID: PMC5420074.

92. Sikora A E, Wierzbicki I H, Zielke R A, Ryner R F, Korotkov K V, Buchanan S K, Noinaj N. Structural and functional insights into the role of BamD and BamE within the beta-barrel assembly machinery in *Neisseria gonorrhoeae. J Biol Chem.* 2018; 293(4):1106-19. Epub 2017/12/13. doi: 10.1074/jbc.RA117.000437. PubMed PMID: 29229778; PMCID: PMC5787791.

Example 2: Immune Recognition of NGO0690, NGO0948 and NGO1701 by Human Sera

Figures 10A, 10B, 10C:
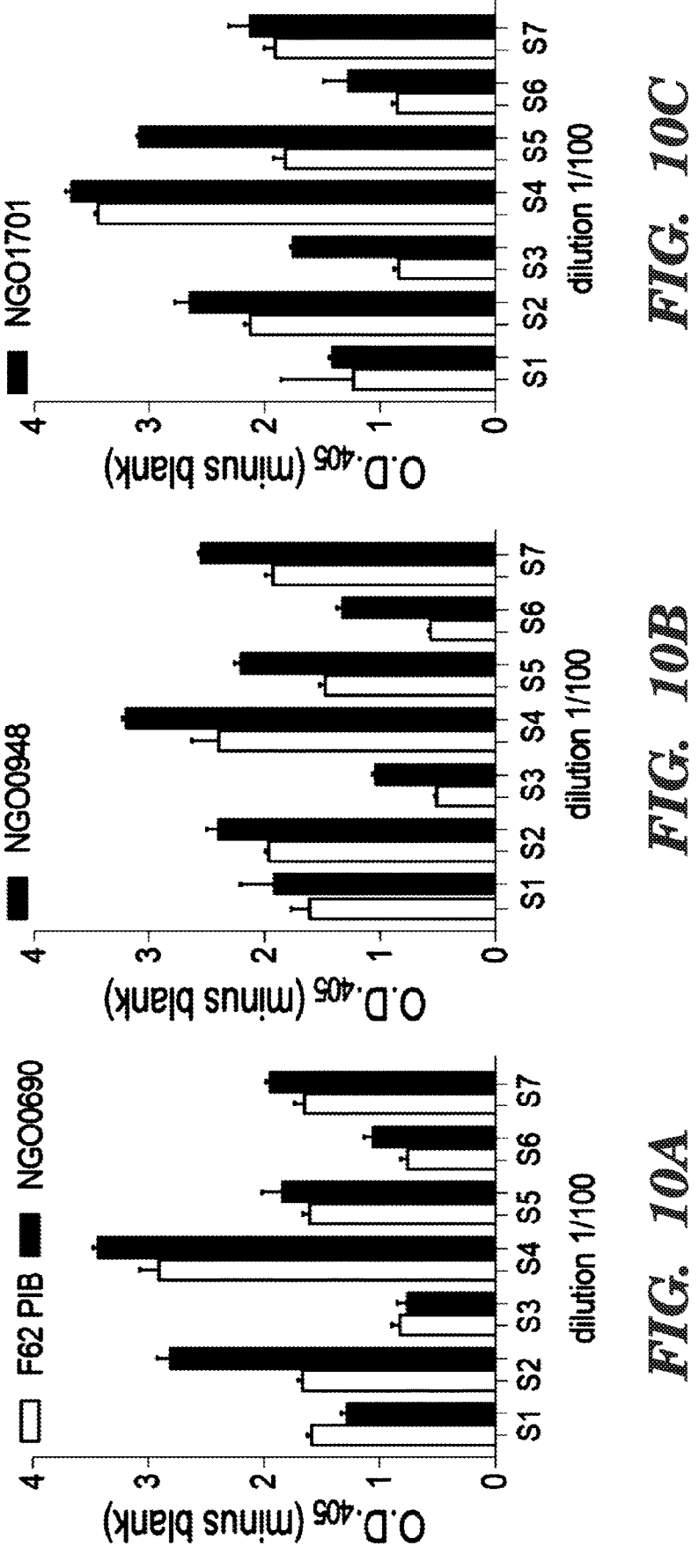
FIG. 10A-10C shows the total antigen-specific IgG in human sera measured against PIB (white bars) and NGO0690 (FIG. 10A, gray bars), NGO0948 (FIG. 10B, gray bars) and NGO1701 (FIG. 10C, gray bars). Plates were coated with 2 µg/ml of purified native gonococcal porin PIB (positive control, white bars) and purified recombinant A) NGO0690, B) NGO0948 and C) NGO1701 (gray bars). Sera from different DGI patients (Si through S7) were used at a 1:100 dilution. Total human IgGs to the proteins were measured with a secondary anti-human AP-linked secondary antibody, detected by ELISA and reported as O.D. 405 reading from quadruplicate wells subtracted of the blank ±SEM).

Immune recognition of recombinant purified antigens, NGO0690, NGO0948, and NGO1701 was validated by hyperimmune human sera from a collection of *N. gonorrhoeae*-naturally infected, convalescent female subjects that developed PID or DGI. These subjects often mount a strong anti-gonococcal antibody response, in contrast to uncomplicated infections {see, e.g., Hedges et al., *J Infect Dis.* 1998 September; 178(3):742-51. doi: 10.1086/515372; and Hook et al., J Clin Microbiol. 1997 August; 35(8): 2129-2132, which are incorporated herein by reference in their entireties}. The antigens were consistently recognized by ELISA similarly to purified *N. gonorrhoeae* F62 PIB porin, a known immunoreactive antigen (FIG. 10A-10C). That is, human patients infected with *N. gonorrhoeae* raised antibodies that bind to the NGO0690, NGO0948 and NGO1701 antigens identified herein. This indicates that not only are these antigens expressed in human infection with different, naturally-occurring strains of the pathogen, they are clearly antigenic in human (in vivo) infection.

Example 3: Antibody Levels to Combined Antigens (NGO0690/NGO1701 AND NGO0690/NGO0948/NGO1701)

Figure 11:
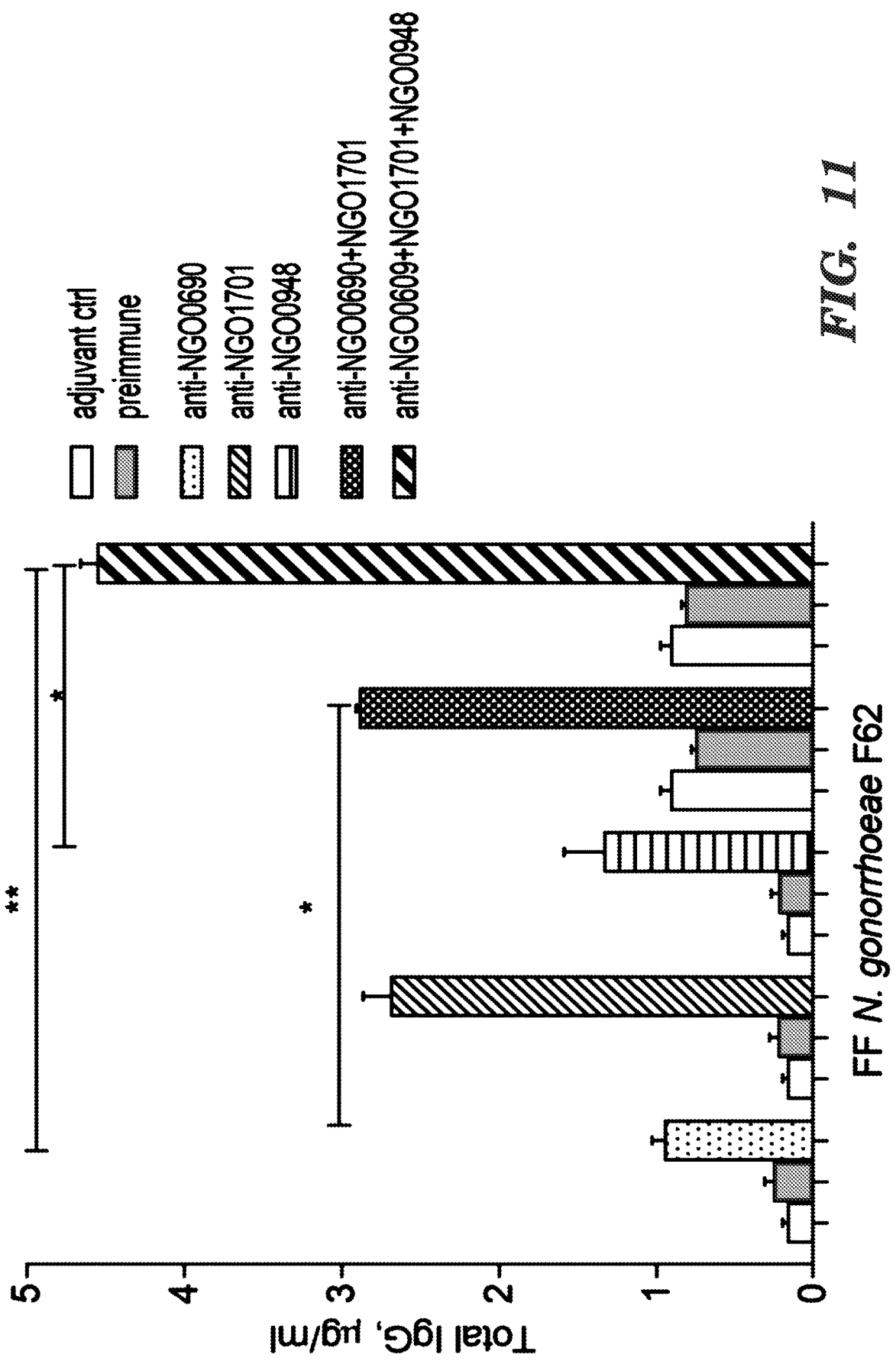
FIG. 11 shows sera from mice immunized with combination antigens recognize *N. gonorrhoeae* F62 organisms better than sera from mice immunized with individual proteins by ELISA. Total IgG (µg/ml±SEM) measured by ELISA of pooled sera from mice immunized with alum alone (white bars), NGO0690 (dotted bar), NGO1701 (thin striped bar), NGO0948 (horizontal striped bar), NGO0690/NGO1701 (checkered bar) and NGO0690/NGO0948/NGO1701 (thick striped bar) against FF *N. gonorrhoeae* strain F62. Preimmune sera, gray bars. *,** p significant by Kruskal Wallis test with Dunn's multiple comparisons test.

Female BALB/c mice were immunized subcutaneously with purified recombinant NGO0690, NGO0948 and NGO1701 as antigens in the following combinations: 1) NGO0690/NGO1701 together and 2) NGO0690/NGO0948/NGO1701 together, using alum as an adjuvant as previously described. Pooled preimmune sera and immune sera were tested for presence and amounts of antigen-specific antibodies by ELISA and compared to those in sera from mice immunized with the individual antigens. Sera from mice immunized with adjuvant alone and preimmune sera served as control; total IgGs were measured against formalin-fixed *N. gonorrhoeae* strain F62 as previously described, and expressed as μg/ml±SEM. A robust production of antigen-specific IgG was induced by the combination antigens as compared to the individual antigens, all of which were higher than the preimmune sera and adjuvant sera controls. FIG. 11 shows the control sera in the white bars (adjuvant alone) and gray bars (preimmune sera); the anti-NGO0690 sera (dotted bar), anti-NGO1701 sera (thin striped bar) and anti-NGO0948 sera (horizontal striped bar), the anti-NGO0690/NGO1701 sera (checkered dotted bar) and the anti-NGO0690/NGO0948/NGO1701 sera (thick striped bar).

Example 4: Serum Bactericidal Activity of Anti-NGO0690/NGO1701 and NGO0690/NGO0948/NGO1701

Figure 8B:
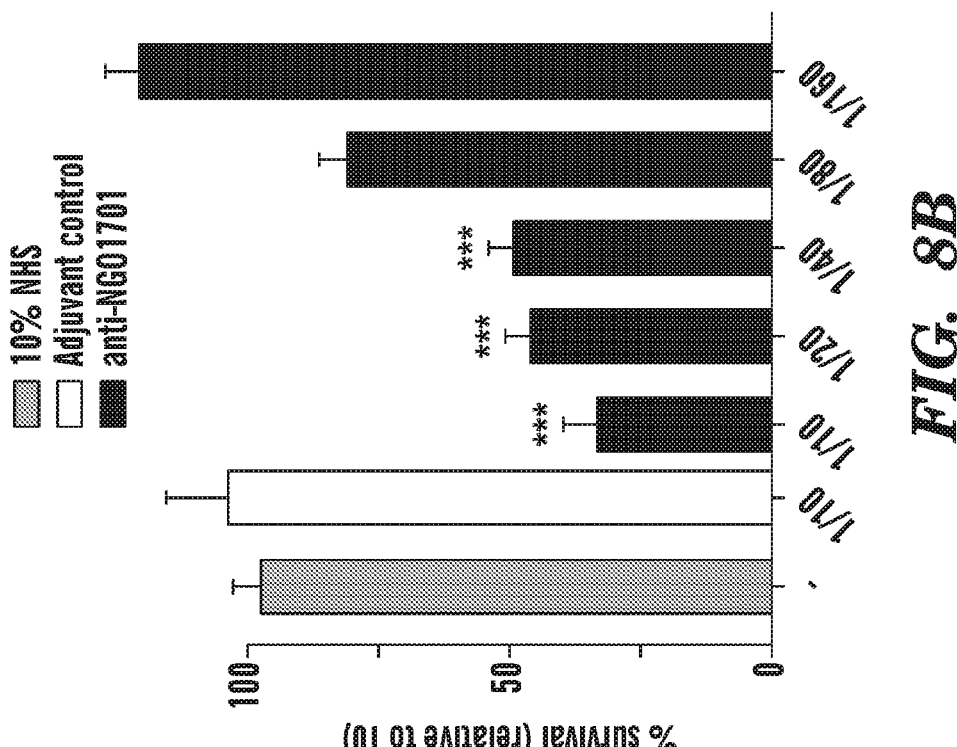
FIG. 8A-8C shows serum bactericidal activity (SBA). Percent survival (CFU at T30/T0±SEM) of *N. gonorrhoeae* F62 incubated with serial dilutions of immune mouse sera to FIG. 8A) NGO0690 and FIG. 8B) NGO1710.
Figure 8A:
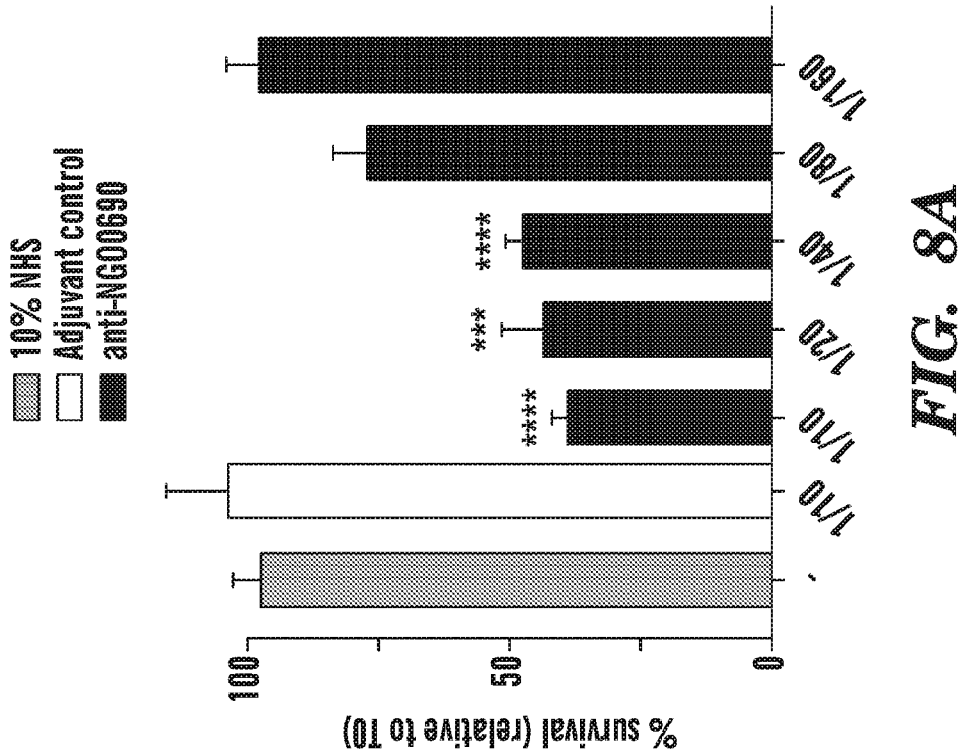
Figure 8C:
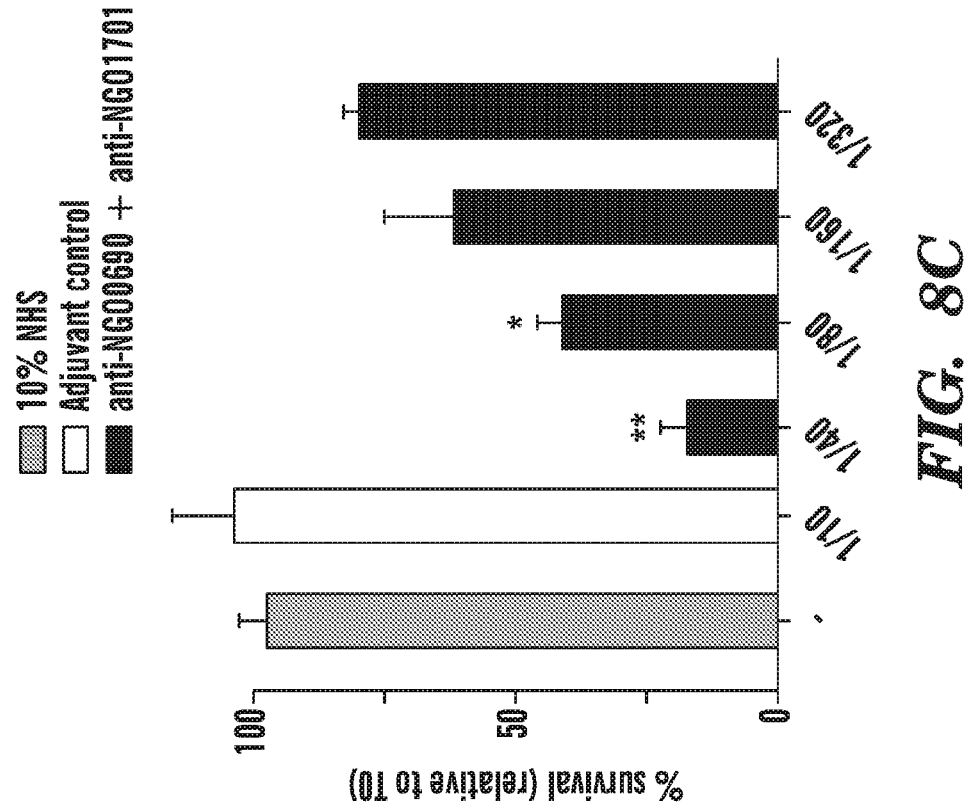
Figures 12A, 12B, 12C:
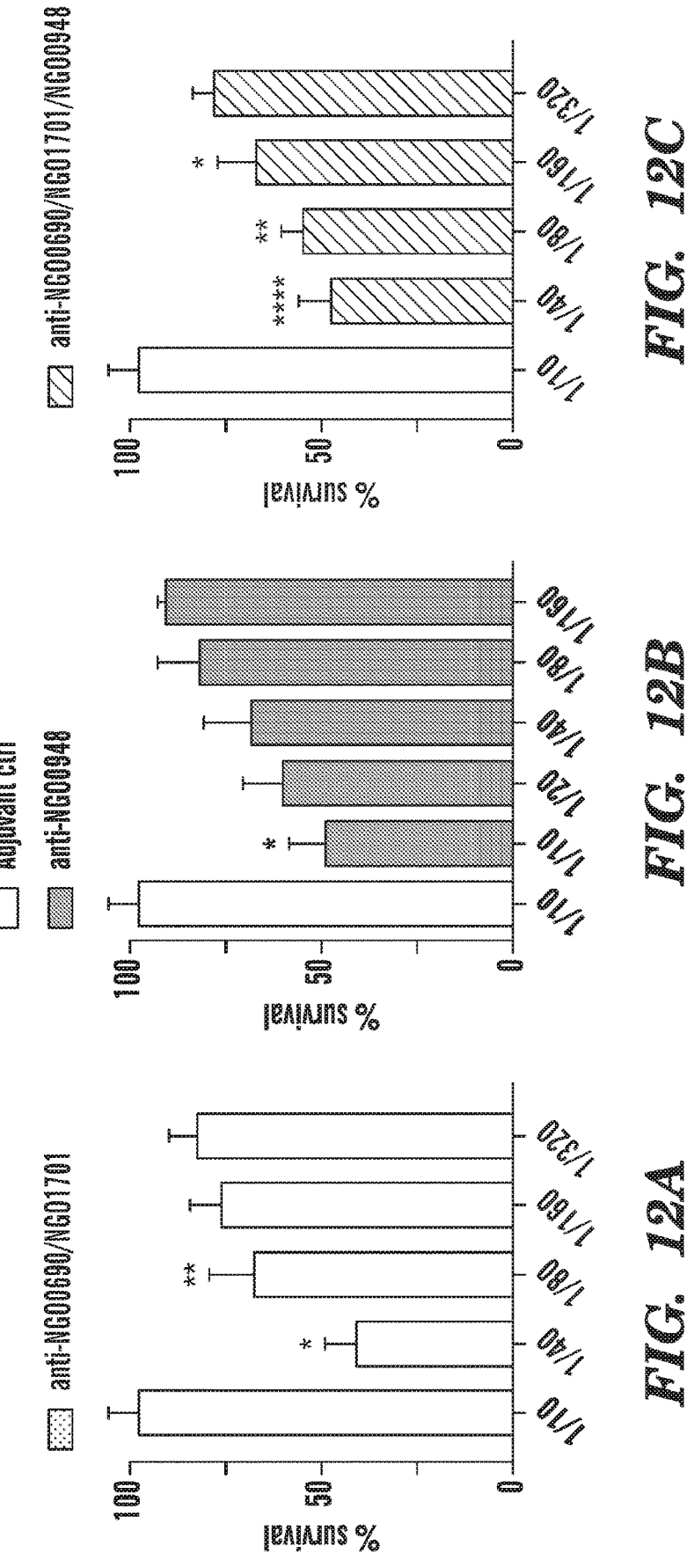
FIG. 12A-12C shows a serum bactericidal assay (SBA). *N. gonorrhoeae* F62 survival (% T30/T0±SEM) with adjuvant control sera (white bars)

The ability of antibodies to kill *N. gonorrhoeae* was shown in Example 1 for sera from mice immunized with NGO0690, NGO0948 and NGO1701 individually, and for the anti-NGO0690+anti-NGO1701 combined (FIGS. 8A-8C). Using the serum bactericidal activity (SBA) assay bacterial killing by mouse sera were evaluated from the combination antigens immunizations and reported % survival as the reciprocal of killing. FIG. 12A shows the % survival of bacteria exposed to sera from mice immunized with NGO0690/NGO1701 at the indicated dilutions (checkered bars). The killing titers remained similar to those of anti-NGO0690+anti-NGO1701 sera together (approx. 1/80, see FIG. 8C). FIG. 12B shows the % of bacteria survival after exposure to anti-NGO0948 individual antigen sera (gray bars) and the corresponding killing titers (1/10, see also Table 2). FIG. 12C shows the % survival and killing titers for sera raised to NGO0690/NGO0948/NGO1701 combined (thick striped bars), which was higher that both the individual antigen antisera and the 2 antigen combination antisera. Bacterial killing by sera from mice immunized with PBS/alum (adjuvant control, FIG. 12A-12C, white bars) and preimmune sera (not shown) remained negligible.

Using established methods, *N. gonorrhoeae* F62 mutants deleted for the NGO0690 or NGO1701 were constructed by allelic replacement of the coding region with a kanamycin (kan) resistance gene and selection on kanamycin plates. Immune recognition of *N. gonorrhoeae* F62 NGO0690 deletion mutant (Δ0690) by mouse immune sera raised to the purified NGO0690 was abrogated and recognition of *N. gonorrhoeae* F62 NGO1701 deletion mutant (A1701) was greatly reduced, as determined by whole-cell ELISA and total IgG quantification in mouse pooled immune sera as compared to WT organisms.

As for antibody recognition, the bactericidal activity of sera raised to NGO0690 and NGO1701 was also abrogated against both *N. gonorrhoeae* F62 deletion mutants, confirming antigen-specific antibody functionality.

```
SEQUENCES
NGO0188 >YP_207355.1 preprotein translocase
subunit YajC [Neisseria gonorrhoeae FA 1090]
                              SEQ ID NO: 1
MNQAVAQFAPLVLIMVVFYFLIMRPQQKKFKAHQAMLAALKAGDKVVLAA

GFKGKVTRVGEQFFTVDIGQGTKIEVEVERNAIAAKVD

NGO0449 >YP_207601.1 membrane protein
[Neisseria gonorrhoeae FA 1090]
                              SEQ ID NO: 2
MTMILSILSLFFIIRLLFLAVSIKHEKALIAKGAKQYGKTNSTVLAAVHT

LYYLACFVWVWLSDTAFNGISLIGTLTVMASFVILSLIIKQLGEIWTVKI

YILPNHQINRSWLFKTFRHPNYFLNIIPELIGIALLCQAWYVLLIGLPIY

LLVLFKRIRQEEQAMATLF

NGO0914 >YP_208022.1 membrane protein
[Neisseria gonorrhoeae FA 1090]
                              SEQ ID NO: 3
MNKEIVGIFFIPMGIISMCMAALWQMYVMMTETYTLNRFKDKELVWRVAL

LFISFSLAVYLLCPNSRKKGIVFFILGGGGAVMYLLARMWLPFSK

NGO1332 >YP_208394.1 hypothetical protein NGO1332
[Neisseria gonorrhoeae FA 1090]
                              SEQ ID NO: 4
MTQETALGAALKSAVQTMSKKKQTEMIADHIYGKYDVFKRFKPLALGIDQ

DLIAALPQYDSALIARVLANHCRRPRYLKALARGGKRFDLNNRFKGEVTP

EEQAIAQNHPFVQQALQQQSAQAAAETPSVEAEAAESSAAE
```

-continued

NGO1377 >YP_208437.1 biopolymer transporter
ExbD [*Neisseria gonorrhoeae* FA 1090]
SEQ ID NO: 5
MAFGSMNSSDDSPMSDINVTPLVDVMLVLLIVFMITMPVLTHSIPLELPT

ASEQANKQDKQPKDPLRLTIDANGGYYVGGDSASKVEIGEVESRLKAAKE

QNENVIVAIAADKAVEYDYVNKALEAARQAGITKIGFVTETKAQ

NGO1543 >YP_208591.1 cell division protein
FtsL [*Neisseria gonorrhoeae* FA 1090]
SEQ ID NO: 6
MNKSNFFLLLAVCVSAFSVVMQQNQYRLNFTALDKAKKQEIALEQDYAQM

RLQQARLANHEAIRAAAEKQNLHPPVSGNTFMVEHQR

NGO1549 >YP_208597.1 cell division protein
FtsN [*Neisseria gonorrhoeae* FA 1090]
SEQ ID NO: 7
MFMNKFSQSGKGLSGFFFGLILATVIIAGILLYLNQGGQNAFKIPAPSKQ

PAETEILKLKNQPKEDIQPEPADQNALSEPDVAKEAEQSDAEKAADKQPV

ADKADEVEEKAGEPEREEPDGQAVRKKALTEEREQTVREKAQKKDAETVK

KQAVKPSKETEKKASKEEKKAAKEKVAPKPTPEQILNSGSIEKARSAAAK

EVQKMKTFGKAEATHYLQMGAYADRRSAEGQRAKLAILGISSEVVGYQAG

HKTLYRVQSGNMSADAVKKMQDELKKHGVASLIRAIEGK

NGO1607 >YP_208647.1 lipopolysaccharide-
assembly protein [*Neisseria gonorrhoeae*
FA 1090]
SEQ ID NO: 8
MKVRWRYGIAFPLILAVALGSLSAWLGRISEVEIEEVRLNPDEPQYTMDG

LDGRRFDEQGYLKEHLSAKGAKQFPENSDIHFDSPHLVFFQEGRLLYEVG

SDEAVYHTENKQVLFKNNVVLTKTADGRRQAGKVETEKLHVDTESQYAQT

DTPVSFQYGASHGQAGGMTYNHKTGMLNFSSKVKAAIYDTKDM

NGO1880 >YP_208913.1 membrane protein
[*Neisseria gonorrhoeae* FA 1090]
SEQ ID NO: 9
MKVLNGWSDRKMWRVLSALPIGVVFFDLIYGFVLNVLQGLDLQRAVPDSE

GVLAVTPDIAFNSLQIVANGGMAAVVCFGLAVVFLLNRSVRRRQVLEIGV

FRMLGLVAVLAFSAPSLWEWANALPLLLKGADVVNTGNARYVLTALCMPF

PAVSCIIGLVGRFRLQTASGRVAKAGGAVKAGG

NGO1948 >YP_208972.1 membrane protein
[*Neisseria gonorrhoeae* FA 1090]
SEQ ID NO: 10
MKIGTTWQTASAMLVLRLFAAYEFLESGLQKWNGENWFSEINDQFPFPFN

LLPDALNWNLAMYAELLLPVLLLLGLATRLSALGLMVVTAVAWAAVHAGS

GYNVCDNGYKMALIYIVVLIPLLFQGAGGWSLDTLLKKLFCPKCRLKQD

NGO2057 >YP_209076.1 mechanosensitive
channel MscS [*Neisseria gonorrhoeae*
FA 1090]
SEQ ID NO: 11
MDFKQFDFLHLISVSGWGHLAEKAWAFGLNLAAALLIFLVGKWAAKRIVA

VMRAAMTRAQVDATLISFLCNVANIGLLILVIIAALGRLGVSTTSVTALI

GGAGLAVALSLKDQLSNFAAGALIILFRPFKVGDFIRVGGFEGYVREIKM

VQTSLRTTDNEEVVLPNSVVMGNSIVNRSSLPLCRAQVIVGVDYNCDLKV

AKEAVLKAAAEHPLSVQNEERQPAAYITALGDNAIEITLWAWANEADRWT

LQCDLNEQVVENLRKVNINIPFPQRDIHIINS

-continued

NGO0416 >YP_207571.1 hypothetical protein
NGO0416 [*Neisseria gonorrhoeae* FA 1090]
SEQ ID NO: 12
MKKCILGILTACAAMPAFADRISDLEARLAQLEHRVAVLESGGNTVKIDL

FGSNSTMYVCSVTPFQKTFEASDRNEGVARQKVRQACNRETSAMFCGDEA

IRCRKFD

NGO0571 >YP_207716.1 hypothetical protein
NGO0571 [*Neisseria gonorrhoeae* FA 1090]
SEQ ID NO: 13
MRYKPLLLALMLVFSTPAVAAHDAAHNRSAEVKKQAKNKKEQPEAAEGKK

EKGKNAAVKDKKTGGKEAAKEFKKTAKNRKEAEKEATSRQSARKGREGDK

ESKAEHKKAHGKPVSGSKEKNAKTQPENKQGKKGAKGQGNPRKGGKAEKD

TVSANKKARSDKNGKAVKQDKKHTEEKNAKTDSDELKAAVAAATNDVENK

KALLKQSEGMLLHVSNSLKQLQEERIRQERIRQERIRQARGNLASVNRKQ

REAWDKFQKLNTELNRLKTEVAATKAQISRFVSGNYKNSRPNAVALFLKN

AEPGQKNRFLRYTRYVNASNREVVKDLEKQQKALAVQEQKINNELARLKK

IQANVQSLLKKQGVTDAAEQTESRRQNAKISKDARKLLEQKGNEQQLNKL

LSNLEKKKAEHRIQDAEAKRKLAEAKLAAAEKARKEAAQQKAEARRAEMS

NLTAEDRNIQAPSVMGIGSADGFSRMQGRLKKPVDGVPTGLFGQNRSGGD

VWKGVFYSTAPATVESIAPGTVSYADELDGYGKVVVIDHGENYISIYAGL

SEISAGKGYTVAAGSKIGTSGSLPDGEEGLYLQIRYRGQVLNPSGWIR

NGO0757 >YP_207884.1 hypothetical protein
NGO0757 [*Neisseria gonorrhoeae* FA 1090]
SEQ ID NO: 14
MPLPAPCRFAKPAASFLSMALLSCQLSHAATAYIPPNDFQPNCDIRRLGL

TQGQHNELRKIRAAFKMAGDRARLKVMHSEHSRRRSVVEIISSDVFNRNE

ARDYVESRYHSSMDFAVDELEIQHRFFHILTPQQQQMWLSSCLK

NGO1215 >YP_208286.1 hypothetical protein
NGO1215 [*Neisseria gonorrhoeae* FA 1090]
SEQ ID NO: 15
MKKLLAAVMMAGLAGAVSAAGVHVEDGWARTTVEGMKMGGAFMKIPNDEA

KQDFLLVGSSPVADRVEVHTHINDNGVMRMREVKGGVPLEAKSVTELKPG

SYHVMFMGLKKQLKEGDKIPVTLKFKNAKAQTVQLEVKTAPMSAMNHGHH

HGEAHQH

NGO1251 >YP_208322.1 hypothetical protein
NGO1251 [*Neisseria gonorrhoeae* FA 1090]
SEQ ID NO: 16
MCFCLLLMPKFYFSCRTICFLKANLIIMAGMKKYLIPLSIAAVLSGCQSI

YVPTLTEIPVNPINTVKTEAPAKGFRLAPSHWADVAKISDEATRLGYQVG

IGKMTKVQAAQYLNNFRKRLVGRNAVDDSMYEIYLRSAVDSQRGEINTEQ

SKLYIENALRGWQQRWKNMDAKPDNPAFTNFLMEVMKMQPLK

NGO1438 >YP_208492.1 protein-disulfide
isomerase [*Neisseria gonorrhoeae* FA 1090]
SEQ ID NO: 17
MKTKLIKILTPFTVLPLLACGQTPVSNANAESAVKAESAGKSVAASLKAR

LEKTYSAQDLKVLSVSETPVKGIYEVVVSGRQIIYTDAEGGYMFVGELIN

IDTRKNLTEERAADLNKIDFASLPLDKAIKEVRGNGKLKVAVFSDPDCPF

-continued

CKRLEHEFEKMTDVTVYSFMMPIAGLHPDAARKAQILWCQPDRAKAWTDW

MRKGKFPVGGSICDNPVAETTSLGEQFGFNGTPTLVFPNGRTQSGYSPMP

QLEEIIRKNQQ

NGO1701 >YP_208734.1 membrane protein
[*Neisseria gonorrhoeae* FA 1090]
SEQ ID NO: 18
MNRRQFLGSAAAVSLASAASFARAHGHADYHHHHDMQPAAASAYTAVRQT

AAHCLDAGQVCLTHCLSLLTQGDTSMSDCAVAVRQMLALCGAVHDLAAQN

SPLTRDAAKVCLEACKQCAKACKEHSAHHAECKACYESCLDCIKECEKLA

A

NGO1868 >YP_208900.1 hypothetical protein
NGO1868 [*Neisseria gonorrhoeae* FA 1090]
SEQ ID NO: 19
MAFITRLFKSIKQWLVLLPILSVLPDAAAEGIAATRAEARITDGGRLSIS

SRFQTELPDQLQQALRRGVPLNFTLSWQLSAPTIASYRFKLGQLIGDDDN

IDYKLSFHPLTNRYRVTVGAFSTDYDTLDAALRATGAVANWKVLNKGALS

GAEAGETKAEIRLTLTSTSKLPKPFQINALTSQNWHLDSGWKPLNIIGNK

NGO2119 >YP_209129.1 organic solvents
ABC transporter auxiliary protein
[*Neisseria gonorrhoeae* FA 1090]
SEQ ID NO: 20
MKKSSFISALGIGILSIGMAFASPADAVGQIRQNATQVLTILKSGDAASA

RPKAEAYAVPYFDFQRMTALAVGNPWRTASDAQKQALAKEFQTLLIRTYS

GTMLKFKNATVNVKDNPIVNKGGKEIVVRAEVGIPGQKPVNMDFTTYQSG

GKYRTYNVAIEGTSLVTVYRNQFGEIIKAKGIDGLIAELKAKNGGK

NGO0227 >YP_207392.1 hypothetical protein
NGO0227 [*Neisseria gonorrhoeae* FA 1090]
SEQ ID NO: 21
MKDSTGQMRLATKDLAEAIKRGEVRSSAFTTKQLKAIEKGKDKIPSYTWH

HHQDTGRMQLVPEWEHSKTGHIGGTAMGKGK

NGO0354 >YP_207510.1 hypothetical protein
NGO0354 [*Neisseria gonorrhoeae* FA 1090]
SEQ ID NO: 22
MNFQDYLATFPSIDHLGGLDVQDAEGKTVHHIPAVQGKLGSLKLYNALAE

RFDGKLGKEAAEQGL1WFAEHVADARAHPGKHPNIDLLENVVQSGETLLL

KPLAAQ

NGO0588 >YP_207731.1 hypothetical protein
NGO0588 [*Neisseria gonorrhoeae* FA 1090]
SEQ ID NO: 23
MMKKILAVSALCLMTAAAQAADTYGYLAVWQNPQDANDVLQVKTTKEDSA

KSEAFAELEAFCKGQDTLAGIAEDEPTGCRSVVSLNNTCVSLAYPKALGA

MRVENAVVITSPRFTSVHQVALNQCIKKYGAQGQCGLETVYCTSSSYYGG

AVRSLIQHLK

NGO0648 >YP_207787.1 membrane protein
[*Neisseria gonorrhoeae* FA 1090]
SEQ ID NO: 24
MKKIIASALIATFALTACQDDTQARLERQQKQIEALQQQLAQQADDTVYQ

LTPEAVKDTIPAQAQANGNNGQPVTGKDGQQYIYDQSTGSWLLQSLIGAA

AGAFIGNALANKFTRAGNQDSPVARRARAAYHQSARPNARTSRDLNTRSL

RAKQQAAQAQRYRPTTRPPVNYRRPAMRGFGRRR

-continued

NGO0678 >YP_207817.1 hypothetical protein
NGO0678 [*Neisseria gonorrhoeae* FA 1090]
SEQ ID NO: 25
MNKLFVTALSALALSACAGTWQGAKQDTARNLDKTQAAAERAAEQTGNAV

EKGWDKTKEAVKKGGNAVGRGISHLGKKIENATE

NGO0690 >YP_207829.1 hypothetical protein
NGO0690 [*Neisseria gonorrhoeae* FA 1090]
SEQ ID NO: 26
MNKTLSILPAAILLGGCAAGGNTFGSLDGGTGMGGSIVKMTVESQCRAEL

DRRSEWRLTALAMSAEKQAEWENKICGCATEEAPNQLTGNDVMQMLNQST

RNQALAALTVKTVSACFKRLYR

NGO0694 >YP_207831.1 hypothetical protein
NGO0694 [*Neisseria gonorrhoeae* FA 1090]
SEQ ID NO: 27
MNQEGITAHGNATITLKAKENNKITVENAAYSSDGISTLINRTGARPGTR

DDGNKIILEAGGDNIVTMKSGDADADYVNNSKVLTETPYYKSKRGSNGIF

AYGDKSLVKLIGENNIVKSEISEKSKALNGGFRHIGIYSWQNAKVELSAK

SDNIVQGGIWGLYSNNSSISLKGKNNVISNPKYNVFAYKKAKVDLTVENK

NTLSDAEFGVYALNTSMVNLSSKDNNEVKSTQVGLYSQDGGSINVDRKDN

IIEGDAVALVGKGGSQNIRASRTNLISSKSLGIHAEQAAKIAITGASNTI

HASNAAIRSLDKSEVKIDGQITIDSNVANLARQDGSIHLNYKDDTRITGA

TVSDKGLVAIKPLNNTNIVADTIHYKGDVLAVNKGKVELDFTPNILLAGR

LDNFSGLTDSKHKNLFENYVANLDSKSAGEINFNLAKDALWTMTGQSWLD

KLEGQGTIDFNNDAKTSGRALHIGELAGANKFLMHLNKDGIHSDMLYVKK

GTSTPQEVVVKNLSEVLDSMNYGERLRFATVTNSKNEFVNGKKYIDDTHL

MEDALTVEYSAHNGDKNNKDDYNKSFNGSEMTAEKAGDDYVNKTYTDNRQ

NVYLVKQATGNPSRNVKNINDMFDSTAHYAFTLDTYAKREGERAFSTLDK

KEGDWIRLTHTRVIQSNAFRFHNNDFEIGYDRFSLNEQEKKRKWGISLDY

GHGRTSLWNTFGKDKIRKYELALYNTTQYIDKEGDETGYIDNVLKIGKLR

NRVIARNHMGQLWGKGKYSNTLFSISTEYGRRKFLDDDKLWRITPQVQLQ

YSYLRGTGYRIDNGINVNLSHANSLIGRLGLDVVRKFDGGKKLFYIKGNI

FHEFLGSRSFKAFEGKSHYAQK

NGO0768 >YP_207895.1 hypothetical protein
NGO0768 [*Neisseria gonorrhoeae* FA 1090]
SEQ ID NO: 28
MWQIRKNRTENLHNAPNYPILLLKQNLFFKENNEYQENLRFVCCCRFYCF

DSLCQRNQNRCQQHALFRSRRAKAGGNGSRYGR

NGO0861 >YP_207975.1 hypothetical protein
NGO0861 [*Neisseria gonorrhoeae* FA 1090]
SEQ ID NO: 29
MKMKKLILLSVAAMLVTACTYADRRFVTQESAAEIQAKSRAIQISERAER

AEYRKERREEMMDAARAIKKANENSPNIYFIR

NGO0891 >YP_208002.1 hypothetical protein
NGO0891 [*Neisseria gonorrhoeae* FA 1090]
SEQ ID NO: 30
MKKLLMITLTGMLAACSTGVNVGRLMVEMPQGERPVVVQVPATNNPLSDA

VAVGMIKTSGSPSASNMIEMLGADNINVGVAGGSQMFNKATALYSLNHAK

KVGNNVSVYMTGDSESDKADLENAANAKNIKLHYFFNQK

-continued

-continued

NGO0948 >YP_208051.1 lipoprotein
[*Neisseria gonorrhoeae* FA 1090]

SEQ ID NO: 31

MPSEPFGRHNMTNTLISITQDDTMTHIKPVIAALALIGLAACSGSKTEQP

KLDYQSRSHRLIKLEVPPDLNNPDQGNLYRLPAGSGAVRASDLEKRRTPA

VQQPADAEVLKSVKGVRLERDGSQRWLVVDGKSPAEIWPLLKAFWQENGF

DIESEEPAIGQMETEWAENRAKIPQDSLRRLFDTVGLGGIYSTGERDKFI

VRIEQGKNGVSDIFFAHKAMKEVYGDKNKDTTMWQPSASDPNLEAAFLTR

FMQYLGVDGRQAENALAKKPTLPAANEMARIEGKSLIVFGDYGRNWRRTG

LALDRIGLTVVGQNTERHAFLVQKAPNESNAVTEQKPGLFKRLLGKGKAE

KPAEQPELIVYAEPVADGSRIVLLNKDGSAYAGKDASALLGKLHSELR

NGO1043 >YP_208127.1 hypothetical protein
NGO1043 [*Neisseria gonorrhoeae* FA 1090]

SEQ ID NO: 32

MKKLLIAAMMAAALAACSQEAKQEVKEAAQAVESDVKDTAASAAESAASA

VEEAKGQVKDAAADAKASAEEAVTEAKDAAAETKEAVSEAAKDTLNKAAD

AAQEAADKMKDAAK

NGO1428 >YP_208483.1 hypothetical protein
NGO1428 [*Neisseria gonorrhoeae* FA 1090]

SEQ ID NO: 33

MKKTSKYLIYTAAFTSFCFAFQENRSEAKQPDITLSASLCEQFNMLNAKD

MDTEQVSLSKECDIIESSHDWEKEYGNLNEQEMLAGVVYE

NGO1729>YP_ 208762.1 hypothetical protein
NGO1729 [*Neisseriagonorrhoeae*FA 1090]

SEQ ID NO: 34

MNIKHLLLTAAATALLGISAPALAHHDGHGDDDHGHAAHQHGKQDKIISR

AQAEKAAWARVGGKITDIDLEHDDGRPHYDVEIVKNGQEYKVVVDARTGR

VISSRRDD

NGO1802 >YP_208832.1 membrane protein
[*Neisseria gonorrhoeae* FA 1090]

SEQ ID NO: 35

MPSEALQTAFRGNIRRSFTMIRLTRAFAAALIGLCCTTGAHADTFQKIGF

INTERIYLESKQARNIQKTLDGEFSARQDELQKLQREGLDLERQLAGGKL

KDAKKAQAEEKWRGLVEAFRKKQAQFEEDYNLRRNEEFASLQQNANRVIV

KIAKQEGYDVILQDVIYVNTQYDVTDSVIKEMNAR

NGO1947 >YP_208971.1 hypothetical protein
NGO1947 [*Neisseria gonorrhoeae* FA 1090]

SEQ ID NO: 36

MNKNIAAALAGALSLSLAAGAVAAHKPASNATGVQKSAQGSCGASKSAEG

SCGASKSAEGSCGAAASKAGEGKCGEGKCGATVKKAHKHTKASKAKAKSA

EGKCGEGKCGSK

NGO0188 >YP_207355.1; NC_002946.2
(189505..189771)

SEQ ID NO: 37

```
  1 atgaatcaag ctgttgcaca atttgctcct ttggtgttga ttatggtggt gttctacttc 61 ctgatcatgc gcccccaaca aaagaaattc aaagcgcatc aggcaatgct tgccgccttg 121 aaagccggcg acaaagtggt cttggcggca ggtttcaagg gtaaggtaac cagagtcggc
```

NGO0449 >YP_207601.1; NC_002946.2
(444039..444548)

SEQ ID NO: 38

```
  1 atgacaatga ttttaagcat tttaagcctg ttttttatca ttagactgtt attttttagcc 61 gtctctatta aacatgaaaa agccttgatt gccaaagggg cgaaacaata cggaaaaacc 121 aattccacgg tgcttgcggc agttcatacg ctttattatt tggcgtgttt tgtttgggta 181 tggctttctg acactgcttt taatggcata tccttgattg gtacactgac ggtgatggct 241 tcatttgtga tattatcatt gattattaag cagttggggg agatttggac ggttaaaatc 301 tatattttgc caaatcatca aattaatcgt tcgtggttgt ttaaaacatt ccgccacccg 361 aattatttt taaacatcat acccgaactg attggcatcg ccttattatg tcaagcgtgg 421 tatgttttat tgattggcct gcccatttat ttgctggtct tatttaagcg tatccgacaa 481 gaagaacagg cgatggcaac actttttaa
```

NGO0914 >YP_208022.1; NC_002946.2
(892771..893058, complement)

SEQ ID NO: 39

```
  1 atgaacaaag aaatagtcgg tattttcttt ataccgatgg gcatcatcag catgtgtatg 61 gccgcattgt ggcagatgta tgtgatgatg accgaaactt atacgctcaa ccgtttcaaa 121 gataaagaat tggtttggcg cgtggcattg ttgtttatca gtttcagcct tgccgtttat 181 ctgctctgtc cgaattcgcg taaaaaaggc atcgtctttt ttattctcgg gggaggcggt 241 gcagtcatgt atctgctggc gcggatgtgg ttgcccttca gtaaatag
```

NGO1332 >YP_208394.1; NC_002946.2
(1290929..1291354)

SEQ ID NO: 40

```
  1 atgacacaag aaaccgcttt gggcgcggca ctgaaatccg ccgtccaaac tatgagcaaa 61 aagaaacaga ccgaaatgat cgccgaccac atctacggca aatacgatgt attcaaacgc 121 ttcaaaccgt tggcgctcgg catcgatcag gatttgattg ccgctttgcc gcaatacgat
```

-continued

```
    181   tccgcactga ttgcacgcgt cctcgccaac cactgccgcc gtccgcgcta tctgaaagcc 241   ttggcgcgcg gcggcaaacg tttcgatttg aacaaccgtt tcaaaggcga agttaccccc 301   gaagaacagg cgattgcgca aaaccatcct ttcgtgcagc aggctttgca acagcagtcc 361   gcccaagctg ccgccgaaac gccgtctgtt gaagccgaag cagccgaatc ttccgcagca 421   gaataa
```

NGO1377 >YP_208437.1; NC_002946.2
(1290929..1291354)

SEQ ID NO: 41

```
      1   atgacacaag aaaccgcttt gggcgcggca ctgaaatccg ccgtccaaac tatgagcaaa 61   aagaaacaga ccgaaatgat cgccgaccac atctacggca aatacgatgt attcaaacgc 121   ttcaaaccgt tggcgctcgg catcgatcag gatttgattg ccgctttgcc gcaatacgat 181   tccgcactga ttgcacgcgt cctcgccaac cactgccgcc gtccgcgcta tctgaaagcc 241   ttggcgcgcg gcggcaaacg tttcgatttg aacaaccgtt tcaaaggcga agttaccccc 301   gaagaacagg cgattgcgca aaaccatcct ttcgtgcagc aggctttgca acagcagtcc 361   gcccaagctg ccgccgaaac gccgtctgtt gaagccgaag cagccgaatc ttccgcagca 421   gaataa
```

NGO1543 >YP_208591.1; NC_002946.2
(1517225..1517488, complement)

SEQ ID NO: 42

```
      1   atgaacaaat cgaatttctt tctgctgctt gcggtgtgcg tttccgcttt ttccgttgtg 61   atgcagcaaa accagtacag gctcaacttc acagctttgg acaaggcgaa aaaacaggaa 121   atcgccttgg agcaggatta tgcgcaaatg aggctgcaac aggcgcgttt ggcgaatcac 181   gaagcgatca gggcggcggc agaaaaacaa aacctccatc cgccggtttc gggcaatacc 241   tttatggtgg aacatcaaag atag
```

NGO1549 >YP_208597.1; NC_002946.2
(1522391..1523260, complement)

SEQ ID NO: 43

```
      1   atgtttatga acaaattttc ccaatccgga aaaggtctgt ccggtttctt cttcggtttg
```

-continued

```
     61   atactggcaa cggtcattat tgccggtatt ttgctttatc tgaaccaggg cggtcaaaat 121   gcgttcaaaa tcccggctcc gtcgaagcag cctgcagaaa cggaaatcct gaaactgaaa 181   aaccagccta aggaagacat ccaacctgaa ccggccgatc aaaacgcctt gtccgaaccg 241   gatgttgcga aagaggcaga gcagtcggat gcggaaaaag ctgccgacaa gcagcccgtt 301   gccgacaaag ccgacgaggt tgaagaaaag gcgggcgagc cggaacggga agagccggac 361   ggacaggcag tgcgcaagaa agcactgacg gaagagcgtg aacaaaccgt cagggaaaaa 421   gcgcagaaga agatgccga aacggttaaa aaacaagcgg taaaaccgtc taaagaaaca 481   gagaaaaaag cttcaaaaga gagaaaaag gcggcgaagg aaaaagttgc acccaaaccg 541   accccggaac aaatcctcaa cagcggcagc atcgaaaag cgcgcagtgc cgctgccaaa 601   gaagtgcaga aaatgaaaac gtttggcaag gcggaagcaa cgcattatct gcaaatgggc 661   gcgtatgccg accgccgag cgcggaaggg cagcgtgcca aactggcaat cttgggcata 721   tcttccgaag tggtcggcta tcaggcggga cataaaacgc tttaccgcgt gcaaagcggc 781   aatatgtctg ccgatgcggt gaaaaaaatg caggacgagt tgaaaaagca tggggttgcc 841   agcctgatcc gtgcgattga aggcaaataa
```

NGO1607 >YP_208647.1; NC_002946.2
(1577171..1577752, complement)

SEQ ID NO: 44

```
      1   atgaaagtaa gatggcggta cggaattgcg ttcccattga tattggcggt tgccttgggc 61   agcctgtcgg catggttggg ccgtatcagc gaagtcgaaa tcgaggaagt caggctcaat 121   cccgacgaac ctcaatacac aatggacggc ttggacggaa ggcggtttga cgaacaggga 181   tacttgaaag aacatttgag cgcgaaaggt gcgaaacagt ttcccgaaaa cagcgacatc 241   cattttgatt cgccgcatct cgtgttcttc caagaaggca ggctgttgta cgaagtcggc 301   agcgatgaag ccgtttacca taccgaaaac aaacaggttc tttttaaaaa caacgttgtg
```

-continued

```
361  ctgaccaaaa ccgccgacgg caggcggcag gcgggtaaag tcgaaaccga aaaactgcac 421  gtcgataccg aatctcaata tgcccaaacc gatacgcctg tcagtttcca atatggcgcg 481  tcgcacggtc aggcgggcgg tatgacctac aaccacaaaa caggcatgtt gaacttctca 541  tctaaagtga aagccgcgat ttatgataca aaagatatgt aa
```

NGO1880 >YP_208913.1; NC_002946.2
(1849888..1850439, complement)

SEQ ID NO: 45

```
  1  atgaaggttt tgaacggttg gtcagatagg aagatgtggc gggttttgag tgctttgccg 61  ataggcgtgg tgtttttga tttgatctac ggttttgtgt tgaatgtgtt gcagggtttg 121  gatttgcagc gtgccgtgcc ggattcggaa ggcgtgttgg cggttacgcc cgatattgcg 181  ttcaacagtt tgcagattgt cgccaacggc ggtatggcgg cggtggtctg tttcgggttg 241  gcgttgtgt ttttgctcaa ccgttcggtg cggcggcggc aggtcttgga aatcggggtg 301  ttccggatgt tggggctggt ggcggtattg gcgttcagcg cgccttcgct gtgggagtgg 361  gcgaacgcgc tgccgctgct gctgaagggc gcggacgtgg tcaatacggg gaatgcgcgt 421  tatgtgctga cggctttgtg tatgcccttt ccggcggtgt cgtgcatcat cgggctggta 481  gggcggttca ggcttcagac ggcatcgggc agggtggcaa aggcagggggg tgcggtcaag 541  gcgggcggat ag
```

NGO1948 >YP_208972.1; NC_002946.2
(1921470..1921919, complement)

SEQ ID NO: 46

```
  1  atgaaaatcg gaacaacttg gcagacggca tccgctatgc tggttttgcg tctatttgcc 61  gcatatgaat ttttggaatc gggtttgcaa aaatggaacg gggagaattg gttttccgaa 121  atcaacgatc agtttccatt cccgttcaac ttgctgccgg acgcgttaaa ctggaatctc 181  gccatgtatg cggagctttt gctgcccgta ctgttgcttt tgggtttggc aacgcgcctg 241  tcggcattgg ggctgatggt cgttaccgcc gtcgcttggg ctgcggttca cgccggttcg
```

-continued

```
301  ggttacaatg tctgcgacaa cggttataaa atggctttaa tttatatcgt ggtattaatc 361  ccgctgcttt tccagggtgc gggcggatgg tcgctggata cgctgctgaa aaaactgttt 421  tgccccaaat gccgtctgaa acaagattga
```

NGO2057 >YP_209076.1; NC_002946.2
(2031669..2032517)

SEQ ID NO: 47

```
  1  atggacttca aacaatttga ttttttacac ctgatcagtg tttccggttg ggggcatctg 61  gctgaaaagg cgtgggcgtt cgggctgaac cttgccgccg cgctgcttat tttcttggtc 121  gggaaatggg cggcgaaacg cattgtcgcc gtaatgaggg cggcgatgac gcgcgcgcag 181  gtcgatgcca cgctgattag ttttttgtgt aatgttgcca atatcggctt attgattttg 241  gtgattattg ccgcattggg acggttgggc gtttccacaa catccgtaac cgccttaatc 301  ggcggcgcgg gtttggcggt ggcgttgtcc ttaaaagacc agctgtccaa ttttgccgcc 361  ggcgcgctga ttatcctgtt ccgcccgttc aaagtcggcg actttatccg tgtcggcggt 421  tttgaaggat atgtccggga aatcaaaatg gtgcagactt ctttgcggac gaccgacaac 481  gaagaagtcg tgctgcccaa cagcgtggtg atgggcaaca gcatcgtcaa ccgttccagc 541  ctgccgcttt gccgcgccca agtgatagtc ggcgtcgatt acaactgcga tttgaaagtg 601  gcgaaagagg cggtgttgaa agccgccgcc gaacacccct tgagcgttca aaacgaagag 661  cggcagcccg ccgcctacat caccgccttg ggcgacaatg ccatcgaaat cacattatgg 721  gcttgggcaa acgaagcaga ccgctggacg ctgcaatgcg acttgaacga acaagtggtc 781  gaaaacctcc gcaaagtcaa tatcaacatc ccgttcccgc aacgcgacat acacatcatc 841  aattcttaa
```

NGO0416 >YP_207571.1; NC_002946.2
(413598..413921)

SEQ ID NO: 48

```
  1  atgaaaaaat gtattttggg cattttgacc gcgtgtgccg ccatgcctgc atttgccgac 61  agaatcagcg atttggaagc acgtctggcg cagttggaac accgtgtcgc cgtattggaa
```

-continued

```
121  agcggcggca ataccgtcaa aatcgacctt ttcggttcaa attccaccat gtatgtatgc 181  agcgttacgc cttttcagaa gacgtttgag gcaagcgatc ggaatgaagg cgtggcgcgg 241  cagaaagtgc gtcaggcgtg caaccgcgaa acttcggcaa tgttttgcgg agatgaggca 301  atccgatgca gaaaattcga ttga
```

NG00571 >YP_207716.1; NC_002946.2
(553869..555665)

SEQ ID NO: 49

```
  1  atgcgctaca aaccccttct gcttgccctg atgctcgttt tttccacgcc cgccgttgcc 61  gcccacgacg cggcacacaa ccgttccgcc gaagtgaaaa aacaggcgaa gaacaaaaaa 121  gaacagcccg aagcggcgga aggcaaaaaa gaaaaaggca aaaatgccgc agtgaaagat 181  aaaaaaacag gcggcaaaga ggcggcaaaa gagttcaaaa aaaccgccaa aaaccgcaaa 241  gaagcagaga aggaggcgac atccaggcag tctgcgcgca aaggacgcga aggggataag 301  gaatcgaagg cggaacacaa aaaggcacat ggcaagcccg tgtccggatc caaagaaaaa 361  aacgcaaaaa cacagcctga aaacaaacaa ggcaaaaaag gggcaaaagg acaggcaat 421  ccgcgcaagg gcggcaaggc ggaaaaagac actgtttctg caaataaaaa agcccgttcc 481  gacaagaacg gcaaagcagt gaaacaggac aaaaaacaca cggaagagaa aaatgccaaa 541  accgattccg acgaattgaa agccgccgtt gccgctgcca ccaatgatgt cgaaaacaaa 601  aaagccctgc tcaaacaaag cgaaggaatg ctgcttcatg tcagcaattc cctcaaacag 661  cttcaggaag agcgtatccg ccaagaacgt atccgccaag agcgtatccg tcaggcgcgc 721  ggcaaccttg cttccgtcaa ccgcaaacag cgcgaggctt gggacaaatt ccaaaaactc 781  aataccgagc tgaaccgttt gaaaacggaa gtcgccgcta cgaaagcgca gatttcccgt 841  ttcgtatcgg ggaactataa aaacagccgg ccgaatgcgg ttgccctgtt cctgaaaaac 901  gccgaaccgg gtcagaaaaa ccgcttttg cgttatacgc gttatgtaaa cgcctccaat
```

-continued

```
 961  cgggaagttg tcaaggattt ggaaaaacag cagaaggctt tggcggtaca agagcagaaa 1021  atcaacaatg agcttgcccg tttgaagaaa attcaggcaa acgtgcaatc cctgctgaaa 1081  aaacagggtg taaccgatgc ggcggaacag acggaaagcc gcagacagaa tgccaaaatc 1141  tccaaagatg cccgaaaact gctggaacag aaagggaacg agcagcagct gaacaagctc 1201  ttgagcaatt tggagaaaaa aaaagccgaa caccgcattc aggatgcgga agcaaaaaga 1261  aaattggctg aagccaaact ggcggcagcc gaaaaagcca gaaaagaagc ggcgcagcag 1321  aaggctgaag cgcgacgtgc ggaaatgtcc aacctgaccg ccgaagacag gaacatccaa 1381  gcgccttcgg ttatgggtat cggcagtgcc gacggtttca gccgcatgca gggacgtttg 1441  aaaaaaccgg ttgacggtgt gccgaccggg cttttcgggc agaaccggag cggcggcgat 1501  gtttggaaag gcgtgttcta ttccactgcg cctgcaacgg ttgaaagcat tgcgccggga 1561  acggtaagct atgcggacga gttggacggc tacggcaaag tggtcgtgat cgatcacggc 1621  gagaactaca tcagcatcta tgccggtttg agcgaaattt ccgccggcaa gggttatacg 1681  gtcgcggcag gaagcaaaat cggcacgagc gggtcgctgc cggacgggga agagggctt 1741  tacctgcaaa tacgttatcg aggtcaggtg ttgaaccctt cgggctggat acgttga
```

NG00757 >YP_207884.1; NC_002946.2
(753640..754074, complement)

SEQ ID NO: 50

```
  1  gtgccgctgc ctgctccctg ccgtttttgcc aaacctgccg cctctttttt aagtatggct 61  ttgctttcct gccagctttc ccacgccgcc acggcttata tcccccgaa cgattttcaa 121  ccgaactgcg acatacgccg gctcgggctg acacagggtc agcacaatga gctgcgtaaa 181  atccgcgccg ccttcaaaat ggcgggcgac agggcgcgtt tgaaggttat gcattccgaa 241  cacagccgcc gccgctctgt cgtcgaaatc atttcttcgg atgttttaa tcggaacgag
```

-continued

```
301  gcgcgcgatt atgtcgaaag ccgctaccac tccagcatgg
     attttgcggt ggacgaattg 361  gaaatccaac accgcttctt ccatattctc acaccgcaac
     agcagcaaat gtggctttct 421  tcctgcctca aataa
```

NGO1215 >YP_208286.1; NC_002946.2
(1165669..1166142, complement)
                                SEQ ID NO: 51
```
  1  atgaaaaaat tattggcagc cgtgatgatg gcaggtttgg
     caggcgcggt ttccgccgcc 61  ggagtccatg tcgaggacgg ctgggcgcgc accactgtcg
     aaggtatgaa aatgggcggc 121  gcgttcatga aaatccccaa cgacgaagcc aaacaagact
     ttttgctcgt cggaagcagc 181  cccgttgccg accgcgtcga agtgcatacc cacatcaacg
     acaacggcgt gatgcgtatg 241  cgcgaagtca aaggcggcgt gcctttggag gcgaaatccg
     ttaccgaact caaacccggc 301  agctatcacg tgatgtttat gggtttgaaa aaacaactga
     aagagggcga caagattccc 361  gttaccctga aatttaaaaa cgccaaagcg caaaccgtcc
     aactggaagt caaaaccgcg 421  ccgatgtcgg caatgaacca cggtcatcac cacggcgaag
     cgcatcagca ctaa
```

NGO1251 >YP_208322.1; NC_002946.2
(1201722..1202300, complement)
                                SEQ ID NO: 52
```
  1  atgtgttttt gcctgcttct gatgccgaaa tttatttttt
     cttgccgaac aatttgtttt 61  ctcaaggcaa acttgattat aatggcgggt atgaaaaaat
     accttatccc tctttccatt 121  gcggcagtcc tttccgggtg ccagtctatt tatgtgccca
     cattgacgga aatccccgtg 181  aatcccatca ataccgtcaa aacggaagca cctgcaaaag
     gtttttcgcct cgccccttcg 241  cattgggcgg atgttgccaa aatcagcgat gaagcgacgc
     gcttgggcta tcaggtgggt 301  atcggtaaaa tgaccaaggt tcaggcggcg caatatctga
     caacttcag aaaacgcctg 361  gtcggacgca atgccgtcga tgacagtatg tatgaaatct
     acctgcgttc ggcggtagac 421  agccagcgcg gcgaaatcaa tacggaacag tccaagctgt
     atatcgagaa tgccttgcgc
```

-continued

```
481  ggctggcagc agcgttggaa aaatatggat gccaaacccg
     ataatcccgc atttaccaac 541  tttttgatgg aagtgatgaa gatgcagccc ttgaaatga
```

NGO1438 >YP_208492.1; NC_002946.2
(1402283..1403068)
                                SEQ ID NO: 53
```
  1  atgaaaacca agttaatcaa aatcttgacc cccttttaccg
     tcctgccgct gctggcttgc 61  gggcaaacgc ccgtttccaa tgccaacgcc gaatccgccg
     tcaaagccga atccgccggc 121  aaatccgttg ccgcttcttt gaaagcgcgt ttggaaaaaa
     cctattccgc ccaagatttg 181  aaagtgttga gcgtcagcga aacaccggtc aaaggcattt
     acgaagtcgt cgtcagcggc 241  aggcagatta tctacaccga tgccgaaggc ggctatatgt
     tcgtcggcga actcatcaac 301  atcgacacgc gcaaaaacct gaccgaagaa cgcgccgccg
     atttgaacaa aatcgacttc 361  gcctccctgc ctttggacaa agccatcaaa gaagtacgcg
     gcaacggcaa gctgaaagtc 421  gccgtcttct ccgaccccga ttgtccgttc tgcaaacgct
     tggaacatga gtttgaaaaa 481  atgaccgacg tgacggttta cagctttatg atgcccattg
     ccggcctgca cccagatgcc 541  gcgcgcaagg cgcaaatctt atggtgtcag cccgaccgtg
     ccaaagcgtg gacggattgg 601  atgcgtaaag gcaaattccc ggtcggcggc agcatctgcg
     acaatcccgt cgcggaaacc 661  acttccttgg gcgaacagtt cggcttcaac ggcacgccga
     ccctcgtctt ccccaacggg 721  cgcacccaaa gcggttacag cccgatgccc caactggagg
     aaatcatccg caaaaaccag 781  cagtaa
```

NGO1701 >YP_208734.1; NC_002946.2
(1658077..1658532)
                                SEQ ID NO: 54
```
  1  atgaaccgtc gtcaattttt gggcagcgcc gctgccgtct
     ctttggcttc cgccgcctct 61  ttcgcgcgtg cgcacggaca cgccgactac caccatcatc
     acgatatgca gcctgccgcc 121  gcatccgcct acaccgccgt ccgccaaact gccgcacact
     gtctggatgc cggacaggtt 181  tgcctgaccc actgcctgtc cctgctcact cagggcgaca
     cgtctatgtc cgactgtgcg
```

-continued

```
241  gttgccgtgc gccagatgct tgccttatgc ggcgcggtgc acgaccttgc cgcacaaaat 301  tcccctctga cacgcgacgc ggcaaaagtg tgcctcgaag cgtgcaaaca gtgtgccaaa 361  gcctgtaaag aacactccgc ccaccatgcg gaatgcaaag cctgttacga gtcctgcctc 421  gactgtatca agaatgcgaa aaaactcgcc gcctga
```

NGO1868 >YP_208900.1; NC_002946.2
(1839566..1840165, complement)

SEQ ID NO: 55

```
  1  atggctttta ttacgcgctt attcaaaagc attaaacaat ggcttgtgct gttgccgata 61  ctctccgttt tgccggacgc ggcggcggag ggcattgccg cgacccgcgc cgaagcgagg 121  ataaccgacg gcgggcggct ttccatcagc agccgcttcc aaaccgagct gcccgaccag 181  ctccaacagg cgttgcgccg gggcgtaccg ctcaacttta ccttaagctg gcagctttcc 241  gccccgacaa tcgcttctta tcggtttaaa ttggggcaac tgattggcga tgacgacaat 301  attgactaca aactaagttt ccatccgctg accaaccgct accgcgttac cgtcggcgca 361  ttttccaccg attacgacac tttggatgcg gcattgcgcg cgaccggcgc ggttgccaac 421  tggaaagtcc tgaacaaagg cgcgttgtcc ggtgcggaag caggggaaac caaggcggaa 481  atccgcctga cgctgtccac ttcaaaactg cccaagcctt tccaaatcaa cgcattgact 541  tctcaaaact ggcatttgga ttcgggttgg aaacctctaa acatcatcgg gaacaaataa
```

NGO2119 >YP_209129.1; NC_002946.2
(2105123..2105713)

SEQ ID NO: 56

```
  1  atgaaaaaat cctccttcat cagcgcattg ggcatcggta ttttgagcat cggcatggca 61  tttgcctccc cggccgacgc agtgggacaa atccgccaaa acgccacaca ggttttgacc 121  atcctcaaaa gcggcgacgc ggcttctgca cgcccaaaag ccgaagccta tgcggttccc 181  tatttcgatt ccaacgtat gaccgcattg gcggtcggca accccttggcg taccgcgtcc 241  gacgcgcaaa acaagcgtt ggccaaagaa tttcaaaccc tgctgatccg cacctattcc
```

-continued

```
301  ggcacgatgc tgaaattcaa aaacgcgacc gtcaacgtca aagacaatcc catcgtcaat 361  aagggcggca aggaaatcgt cgtccgtgcc gaagtcggca tccccggtca gaagcccgtc 421  aatatggact ttaccaccta ccaaagcggc ggcaaatacc gtacctacaa cgtcgccatc 481  gaaggcacga gcctggttac cgtgtaccgc aaccaattcg gcgaaatcat caaagccaaa 541  ggcatcgacg ggctgattgc cgagttgaaa gccaaaaacg gcggcaaata a
```

NGO0227 >YP_207392.1; NC_002946.2
(230200..230445)

SEQ ID NO: 57

```
  1  ttgaaggatt ctacagggca aatgaggctg gcaaccaagg atttggcgga agccattaaa 61  cgaggagaag tacgtagttc tgcttttaca acaaagcaac taaaggcaat cgaaaaaggc 121  aaagacaaaa tccctagcta cacttggcat catcatcaag atacagggag aatgcagctt 181  gtgcctgaat gggaacattc taaaaccggt cacataggag ggacggcaat ggggaagggt 241  aaataa
```

NGO0354 >YP_207510.1; 002946.2
(346195..346515)

SEQ ID NO: 58

```
  1  atgaatttcc aagactatct cgccacattt ccttcaatcg accatctggg cggtttggat 61  gttcaggatg ccgaaggcaa aacggttcac cacattcccg ccgttcaggg caagctcggt 121  tcgctcaagc tgtacaatgc cttggcggaa cgttttgatg gaaaattggg taaagaagcg 181  gcagaacagg gtttgatatg gtttgccgaa catgttgccg acgcgcgcgc ccatccgggg 241  aagcatccga acatcgattt gctggaaaat gtcgtgcaaa gcggcgaaac cctcctgctc 301  aaaccgcttg ccgcgcaata a
```

NGO0588 >YP_207731.1; NC_002946.2
(573500..573982)

SEQ ID NO: 59

```
  1  atgatgaaaa agatactggc agtatcggca ctatgcctga tgactgcggc ggcacaggct 61  gccgatactt acggctatct cgccgtttgg cagaatccgc aggatgcaaa cgatgttttg 121  caggttaaaa ccacaaaaga agattcggcg aaaagcgaag cgtttgccga gttggaagcc
```

-continued

```
181    ttttgcaaag gtcaggacac gcttgcgggc attgccgaag acgagccgac cggatgccgg 241    tcggtcgtgt cgctgaacaa tacctgtgtc tcgctggcat acccgaaagc cttgggcgcg 301    atgcgcgttg aaaacgccgt cgtgattact tctccgcgtt ttacgagcgt tcatcaggtc 361    gcactcaacc agtgcataaa aaaatacggc gcacagggac aatgcggctt ggaaacagtg 421    tattgcacgt catcttctta ttacggcggg gctgttcgct ccttaatcca acacctgaaa 481    taa
```

NGO0648 >YP_207787.1; NC_002946.2
(638163..638717)
                                    SEQ ID NO: 60
```
  1    atgaaaaaaa tcatcgcctc cgcgcttatc gcaacattcg cactcaccgc ctgccaagac 61    gacacgcagg cgcggctcga acggcagcag aaacagattg aagccctgca acagcagctc 121    gcacagcagg cagacgatac ggtttaccaa ctgactcccg aagcagtcaa agacaccatt 181    cctgcccagg cgcaggcaaa cggcaacaac ggtcagcccg ttaccggcaa agacgggcag 241    cagtatattt acgaccaatc gacaggaagc tggctgctgc aaagcctgat tggcgcggcg 301    gcaggcgcgt ttatcggcaa cgcgctggca aacaaattca cacgggcggg caaccaagac 361    agccccgtcg cccgtcgcgc gcgtgctgcc taccatcagt ccgcacgccc caatgcgcgc 421    accagcaggg atttgaacac gcgcagcctc cgtgcaaaac aacaggcggc gcaggcgcag 481    cgttaccgcc cgacaacgcg cccgcccgtc aattaccgcc gtcccgctat cgcgcggtttc 541    ggcagaaggc ggtaa
```

NGO0678 >YP_207817.1; NC_002946.2
(666979..667233, complement)
                                    SEQ ID NO: 61
```
  1    atgaacaaac ttttcgttac cgccctgtcc gccctcgcct tgtccgcctg cgccggcact 61    tggcagggcg cgaaacaaga caccgcccgc aaccttgaca aaacacaggc cgccgccgaa 121    cgcgccgccg aacaaacagg caacgccgtc gaaaaaggtt gggacaaaac caaagaagcc
```

-continued

```
181    gtcaaaaaag gcggcaatgc cgtcggacgc ggcatttccc atctcggcaa aaaaatcgaa 241    aacgccaccg aataa
```

NGO0690 >YP_207829.1; NC_002946.2
(680960..681328, complement)
                                    SEQ ID NO: 62
```
  1    atgaataaaa ccttgtctat tttgccggcg gcaatcttac tcggcgggtg cgccgccggc 61    ggcaacacat tcggcagctt agacggcggc acgggtatgg gtggcagcat cgtcaaaatg 121    acggtagaaa gccaatgccg tgcggaattg gacaggcgca gcgaatggcg tttgaccgcg 181    ctggcgatga gtgccgaaaa acaggcggaa tgggaaaaca agatttgcgg ctgcgctacc 241    gaagaagcac ctaaccagct gaccggcaac gatgtgatgc agatgctgaa ccagtccacg 301    cgcaatcagg cacttgccgc cctgaccgtc aaaacggttt ccgcctgctt caaacgcctg 361    taccgctaa
```

NGO0694 >YP_207831.1; NC_002946.2
(684728..687346, complement)
                                    SEQ ID NO: 63
```
  1    atgaaccaag aaggggattac cgctcacgga aatgccacga ttaccctcaa ggcgaaagaa 61    aacaataaaa ttaccgtgga aaacgccgca tacagcagcg acggcatttc gactctgatt 121    aacagaacgg gggcaagacc cggaacaagg gatgatggaa ataaaatcat actggaagcc 181    ggcggcgata atattgttac catgaaatcc ggcgatgcgg atgcggatta tgtaaacaat 241    tccaaagtat taacggagac accatattat aaaagcaaac gaggttccaa cggcatttttt 301    gcctatgcg acaaatcgct ggtcaaactg attggcgaga ataatatcgt taagagtgaa 361    atcagtgaaa aatctaaggc attaaatggg ggatttcgcc atatcggcat ttattcatgg 421    caaaacgcga aagtcgaatt gtctgcgaag agcgacaata tcgtacaagg cggaatttgg 481    ggcttatact ccaacaactc ctcaatttcc ctcaagggga aaaataatgt gatttcaaac 541    ccgaaatata atgttttcgc ctacaaaaag gcaaaggtgg atttgactgt cgaaaataaa
```

-continued

```
 601  aacacattat ctgatgcgga atttggcgta tatgccttaa
       acacaagtat ggttaatttg 661  tcttcaaaag ataataacga ggtaaaaagc acccaagtgg
       gtctgtattc gcaagacggc 721  ggttcaatca atgtagatag gaaggataat attattgaag
       gcgacgcggt tgccttggtg 781  ggaaaaggtg gaagtcaaaa cattcgggca agccgtacaa
       acctgattag ttcaaaaagc 841  ttaggaattc atgctgaaca agctgcaaaa atagccataa
       ccggcgcaag caatacaatt 901  catgcaagca atgccgctat tcgttcatta gacaaaagcg
       aagttaagat tgacggtcaa 961  attaccattg actccaacgt tgccaatctt gcaaggcaag
       atggttcaat tcatttgaat 1021  tataaagacg atacccgtat cacaggggca accgtatctg
       ataagggttt ggtagccatc 1081  aaacctttga ataacacgaa tattgttgcc gacactattc
       actataaagg cgatgtcttg 1141  gcggtaaata agggtaaagt ggaattagat ttcacgccga
       acatcctttt agcgggacgt 1201  ttggataatt ttagcggctt aaccgattcc aaacataaaa
       atttattcga aaactatgtt 1261  gcaaatttag acagcaaaag tgcgggcgaa attaacttta
       atttagccaa agacgcatta 1321  tggacgatga caggtcaaag ctggctggat aaattggaag
       gacaaggcac tatcgatttt 1381  aataatgatg ctaaaacaag tggacgcgcc ttacatatcg
       gcgaattggc gggtgccaat 1441  aaattcttga tgcatctgaa taaagacggc attcacagcg
       atatgctcta tgtgaaaaaa 1501  ggcacttcga caccgcaaga agtcgtcgtc aaaaatctgt
       ccgaagtgct cgacagtatg 1561  aattacggcg aacgtttgcg tttcgctaca gtaacaaact
       caaaaaatga atttgtgaac 1621  ggtaaaaaat atattgacga tacgcacctt atggaggatg
       ccctgactgt cgaatactcc 1681  gcacataacg gcgataaaaa caacaaggat gactataata
       aatcctttaa cggctctgaa 1741  atgacggcgg aaaaagctgg agacgattat gtcaataaaa
       cctataccga caacaggcaa
```

-continued

```
1801  aatgtctatt tggtcaaaca ggctaccggc aatccgagcc
       gaaatgtcaa aaatatcaat 1861  gatatgttcg attcaaccgc acattatgcg ttcactttgg
       atacttatgc caaacgcgaa 1921  ggggagcggg cttttttcaac gttggataaa aaagaaggcg
       attggataag gctgacgcat 1981  acccgtgtga ttcaatccaa tgcgtttagg tttcataaca
       acgattttga aatcggatat 2041  gaccgattca gcctcaacga gcaggagaaa aaacgcaaat
       ggggcataag tctcgactac 2101  ggccacggca ggacatcatt atggaatacg tttggcaagg
       acaaaatcag gaaatatgaa 2161  ttggctctgt acaatactac ccaatacata gataaagaag
       gagacgaaac agggtatatc 2221  gacaatgtat taaaaatagg aaaactgcgt aaccgtgtga
       ttgcacgaaa tcatatgggg 2281  caattatggg gcaagggaaa atatagcaac accctattct
       ctatcagcac cgaatacggc 2341  cgccgtaaat ttttggatga cgataaattg tggcggatta
       caccgcaagt acagttgcaa 2401  tattcctatt tgagaggtac cggctatcgg atcgataacg
       gcataaacgt caatttaagc 2461  cacgcaaaca gcctgatagg ccgcttgggt ttggatgtcg
       tgagaaaatt tgacggaggc 2521  aaaaaacttt tctatatcaa aggcaatatc tttcatgaat
       ttttgggcag tcgttccttt 2581  aaggcatttg agggcaaaag tcattatgct caaaaatga
```

NG00768 >YP_207895.1; NC_002946.2
(762907..763158, complement)

SEQ ID NO: 64
```
   1  atgtggcaaa ttcggaaaaa caggacggaa aacttgcaca
       acgcgccgaa ctaccctatc 61  cttctcttga aacaaaacct tttctttaag gaaaacaatg
       aatatcagga aaatctccgc 121  tttgtgtgct gttgccgttt ttactgtttc gacagcctat
       gccaaagaaa tcaaaatcga 181  tgccaacaac acgccttatt ccgaagccga cgcgcaaaag
       ctggcggcaa cggcagtcgg 241  tatgggcgtt aa
```

NG00861 >YP_207975.1; NC_002946.2
(844152..844400, complement)

SEQ ID NO: 65
```
   1  atgaaaatga agaaactgat tttgttgtcg gtggctgcga
       tgttggtgac ggcatgtact
```

-continued

```
   61   tacgcagacc gccgttttgt aactcaagaa tctgcagcgg aaatacaggc gaaaagtcgt 121   gccattcaga taagcgagcg tgccgagcgt gccgaataccc gtaaagaacg ccgggaagaa 181   atgatggatg cggcacgcgc catcaaaaag gcaaacgaaa attcacccaa tatttatttt 241   atccgataa
```

NGO0891 >YP_208002.1; NC_002946.2
(870109..870528, complement)

SEQ ID NO: 66

```
    1   atgaaaaaac ttctaatgat aaccctcacc ggtatgcttg cagcttgttc aacaggtgtc 61   aatgtcggcc ggttgatggt tgaaatgccg cagggagaac gccctgttgt cgtgcaggtt 121   cccgcgacga ataacccgct ttccgatgcg gtggctgtcg gaatgattaa aacatccgga 181   tcgccttcgg catcaaatat gattgaaatg ctcggcgcgg acaatatcaa cgtcggcgtg 241   gcgggaggca gccaaatgtt taataaggcg accgcacttt attccttaaa ccatgcaaag 301   aaagtcggaa ataatgtcag tgtctatatg acgggcgata gcgaaagcga caaggccgat 361   ttggaaaacg cggcaaatgc caaaaatatt aaattacatt atttctttaa ccaaaaataa
```

NGO0948 >YP_208051.1; NC_002946.2
(922329..923525)

SEQ ID NO: 67

```
    1   atgccgtctg aaccgttcgg acggcataac atgacaaaca ctttaatatc catcacacag 61   gatgacacga tgacccatat caaacccgtc attgccgcgc tcgcactcat cgggcttgcc 121   gcctgctccg gcagcaaaac cgaacagccc aagctcgact accaaagccg gtcgcaccgc 181   ctgatcaaac tcgaagtccc ggctgatttg aacaaccccg accaaggcaa cctctaccgc 241   ctgcctgccg gttcgggagc cgtccgcgcc agcgatttgg aaaaacgccg cacacccgcc 301   gtccaacagc cagccgatgc cgaagtattg aaaagcgtca aaggcgtccg cctcgagcgc 361   gacggcagcc aacgctggct tgtcgttgac ggcaaatccc ccgccgaaat ctggccgctt 421   ctgaaagcct tttggcagga aaacggcttc gacatcgaat ccgaagaacc cgccatcgga
```

-continued

```
  481   caaatggaaa ccgagtgggc ggaaaaccgt gccaaaatcc cccaagacag cttgcgccgc 541   ctattcgaca cagtcggttt gggcggcatc tactccaccg gcgagcgcga caaattcatc 601   gtccgtatcg aacagggcaa aaacggcgtt tccgacatct tcttcgccca caaagcgatg 661   aaagaagtgt atggcgacaa aaacaaagac acgaccatgt ggcagccttc cgcttccgac 721   cccaaccttg aggccgcttt cctgacgcgc tttatgcaat atttgggcgt tgacggacgg 781   caggcggaaa acgcattggc aaaaaaaccg accccttcccg ccgccaacga aatggcgcgt 841   atcgaaggca aaagcctgat tgtctttggc gactacggca gaaactggcg gcgcaccggc 901   cttgccctcg accgcatcga actgaccgtc gtcggtcaaa acaccgaacg ccacgccttc 961   ctggttcaaa aagccccgaa cgaaagcaat gcagttaccg aacaaaaacc ggggctgttc 1021   aaacgcctac tgggcaaagg caaagcggag aaacctgccg aacagccgga actgattgtc 1081   tatgccgagc ctgtcgccga cggttcgcgc atcgtcctgc tcaacaaaga cggcagcgca 1141   tatgccggca aagacgcatc cgcactgtta ggcaaactcc attccgaact gcgttaa
```

NGO1043 >YP_208127.1; NC_002946.2
(1003573..1003917, complement)

SEQ ID NO: 68

```
    1   atgaaaaaat tattgattgc cgcaatgatg gcggctgcct tggcagcttg ttcgcaagaa 61   gccaaacagg aggttaaaga agcggcccaa gccgttgagt ccgatgttaa agacactgcg 121   gcttctgccg ccgagtctgc cgcttctgcc gtcgaagaag cgaaaggcca agtcaaagat 181   gctgcggctg atgcaaaggc aagtgccgag gaagctgtaa ctgaagccaa agacgcggca 241   gccgaaacca agaagcggt aagcgaagcg gctaaagaca ctttgaacaa agctgccgac 301   gcggctcagg aagcggcaga caaaatgaaa gacgccgcca aataa
```

NGO1428 >YP_208483.1; NC_002946.2
(1390072..1390344)

SEQ ID NO: 69

```
    1   atgaagaaaa ccagcaaata tcttatctat actgcggcat ttacctcatt ctgctttgcc
```

-continued

```
   61   ttccaagaaa accgttctga agccaaacag cccgacatca ctttatccgc atccctgtgc 121   gaacaattca acatgctgaa cgccaaagat atggatacag aacaagtctc cctttccaaa 181   gaatgcgaca tcatcgagtc ttcacacgac tgggaaaaag agtacggcaa cttgaacgaa 241   caggaaatgc tcgccggcgt cgtctatgaa taa
```

NGO1729 >YP_208762.1; NC_002946.2
(1689736..1690062)
SEQ ID NO: 70
```
    1   atgaacatca aacaccttct cttgaccgcc gccgcaaccg cactgttggg catttccgcc 61   cccgcactcg cccaccacga cggacacggc gatgacgacc acggacacgc cgcacaccaa 121   cacggcaaac aagacaaaat catcagccgc gcccaagccg aaaaagcggc ttgggcgcgt 181   gtcggcggca aaatcaccga catcgatctc gaacacgacg acggccgtcc gcactatgat 241   gtcgaaatcg tcaaaaacg acaggaatac aaagtcgttg tcgatgcccg taccggccgc 301   gtgatttcct cccgccgcga cgactga
```

NGO1802 >YP_208832.1; NC_002946.2
(1776008..1776565)
SEQ ID NO: 71
```
    1   atgccgtctg aagcccttca gacggcattt cgcggcaaca tccgaaggag ttttaccatg 61   atccgtttga cccgcgcgtt tgccgccgcc ctgatcggtt tatgctgcac cacaggcgcg
```

-continued

```
  121   cacgccgaca ccttccaaaa aatcggcttt atcaacaccg agcgcatcta cctcgaatcc 181   aagcaggcgc gcaacatcca aaaaacgctg gacggcgaat tttccgcccg tcaggacgaa 241   ttgcaaaaac tgcaacgcga aggcttggat ttggaaaggc agctcgccgg cggcaaactt 301   aaggacgcaa aaaaggcgca agccgaagaa aaatggcgcg ggctggtcga agcgttccgc 361   aaaaaacagg cgcagtttga agaagactac aacctccgcc gcaacgaaga gtttgcctcc 421   ctccagcaaa acgccaaccg cgtcatcgtc aaaatcgcca aacaggaagg ttacgatgtc 481   attttgcagg acgtgattta cgtcaacacc caatacgacg ttaccgacag cgtcattaaa 541   gaaatgaacg cccgctga
```

NGO1947 >YP_208971.1; NC_002946.2
(1921058..1921396, complement)
SEQ ID NO: 72
```
    1   atgaacaaaa atattgctgc cgcactcgcc ggtgctttat ccctgtctct ggccgccggc 61   gccgttgccg cccacaaacc ggcaagcaac gcaacaggcg ttcaaaaatc cgcccaaggc 121   tcttgcggcg catccaaatc tgccgaaggt tcgtgcggcg catccaaatc tgccgaaggt 181   tcgtgcggcg cggctgcttc taaagcaggc gaaggcaaat gcggcgaggg caaatgcggt 241   gcaactgtaa aaaaagccca caaacacacc aaagcatcta aagccaaagc caaatctgcc 301   gaaggcaaat gcggcgaagg caaatgcggt tctaaataa
```

---

The invention claimed is:

1. A composition comprising:

a) two or more purified antigens, wherein the two or more purified antigens are selected from the group consisting of:

NGO0188, NGO0449, NGO0914, NGO1332, NGO1377, NGO1543, NGO1549, NGO1607, NGO1880, NGO1948, NGO2057, NGO0416, NGO0571, NGO0757, NGO1215, NGO1251, NGO1438, NGO1701, NGO1868, NGO2119, NGO0227, NGO0354, NGO0588, NGO0648, NGO0678, NGO0690, NGO0694, NGO0768, NGO0861, NGO0891, NGO0948, NGO1043, NGO1428, NGO1729, NGO1802, and NGO1947; and b) at least one adjuvant;

wherein the composition induces the production of antibodies with bactericidal activity.

2. The composition of claim 1, wherein the bactericidal activity is bactericidal activity against *Neisseria gonorrhoeae*.

3. The composition of claim 1, comprising:

at least one further antigen.

4. The composition of claim 3, wherein the at least one further antigen is selected from the group consisting of:

porin, pilin, transferrin binding protein A (TbpA), transferrin binding protein B (TbpB), Lipooligosaccharide (LOS), MetQ/NlpA family ABC transporter substrate-binding protein Q (MetQ) surface-exposed lysozyme inhibitor of c-type (SliC), Multidrug efflux transporter outer membrane subunit E (MtrE), β-Barrel Assembly Machinery protein A (BamA), and Adhesin Complex Protein (ACP).

5. The composition of claim 1, wherein at least one purified antigen is a lipoprotein.

6. The composition of claim 1, wherein the composition induces the production of antibodies with bactericidal activity against multiple strains of *Neisseria gonorrhoeae*.

7. The composition of claim 1, wherein the composition is a recombinant subunit composition.

8. The composition of claim 1, wherein at least one purified antigen is a soluble polypeptide.

9. A method of provoking an immune response to a pathogenic bacterium in a subject, the method comprising: administering to a subject a composition of claim 1.

10. The method of claim 9, wherein the composition provokes an immune response that is protective against a plurality of strains of the bacteria.

11. The method of claim 9, wherein the composition provokes an immune response that is protective against multiple strains of *Neisseria gonorrhoeae*.

12. A composition comprising:

a purified NGO0690 polypeptide;

a purified NGO1701 polypeptide; and at least one adjuvant.

13. A composition comprising:

a purified NGO690 polypeptide;

a purified NGO0948 polypeptide;

a purified NGO1701 polypeptide; and at least one adjuvant.

* * * * *